(12) United States Patent
Huang et al.

(10) Patent No.: US 11,219,694 B2
(45) Date of Patent: Jan. 11, 2022

(54) METHODS AND COMPOSITIONS FOR REDUCING METASTASES

(71) Applicant: THE UNIVERSITY OF NORTH CAROLINA AT CHAPEL HILL, Chapel Hill, NC (US)

(72) Inventors: Leaf Huang, Durham, NC (US); Tyler Goodwin, Chapel Hill, NC (US); Rihe Liu, Chapel Hill, NC (US); Lei Miao, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 199 days.

(21) Appl. No.: 15/763,065

(22) PCT Filed: Sep. 15, 2016

(86) PCT No.: PCT/US2016/051966
§ 371 (c)(1),
(2) Date: Mar. 23, 2018

(87) PCT Pub. No.: WO2017/053170
PCT Pub. Date: Mar. 30, 2017

(65) Prior Publication Data
US 2019/0381184 A1 Dec. 19, 2019

Related U.S. Application Data

(60) Provisional application No. 62/232,169, filed on Sep. 24, 2015.

(51) Int. Cl.
| | | |
|---|---|---|
| *A61K 47/68* | (2017.01) | |
| *A61K 47/65* | (2017.01) | |
| *A61K 48/00* | (2006.01) | |
| *C07K 14/47* | (2006.01) | |
| *C07K 16/28* | (2006.01) | |
| *C12N 15/62* | (2006.01) | |

(52) U.S. Cl.
CPC .......... *A61K 47/6881* (2017.08); *A61K 47/65* (2017.08); *A61K 48/005* (2013.01); *C07K 14/47* (2013.01); *C07K 16/2818* (2013.01); *C07K 16/2827* (2013.01); *C12N 15/62* (2013.01); *C07K 2317/31* (2013.01); *C07K 2319/035* (2013.01)

(58) Field of Classification Search
None
See application file for complete search history.

(56) References Cited

U.S. PATENT DOCUMENTS

| 8,512,701 B2 | 8/2013 | Lillard et al. | |
|---|---|---|---|
| 2005/0009149 A1* | 1/2005 | West ....................... | A61P 43/00 435/69.7 |
| 2006/0110383 A1* | 5/2006 | Honjo ..................... | A61P 31/22 424/133.1 |
| 2014/0086835 A1* | 3/2014 | Liu ......................... | C07K 14/47 424/1.69 |
| 2015/0203579 A1* | 7/2015 | Papadopoulos ........... | A61P 7/04 424/142.1 |

FOREIGN PATENT DOCUMENTS

| CN | 102250254 A | 11/2011 |
|---|---|---|
| CN | 103857699 A | 6/2014 |
| CN | 107108707 A | 8/2017 |
| CN | 108079301 A | 5/2018 |
| JP | 2015-57442 A | 3/2015 |
| WO | WO 2001/83750 A3 | 5/2002 |
| WO | WO-2013-071068 A2 | 5/2013 |
| WO | WO 2014/121085 A1 | 8/2014 |
| WO | WO 2015/118175 A2 | 8/2014 |
| WO | WO-2015-019284 A2 | 2/2015 |
| WO | WO 2017/053170 A1 | 3/2017 |
| WO | WO 2018/160572 A1 | 9/2018 |

OTHER PUBLICATIONS

EP 16849370.8 Extended European Search Report dated Feb. 26, 2019.
Feig, et al., "Targeting CXCL12 from FAP-expressing carcinoma-associated fibroblasts synergizes with anti-PD-L1 immunotherapy in pancreatic cancer," PNAS, vol. 110, No. 50, 20212-20217, (Dec. 10, 2013).
Miao, et al., "Transient and Local Expression of Chemokine and Immune Checkpoint Traps to Treat Pancreatic Cancer," ACS Nano, 11, 8690-8706, (2017).
Goodwin, et al., "Liver specific gene immunotherapies resolve immune suppressive ectopic lymphoid structures of liver metastases and prolong survival," Biomaterials, 141, 258-271, (2017).
International Search Report and Written Opinion for corresponding International Application No. PCT/US2016/051966, dated Mar. 30, 2017, 15 pages.
Zhong et al., Development and Preclinical Characterization of A Humanized Antibody Targeting CXCL12, Clinical Cancer Research, 2012, vol. 19, No. 16, pp. 4433-4445.

(Continued)

*Primary Examiner* — Nelson B Moseley, II
(74) *Attorney, Agent, or Firm* — Alston & Bird LLP

(57) ABSTRACT

The subject matter described herein is directed to methods of modifying the micro-environment of a target cell or The methods comprise systemically administering to a subject a composition comprising a vector, wherein the vector comprises a construct for the expression of a trap in the target cell, wherein the trap is expressed in the target cell thereby modifiying the micro-environment. Also described herein are methods of reducing metastasis of a cancer comprising, systemically administering to a subject suffering from the cancer, a composition comprising a vector, wherein the vector comprises a construct for the expression of a trap, wherein the trap is delivered to and then expressed in tissue susceptible to metastasis, wherein metastasis of the cancer to the tissue is reduced. Compositions for carrying out the methods are also described.

5 Claims, 42 Drawing Sheets

Specification includes a Sequence Listing.

(56) References Cited

OTHER PUBLICATIONS

Harris et al., Inhibiting CXCL12 Blocks Fibrocyte Migration and Differentiation and Attenuates Bronchiolitis Obliterans in a Murine Heterotopic Tracheal Transplant Model, The Journal of Thoracic and Cardiovascular Surgery, 2013, vol. 145, No. 3, pp. 845-861.
*Crystal structure of the complex between programmed death-1 (PD-1) and its ligand PD-L2* by Lazar-Molnar et al., PNAS, Jul. 29, 2008, vol. 105, No. 30, pp. 10483-10488.
*The Crystal Structure of the Costimulatory OX40-OX40L Complex*, Compaan et al., Structure 14, pp. 1321-1330, Aug. 2006, Elsevier Ltd.
Accession 2M2D_A, NCBI Chain A, Programmed Cell Death Protein 1 (May 15, 2013).
Accession 3BIK_A, NCBI Chain A, Programmed Cell Death Protein 1 (Oct. 10, 2012).
Zhu Jiang, "The function and regulation of PD-L1 in keratinocytes and the intervention of indirubin," 1-64, Wanfang dissertation database, (Sep. 17, 2008), English Abstract.
Xue Xiaochuan, "The function and regulation of PD-L1 in keratinocytes and the intervention of indirubin," 1-115, Wanfang dissertation database, (Jun. 18, 2019), English Abstract.

* cited by examiner

Figure 1A-B
A
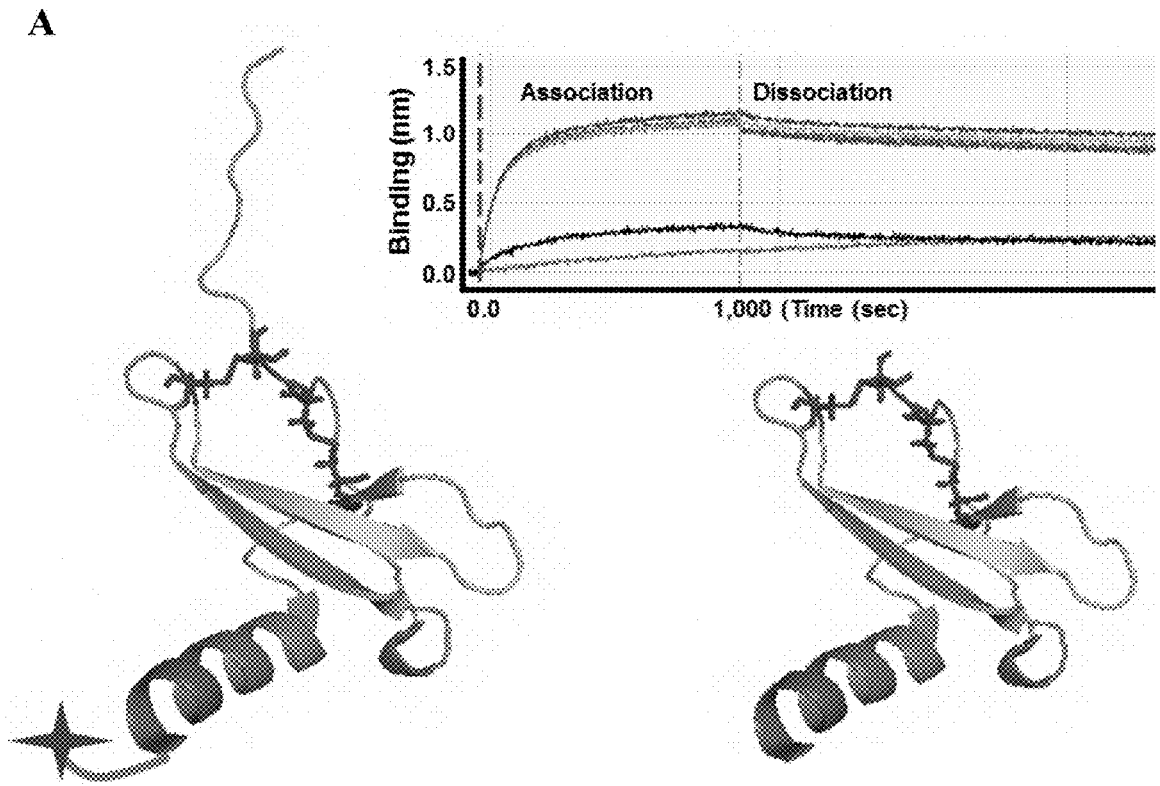
B
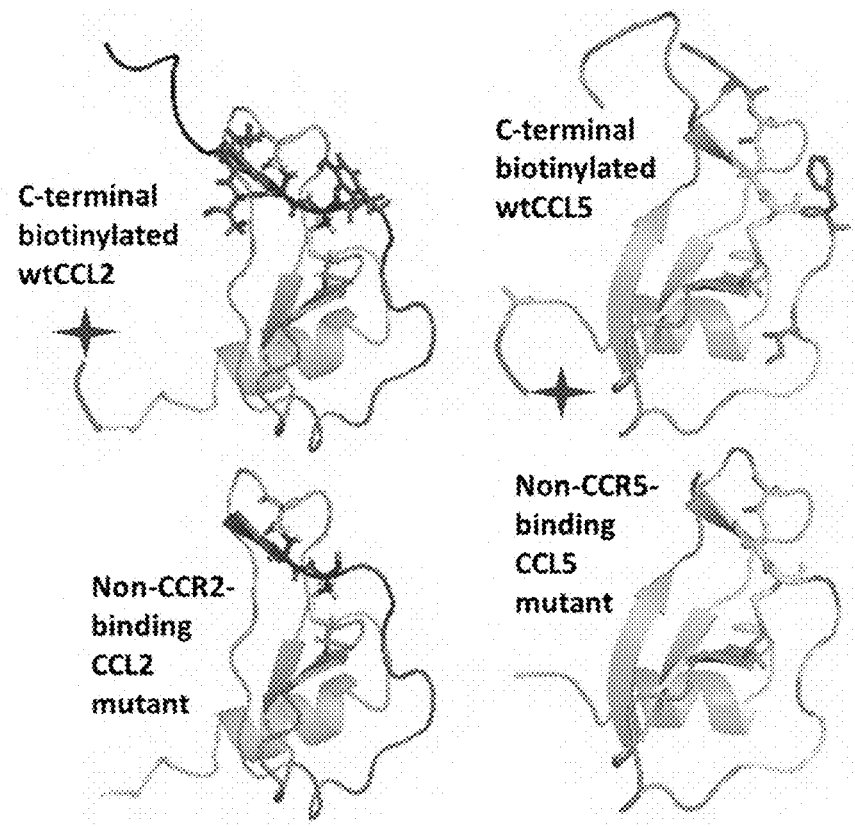

Figure 1D
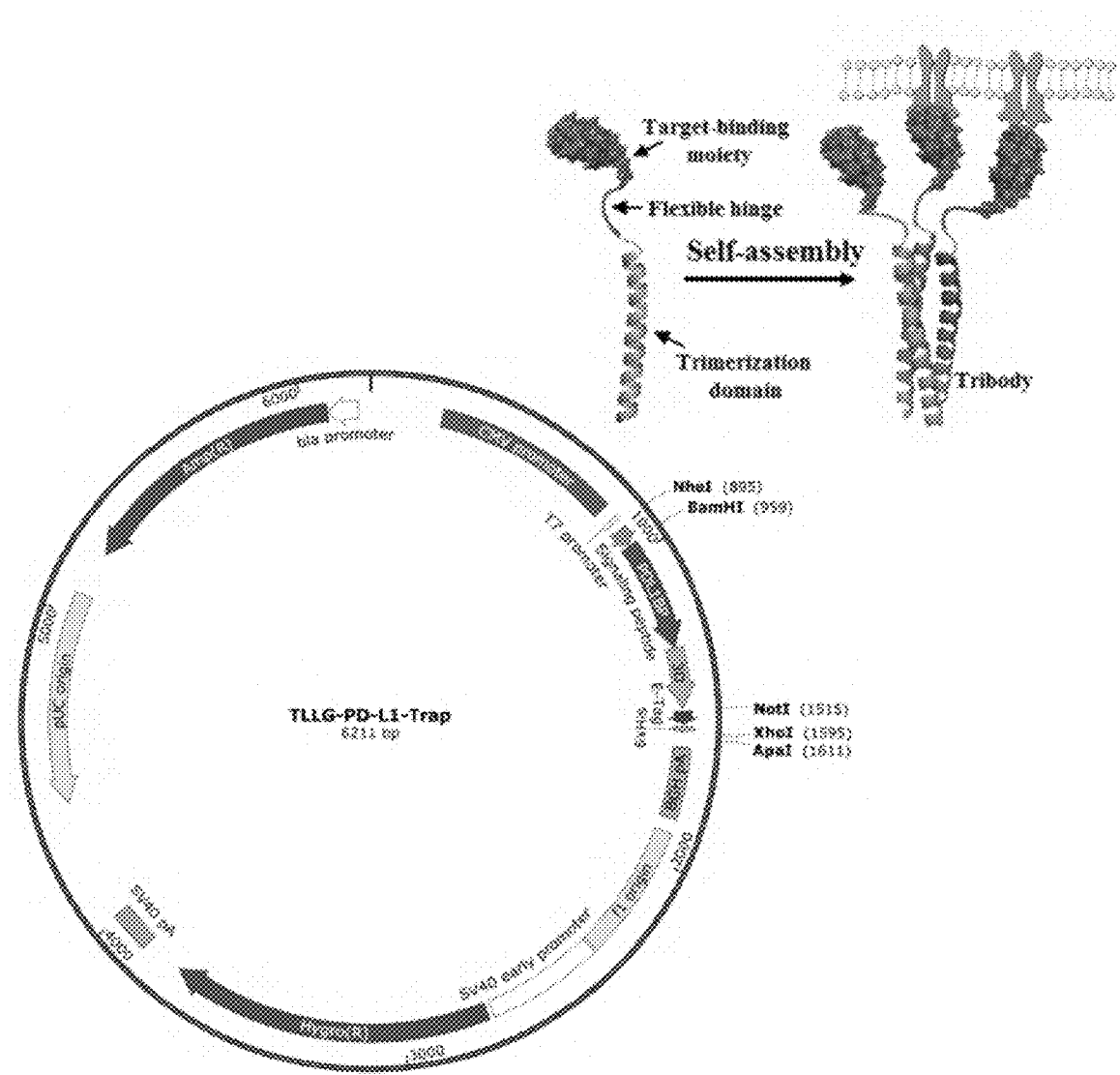
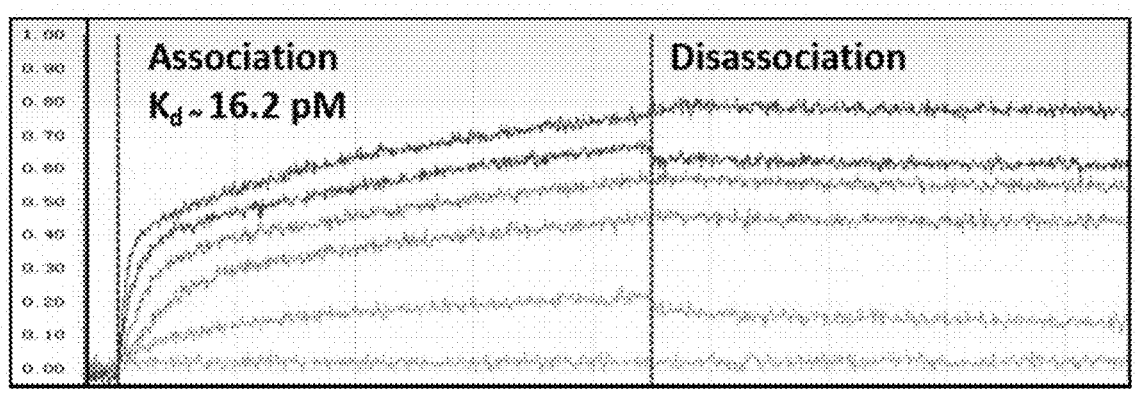

Figure 2A-C
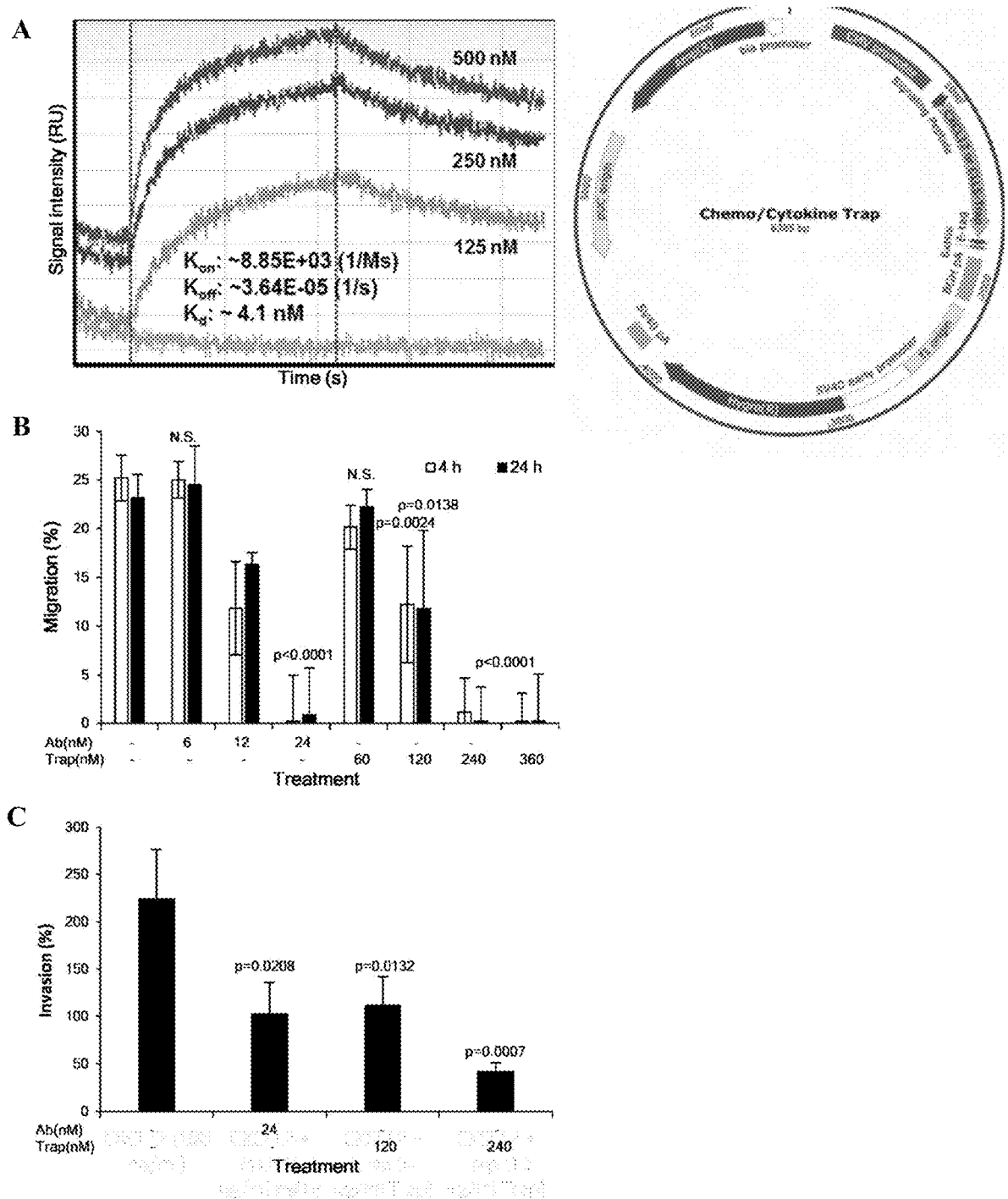

Figure 3A-B
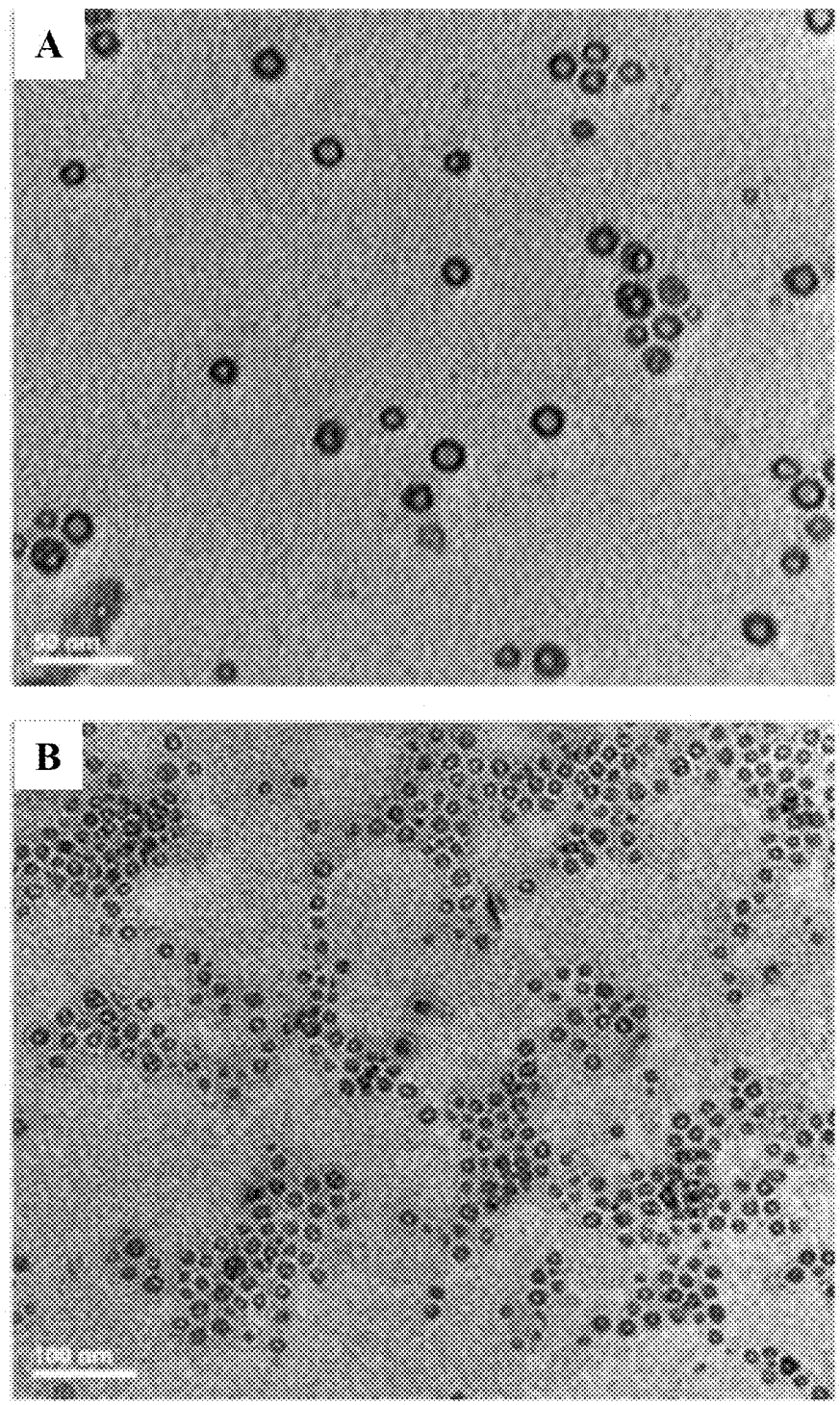

Figure 3D-E
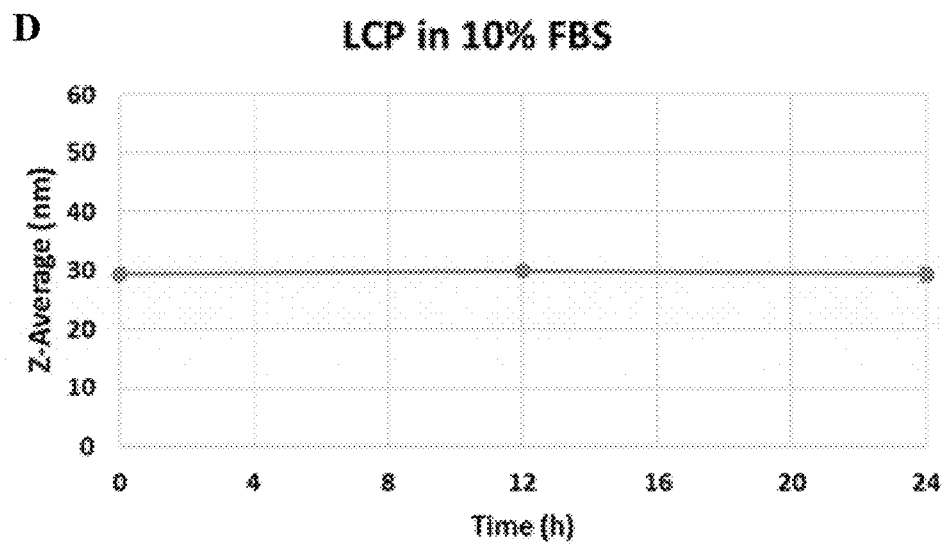
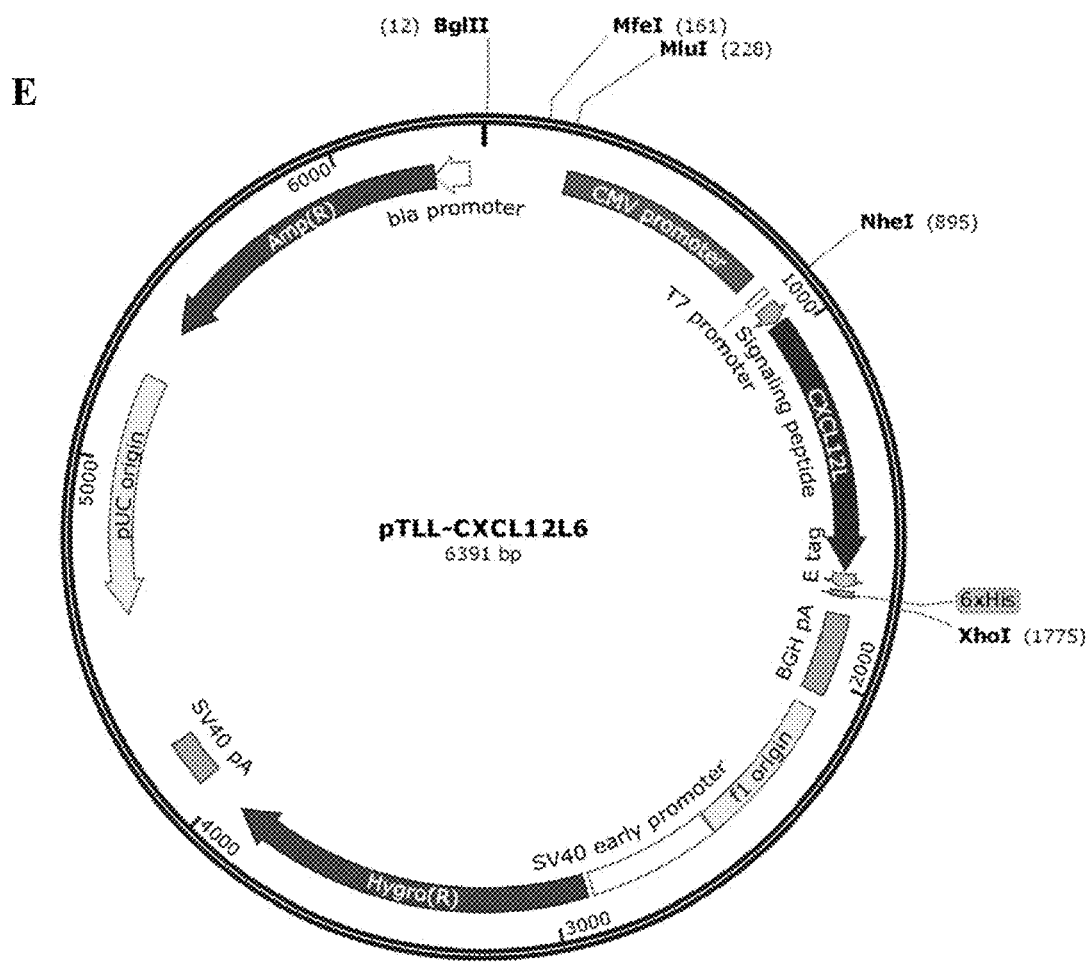

Figure 3F

GTTGACATTGATTATTGACTAGTTATTAATAGTAATCAATTACGGGGTCATTAGTTCATAGCCC
ATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCAT
TGACGTCAATGGGTGGACTATTTACGGTAAACTGCCCACTTGGCAGTACATCAAGTGTATCAT
ATGCCAAGTACGCCCCCTATTGACGTCAATGACGGTAAATGGCCCGCCTGGCATTATGCCCAG
TACATGACCTTATGGGACTTTCCTACTTGGCAGTACATCTACGTATTAGTCATCGCTATTACCA
TGGTGATGCGGTTTTGGCAGTACATCAATGGGCGTGGATAGCGGTTTGACTCACGGGGATTTC
CAAGTCTCCACCCCATTGACGTCAATGGGAGTTTGTTTTGGCACCAAAATCAACGGGACTTTCC
AAAATGTCGTAACAACTCCGCCCCATTGACGCAAATGGGCGGTAGGCGTGTACGGTGGGAGGT
CTATATAAGCAGAGCTCTCTGGCTAACTAGAGAACCCACTGCTTACTGGCTTATCGAAATTAAT
ACGACTCACTATAGGGAGACCCAAGCTGGCTAGCCACCATGAAATGGGTCACCTTTATCAGCC
TGCTGTTCCTGTTCAGCAGCGCCTACAGCGGATCCGAGGTGCAGCTGGTGGAATCTGGCGGAG
GACTGGTGCAGCCTGGCGGCTCTCTGAGACTGTCTTGTGCCGCCAGCGGCTTCAGCCTGACCGT
GTACTCTGTGCACTGGGTGCGCCAGGCCCCAGGCAAAGGACTGGAATGGGTGGGAGCCCTGTG
GGGCTCTGGCGGAACCGAGTACAACAGCAACCTGAAGTCCCGGTTCACCATCAGCCGGGACA
CCAGCAAGAACACCGTGTACCTGCAGATGAACAGCCTGCGGGCCGAGGACACCGCCGTGTAC
TATTGCGCCAGAGATCAGGGCCTGAACTACGGCAGCCTGTTCGACTATTGGGGCCAGGGCACA
CTCGTGACCGTGTCTAGCGGAGGCGGAGGAAGTGGCGGAGGGGGATCTGGCGGCGGAGGCAG
CGATATTCAGATGACCCAGTCCCCCAGCAGCCTGAGCGCCTCTGTGGGCGACAGAGTGACCAT
CACCTGTCGGGCCAGCGAGAGCATCAGCTACAGCCTGTCCTGGTATCAGCAGAAGCCCGGCAA
GGCCCCCAAGCTGCTGATCTACAACGCCGTGAAGCTGGAAAGCGGCGTGCCCAGCAGATTTTC
CGGCAGCGGCTCTGGCACCGACTTCACCCTGACCATCAGCTCCCTGCAGCCCGAGGACTTCGC
CACCTACTACTGCAAGCAGTACTGGAACACCCCTTCACCTTCGGACAGGGCACCAAGGTGGA
AATCAAGAGAGCGGCCGCTGGCGCCCCTGTGCCTTATCCTGATCCCCTGGAACCTAGAGGCGG
CAGCCACCACCACCATCACCACTGATGA (SEQ ID NO: 63)

Figure 4A-B
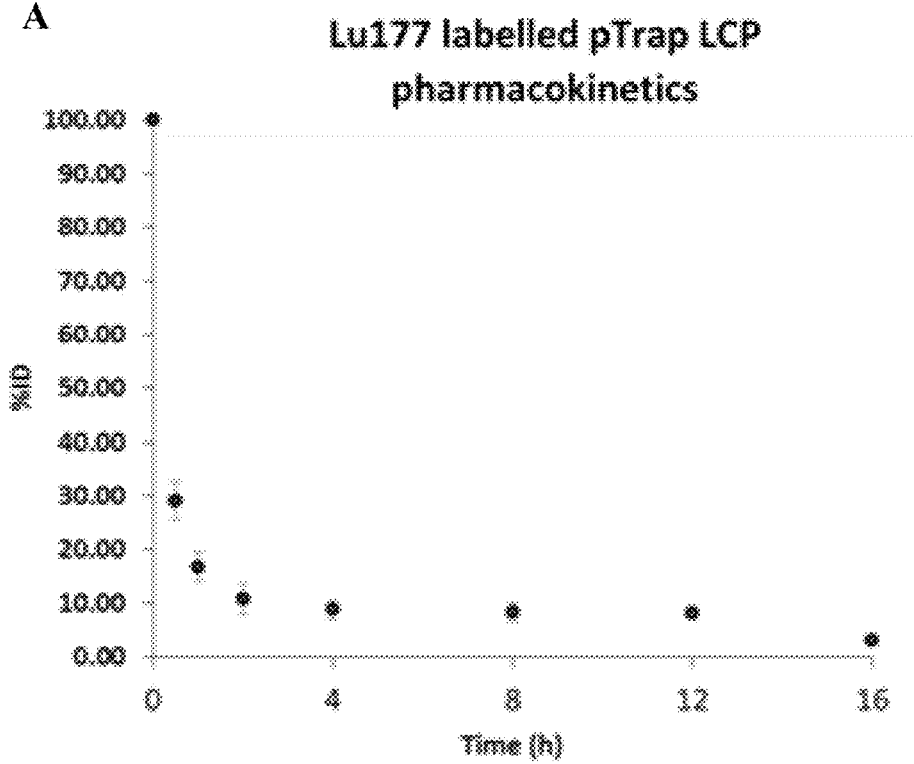
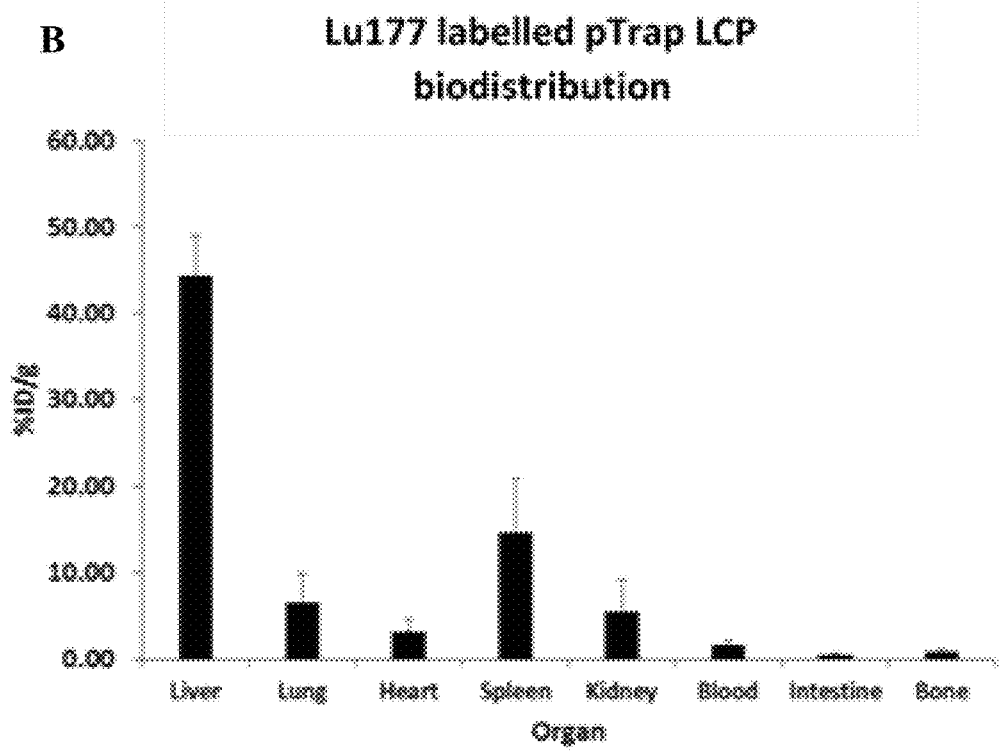

Figure 5A
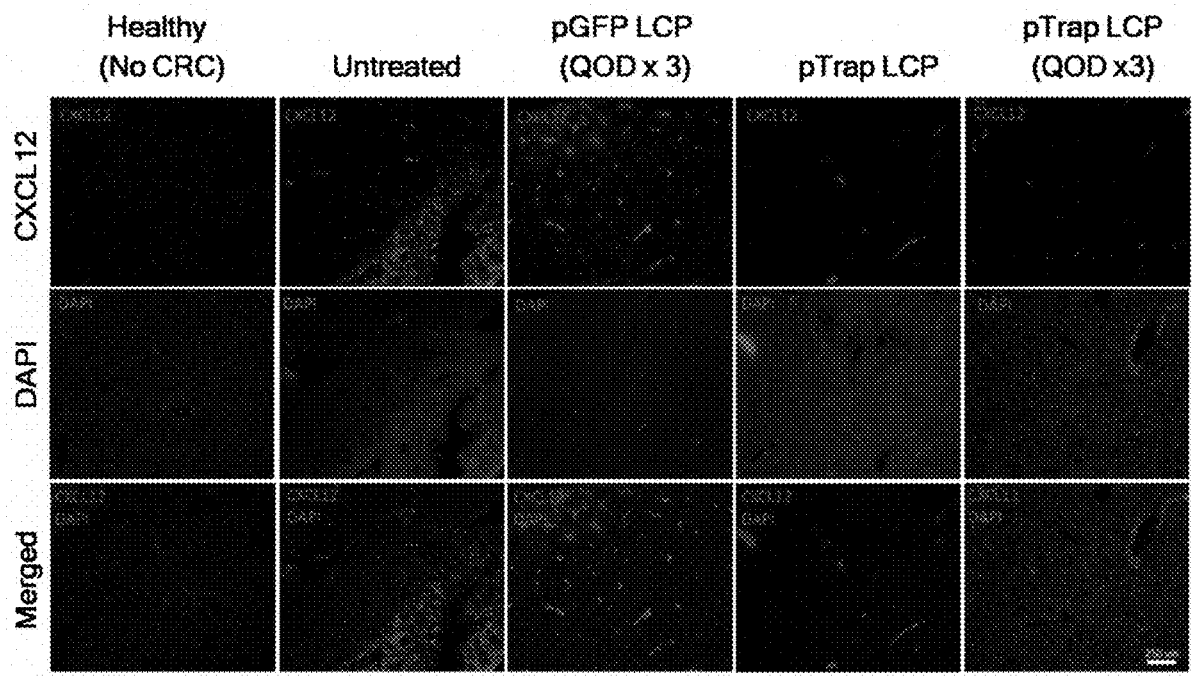
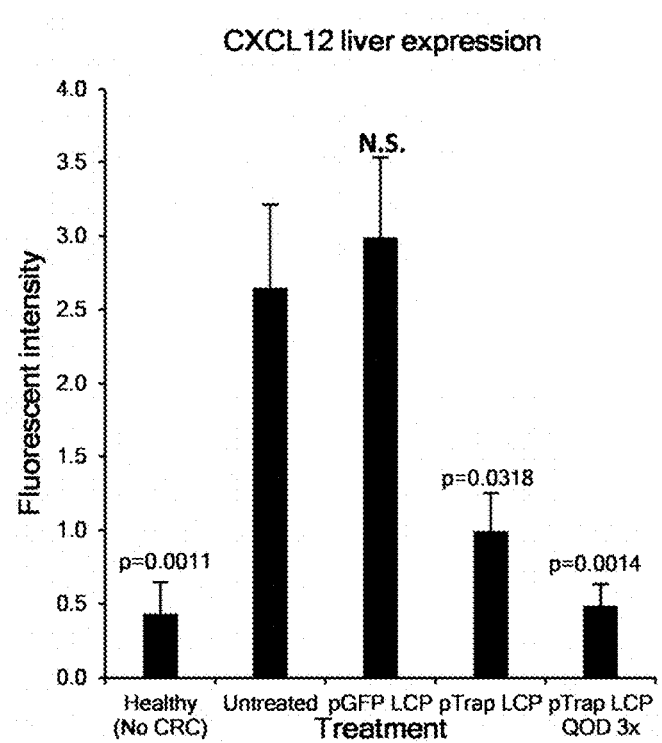

Figure 5B
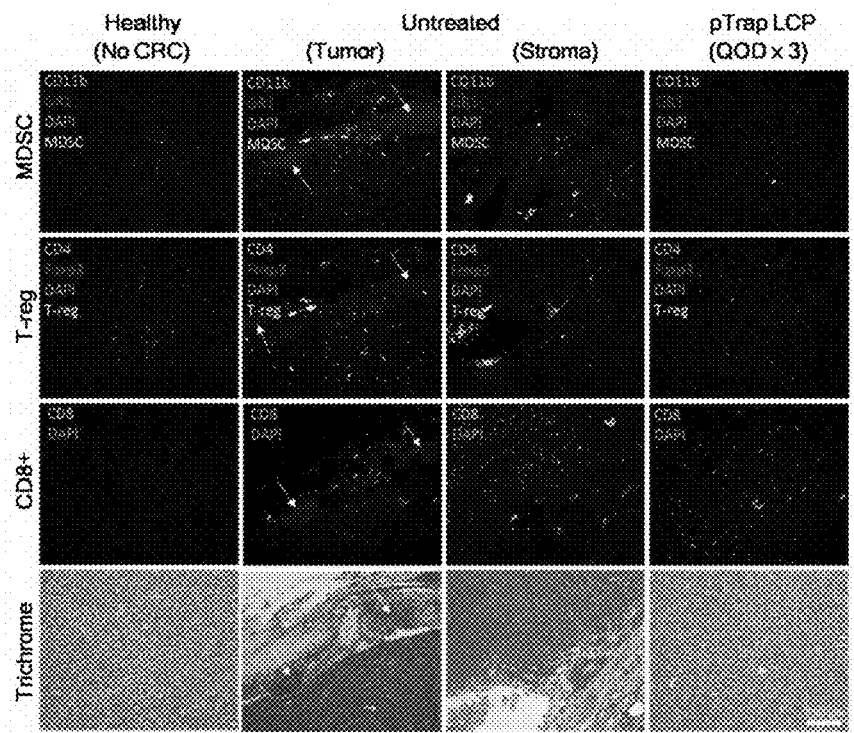
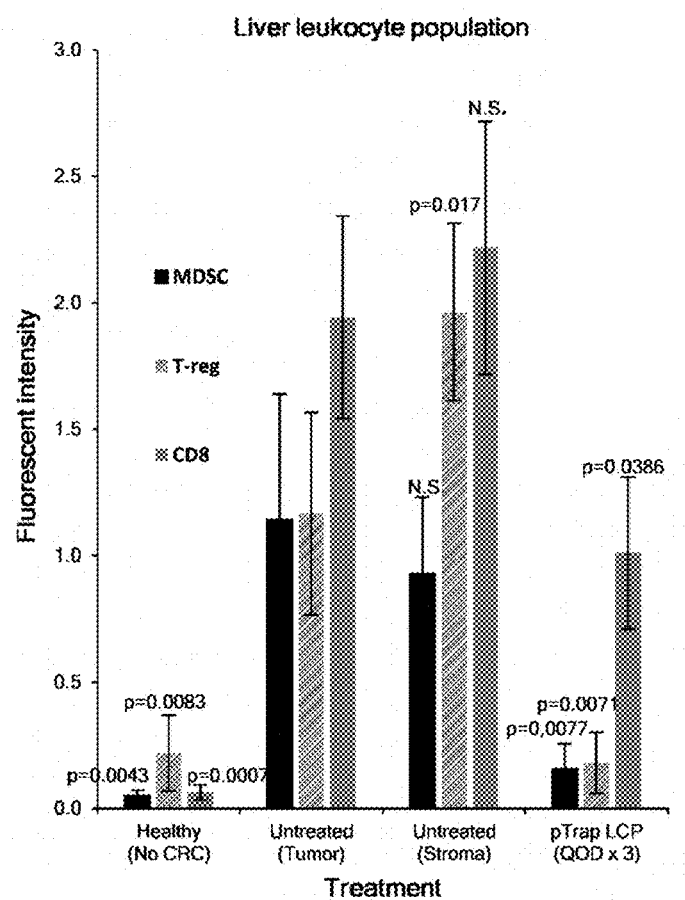

Figure 5C
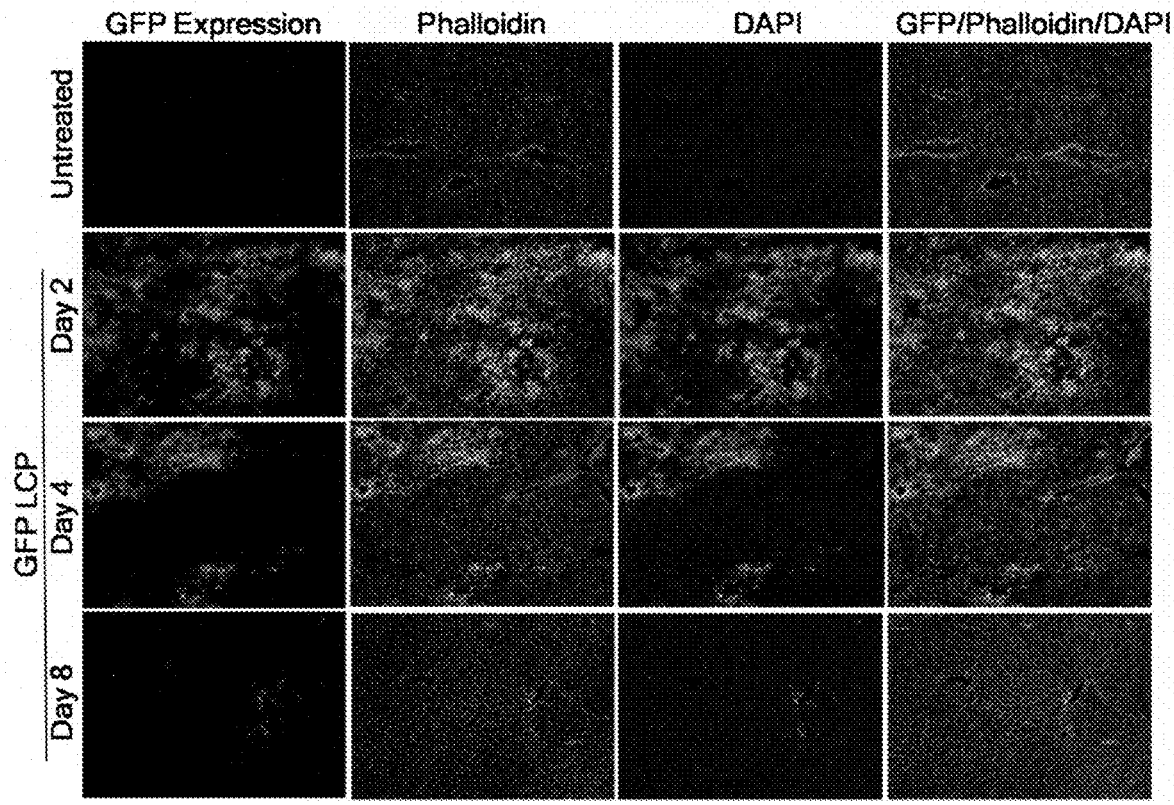
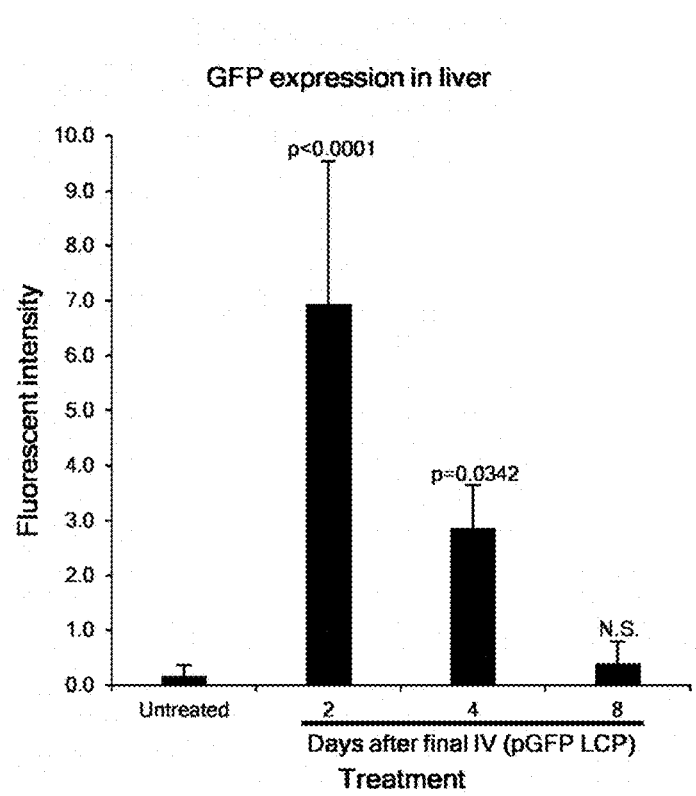

Figure 5D-E
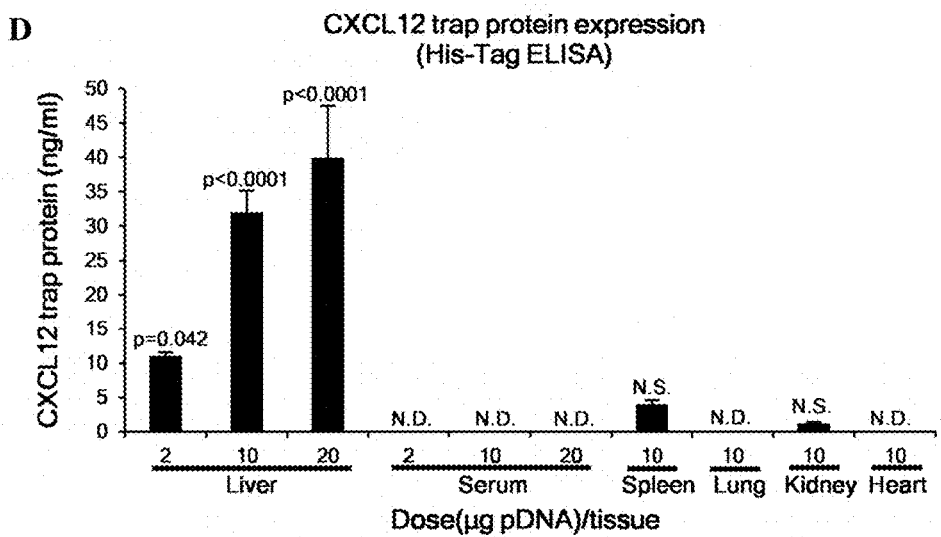
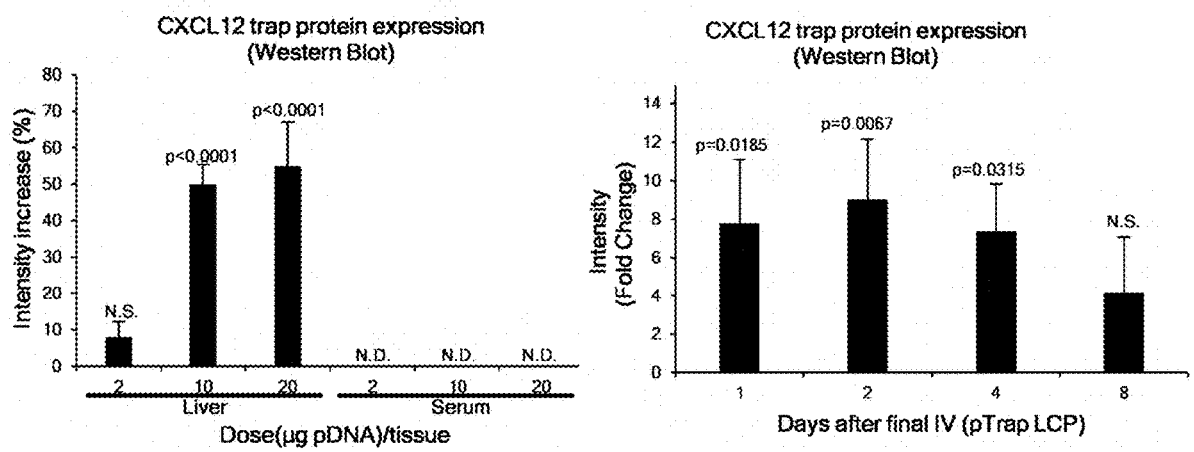

Figure 6B
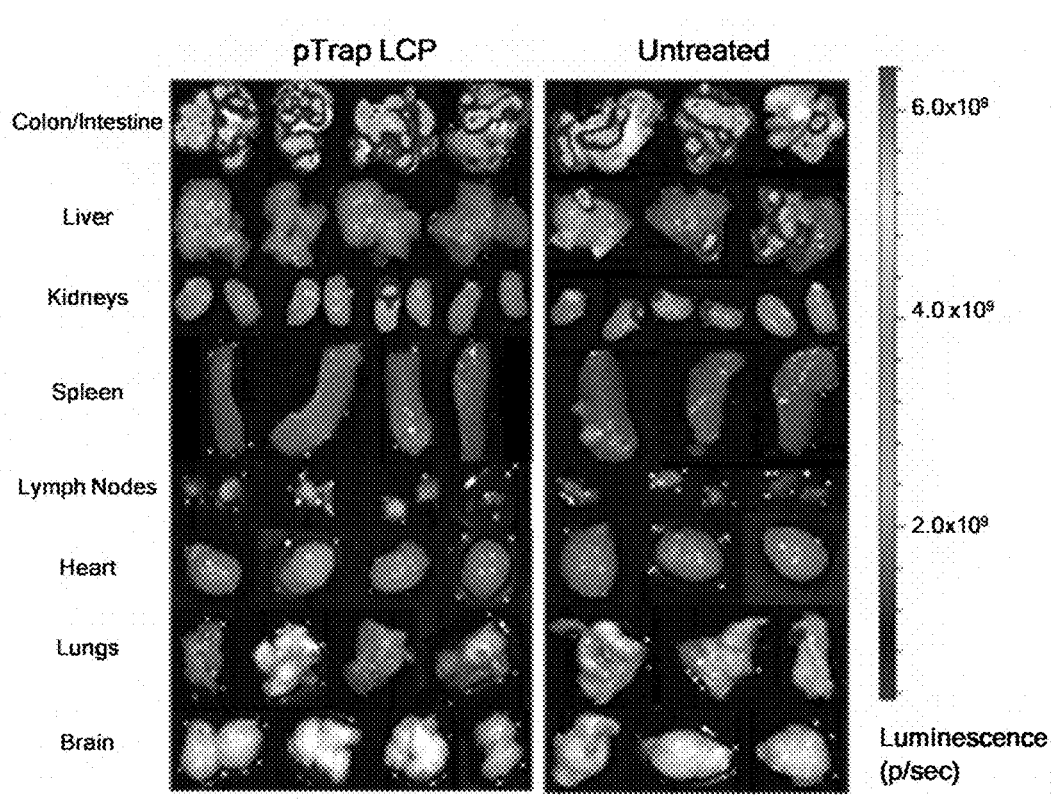
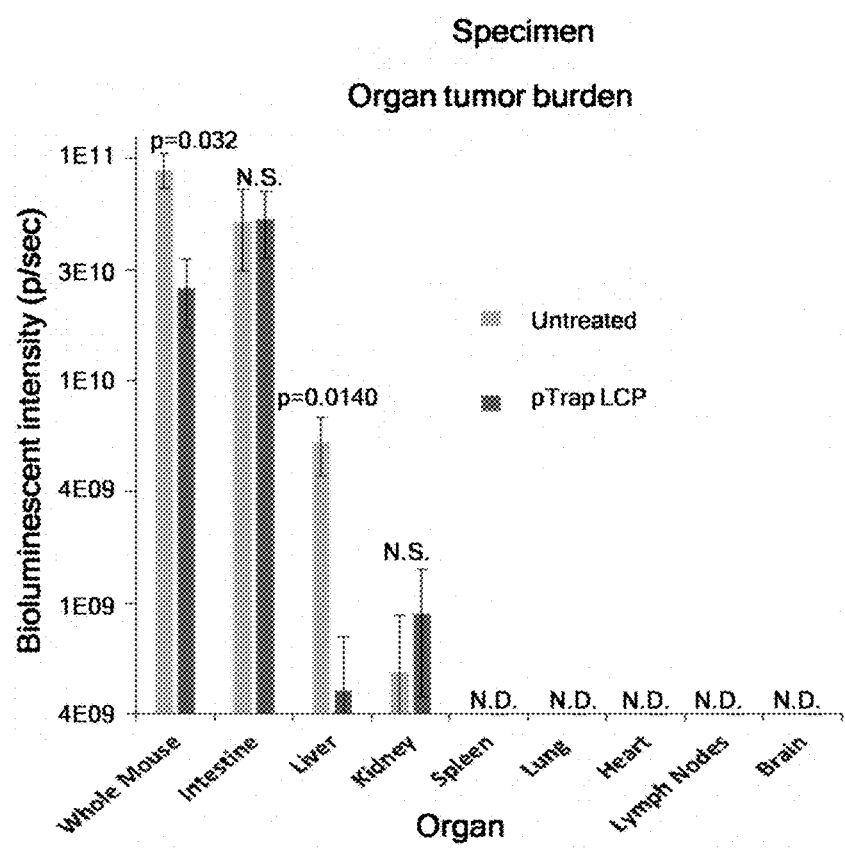

Figure 6C
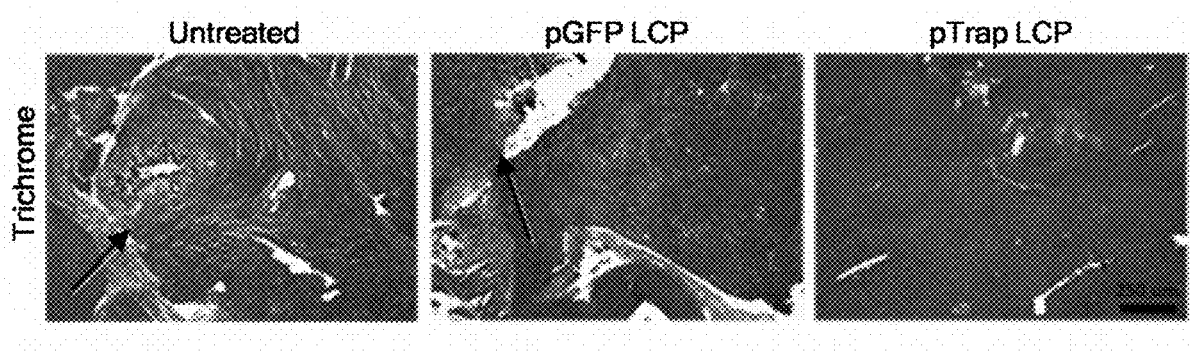
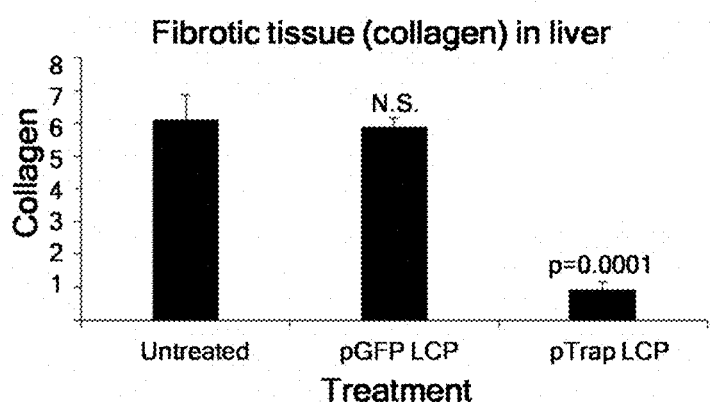

Figure 7
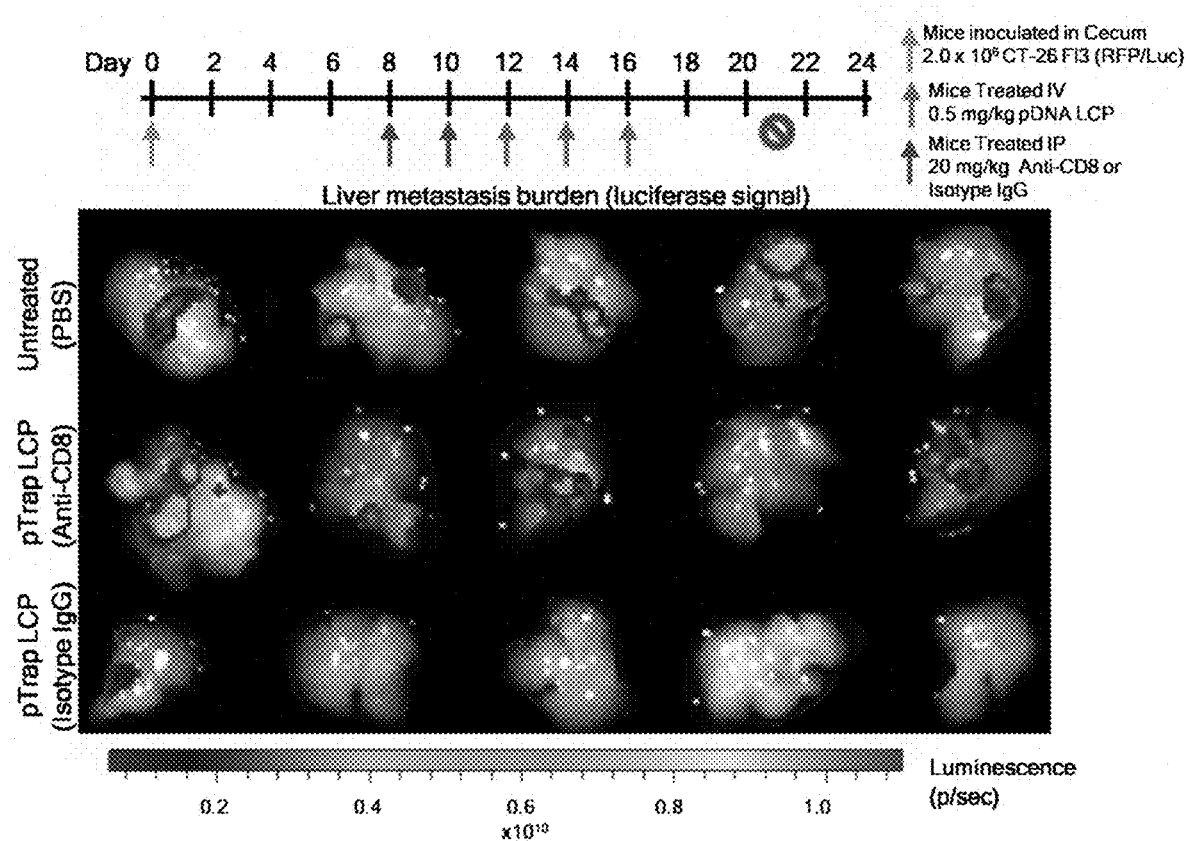
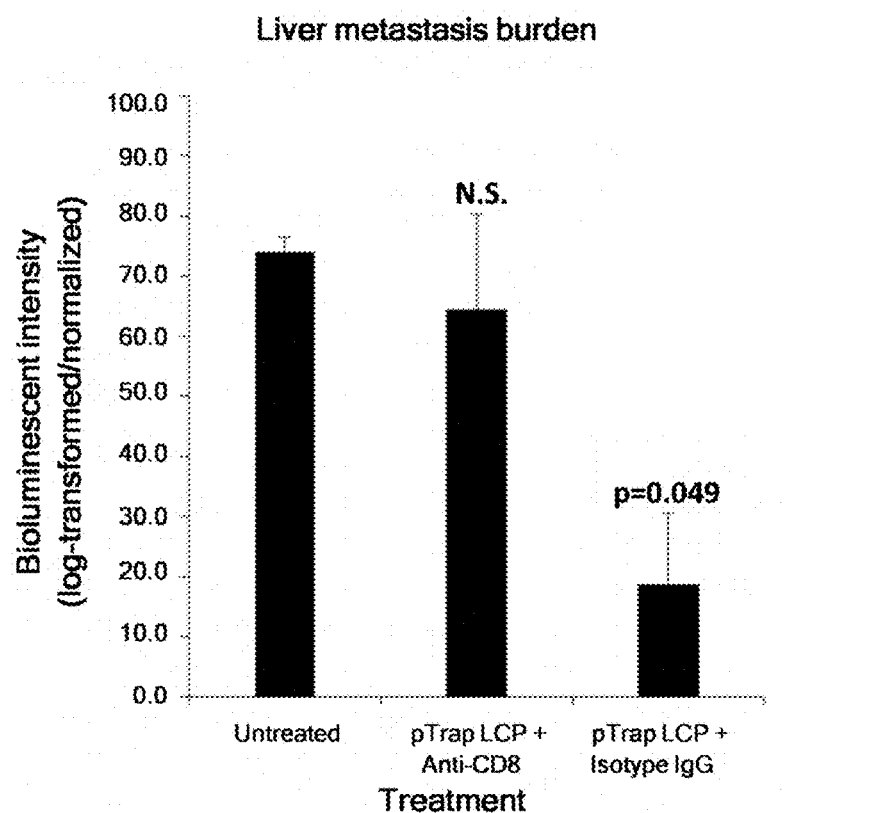

Figure 8B-C
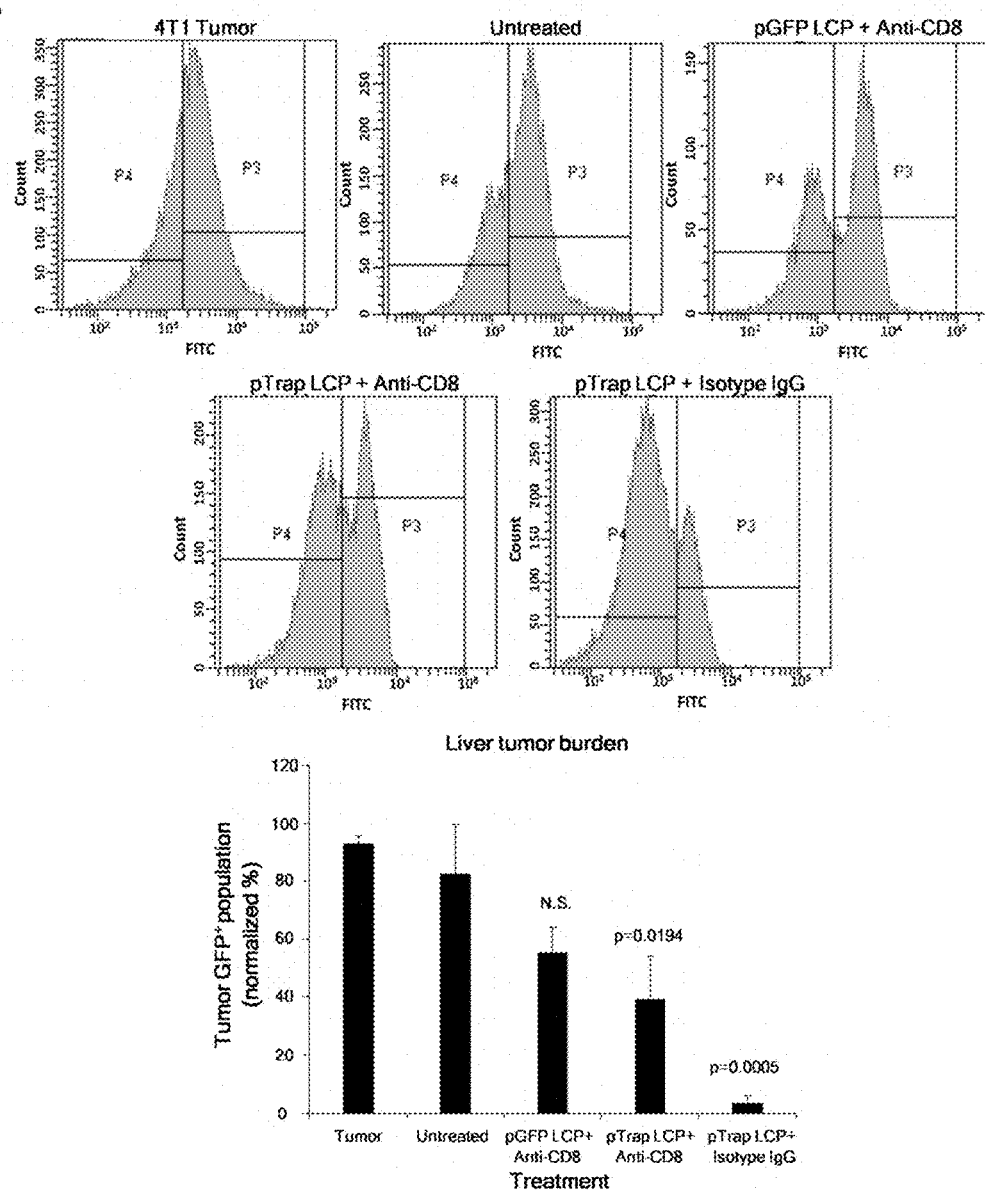
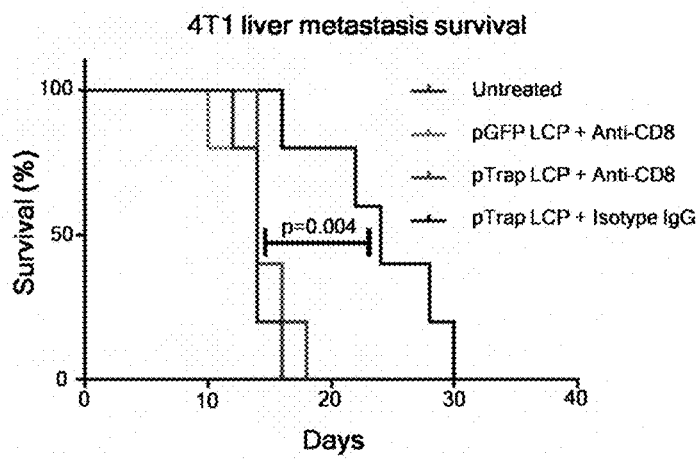

Figure 9A-B
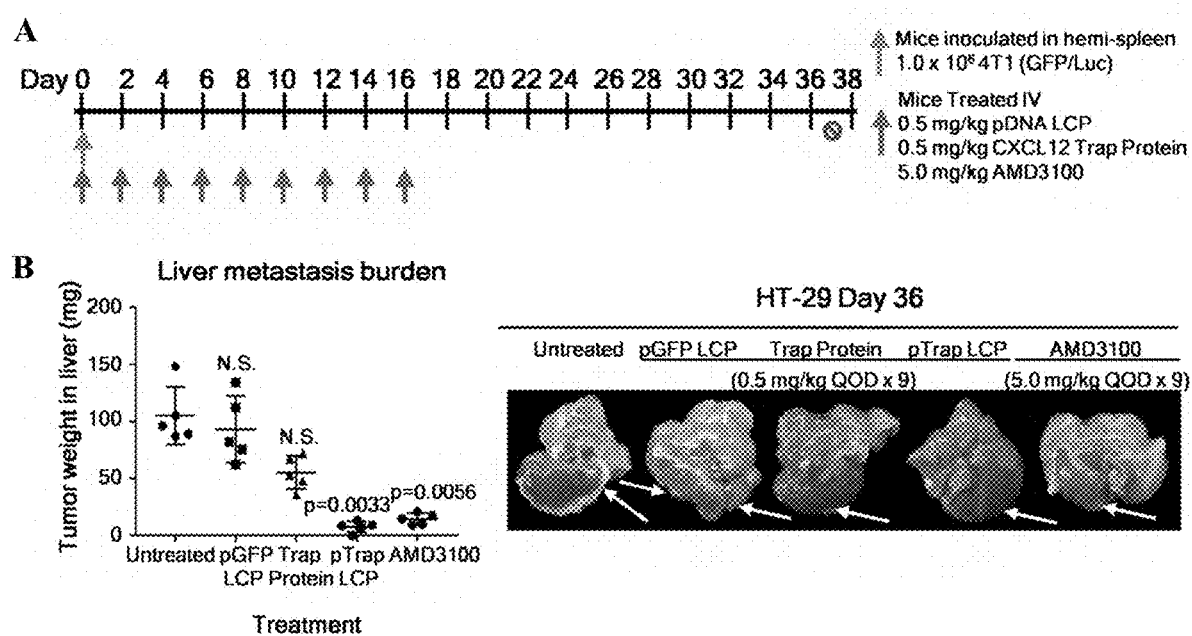

Figure 14A-C
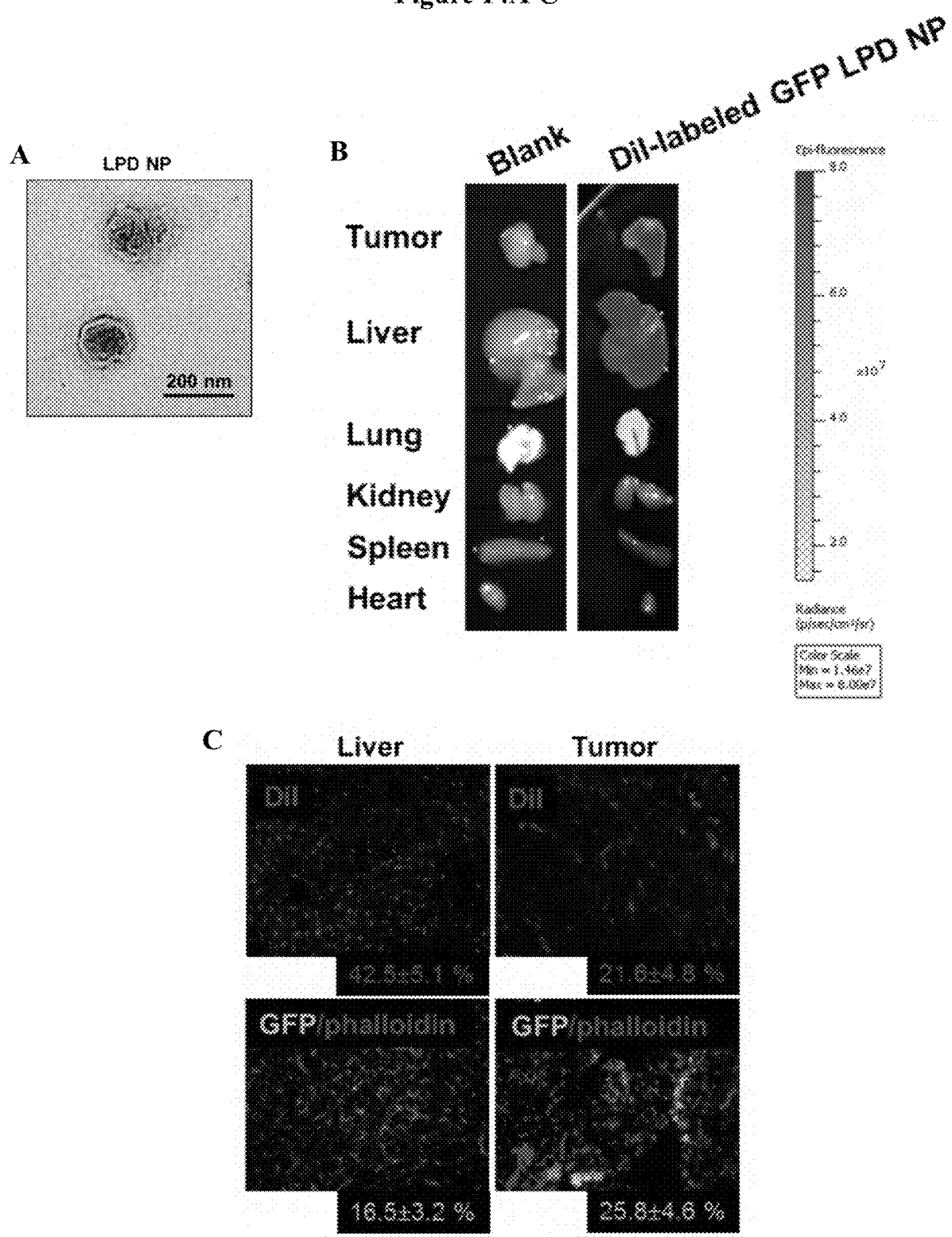

Figure 14D
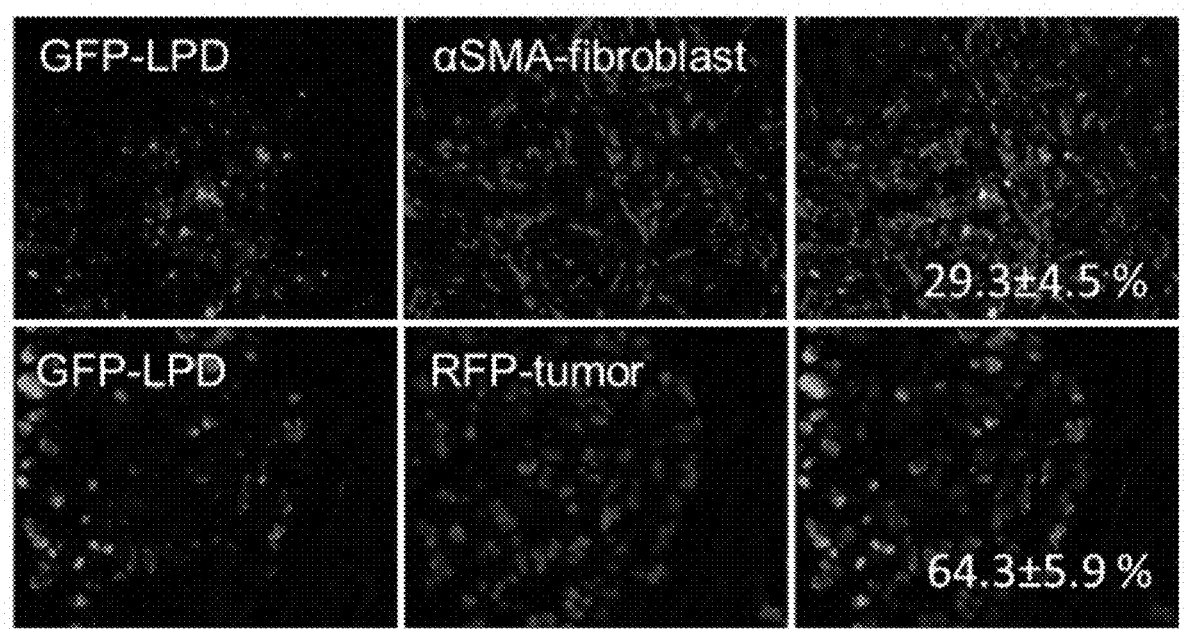
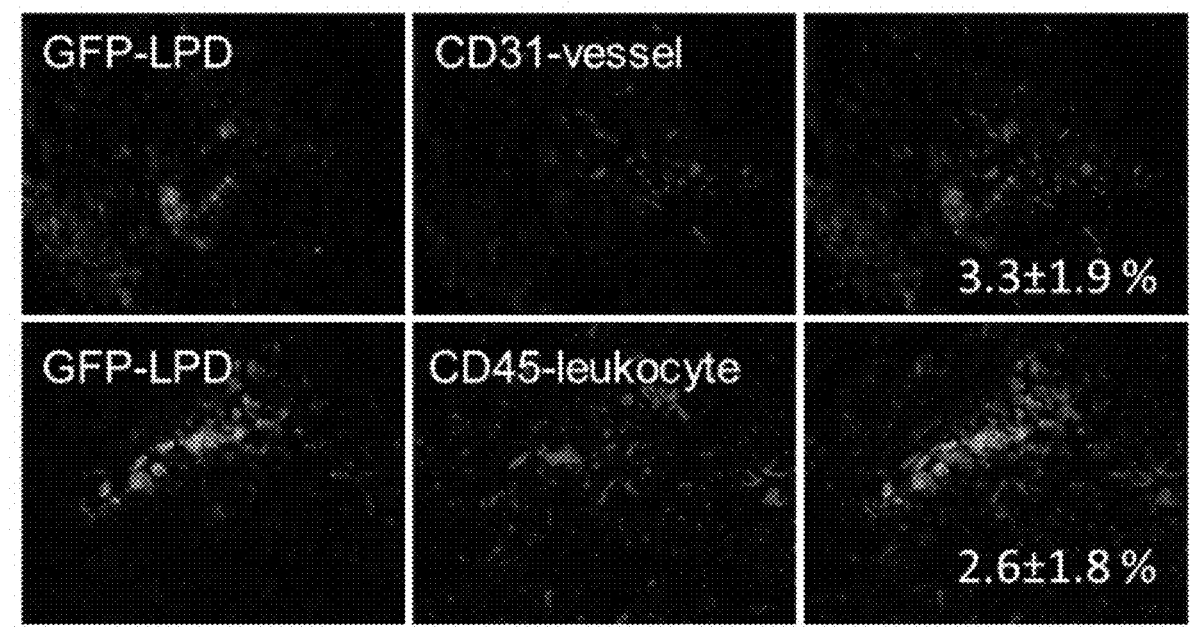

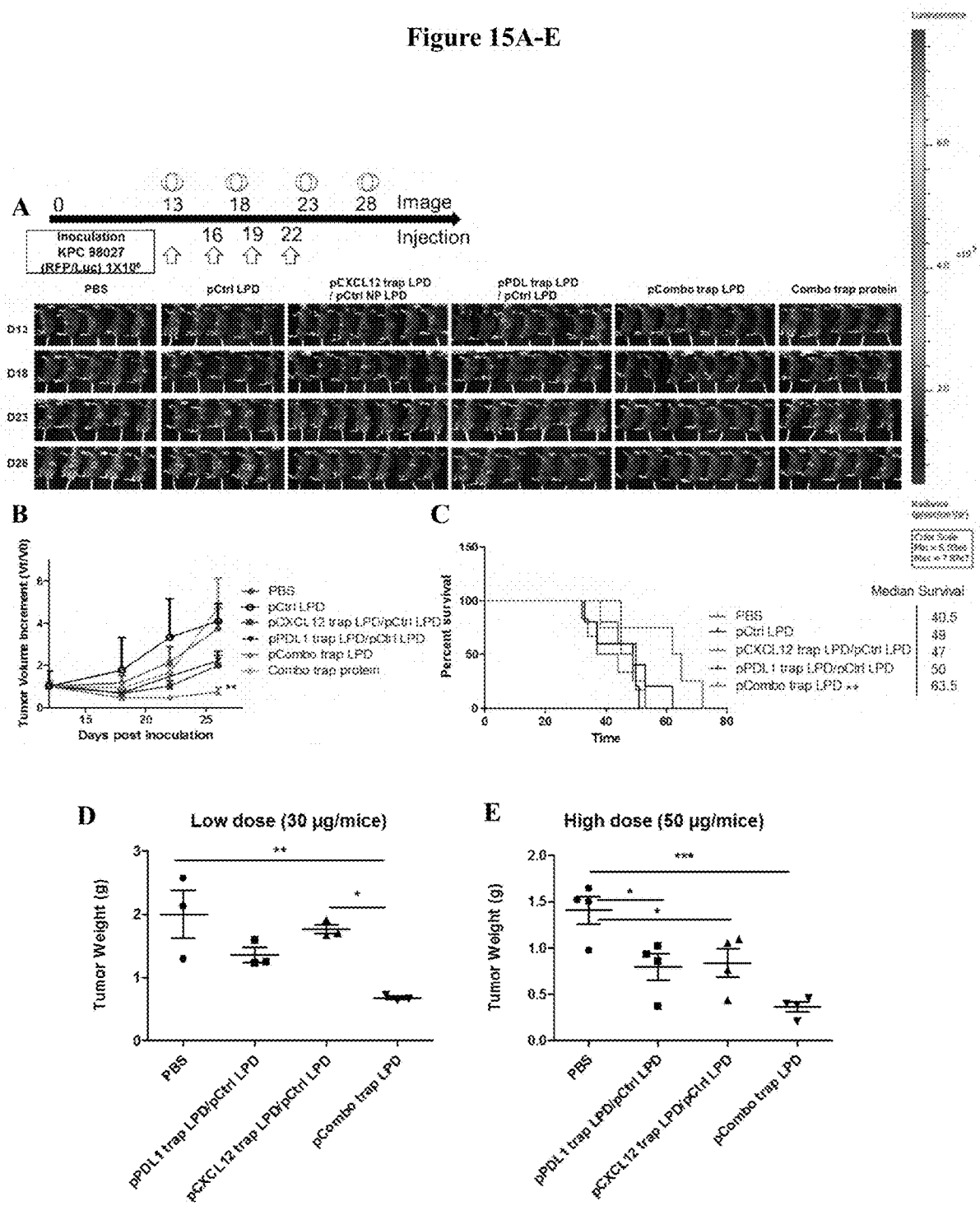
Figure 15A-E

Figure 16A-B
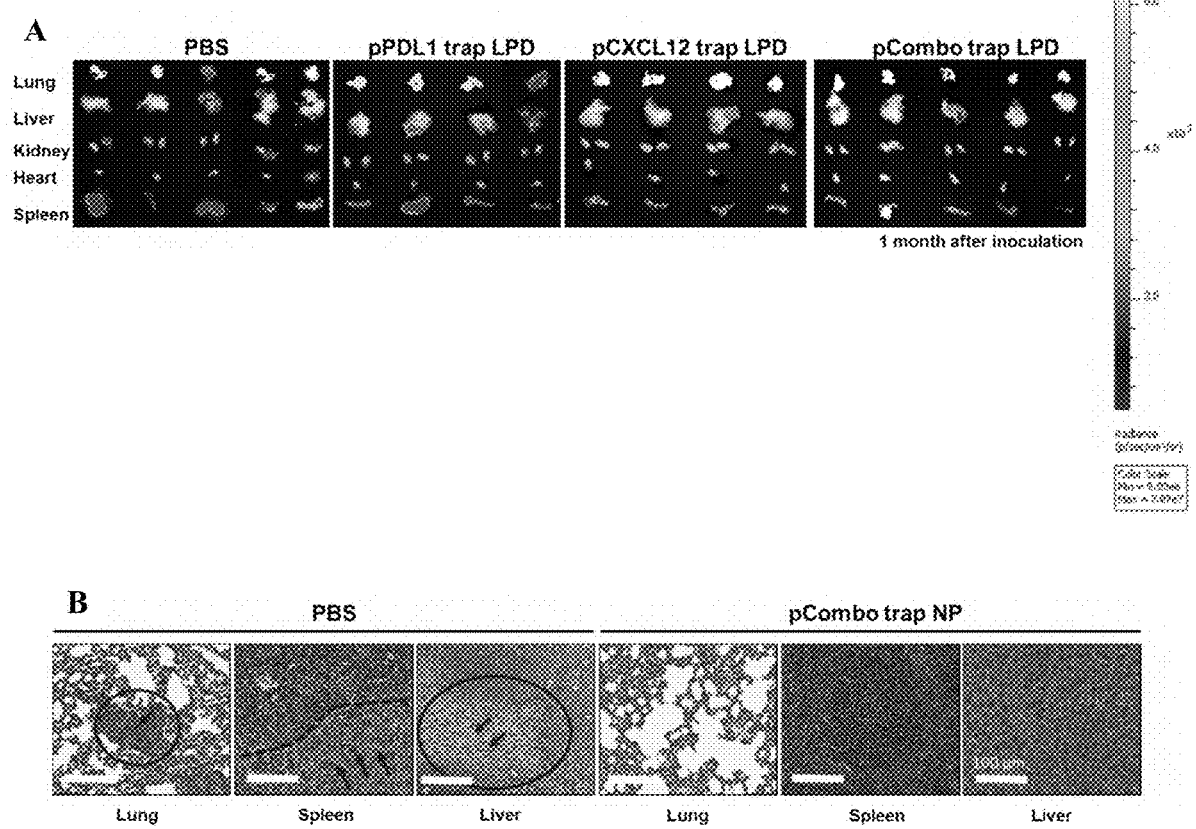

Figure 17A-B
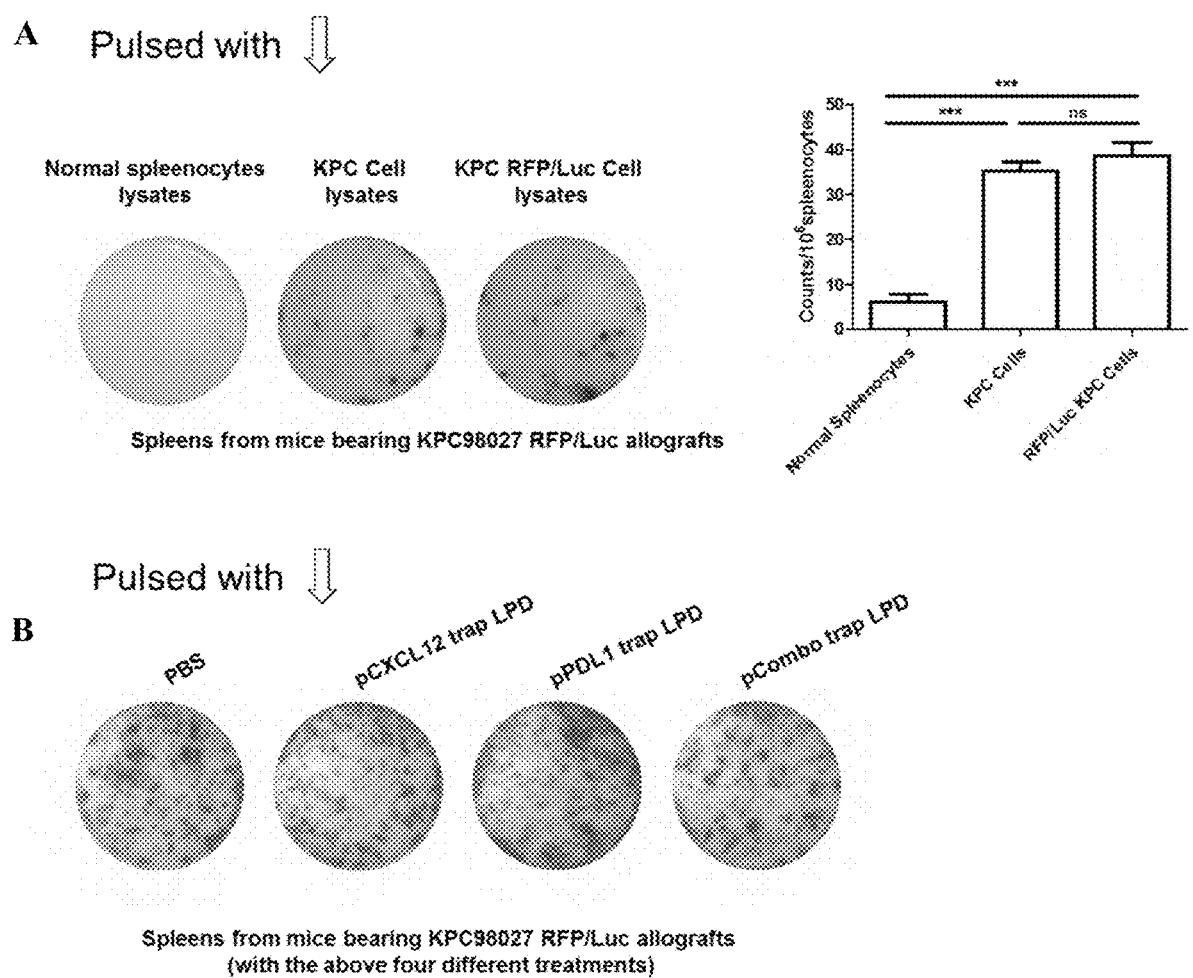

Figure 18B-C
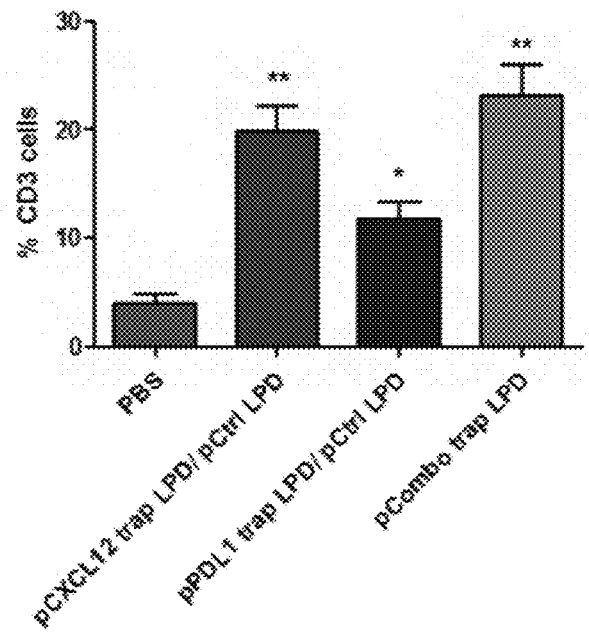
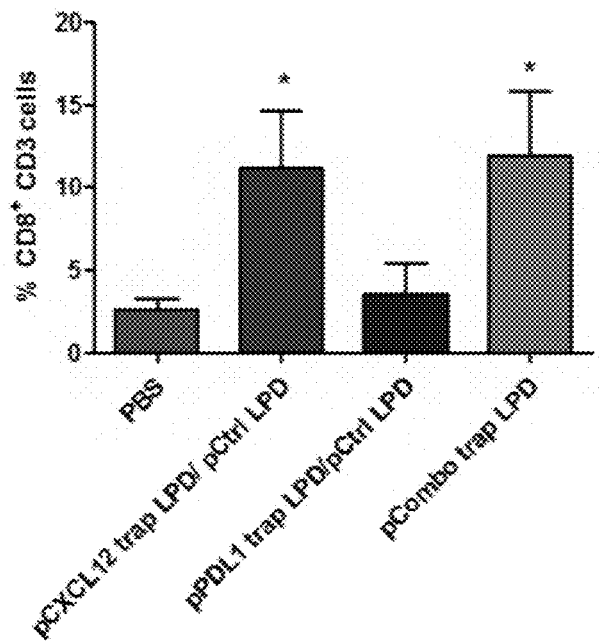

Figure 18D-E
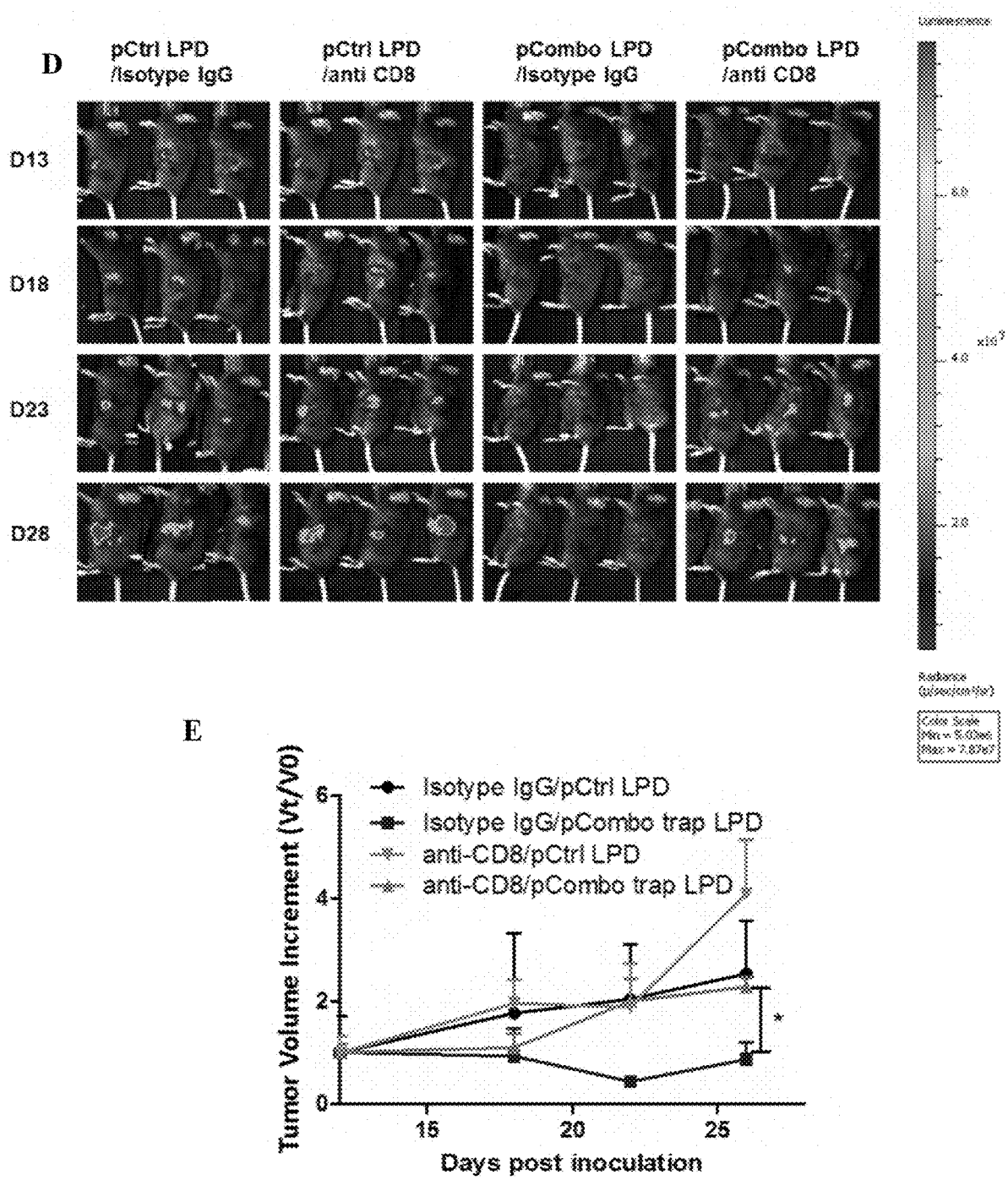

Figure 20A-B
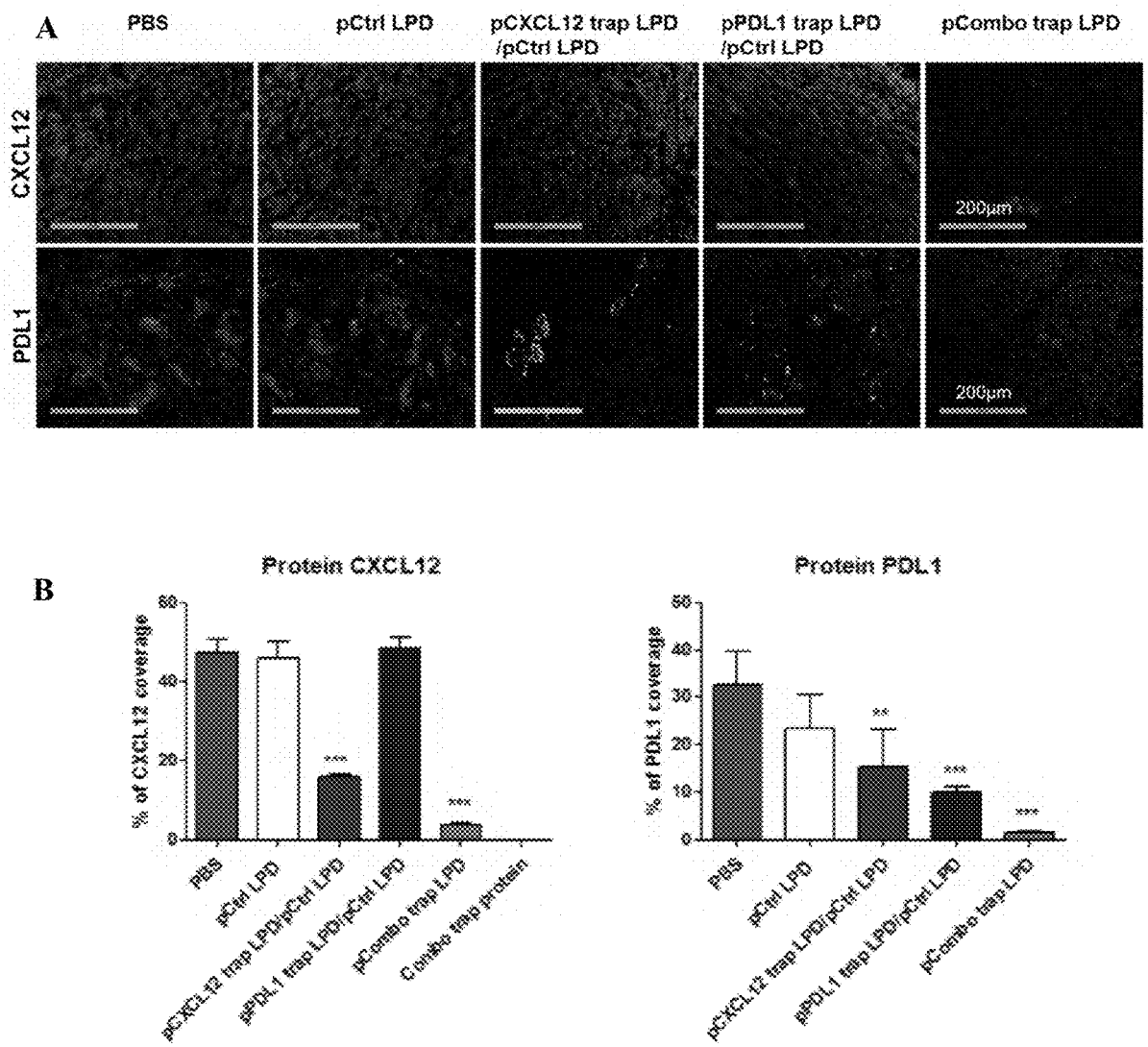

Figure 22A-B

Figure 24
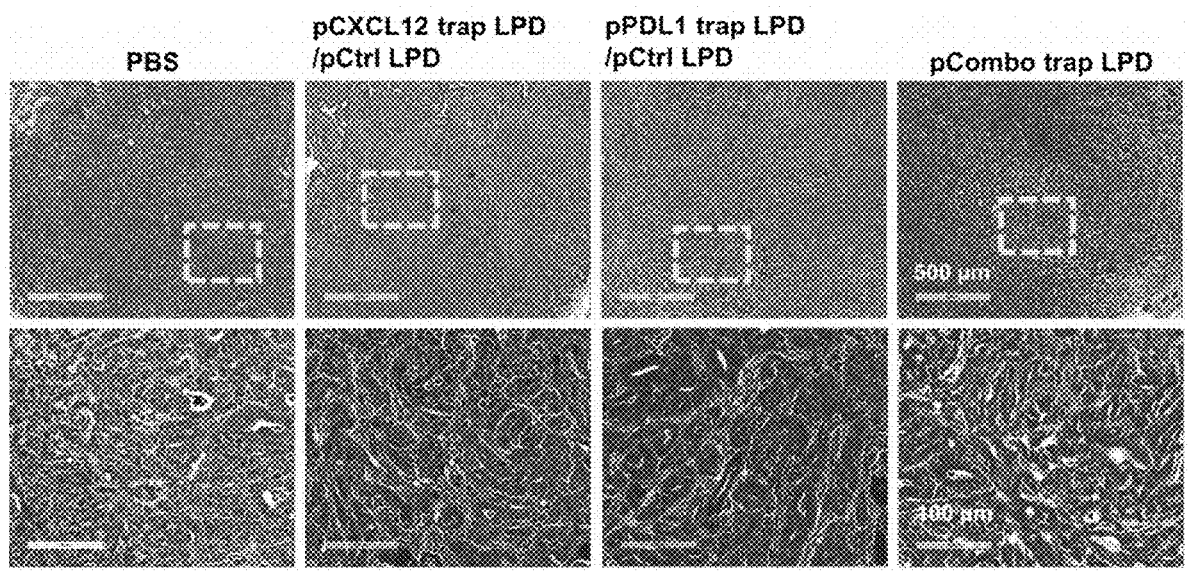
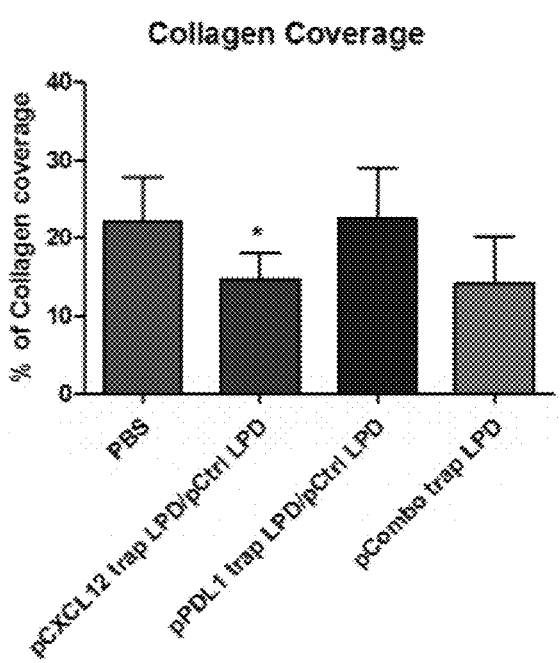

METHODS AND COMPOSITIONS FOR REDUCING METASTASES

CROSS REFERENCE TO RELATED APPLICATIONS

This application is a US national stage of PCT/US2016/051966 filed Sep. 15, 2016, which claims priority from and the benefit of U.S. 62/232,169 filed Sep. 24, 2015 all of which are incorporated herein by reference.

STATEMENT OF GOVERNMENT SUPPORT

This invention was made with government support under Grant Nos. CA151652, CA149387, CA198999, CA157738, and DK100664 awarded by the National Institutes of Health. The government has certain rights in the invention.

REFERENCE TO SEQUENCE LISTING

This application includes an electronic sequence listing in a file named 512227_SEQLST.txt, created on Mar. 23, 2018 and containing 77,736 bytes, which is hereby incorporated by reference in its entirety for all purposes.

REFERENCE TO A SEQUENCE LISTING SUBMITTED AS A TEXT FILE VIA EFS-WEB

The sequence listing written in the file 482902_seqlisting.txt is 77,671 bytes, and was created on Sep. 14, 2016 and is hereby incorporated by reference.

FIELD OF THE INVENTION

The subject matter described herein is directed to treatments that prevent or reduce the occurrence of metastatic cancer by modifying cellular micro-environment factors in tissues susceptible to metastases.

BACKGROUND

In treating cancer, early diagnosis and treatment before metastasis is critical since once a cancer has metastasized, the success rates of therapy are substantially lower. In particular, colorectal cancer (CRC) is the third most prevalent cancer diagnosed worldwide, leading to the third most cited deaths. In the United States alone, approximately 143,460 patients are diagnosed, resulting in 51,690 patient deaths yearly (American Cancer Society. Cancer Facts and Figures 2012. Atlanta: *American Cancer Society;* 2012. p. 25-6). However, the cause of death is rarely due to the primary colon cancer burden, in which local resection of the colon where the primary cancer resides is quite efficient. Unfortunately, the occurrence of liver metastasis is the leading cause of death in CRC patients (American Cancer Society. Cancer Facts and Figures 2012. Atlanta: *American Cancer Society;* 2012. p. 25-6).

At early stages of colorectal cancer detection, the five-year survival rate is approximately 90%. Unfortunately, this rate drops drastically to less than 12% survival once the liver metastasis has occurred. Studies have also found that upon diagnosis, 20% of patients have already developed liver metastasis, with this number reaching up to 60-70% of patients having developed metastatic lesions in the liver at time of death (Schima W, Kulinna C, Langenberger H, et al. Liver metastases of colorectal cancer: US, CT or MR? Cancer imaging. *International Cancer Imaging Society.* 2005; 5(SpecNo A): S149-56).

Yet, treatments for diseases such as cancer, for which the ultimate therapeutic goal is to kill the diseased cell or prevent or inhibit its reproduction, include the administration of cytotoxic drugs. Cytotoxic drugs include many chemotherapeutic agents that are used in the treatment of cancers, including alkylating agents, antimetabolites, and toxins. Most cytotoxic drugs are non-selective, killing healthy cells as well as diseased cells, which contributes to undesirable side effects when these agents are delivered systemically. Thus, a need exists for alternate therapies that do not rely on systemic administration of toxic agents.

The subject matter herein addresses the shortcomings of known therapies by modifying the micro-environment of tissues that are susceptible to metastases. In doing so, metastasis is prevented or reduced and the use of cytotoxic agents can be avoided.

BRIEF SUMMARY OF THE INVENTION

In an embodiment, the subject matter described herein is directed to a method of modifying the micro-environment of a target cell comprising, systemically administering to a subject a composition comprising a vector, wherein the vector comprises a construct for the expression of a trap, wherein the trap is expressed in the target cell thereby modifying the micro-environment.

In an embodiment, the subject matter described herein is directed to a method of reducing metastasis of a cancer comprising, systemically administering to a subject having cancer a composition comprising a vector, wherein the vector comprises a construct for the expression of a trap, wherein the trap is expressed in tissue susceptible to metastasis thereby modifying the micro-environment of the tissue and reducing metastasis of the cancer to the tissue.

In an embodiment, the subject matter described herein is directed to a method of treating cancer in a patient comprising, administering to the patient a composition comprising a nucleic acid sequence that encodes a polypeptide capable of binding CXCL12, wherein the polypeptide comprises a signaling peptide for desired extracellular or intracellular localization and an affinity or trap region that interacts with CXCL12 and disrupts its interaction with its endogenous receptor(s), and wherein said polypeptide is transiently expressed.

In another embodiment, the subject matter described herein is directed to a method further comprising administering a second composition comprising a nucleic acid encoding a polypeptide capable of binding PD-L1, wherein the polypeptide comprises a signaling peptide for desired extracellular or intracellular localization and an affinity or trap region that interacts with PD-L1 and disrupts its interaction with its endogenous receptor(s), and wherein said polypeptide is transiently expressed.

In another embodiment, a method further comprising administering a second composition comprising a nucleic acid encoding a polypeptide capable of binding PD-1, wherein the polypeptide comprises a signaling peptide for desired extracellular or intracellular localization and an affinity or trap region that interacts with PD-1 and disrupts its interaction with its endogenous receptor(s), and wherein said polypeptide is transiently expressed.

These and additional embodiments are fully disclosed herein.

BRIEF DESCRIPTION OF THE FIGURES

FIG. 2 depicts development and effect of engineered CXCL12 trap protein on CT-26 FL3 cellular migration and invasion. (A) The plasmid vector map of pCXCL12 Trap DNA sequence. The coding sequences of the CXCL12-binding VH and VL domains were used for assembly of the trap gene. The final sequence for the CXCL12 trap codes for a signaling peptide, VH domain, a flexible linker, VL domain, E tag, and His(6×) tag, respectively. The complete cDNA was cloned into pCDNA3.1 between Nhe I and Xho I sites and the accuracy was confirmed by DNA sequencing. The binding affinity between CXCL12 trap and CXCL12 by using Bio-Layer Interferometry. CXCL12 was immobilized on the AR2G biosensor and different concentrations of CXCL12 trap were used to measure the binding kinetics, in which the CXCL12 trap was found to have a Kd=4 nM. (B) The engineered CXCL12 trap was found to have one-half maximal inhibition [ND50] against biological active CXCL12 (100 ng/ml) at a concentration of approximately 120 nM. Analysis of CT-26 FL3 cell migration stimulated with CXCL12 (100 ng/ml; 10 nM) in the presence or absence of CXCL12 trap (2, 4, 8, or 12 µg/ml; 60, 120, 240, or 360 nM respectively) or positive control CXCL12 Ab (1, 2 or 4 µg/ml; 6, 12, or 24 nM respectively). (C) Analysis of CT-26 FL3 cell invasion after stimulation with CXCL12 (100 ng/ml; 10 nM) in the presence or absence of CXCL12 trap (4 or 12 µg/ml; 120 or 360 nM) or positive control CXCL12 Ab (4 µg/ml; 24 nM). Data was expressed as mean±s.d., calculated from samples ran in triplicate and as a percentage of untreated (no CXCL12 or treatment protein) control. *p<0.05, **p<0.01, compared to CXCL12 (100 ng/ml, 10 nM) stimulate cells (without protein trap or Ab treatment) control. NS, not significant.

FIG. 4 depicts the pharmacokinetic and organ biodistribution analysis of galactose-LCP-pCXCL12 Trap/mcCR8C with $^{177}$Lu incorporated into the LCP core. Approximately 250,000 counts were administered into the mice by tail vein injection. (A) Blood samples collected via tail vein cut were collected, weighed, and measured for radioactive counts to determine the percentage of injected dose (% ID) remaining in circulation. A biphase distribution is observed, yielding $T_{1/2}\alpha$ and $T_{1/2}\beta$ of 20 min and 1,054 min, respectively. (B) LCP biodistribution/organ accumulation was measured at 16 hours after tail vain injection (a time when blood radiation counts reached background signal). Approximately 40-50% of the injected dose per gram of tissue was found to accumulate in the liver. Data were expressed as mean±s.d., calculated from samples ran in triplicate.

Figure 1C:
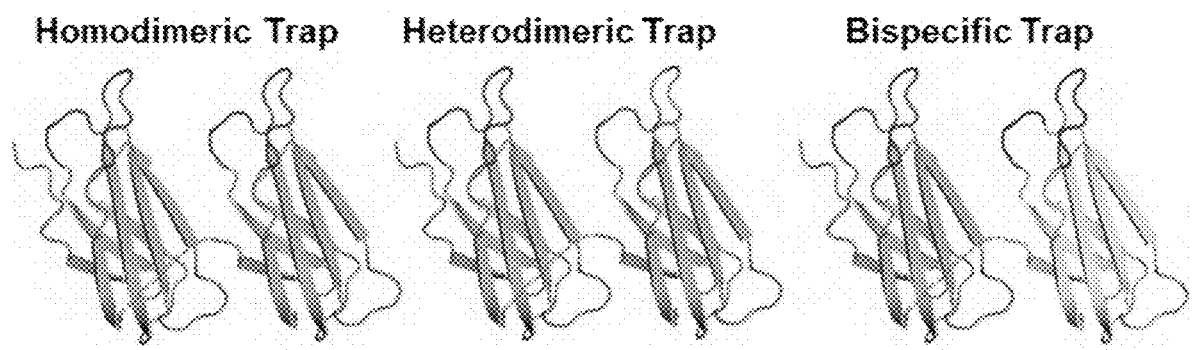
FIG. 1 depicts the endogenous protein structures of the chemokine CXCL12 used to establish a trap against wild-type CXCL12 with C-terminal biotin as target for positive selection. (A) The Structure of CXCL12 mutant with CXCR4-interacting with the N-terminus motif deleted for negative selection. (B) The structures of wild-type CCL2 and CCL5 and their non-receptor-binding mutants used for positive and negative selections. (C) Schematics of homodimeric, heterodimeric, and bispecific chemo/cytokine traps which can be used for single or combination therapies. (D) The trivalent PD-L1 trap as well as the self-assembly process of the trivalent trap. Furthermore, the binding kinetics of the trivalent PD-L1 trap with PD-L1 using Octet is displayed along with the plasmid map of the PD-L1 trap used for gene delivery based on the nanoparticle system.

FIG. 6 depicts Decreased incidence of liver metastasis after pCXCL12 Trap LCP treatment. (A) Mice were inoculated with $2 \times 10^6$ CT-26(FL3) RFP/Luc cells into the cecum wall. Treatment schedule is shown above. Treatment, 10 µg (0.5 mg/kg) pDNA, was administered through the tail vein IV on days 10, 12, and 14. Groups included PBS (untreated; n=7) and pGFP LCP (10 µg every other day×3; n=6), as well as pCXCL12 Trap LCP (10 µg every other day×3; n=7). Progression of overall tumor mass was followed by administration of 200 µl luciferin (10 mg/ml) IP. Luciferase bioluminescent imaging was recorded 10 min after administration of luciferin. Whole mouse and liver tumor burden were recorded. All data were expressed as mean±s.d., and reported as bioluminescent intensity. N.S. denotes no significance, N.D. denotes under detection limit. The p-values of individual groups compared to corresponding untreated control are displayed in graph. (B) Total organ tumor burden of untreated (n=3) and therapeutic pCXCL12 Trap LCP (n=4) groups. Quantification of tumor burden in organs was performed with IVIS/Kodak software. All data were expressed as mean±s.d., and reported as bioluminescent intensity. N.S. denotes no significance, N.D. denotes under detection limit. The p-values of individual groups compared to corresponding untreated control are displayed in graph. (C) Paraffin-embedded liver sections were stained with trichrome. Large tumor burden (indicated by black arrows) and cirrhosis/fibrosis (blue stain, collagen) are clearly seen in the PBS (untreated) and pGFP LCP treatment groups. The pCXCL12 Trap LCP treated livers have normal healthy liver morphology and no detectable metastatic burden. Scale bar is 250 µm. Collagen quantification in liver section was recorded. All data were expressed as mean s.d. N.S. denotes no significance, N.D. denotes under detection limit. The p-values of individual groups compared to corresponding untreated control are displayed in graph.

FIG. 7 depicts a decreased incidence of liver metastasis and enhanced T cell killing after pCXCL12 trap LCP therapy. Mice were inoculated with $2 \times 10^6$ CT-26(FL3) RFP/Luc cells into the cecum wall. Treatment, 10 µg (0.5 mg/kg) pDNA, was administered through tail vein IV on days 10, 12, and 14. Groups included PBS (untreated; n=5) and pCXCL12 Trap LCP (10 µg every other day×3; n=5) with either anti-Lyt2.2 or isotype IgG control administered on days 8 and 10 IP (400 µg, 20 mg/kg). Inoculation and treatment schedule/dose and liver tumor mass on day 21 are shown above. Mice were administered 200 µl (10 mg/ml) luciferin IP. After 5 min, mice were euthanized and livers were extracted, rinsed in PBS, and placed in a solution of luciferin (1 mg/ml). The bioluminescent images were recorded using IVIS kinetic with Kodak camera. Quantification of tumor burden in the liver was performed with IVIS/Kodak software. Data were expressed as log-transformed mean, normalized±s.e. N.S. denotes no significance, N.D. denotes under detection limit. The p-values of individual groups compared to corresponding untreated control are displayed in graph. ROI=region of interest.

FIG. 8 depicts a decreased incidence of 4T1 (Breast Cancer) liver metastasis and increased survival after pCXCL12 Trap LCP treatment. (A) The figure shows the inoculation and treatment schedule and doses, as well as bioluminescent signal detection and tumor burden quantification 7 days after inoculation. Treatment groups included PBS (untreated; n=5), pGFP LCP/anti-CD8 (n=5), pTrap LCP/anti-CD8 (n=5), pTrap LCP/Isotype IgG (n=5). Data were expressed as log-transformed mean, normalized±s.e. N.S. denotes no significance, N.D. denotes under detection limit. The p-values of individual groups compared to corresponding untreated control are displayed in graph. ROI=region of interest. (B) Flow cytometry analysis of tumor burden and quantification on day 10 (n=3 per group). Gating consists of GFP positive tumor cells (P3) versus non-GFP positive cells (P4) Data were expressed as mean, normalized±s.d. N.S. denotes no significance, N.D. denotes under detection limit. The p-values of individual groups compared to corresponding untreated control are displayed in graph. (C) Kaplan-Meier survival curve including all 4 treatment groups (n=5 per group). Survival was determined by evaluating mouse weight, activity, and quality of life. N.S. denotes no significance, N.D. denotes under detection limit. The p-values of individual groups compared to corresponding untreated control are displayed in graph.

FIG. 9 depicts a comparison of therapeutic strategies for reducing incidence of colorectal cancer (HT-29) liver metastasis. (A) The timeline at the top shows the inoculation and treatment schedule and dosing for the HT-29. Treatments were administered every other day on days 0-16, through tail vein IV. Treatment groups included PBS (untreated; n=5), pGFP LCP (10 µg, 0.5 mg/kg pDNA; n=5), pTrap LCP (10 µg, 0.5 mg/kg pDNA; n=5), free CXCL12 trap protein (10 µg, 0.5 mg/kg protein; n=5), and AMD3100 (100 µg, 5.0 mg/kg; n=5). (B) Tumor burden analysis and quantification on day 36 (n=5 per group). Liver metastasis burden was quantified by resection and weighing of tumor nodules (in mg). Image of liver from each treatment group with metastatic burden shown, white arrows indicate metastatic lesion. Survival was determined by evaluating mouse weight, activity, and quality of life. Data were expressed as individual data points with mean±s.d. N.S. denotes no significance, N.D. denotes under detection limit. The p-values of individual groups compared to corresponding untreated control are displayed in graph.

FIG. 10 depicts the reduction in toxicity via LCP delivery. (A) ALT, AST, creatinine, and BUN measurements and blood leukocyte cell counts 24 hours after final treatment with PBS (untreated), 10 µg pGFP LCP every other day×3, 10 µg pCXCL12 Trap LCP every other day×3, or free CXCL12 trap protein (20 µg every other day ×3), in which mice were sacrificed on days 1, 7, and 14 after final administration. All data were expressed as mean±s.d. from samples run in triplicate. N.S. denotes no significance, N.D. denotes under detection limit. The p-values of individual groups compared to corresponding untreated control are displayed in graph. (B) Trichrome histology sections of different organs 24 hours after final treatment with PBS (untreated), 10 µg pGFP LCP every other day×3, 10 µg pCXCL12 Trap LCP every other day×3, or free CXCL12 trap protein (20 µg every other day×3), in which mice were sacrificed on days 1, 7, and 14 after final administration. All trichrome histology sections show no toxicity in any major organ including: heart, lung, spleen, kidney, and liver. Scale bar=100 µm.

Figure 11:
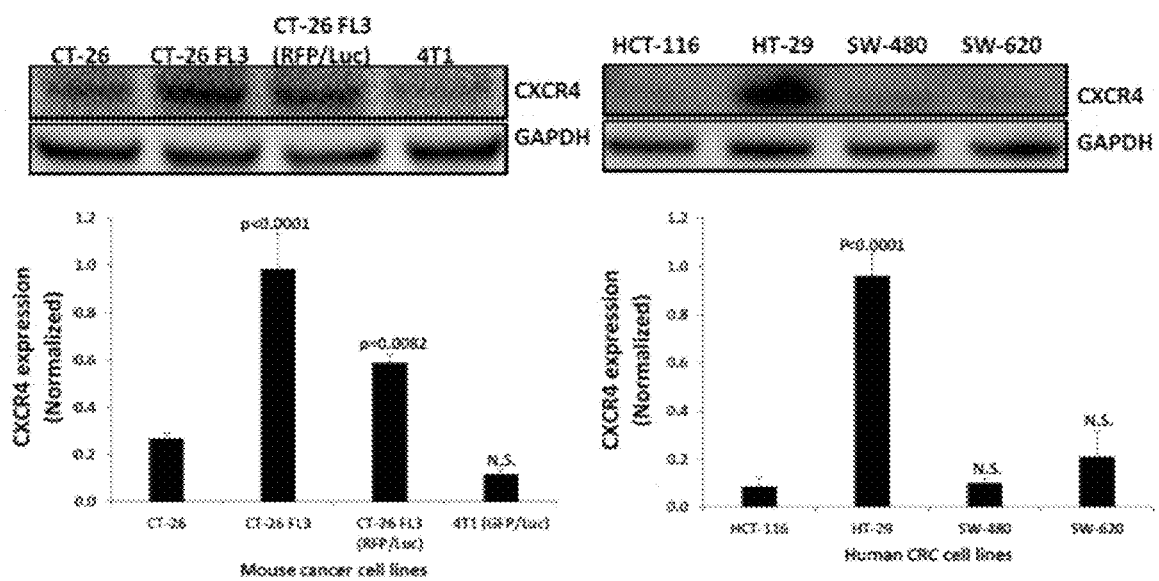

FIG. 11 depicts the western blot analysis to evaluate endogenous CXCR4 expression in mouse and human cancer cell lines. Cells were cultured according to the conditions recommended by ATCC, lysed, and normalized by BCA for accurate protein loading. Each lane received 30 μg of total protein. All samples were run on same gel to ensure accurate exposure and relative expression. Protein was identified at 42 kDa using a protein standard ladder. Data were expressed as mean±s.d., calculated from samples ran in triplicate and reported as a relative intensity to the highest intensity sample [CT-26(FL3) and HT-29] and normalized by GAPDH intensity. N.S. denotes no significance, N.D. denotes under detection limit, p-values represent significance to first cell line in graph.

Figure 12:
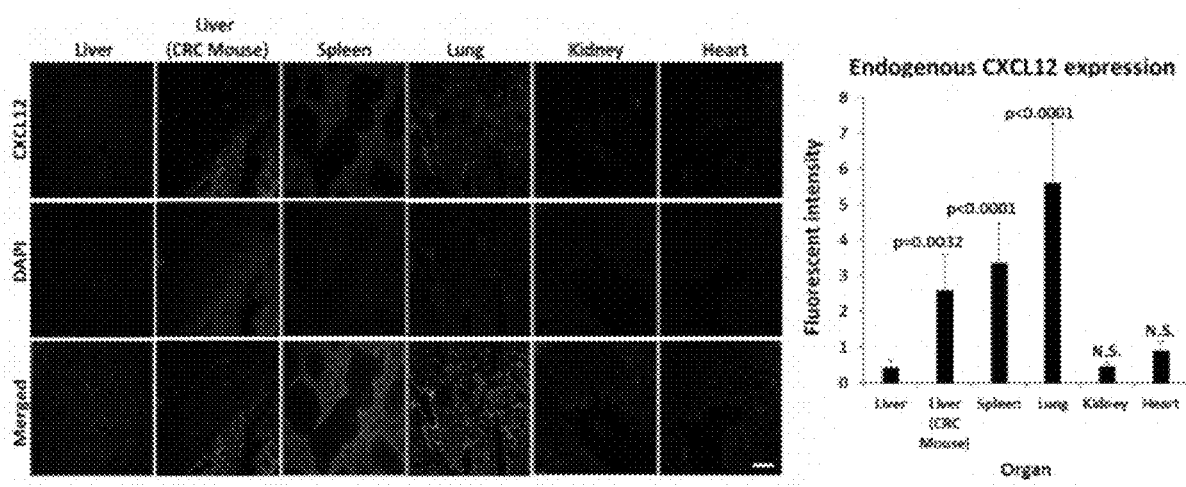

FIG. 12 depicts the endogenous CXCL12 in major organs of mice (without CRC) and in the liver of a CRC mouse. Endogenous CXCL12 expression in different organs from BALB/c mice. The images show immunofluorescent staining against CXCL12 (red), along with DAPI nuclear stain (blue). Data were expressed as mean±s.d., calculated from at least triplicated samples and reported as a fluorescent intensity. N.S. denotes no significance, N.D. denotes under detection limit, p-values represent significance to liver sample. Scale bar 250 μm.

Figure 13:
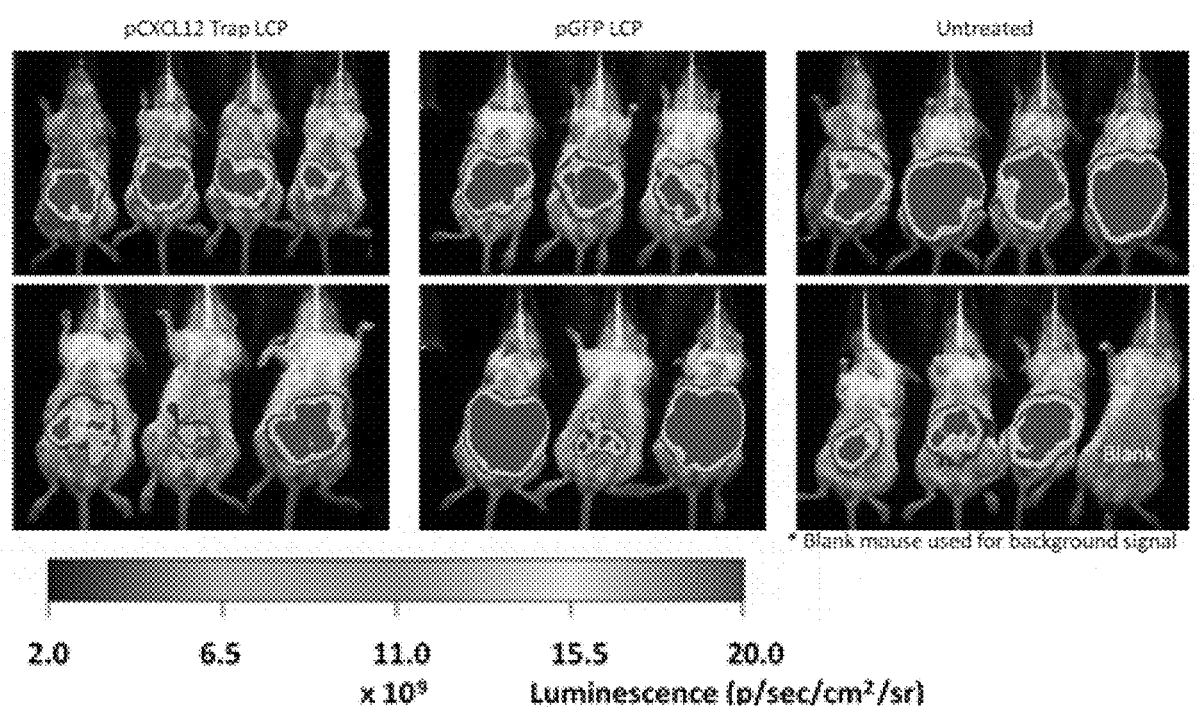

FIG. 13 depicts the total mouse tumor burden on day 24 after cecal inoculation. Mice were inoculated with $2\times10^6$ CT-26 F3 RFP/Luc cells into the cecum wall. Treatment consisting of 10 μg pDNA was administered through tail vein IV on days 10, 12, and 14. Groups included PBS (untreated; n=7), pGFP DNA LCP (10 every other day×3; n=6), and pCXCL12 trap LCP (10 μg every other day×3; n=7). Progression of tumor mass was followed by administration of 200 μl luciferin (10 mg/ml) IP. Luciferase bioluminescent imaging was performed 10 min after administration of luciferin.

FIG. 14 depicts (A) TEM image of LPD NP (vector for encapsulating plasmid). (B) Biodistribution of DiI-labeled LPD NP (24 h post injection) in mice bearing KPC orthotopic tumor. (C) Fluorescence images of DiI distribution in liver and tumor (white numbers indicate % cells taken up DiI in the organ). Two daily doses of GFP LPD NPs were intravenous injected into mice bearing tumors. The GFP expression in liver and tumor are shown (green numbers). Phalloidin labelled cellular actin. Results suggest that though liver is the major organ taken up NPs, plasmid expression is mainly in the tumor (n=3). (D) GFP expression in different cell populations within tumor. The % of GFP positive cells in each cell population was quantified (white numbers). αSMA positive fibroblasts and RFP positive tumor cells are major GFP producing cells within the tumor microenvironment. (E) Transient expression of His-tag labeled trap plasmid were quantified by His-tag ELISA. The expression of trap was transient within one week. And again, tumor is the major producing organs. Compared to trap protein, the plasmid delivery prolonged trap expression in tumor (n=4).

FIG. 15 depicts the tumor growth inhibition and host survival. (A) Dosing schedule of different treatments on mice bearing KPC allograft are shown in the upper panel. IVIS images of KPC tumor after different treatments (n=5~7) are shown in the lower panel. (B) Tumor inhibition curve of KPC (n=6-10). (C) The survival proportions of the treated groups. Data show mean±SD, n=5-8. (D&E). The end time point tumor weight of mice bearing KPC with low dose plasmid treatment (30 μg/mice, 4 times, D) and high dose plasmid treatment (50 μg/mice, 4 times, E). n=4. * $p<0.05$,  $p<0.01$, * $p<0.001$. The statistical analyses were calculated by comparison with the control group if not specifically mentioned.

FIG. 16 depicts the long-term metastasis study. (A) Metastasis of KPC cells in major organs 1 month after different treatments (n=4~5). Liver, lung and spleen are major organs for KPC metastasis. (B) H&E staining shown the histology of tumor metastasis in the major organs of the PBS control group. Metastasis was significantly inhibited when mice were treatment with combo trap NP. Blue circles and arrows indicate metastatic tumor growth in lung, spleen and liver. Bars in B represent 100 μm.

FIG. 17 depicts the IFN-γ ELISpot assay of splenocytes from mice bearing orthotopic KPC pancreatic cancer with different treatment. (A) Spleens were harvested from tumor bearing animals. Splenocytes were re-stimulated with extracts from normal splenocytes (control), KPC cells or KPC cells transduced with RFP and Luciferase markers. Cells secreted IFN-γ were stained with anti-IFN-γ antibody. Results are quantified and shown in the right panel. ns: not significant, *** $p<0.001$. n=4. B. Spleens were harvested from tumor bearing animals with different treatments: PBS, CXCL12 trap NP, PDL1 trap NP and Combo trap NP. Splenocytes were re-stimulated with extracts from KPC RFP/Luc. Cells secreted IFN-γ were stained with anti-IFN-γ antibody. No significant differences were found among different treatments (n=4).

FIG. 18 depicts the combo trap NP facilitate T cells infiltration into tumor microenvironment. (A) Tissue sections from KPC allografts with different treatments were stained for CD3 (green), p53 (red), and DAPI (blue) and then analyzed by IF microscopy. Adjacent H&E stainings show the stroma architecture of the regions. Yellow dotted lines demonstrate the edge of tumor cells' invasion into normal pancreas. Orange-rectangle areas are zoomed in for better visualization. Tumor regions are also presented in lower magnification. Scale bars indicate 400 μm. (B) The percentage of CD3+ cells within tumor regions were quantified with image J of 5 representative images from each treatment. (C) Single-cell suspensions of KPC allograft tumors (within the tumor regions) after different treatments (n=5) were stained with antibodies for CD3 and CD8. The percentage of CD3$^+$CD8 cells are quantified by flow cytometry. * $p<0.05$. ** $p<0.01$. D and E. Mice bearing KPC98027 tumors were pretreated with 3 daily injections of CD8 mAb (300 μg/mice) to deplete the CD8+ T-cells in the mice. Isotype mAb were used as control. The efficacy of combo trap NP in mice with or without CD8 depletion were compared by imaging (D) and quantified (E).

FIG. 19 depicts the changes of tumor-infiltrating immune cells in tumor microenvironment. The KPC murine tumor bearing mice were divided into four groups and treated with either PBS, CXCL12 trap/Ctrl NP, PDL1 trap/Ctrl NP or Combo trap NP. At the end of treatment, mice were euthanized and tumor tissues were collected for (A) immunostaining evaluation and (B) flow cytometry assay: the first panel shows the MDSC (yellow); the second panel shows the Treg cells (yellow) and the third panel shows the macrophages (red). Numbers showing in white indicate the average % of each cell type in the tumor. Bars in A represent 200 μm. * $p<0.05$; ** $p<0.01$. The statistical analyses were calculated by comparison with the untreated group if not specifically mentioned.

FIG. 20 depicts the changing of CXCL12 and PD-L1 coverage after trap plasmid treatment. Both fluorescence image (A) and quantification (B) are presented (n=5). Bars in A represent 200 μm. The statistical analyses were calculated by comparison with the control group if not specifically mentioned. All data show mean±SEM (n=4), *p<0.05;  p<0.01, *p<0.001.

Figure 21:
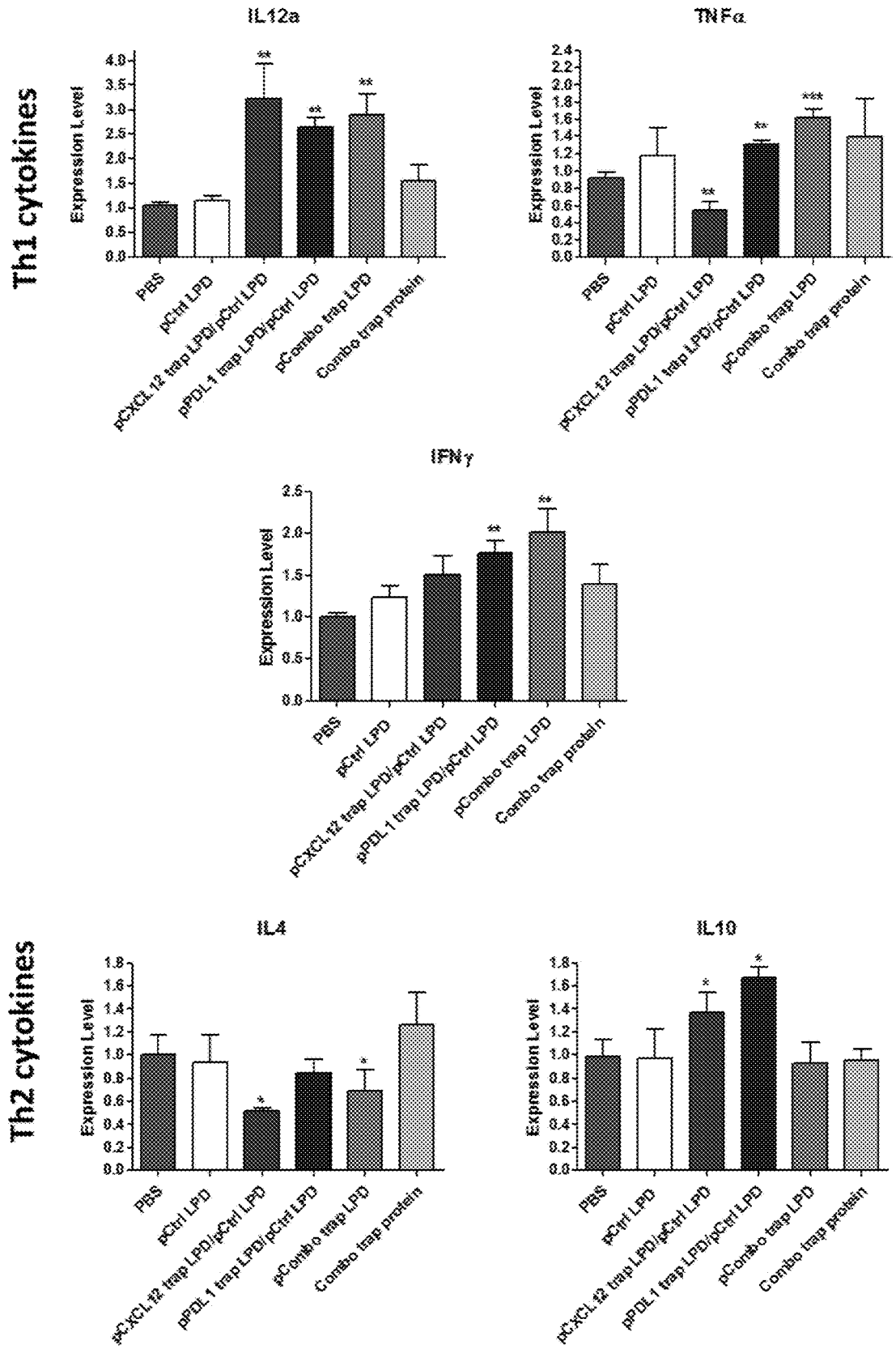

FIG. 21 depicts the changes of cytokines in tumor microenvironment. Cytokine level were detected using quantitative RT-PCR. The statistical analyses were calculated by comparison with the control group if not specifically mentioned. All data show mean±SEM (n=4), *p<0.05;  p<0.01, *p<0.001.

Figure 22:
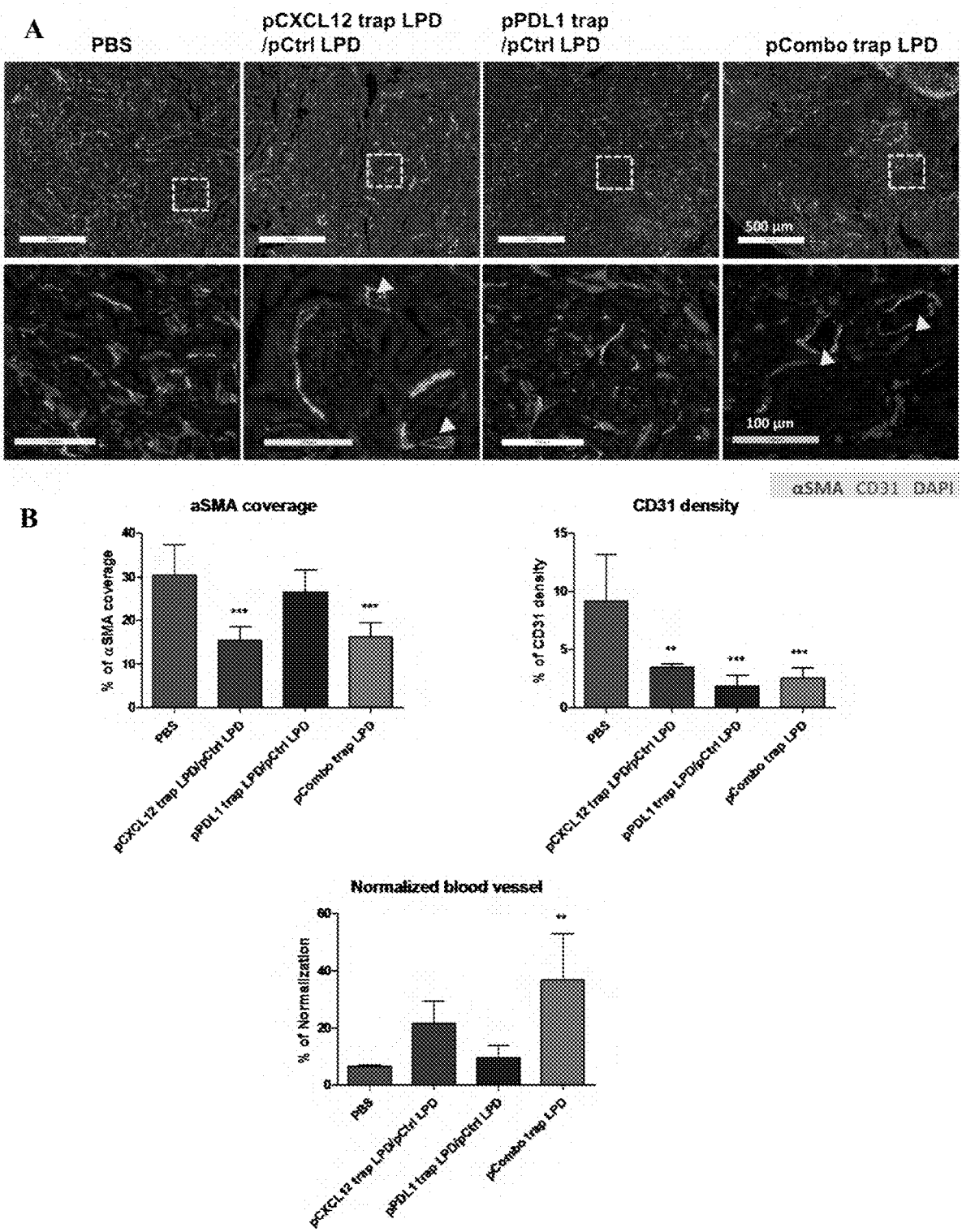

FIG. 22 depicts the tumor microenvironment changes after various treatments. (A) The KPC bearing mice were divided into 4 groups and treated with either PBS, CXCL12 trap/Ctrl NP, PDL1 trap/Ctrl NP or Combo trap NP. At the end of treatment, mice were euthanized and tumor tissues were harvested for double fluorescence staining of CD31 (shown as green) and αSMA (fibroblast staining, shown as red). Representative locations (yellow dotted square) are zoomed in (yellow square). Blood vessels were decompressed and normalized after CXCL12 trap or Combo trap treatment. Yellow arrow indicates the normalized blood vessels. Lower panel images are enlarged from the boxed areas in the corresponding upper panel images. Bars in upper and lower panels represents 500 and 100 μm, respectively. (B) The % of αSMA coverage, CD31 density and normalized blood vessels were quantified using Image J from 5 representative images of each group. The statistical analyses were calculated by comparison with the control group if not specifically mentioned. All data show mean±SD (n=5),  p<0.01, * p<0.001.

Figure 23:
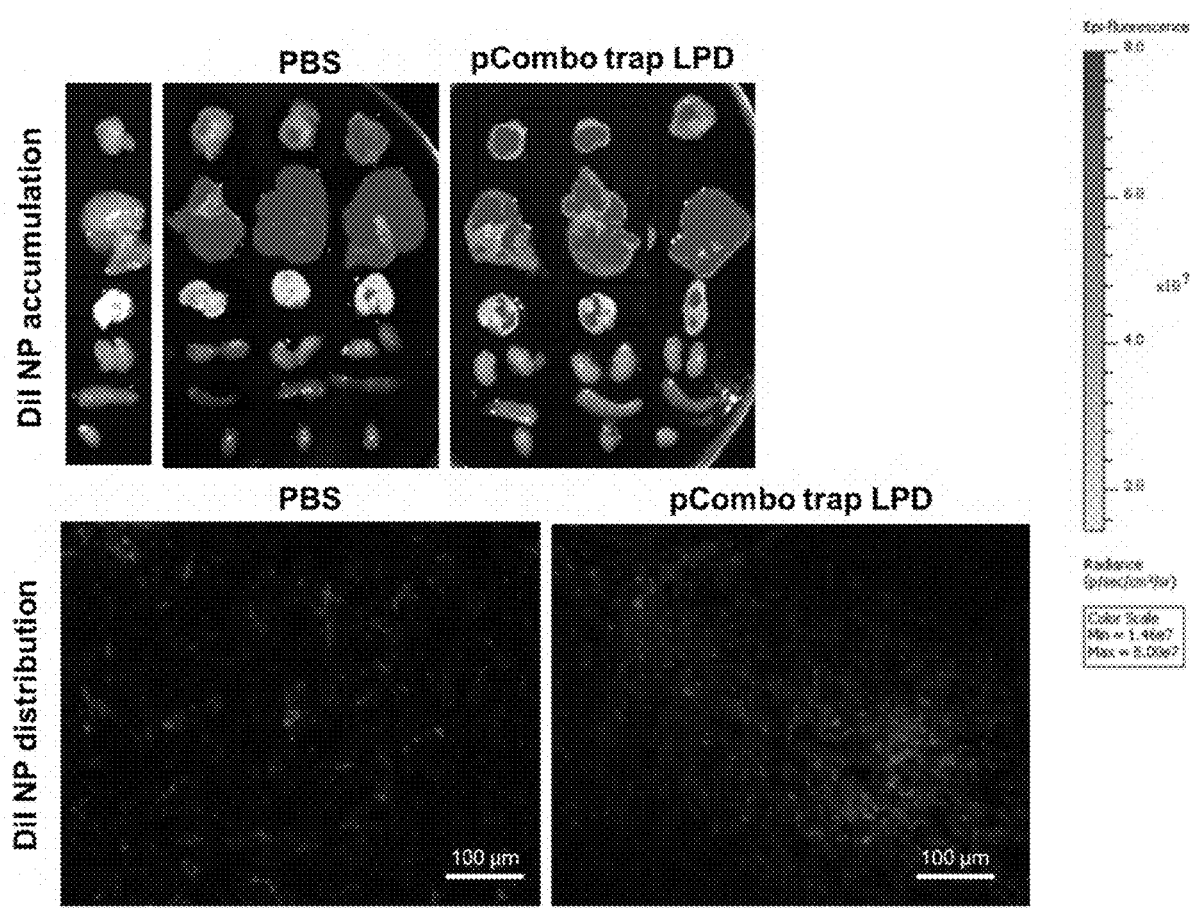

FIG. 23 depicts the accumulation (A) and distribution (B) of DiI labeled LPD NPs in different organs and tumors respectively, from mice bearing KPC allografts treated with either PBS or combo trap NPs.

FIG. 24 depicts the collagen coverage within tumors from mice treated with PBS, CXCL12 trap/Ctrl NP, PDL1 trap/ Ctrl NP and Combo trap NP, respectively.

Figure 25:
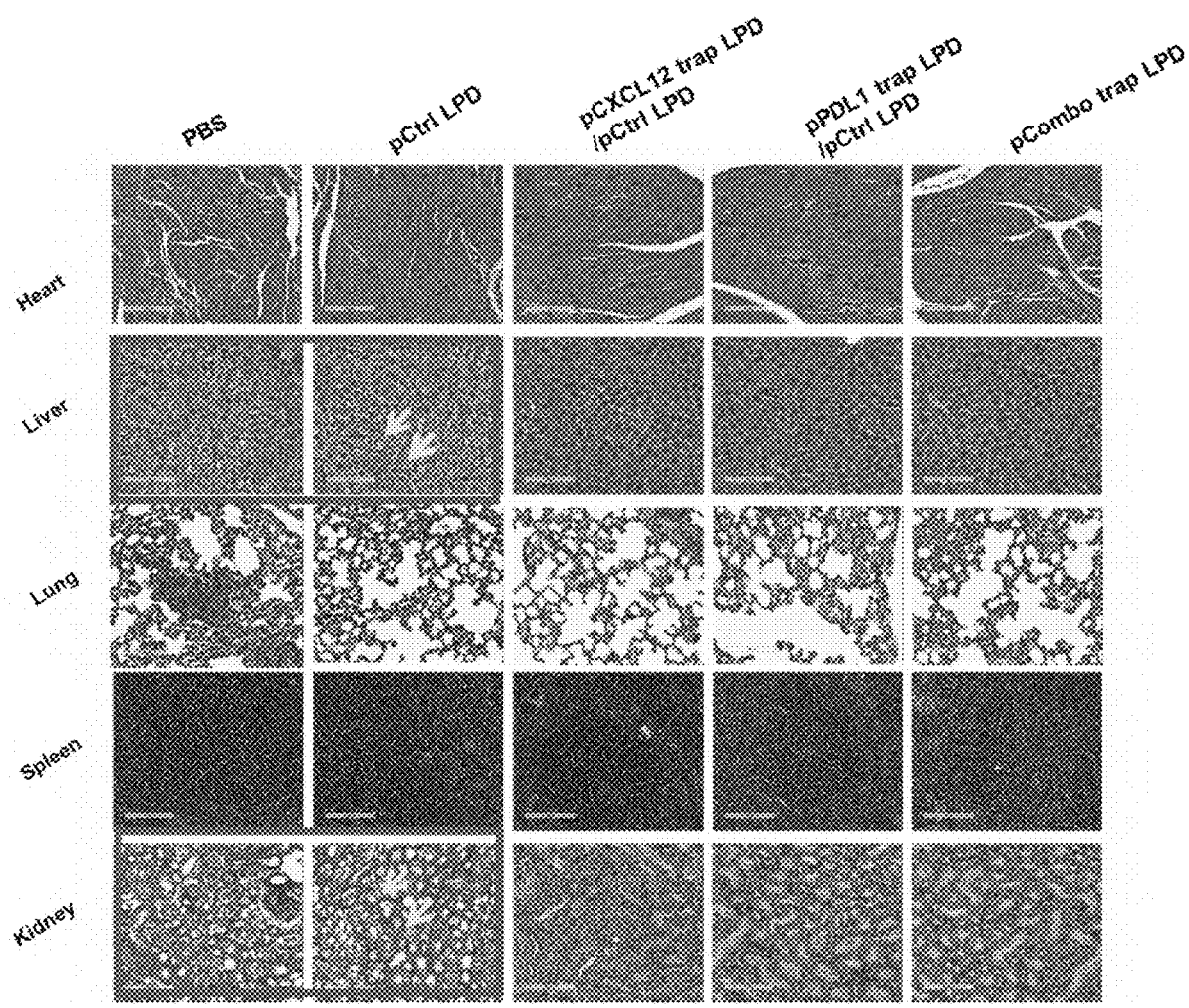

FIG. 25 depicts the H&E morphology of the KPC bearing mice which were divided into 5 groups and treated with 4 doses of PBS, Ctrl NP, CXCL12 trap/Ctrl NP, PD-L1 trap/Ctrl NP and Combo trap NP every two days. At the end of the treatments, mice were euthanized and the major organs were harvested for H&E pathology staining. Blue rectangle highlights the liver and kidney of PBS and Ctrl NP groups, indicating severe liver and kidney toxicities. Cellular vacuolization, desquamated-degenerative cells and focal necrosis (yellow arrows) were observed in these organs.

DETAILED DESCRIPTION

As disclosed herein, improving the survival rate and treatment of cancer patients rests in preventing or decreasing the occurrence of metastases. In particular, colorectal cancer (CRC) patients tend to develop liver metastases. Studies have shown that the relationship between the chemokine receptor (CXCR4) expressed on colon cancer cells and the chemokine ligand (CXCL12) secreted by the hepatic stellate cells (HSC) plays a significant role in CRC liver metastasis (Zeelenberg I, Ruuls-Van Stalle L, Roos E. The Chemokine Receptor CXCR4 Is Required for Outgrowth of Colon Carcinoma Micrometastases. *Cancer Res.*, 63: 3833-3839, 2003). These hepatic stellate cells are resident perisinusoidal cells which have shown to produce high levels of endogenous CXCL12 for recruitment of lymphocytes to areas of inflammation. Migration and invasion studies have shown that in the presence of high levels of CXCL12, colorectal cancer cells (CXCR4 positive) migrate and invade via the CXCL12 concentration gradient. Further studies of human colorectal cancer samples have also found that poor prognosis and a higher rate of liver metastasis correlates with high levels of CXCR4 expression on the cancer cells (Zeelenberg I, Ruuls-Van Stalle L, Roos E. The Chemokine Receptor CXCR4 Is Required for Outgrowth of Colon Carcinoma Micrometastases. *Cancer Res.*, 63: 3833-3839, 2003). As described herein, a method of disrupting this CXCL12 gradient (prophylactically) at the future site of metastasis (liver), can decrease the occurrence of colorectal liver metastasis.

As described herein, the present methods avoid the problems of known therapies. The treatment of animals with AMD3100, a small molecule CXCR4 antagonist, has demonstrated that disrupting the CXCL12/CXRC4 axis can decrease the occurrence of colorectal liver metastasis (Matsusue R, Kubo H, Hisamori S, Okoshi K, Takagi H, Hida K, Nakano K, Itami A, Kawada K, Nagayama S, Sakai Y. epatic stellate cells promote liver metastasis of colon cancer cells by the action of SDF-1/CXCR4 axis. *Ann Surg Oncol.* 16(9):2645-53, 2009). Subsequently, many CXCR4 antagonists have been developed. However, the endogenous role of CXCL12 and CXCR4 in the immune system is vital for normal homeostasis. Therefore, these traditional treatments which include small molecule and protein therapies come with systemic off-target toxicity concerns. Furthermore, to our knowledge no therapies targeting CXCL12 have been developed or reported to reduce the occurrence of metastatic lesions.

As disclosed herein, a unique anti-cancer strategy can be accomplished, in which delivery of genes (encoding CXCL12 trap) to the liver can alter the liver micro-environment, for example, the protein factor levels therein. The methods described herein result in local and transient modification of the micro-environment, thus sparing other cells from undesirable toxicity. Delivery of such genes can achieve reduced concentrations of factors such as CXCL12, priming the liver to resist the migration/invasion of the colorectal cancer cells. The association between CXCL12 and CXCR4 plays a crucial role in liver metastasis, in which over-expression of CXCR4 is characteristic of highly metastatic human colorectal liver metastasis lesions, as well as the high levels of CXCL12 expressed in the liver (Shan-shan Zhang, Zhi-peng Han, Ying-ying Jing, et al., CD133+ CXCR4+ colon cancer cells exhibit metastatic potential and predict poor prognosis of patients. *BMC Med.* 10: 85, 2012).

The subject matter described herein is not limited to any particular tissue or target cell. As disclosed herein, targeting the micro-environment is a unique anti-cancer paradigm, in which the metastatic lesions are not specifically targeted, but instead the environment is primed to be unsuitable for the metastasis to form or progress, ultimately allowing for decreased growth and occurrence of metastasis. Through incorporation of a targeting moiety, for example, the galactose targeting moiety for local liver expression of the therapeutic protein, it is possible to target the desired tissue with no expression found in off-target organs or serum. Since this approach can be used in many tissues besides the liver and with other traps besides CXCL12, other metastatic tissue, such as breast, lung, lymph node, prostate, brain, pancreas, and bone can be targeted.

Other micro-environment factors can play a role in migration, invasion, and proliferation of cancer metastasis. These factors become more pronounced in the organ of interest when inflammation is induced. This inflammation can be associated with many different environmental factors varying from secreted proteins from the primary cancer to a patient's diet. Therefore, targeting these factors is also contemplated in the subject matter described herein. Accordingly, targeting factors in high metastatic tissue or tissue that is susceptible to metastases is a promising therapy for reducing the occurrence/progression of metastasis in many organs.

The insufficient target specificity of most approaches in treating diseases has limited the applications for successful treatment of these diseases in the clinic. Furthermore, the shortcomings of gene therapy, due to the numerous extracellular and intracellular barriers have truly hampered clinical treatments of many diseases. Therefore, in order to overcome these barriers we have developed a vector for clinical applications with high specificity, accumulation, and delivery into the nucleus of the target cell. The subject matter described herein overcomes the problems of prior therapies and can not only treat liver metastasis and primary cancers, but numerous other liver diseases such as HBV, fatty liver, liver cirrhosis and many others. Further, in addition to liver diseases, through incorporation of different targeting moieties, such as adenosine analogs, targeting highly expressed Adenosine A2B receptors on lung epithelial cells, primes the vector to accumulate and deliver traps, such as pDNA traps against CXCL12 or other micro-environment factors, that play a role in other tissues susceptible to metastases. Accordingly, the methods and compositions described herein can be used to prime the micro-environment factors of numerous tissues known to have high rates of metastasis such as the lung, lymph node, breast, bone, and others.

Another type of recalcitrant cancer is pancreatic tumor, which is known to be resistant to immunotherapy due to its strong immune suppressive tumor microenvironment (TME). CXCL12 and PD-L1 are two molecules that control the suppressive TME. Fusion proteins, also referred to herein as one type of trap, that bind one of these two molecules with high affinity (Kd=4 nM and 16 pM, respectively) were manufactured and tested for specific binding with the target. Plasmid DNA encoding for each trap was formulated in LPD nanoparticles and injected IV to mice bearing KPC orthotopic pancreatic cancer. Expression of traps was mainly in the tumor and secondarily in the liver. Combination trap therapy shrunk the tumor and significantly prolonged the host survival by 57%. Either trap alone only brought in a partial therapeutic effect. We also found that CXCL12 trap allowed T-cell penetration into the tumor and PD-L1 trap allowed the infiltrated T-cells to kill the tumor cells. Combo trap therapy also significantly reduced metastasis of the tumor cells to other organs. No toxicity was found in all major organs including the liver and the kidney. Accordingly, combination trap therapy significantly modified the suppressive TME to allow the host immune system to kill the tumor cells.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

The term "microenvironment" refers to the target cell and its adjacent milieu.

The term "construct" refers to an artificially constructed segment of genetic material, such as a nucleic acid sequence, that is to be expressed in a target tissue or cell. It can contain the genetic insert, and any necessary promoters, etc. will also be present in the vector.

The term "susceptible" refers to a tissue or cell that because of its micro-environment certain types of cancers tend to grow or metastasize in the tissue or cell. By way of a non-limiting example, colorectal cancers tend to metastasize and grow in the liver as a result of the micro-environment of liver cells. Other cancers are known to metastasize to particular tissues and cells in the body. In another non-limiting example, breast cancer tends to metastasize in the liver, brain, and regional lymph nodes, and the bone. Thus, these tissues and cells are susceptible as used herein.

As used herein, "reducing metastasis" refers to the inhibition or lessening of metastasis to susceptible tissues and cells. Numerous ways of determining a reduction in metastasis can be used. By way of a non-limiting example, subjects with a type of cancer that is typically known to metastasize and would be expected to metastasize who show little or no metastasis after treatment will have shown a reduction in metastasis. In particular, the subject matter described herein provides reducing metastasis of any cancer to the liver.

As used herein, the term "trap" refers to an expression product that binds, inhibits, or reduces the biological activity of the target molecule in the micro-environment. The trap is delivered by vectors, which can be viral, non-viral, synthetic, such as, nanoparticles, and the like, each of which comprises the necessary materials for subcloning and expression of the trap. The trap can also be delivered by liposomes or living cells including monocytes and stem cells. The inhibition can be measured by $K_d$, for example, or by showing a reduction in the activity of the target, from 1, 5, 10, 15, 20, 25, 30, 35, 40, 45, 50, 55, 60, 70, 75, 80, 85, 90 or 95% or more. The trap is designed to work on a desired target molecule, which in many instances is a trappable protein as is known in the art in view of the subject matter described herein.

The term "transient" refers to an effect that is non-permanent.

The term "subject" refers to animals such as mammals, including, but not limited to, primates (e.g., humans), cows, sheep, goats, horses, dogs, cats, rabbits, rats, mice and the like. In certain embodiments, the subject is a human. In embodiments, the subject has been diagnosed with a disease such as cancer or a liver disease.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of the trap that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer.

The terms "cancer" refers to or describe the physiological condition in mammals that is typically characterized by unregulated cell growth. A "tumor" comprises one or more cancerous cells.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

As used herein, the term "deliver" refers to the transfer of a substance or molecule (e.g., a polynucleotide) to a physiological site, tissue, or cell. This encompasses delivery to the intracellular portion of a cell or to the extracellular space. Delivery of a polynucleotide into the intracellular portion of a cell is also often referred to as "transfection."

As used herein, the term "intracellular" or "intracellularly" has its ordinary meaning as understood in the art. In general, the space inside of a cell, which is encircled by a membrane, is defined as "intracellular" space. Similarly, as used herein, the term "extracellular" or "extracellularly" has its ordinary meaning as understood in the art. In general, the space outside of the cell membrane is defined as "extracellular" space.

A fibroblast is a cell that synthesizes extracellular matrix and collagen, the structural framework (stroma) for animal tissues. The main function of fibroblasts is to maintain the structural integrity of connective tissues by continuously secreting precursors of the extracellular matrix. In embodiments, fibroblasts are a stroma target for the vectors described herein.

The following abbreviations may be used herein. Some abbreviations are defined where they occur in the text of this document.

ALT Alanine Aminotransferase
AST Aspartate Aminotransferase
BLI Bio-Layer Interferometry
BUN Blood Urea Nitrogen
CMV Cytomegalovirus
CRC Colorectal Cancer
DLS Dynamic Light Scattering
DAPI 4',6-diamidino-2-phenylindole
DOPA 1,2-dioleoyl-sn-glycero-3-phosphate
DOTAP 1,2-dioleoyl-3-trimethylammonium-propane
DSPE 1,2-distearoyl-sn-glycero-3-phosphatidylethanolamine
ELISA Enzyme Linked Immunosorbent Assay
GFP Green Fluorescent Protein
LCP Lipid Calcium Phosphate
mc Mono-cyclic
NHS N-Hydroxysuccinimide
PBS Phosphate Buffered Saline
PEG Polyethylene Glycol
PK Pharmacokinetics
pTrap Galactose-PEG-LCP w/pCXCL12 trap/mc-CR8C
TEM Transmission Electron Microscopy An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, Md., 1987 and 1991), The Chothia definition (Chothia & Lesk, *J. Mol. Biol.* 196:901-917, 1987; Chothia et al., *Nature* 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|---|---|---|---|---|---|
| L1 | L24 - - - L34 | L24 - - - L34 | L24 - - - L34 | L24 - - - L34 | L30 - - - L36 |
| L2 | L50 - - - L56 | L50 - - - L56 | L50 - - - L56 | L50 - - - L56 | L46 - - - L55 |
| L3 | L89 - - - L97 | L89 - - - L97 | L89 - - - L97 | L89 - - - L97 | L89 - - - L96 |
| H1 | H31 - - - H35B | H26 - - - H32 . . . H34* | H26 - - - H35B* | H26 - - - H35B | H30 - - - H35B |
| H2 | H50 - - - H65 | H52 - - - H56 | H50 - - - H65 | H50 - - - H58 | H47 - - - H58 |
| H3 | H95 - - - H102 | H95 - - - H102 | H95 - - - H102 | H95 - - - H102 | H93 - - - H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996). The epitope can be linear. The epitope can also be a conformational epitope. It is to be noted that the term "a" or "an" entity refers to one or more of that entity; for example, "a cationic lipid" is understood to represent one or more cationic lipids. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Additional definitions are set forth below.

II. Methods

In an embodiment, the present subject matter is directed to a method of modifying the micro-environment of a target cell comprising, systemically administering to a subject a composition comprising a vector, wherein the vector comprises a construct for expression of a trap in the target cell, wherein the trap is expressed in the target cell, wherein the micro-environment of the target cell is modified.

As described herein, expression of the trap results in the presence of an effective amount of the expressed trap to modify the micro-environment of the target cell.

Modifying the micro-environment of a target cell comprises reducing the amount of a target molecule that is normally present in the micro-environment. As used herein, reducing the amount refers to a 1, 2, 3, 4, 5, 6, 7, 8, 9, 10, 11, 12, 13, 14, 15, 16, 17, 18, 19 20, 25, 30, 35, 40, 45, 50, 55, 60, 65, 70, 75, 80, 85, 90, 95% or more lowering of the amount of the target molecule as compared to the amount in the absence of the trap.

Useful target molecules include proteins, such as enzymes, chemokines, cytokines, protein factors, and combinations thereof. Suitable targets include those in Table 2 below.

TABLE 2

| CXC (alpha chemokines) | | |
|---|---|---|
| CXCL1 | GRO-α/SCYB-1/MGSA/GRO-1/NAP-3 (MIP-2α/KC) | CXCR1, CXCR2 |
| CXCL2 | GRO-β/SCYB-2/GRO-2/MIp-2 α (MIP-2 β/KC) | CXCR2 |
| CXCL3 | GRO-γ/SCYB-3/GRO-3/MIp-2 β (KC) | CXCR2 |
| CXCL4 | PF-4/SCYB-4 | Unknown |
| CXCL5 | ENA-78/SCYB-5 (LIX) | CXCR2 |
| CXCL6 | GCP-2/SCYB-6 | CXCR1, CXCR2 |
| CXCL7 | NAP-2/(SCYB-7/PBP/CTAP-III/β-TG | CXCR1, CXCR2 |
| CXCL8 | SCYB-8/GCP-1/NAP-1/MDNCF | CXCR1, CXCR2 |
| CXCL9 | MIG/SCYB-9 | CXCR3 |
| CXCL10 | IP-10/SCYB-10 | CXCR3, KSHV-GPCR |
| CXCL11 | I-TAC/SCYB-11/β-R1/H174/IP-9 | CXCR3 |
| CXCL12 | SDF-1/SCYB-12/PBSF | CXCR4 |
| CXCL13 | BCA-1/SCYB-13 | CXCR5 |
| CXCL14 | BRAK/SCYB-14/Bolekine | Unknown |
| CXCL16 | Small inducible cytokine B6 | CXCR6 |

TABLE 2-continued

C (gamma chemokines)

| | | |
|---|---|---|
| XCL1 | Lymphotactin/SCYC1/SCM-1α/Lymphotactin α | XCR1 |
| XCL2 | SCM-1b/SCYC2/ymphotactin β | XCR1 |

CX₃C (delta chemokines)

| | | |
|---|---|---|
| CX₃CL1 | Fractalkine/SCYD1 | CX3CR1 |
| CCL1 | I-309/SCYA1 (TCA-3) | CCR8 |
| CCL2 | MCP-1/SCYA2/MCAF/HC11 (JE) | CCR2, CCR5, CCR10 |
| CCL3 | MIP-1α/SCYA 3/LD78α/SIS- α | CCR1, CCR5 |
| CCL4 | MIP-1β/SCYA4/ACT-2/G-26/HC21/LAG-1/SIS-γ | CCR5, CCR10 |
| CCL5 | RANTES/SCYA5/SIS-δ | CCR1, CCR3, CCR5, CCR10 |
| CCL7 | MCP-3/SCYA7 | CCR1, CCR2, CCR3 CCR5, |
| CCL8 | MCP-2/SCYA8/HC14 (MARC) | CCR2, CCR3, CCR5 CCR1, |
| CCL11 | Eotaxin/SCYA11 | CCR3 |
| CCL13 | MCP-4/SCYA13/Ck β10/NCC-1 | CCR1, CCR2, CCR3, CCR5 |
| CCL14 | HCC-1/SCYA14/Ck β1/MCIF/NCC-2/CC-1 | CCR1 |
| CCL15 | MIP-1 δ/SCYA 15/Lkn-1/HCC-2/MIP-5/NCC-3/CC-2 | CCR1, CCR3 |
| CCL16 | HCC-4/SCYA16/Ck β12/LEC/LCC-1/NCC-4/ILINCK/LMC/Mtn-1 | CCR1 |
| CCL17 | TARC/SCYA17 (ABCD-2) | CCR4 |
| CCL18 | PARC/SCYA18/Ckβ7/DC-CK1/AMAC-1/MIP-4/DCtactin | Unknown |
| CCL19 | MIP-3β/SCYA19/Ckβ11/ELC/Exodus-3 | CCR7 |
| CCL20 | MIP-3α/SCYA20/LARC/Exodus-1 | CCR6 |
| CCL21 | 6Ckine/SCYA21/Ckβ9/SLC/Exodus-2 | CCR7 |
| CCL22 | MDC/SCYA22 (ABCD-1) | CCR4 |
| CCL23 | MPIF/SCYA23/Ckβ8/Ckβ8-1/MIP-3/MPIP-1 | CCR1 |
| CCL24 | Eotaxin-2/SCYA24/Ckβ6/MPIF-2 | CCR3 |
| CCL25 | TECK/SCYA25/Ckβ15 | CCR9 |
| CCL26 | Eotaxin-3/SCYA26/MSP-4α/TSC-1/IMA | CCR3 |
| CCL27 | CTACK/SCYA27/ESkine/Skinkine | CCR3, CCR2, CCR10 |
| CCL28 | CCL28/SCYA28/MEC | CCR10, CCR3 |

A particularly useful target molecule is CXCL12. Other Protein Factors include: EGF, Neuregulin, FGF, HGF, VEGF, VEGFR and NRP-1, Ang1 and Ang2, PDGF (BB-homodimer) and PDGFR, TGF-β, endoglin and TGF-β receptors, MCP-1, Histamine, Integrins α2β1, αVβ, αVβ5, αVβ6, α6β4 and α5β1, VE-cadherin and CD31, ephrin, plasminogen activators, plasminogen activator inhibitor-1, eNOS and COX-2, AC133, ID1/ID3, LOX, and HIF.

Inhibitory and Blocking Traps and their Targets: Inhibitory traps for macromolecule targets include traps that can be protein molecules that specifically bind and further inhibit or block the biological functions of a target of interest. The targets of the inhibitory or blocking traps can be cyto/chemokines and their corresponding receptors, including but not limited to IL-1, IL-6, IL-7, IL-8, IL-10, IL-15, IL-21 (and IL receptors), TNF-alpha (and TNF-alpha receptor), TGF-beta (and TGF-beta receptor), CSF-1 (and CSF-1 receptor), CXCR1 and its ligands (CXCL5, CXCL6, CXCL8), CXCR2 and its ligands (CXCL1, CXCL2, CXCL3, CXCL5, CXCL6, CXCL7 and CXCL8), CXCR3 and its ligands (CXCL4, CXCL9, CXCL10, CXCL11), CXCR4 and its ligand (CXCL12), CXCR5 and its ligand (CXCL13), CX3CR1 and its ligand (CX3CL1), CCR1 and its ligands (CCL3, CCL4, CCL5, CCL6, CCL7, CCL8, CCL13, CCL14, CCL15, CCL16, CCL23), CCR2 and its ligands (CCL2, CCL5, CCL7, CCL8, CCL13, CCL16), CCR3 and its ligands (CCL4, CCL5, CCL7, CCL11, CCL13, CCL15, CCL24, CCL26, CCL28), CCR4 and its ligands (CCL17, CCL22), CCR5 and its ligands (CCL3, CCL4, CCL5, CCL7, CCL14, CCL16), CCR6 and its ligand (CCL20), CCR7 and its ligands (CCL19, CCL21), CCR9 and its ligand (CCL25), CCR10 and its ligands (CCL27 and CCL28), ACKR3 and its ligands (CCL11, CCL12), ACKR6 and its ligand (CCL18).

The targets of the inhibitory traps can be immune checkpoint related proteins, including but not limited to CTLA-4, PD-1, PD-L1, PD-L2, B7-H3 (CD276), B7-H4 (VTCN1), HVEM (CD270 or TNFRSF14), BTLA (CD272), TIM-3, GALS, TIGIT, A2aR, LAG-3, KIRs and MHC class I or II.

Targets also include those whose up- or downregulation by inhibitory trapping will suppress the expression or reduce the biological activity of IDO, TDO, arginase-1/2, adenosine receptors, CD39, CD73, COX2, EP receptors, and iNOS that are involved in catabolism (by IDO, TDO, ARG1/2) of amino acids (i.e. tryptophan, arginine, cysteine, glutamine, and phenylalanine), generation of adenosine (by CD39, CD73, and mediated through adenosine receptors), prostaglandin E2 (by COX2), reactive oxygen species (ROS) and reactive nitrogen species (RNS) (by iNOS), all resulting in the immunosuppression of TME.

Inhibitory traps for small molecule metabolites: The targets of the inhibitory traps can also be small molecules, including but not limited to tryptophan metabolites (i.e. kynurenine that is produced by IDO or TDO and signals through the aryl hydrocarbon receptor), cAMP and adenosine, which play critical roles in the inhibition of T cells, recruitment and/or expansion of immunosuppressive cells and consequently the immunosuppressive tumor microenvironment.

Stimulatory Traps and their Targets: The traps can also be simulative, including those that agonistically act on immune checkpoint targets CD28, ICOS (CD278), 4-1BB (CD137 or TNFRSF9), OX40 (CD134 or TNFRSF4), GITR (CD357 or TNFRSF18), CD27 (TNFRSF7), and CD40 (TNFRSF5). The stimulatory traps can also be those that possess or mimic the agonistic effects of the ligands of the above receptors, including but not limited to B7.1 (CD80), B7.2 (CD86), B7-H5 (VISTA or Gi24), ICOSL (B7H2 or CD275), 4-1BBL (CD137L), OX40L (CD252), GITRL, CD27L (CD70), and CD40L (CD154). The targets for agonistic traps also include some toll-like receptors, including but not limited to TLR4, TLR7, TLR8, and TLR9 that play critical roles in the activation of T cells. Traps can be based on antibody-like domains or fragments. It has been found that the local and transient expression of the chemo/cytokine traps results in desired biological activity and low toxicity. Most of the target-binding biologics rely on a full-length monoclonal antibody that has long half-life. Indeed, systemic and prolonged administration of a CXCL12 trap can result in transient liver damage and reduced white blood cell count, as demonstrated in our in vivo data. In addition, due to the large size, complex structure, and sophisticated post-translational modifications, full-length antibodies have several intrinsic disadvantages in serving as chemo/cytokine traps, including inefficiency in tissue penetration to access TME, difficult to engineer and optimize the target-trapping properties such as disruption of receptor binding, high stability, bispecificity (if necessary), and Fc-induced side effects. Our strategy to address the challenge is to develop novel trapping molecules with desired features from protein libraries based on small protein domains, including but not limited to the immunoglobulin VH domain, immunoglobulin VL domain, a VH and VL fusion protein, scFv, a peptide or protein derived from a binding and/or framework region of an antibody, a non-immunoglobulin target-binding domain such as a single domain antibody mimic based on a non-immunoglobulin scaffold (such as an FN domain-based monobody, Z domain-based affibody, DARPINs), singly and in any combination.

Some known target-binding antibodies can be altered and engineered to serve as the trap for the local and transient gene delivery approach described in this work. To compete effectively with the natural receptor(s), a trap should possess unusually high binding specificity and affinity against the receptor-binding site, a property that is more likely to achieve through directed protein selection from a protein or antibody fragment library with a high diversity at the surface loops or residues that could be utilized in the interaction with a target of interest, using protein/peptide display and selection technologies such as phage display, cell surface display, mRNA display, DNA display, ribosome display that are widely used in the in vitro protein selections.

As described herein, local and transient blockade of signaling pathways mediated by certain key chemo/cytokines, e.g., CXCL12, a chemokine that has been implicated in playing a pivotal role in the migration/invasion of CXCR4 positive colorectal cancer cells to the liver, can significantly prevent CRC metastasis. We first engineered a CXCL12 trap gene based on an anti-CXCL12 antibody sequences, by fusing a VH and a VL domain through a protease-resistant flexible linker. To achieve efficient secretion from liver hepatocytes after expression, a strong signal peptide was incorporated at the N-terminus, whereas affinity tags were introduced at the C-terminus to facilitate protein purification and detection. The coding sequence of the resulting CXCL12 trap was cloned into an expression vector pCDNA3.1 driven by a CMV promoter. The resulting CXCL12 trap expressed in and purified from 293T cells was found to have a $K_d$ of 4 nM with CXCL12 (FIG. 2A), whereas its binding with CXCL1, CXCL8 and CXCL10 were not detectable. This CXCL12 trap greatly suppressed the migration and invasion of CT-26 FL3 cells stimulated with CXCL12 (FIG. 2B-C). Local and transient expression of this CXCL12 trap was tested using the gene delivery system based on the lipid calcium phosphate (LCP) nanoparticle (FIG. 5). As detailed below, three treatments with the pCXCL12-trap pDNA formulated in LCP almost completely resolved any occurrence of CT26-FL3 colorectal liver metastasis with no sign of cancer spread to other organs (FIG. 6).

To generate a CXCL12 trap that has much higher potency, we developed a CXCL12 trap based on the VH domain library. To facilitate the in vitro protein selection, we expressed and purified the wild-type recombinant CXCL12 containing a C-terminal biotin tag (wtCXCL12-biotin, FIG. 1A), as well as a CXCL12 mutant (ΔCXCL12, FIG. 1A) in which the N-terminal 8 residues (highlighted in cyan in FIG. 1A) that are implicated in CXCR4-binding were deleted. wtCXCL12-biotin was used as target for positive selection, whereas ΔCXCL12 was used to remove sequences that bind to non-desired sites through competitive washing. Similar strategies were used to develop single domain traps against other chemokines, as illustrated in FIG. 1B for CCL2 and CCL5.

In brief, displayed $V_H$ domain library pre-cleared with a streptavidin-agarose column was incubated with an appropriate amount of biotinylated wtCXCL12 in a binding buffer facilitating the formation of disulfide bond. The mixture was incubated at room temperature for 1 hr, followed by addition of pre-washed streptavidin agarose beads to capture VH sequences. The resulting beads were first washed with binding buffer to remove nonspecifically bound sequences, followed by competitive washing with large excess of ΔCXCL12 to remove the VH sequences that bound CXCL12 at sites away from the CXCR4-binding N-terminus. The enriched pool was regenerated for a new round of selection. Extensive competitive washing was performed to facilitate the enrichment of sequences that bind to the N-terminal CXCL12 with very slow off-rate. After five rounds of selection, we successfully identified 6 VH sequences that tightly and specifically bind to wtCXCL12, but not ΔCXCL12. As shown in FIG. 1A, these sequences have very slow off-rates, with a wtCXCL12-binding affinity in the range of low nanomolars to picomolars.

Bivalent Traps with Synergistic Chemo/Cytokine Trapping Effects

Chemokines exist as monomers and dimers under physiological conditions, and compelling evidence suggests that both forms regulate in vivo function. It was hypothesized that chemokine dimerization perturbs the distribution of the conformational substates, which in turn differentially affects the activation of various downstream signaling pathways. CXCL1, CXCL12, CCR2, CCR5, and IL-6 have all been reported to adopt dimeric or oligomeric structures to interact with their pairing receptors.

In general, CXC chemokines dimerize using the first β-strand and α-helix forming a globular structure, with the dimer interface located away from the receptor binding N-terminal and N-loop regions. CC chemokines dimerize using their N-loop residues and form an extended structure, and so their dimerization and receptor binding domains overlap. CXCL12, for example, forms under physiological conditions both monomer and dimer, which possesses distinct effects on cell signaling and function (Ray P 2012 PMID22142194). While monomeric CXCL12 preferentially activates CXCR4 signaling through Gαi and Akt, the dimeric form more effectively promotes recruitment of β-arrestin 2 to CXCR4 and chemotaxis of CXCR4-expressing cancer cells. Significantly, the dimeric CXCL12 preferentially bind to CXCR4 over CXCR7. These findings indicate that trapping dimeric CXCL12 could more effectively block CXCR4-mediated signaling pathways. Homodimeric or heterodimeric traps can be easily generated through genetic fusion (FIG. 1C). To generate homodimeric chemo/cytokine traps, each single domain trap can be genetically fused with itself through a flexible linker as a recombinant fusion protein. Similarly, heterodimeric traps that bind a chemokine of interest at two unique sites can be generated using two traps that bind to nonoverlapping sites with similar affinities.

Bispecific Traps that Block Signalings Mediated by Two Different Chemo/Cytokines.

The redundancy of the chemokine network involved in tumor metastasis and TME immunosuppression indicates that a trapping therapy that acts on more than one signaling pathways should be more effective. Bispecific traps that can simultaneously block the signaling pathways mediated by two different chemo/cytokines can be generated by genetically linking two traps with unique specificity through a length tunable flexible linker (FIG. 1C).

Trivalent PD-L1 Traps with Very Potent Target-Trapping Efficiency

One of the most effective ways to develop a high quality ligand that binds to a target of interest is by converting the target-binding domain to its multivalent form, as observed in almost all types of antibodies and numerous multimeric interactive proteins. To minimize possible immunogenicity, highly stable trimerization domains from abundant extracellular proteins in mouse, human, or other organisms or trimerization domains based on such proteins can be used for the generation of trivalent traps for the local and transient gene delivery purpose. We chose to use a trimerization domain from human CMP-1. The strong hydrophobic and ionic interactions within the C-terminus of mouse or human CMP-1 result in a parallel, disulfide-linked, and rod-shaped trimeric structure with high stability. We developed a robust technology platform that allows for facile conversion of a target-binding domain from endogenous proteins (such as PD-L1, PD-1) or an affinity domain from protein selection into its trivalent form by genetically fusing with the trimerization domain, resulting in trivalent traps with high stability and significantly enhanced avidity. Typically, trivalent traps that bind to a target of interest with low nanomolar to picomolar binding affinities can be easily generated from monomeric domains that are 1,000 times weaker. The mouse sequence of this trimerization domain is highly homologous to that of human CMP-1, making it easy to switch to the human version if translational application is desired. Since the trimeric trap is formed through self-assembly of three identical monomers, it only requires a cDNA that codes for the monomer, making the gene to be delivered much shorter and easier to deliver. Using this strategy, we developed a potent PD-L1 trap by genetically fusing the mouse or human extracellular domain of PD-1 that binds to PD-L1 with a stable trimerization domain that is very abundant in mouse and human cartilages (FIG. 1D). The resulting trivalent protein bound PD-L1 with a Kd at about 16 picomolar, which is 10,000-higher than that between endogenous PD-1 and PD-L1 (FIG. 1D). Furthermore, in an immune competent KPC model of pancreatic cancer, plasmid DNA encoding this trimeric trap (FIG. 15) efficiently induced tumor shrinkage after IV administration of NPs, when used together with a trap against CXCL12.

In another embodiment, a trimer formed from three fusion polypeptides, wherein each fusion polypeptide comprises a PD-1 extracellular domain, a flexible linker, and a trimerization domain, said trimer capable of binding PD-L1, wherein the fusion polypeptide is encoded by a nucleic acid sequence with at least 70%, 75%, 80%, 85%, 90%, 95%, 96%, 97%, 98% or 99% sequence identity to SEQ ID NO: 25.

In embodiments, useful traps include receptors. Cytokine receptors exist in structurally related families and comprise high-affinity molecular signaling complexes that facilitate cytokine-mediated communication. Type I cytokine receptors have certain conserved motifs in their extracellular amino-acid domain, and lack an intrinsic protein tyrosine kinase activity. This family includes receptors for IL2 (beta-subunit), IL3, IL4, IL5, IL6, IL7, IL9, IL11, IL12, GM-CSF, G-CSF, Epo, LIF, CNTF, and also the receptors for Thrombopoietin (TPO), Prolactin, and Growth hormone. Type I cytokine receptor family is subdivided into three subsets on the basis of the ability of family members to form complexes with one of three different types of receptor signaling components (gp130, common beta, and common gamma— the gamma-chain of the IL2 receptor).

Type II cytokine receptors are multimeric receptors composed of heterologous subunits, and are receptors mainly for interferons. This family includes receptors for IFN-alpha, IFN-beta, IFN-gamma, IL10, IL22, and tissue factor. The extracellular domains of type II cytokine receptors share structural similarities in their ligand-binding domain. Several conserved intracellular sequence motifs have been described, which probably function as binding sites for the intracellular effector proteins JAK and STAT proteins.

Chemokine receptors are G protein-coupled receptors with 7 transmembrane structure and couple to G-protein for signal transduction. Chemokine receptors are divided into different families: CC chemokine receptors, CXC chemokine receptors, CX3C chemokine receptors, and XC chemokine receptor (XCR1).

Tumor necrosis factor receptor (TNFR) family members share a cysteine-rich domain (CRD) formed of three disulfide bonds surrounding a core motif of CXXCXXC creating an elongated molecule. TNFR is associated with pro-caspases through adapter proteins (FADD, TRADD, etc.) that can cleave other inactive procaspases and trigger the caspase cascade, irreversibly committing the cell to apoptosis.

TGF-beta receptors are single pass serine/threonine kinase receptors. TGF-beta receptors include TGFBR1, TGFBR2, and TGFBR3 which can be distinguished by their structural and functional properties.

Though the methods include systemic administration, the methods are locally acting, in that, the effect on the microenvironment is generally isolated in or around the target cells. This can be accomplished by incorporating a targeting ligand onto the vector as described elsewhere herein.

The methods are also transient. That is, the effect of the method lasts for about three (3) days or less. In embodiments, the effect lasts for about 20 hours or less. In embodiments, the effect lasts for about 16 hours or less. In embodiments, the effect lasts for about 12 hours or less. In embodiments, the effect lasts for about 10 hours or less. In embodiments, the effect lasts for about 8 hours or less. In embodiments, the effect lasts for about 6 hours or less. In embodiments, the effect lasts for about 4 hours or less. In embodiments, the effect lasts for about 3 hours or less. In embodiments, the effect lasts for about 3 hours or less. In embodiments, the effect lasts for about 1 hour or less.

In another embodiment, the present subject matter is directed to a method of reducing metastasis of a cancer comprising, systemically administering to a subject suffering from the cancer, a composition comprising a vector, wherein the vector comprises a trap, wherein the trap is delivered to and then expressed in and released out of the tissue susceptible to metastasis, wherein metastasis of the cancer to the tissue is reduced.

In this embodiment, the methods include all the variables described above.

Additionally, the methods are particularly useful in cancers as described elsewhere herein.

The reduction of metastasis can be from a total inhibition, i.e., undetectable, up to a level of metastasis that is lower than expected given the type and aggressiveness of the cancer and/or tumor. Such types and tumors are known to those of skill in the art. Data showing metastasis that is lower than a control or comparator also evidence the methods described herein. The reduction can be from 1, 2, 3, 4, 5, 6, 7, 8, 9, 10, 11, 12, 13, 14, 15, 16, 17, 18, 19 20, 25, 30, 35, 40, 45, 50, 55, 60, 65, 70, 75, 80, 85, 90, 95% or more.

In another embodiment, the present subject matter is directed to a method of treating cancer comprising, systemically administering to a subject suffering from the cancer, a composition comprising a vector, wherein the vector comprises a trap.

In another embodiment, the present subject matter is directed to a method of treating cancer comprising, systemically administering to a subject suffering from the cancer, a combination, wherein the combination comprises at least two vectors, wherein one of the vectors comprises a trap for a cytokine/chemokine, and another vector comprises a trap for a target associated with the cancer. In a particular aspect, the combination comprises a trap for a CXCL12 chemokine and a trap for PD-L1, and the cancer is pancreatic cancers, such as, pancreatic ductal adenocarcinoma. In another aspect, the combination comprises a trap for a CXCL12 chemokine and a trap for PD-1, and the cancer is pancreatic cancers, such as, pancreatic ductal adenocarcinoma. In another embodiment, the combinations include CXCL12 trap with PD-1 trap, CXCL12 trap with PD-L1 trap, CXCL12 trap with PD-L2 trap, CXCL12 trap with agonistic CD27 trap, CXCL12 trap with agonistic CD28 trap, CXCL12 trap with agonistic ICOS trap, CXCL12 trap with agonistic CD40 trap, CXCL12 trap with agonistic OX40 trap, CXCL12 trap with agonistic CD137 trap, CXCL12 trap with IDO trap, CXCL12 trap with TDO trap, CXCL12 trap with ARG1 trap, CXCL12 trap with NOS trap, CXCL12 trap with TGF-beta trap, CXCL12 trap with B7-H3 trap, CXCL12 trap with B7-H4 trap, CXCL12 trap with CTLA4 trap, CXCL12 trap with HVEM trap, CXCL12 trap with BTLA trap, CXCL12 trap with LAG3 trap, CXCL12 trap with KIR trap, CXCL12 trap with TIM3 trap, CXCL12 trap with GALS trap, CXCL12 trap with A2aR trap, PD-1 or PD-L1 trap with CXCR1 trap, PD-1 or PD-L1 trap with CXCR2 trap, PD-1 or PD-L1 trap with CXCR4 trap, PD-1 or PD-L1 trap with CXCR5 trap, PD-1 or PD-L1 trap with CXCR7 trap, PD-1 or PD-L1 trap with CCR2 trap, PD-1 or PD-L1 trap with CCR4 trap, PD-1 or PD-L1 trap with CCR5 trap, PD-1 or PD-L1 trap with CCR7 trap, PD-1 or PD-L1 trap with CCR9 trap, PD-1 or PD-L1 trap with CXCL1 trap, PD-1 or PD-L1 trap with CXCL8 trap, PD-1 or PD-L1 trap with CXCL10 trap, PD-1 or PD-L1 trap with CCL2 trap, PD-1 or PD-L1 trap with CCL5 trap, PD-1 or PD-L1 trap with CCL22 trap, PD-1 or PD-L1 trap with IL-6 trap, PD-1 or PD-L1 trap with IL-10 trap, PD-1 or PD-L1 trap with TGF-beta trap, PD-1 or PD-L1 trap with CSF1 trap, PD-1 or PD-L1 trap with B7-H3 trap, PD-1 or PD-L1 trap with B7-H4 trap, PD-1 or PD-L1 trap with CTLA4 trap, PD-1 or PD-L1 trap with HVEM trap, PD-1 or PD-L1 trap with BTLA trap, PD-1 or PD-L1 trap with LAG3 trap, PD-1 or PD-L1 trap with KIR trap, PD-1 or PD-L1 trap with TIM3 trap, PD-1 or PD-L1 trap with GALS trap, PD-1 or PD-L1 trap with A2aR trap, PD-1 or PD-L1 trap with CCR4 trap, PD-1 or PD-L1 trap with IDO-1 trap, PD-1 or PD-L1 trap with TDO trap, PD-1 or PD-L1 trap with ARG1 trap, PD-1 or PD-L1 trap with NOS trap, PD-1 or PD-L1 trap with PI3K trap, PD-1 or PD-L1 trap with agonistic CD27 trap, PD-1 or PD-L1 trap with agonistic CD28 trap, PD-1 or PD-L1 trap with agonistic ICOS trap, PD-1 or PD-L1 trap with agonistic CD40 trap, PD-1 or PD-L1 trap with agonistic OX40 trap, and PD-1 or PD-L1 trap with agonistic CD137 trap.

In another embodiment, the CXCL12 trap comprises a VH region from an anti-human CXCL12 antibody. In another embodiment, the CXCL12 trap comprises a VL region from an anti-human CXCL12 antibody. In another embodiment, the CXCL12 trap comprises a fusion protein comprising a VH and VL region from an anti-human CXCL12 antibody. In another embodiment, the CXCL12 trap comprises a non-immunoglobulin domain that mimics antibodies, including but not limited to FN domain-based monobody, Z domain-based affibody, and DARPINs.

In another embodiment, the human CXCL12 is set forth in GenBank Accession No. AAH39893 (SEQ ID NO:64) or GenBank Accession No. AAV49999 (SEQ ID NO:65). In another embodiment, the nucleic acid sequence of human CXCL12 is set forth in GenBank Accession No. AY802782 (SEQ ID NO:66).

In another embodiment, the CXCL12 trap comprises a VH region, wherein said VH region has at least at least 90%, 95%, 96%, 97%, 98% or 99% identity to to a sequence selected from the group consisting of SEQ ID NOs: 2, 7, 12, and 17.

In another embodiment, the CXCL12 trap comprises a VH region, wherein said VH region has at least at least 90%, 95%, 96%, 97%, 98% or 99% identity to SEQ ID NO:17 and a VL region, wherein said VL region has at least at least 90%, 95%, 96%, 97%, 98% or 99% identity to SEQ ID NO:18.

In another embodiment, the CXCL12 trap consists essentially of a VH region, wherein the VH region has at least 90% identity to a corresponding VH region of SEQ ID NO: 17. In another embodiment, the CXCL12 trap consists essentially of a VL region, wherein the VL region has at least 90% identity to a corresponding VL region of SEQ ID NO: 18.

In another embodiment, the CXCL12 trap comprises a VH region having three complementarity determining regions (CDRs) wherein the three CDRs are (a) SEQ ID NOS: 3-5, respectively; (b) the three CDRs are SEQ ID NOS: 8-10, respectively; (c) the three CDRs are SEQ ID NOS: 13-15, respectively; or (d) the three CDRs are SEQ ID NOS: 19-21, respectively and a VL region having three complementarity determining regions (CDRs), wherein the CDRs are SEQ ID NOS: 22, 23, and 24, respectively.

In another embodiment, a polypeptide capable of binding CXCL12 encoded by a nucleic acid sequence having at least 70%, 75%, 80%, 85%, 90%, 95%, 96%, 97%, 98% or 99% identity to SEQ ID NO: 63.

Pancreatic ductal adenocarcinoma is a deadly disease that kills 330,000 people globally each year (American Cancer Society. Cancer Facts and Figures 2012. Atlanta: *American Cancer Society;* 2012. p. 25-6). The five-year survival rate is only about 12%. The disease is known to be resistant to chemo and radiation therapies. It is also resistant to the check-point inhibitors. Greater than 90% PDAC is KRas mutated and most also contain additional mutations in the p53 gene. A genetically modified mouse model that contains both the KRas and p53 mutations, i.e. the KPC mice, spontaneously develops PDAC which closely mimic the clinical disease has been developed. We have used a cell line derived from KPC tumor, called KPC98027, which was inoculated orthotopically in the tails of the pancreas in the syngeneic C57BL6 mice. The tumor cell line was stably transduced with luciferase and red fluorescence protein using a lentivirus vector.

Since the tumor is resistant to immunotherapy including the check-point inhibitors, we hypothesized that suppressive immune TME can be modified by locally expressing trap proteins that target key molecules in the tumor. From the work of Feig et al, CXCL12 seems to be a key chemokine that does not allow T-cells to infiltrate the tumor (Feig et al., Targeting CXCL12 from FAP-expressing carcinoma-associated fibroblasts synergizes with anti-PD-L1 immunotherapy in pancreatic cancer, *PNAS,* 2013 Dec. 10; 110(50): 20212-7). A CXCL12 trap expressed locally in the tumor should alleviate the problem. KPC tumor over-expresses PD-L1, which is a check-point in the immune system. Over-expression of PD-L1 in the tumor cells will result in the killing of T-cells via the PD-1/PD-L1 axis interaction. Thus, we decided to deliver both traps to the tumor via gene therapy. The well-established Lipid-Protamine-DNA (LPD) nanoparticle (NP) was used to deliver plasmid DNA encoding the trap to the tumor.

The combination can be synergistic. The term "synergistic" as used herein refers to a therapeutic combination which is more effective than the additive effects of the two or more single therapeutic agents. A determination of a synergistic interaction between, e.g., a cytokine trap and PD-L1 trap, can be based on the results obtained from the assays described herein. For example, the in vivo or in vitro methods disclosed herein. The results of these assays can be analyzed using the Chou and Talalay combination method and Dose-Effect Analysis with CalcuSyn software in order to obtain a Combination Index (Chou and Talalay, 1984, *Adv. Enzyme Regul.* 22:27-55). The combinations provided can be evaluated in one or more assay systems, and the data can be analyzed utilizing a standard program for quantifying synergism, additivism, and antagonism among anticancer agents. An example program is that described by Chou and Talalay, in *New Avenues in Developmental Cancer Chemotherapy*, Academic Press, 1987, Chapter 2. Combination Index values less than 0.8 indicate synergy, values greater than 1.2 indicate antagonism and values between 0.8 to 1.2 indicate additive effects. The combination therapy may provide "synergy" and prove "synergistic", i.e., the effect achieved when the active agents used together is greater than the sum of the effects that results from using the compounds separately. A synergistic effect may be attained when the active agents are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active agent is administered sequentially, i.e., serially, whereas in combination therapy, effective dosages of two or more active agents are administered together. Combination effects can be evaluated using both the BLISS independence model and the highest single agent (HSA) model (Lehar et al., *Molecular Systems Biology,* 3:80 (2007)). BLISS scores quantify degree of potentiation from single agents and a positive BLISS score (greater than 0) suggests greater than simple additivity. A cumulative positive BLISS score greater than 250 is considered strong synergy observed within the concentration ranges tested. An HSA score (greater than 0) suggests a combination effect greater than the maximum of the single agent responses at corresponding concentrations.

Specific embodiments described herein include:

1. A method of modifying the micro-environment of a target cell comprising, systemically administering to a subject a composition comprising a vector, wherein the vector comprises a construct for expression of a trap in the target cell, wherein the trap is expressed in the target cell, wherein the micro-environment of the target cell is modified.

2. The method of embodiment 1, wherein the modifying the micro-environment comprises reducing the amount of a target molecule in the micro-environment.

3. The method of embodiments 1-2, where the target molecule is selected from the group consisting of a protein, a protein factor, a chemokine, and a cytokine, or combinations thereof.

4. The method of embodiments 1-3, wherein the target molecule is a chemokine.

5. The method of embodiments 1-4, wherein the chemokine is CXCL12.

6. The method of embodiments 1-5, wherein the construct comprises a polynucleotide of interest.

7. The method of embodiments 1-6, wherein the trap is a CXCL12 trap.

8. The method of embodiments 1-7, wherein the target cell is an organ cell.

9. The method of embodiments 1-8, wherein the cell is selected from the group consisting of liver, lung, brain, and breast.

10. The method of embodiments 1-9, wherein the expression of the trap is transient.

11. The method of embodiments 1-10, wherein the modifying of the micro-environment is transient.

12. A method of reducing metastasis of a cancer comprising, systemically administering to a subject having the cancer, a composition comprising a vector, wherein the vector comprises a construct for the expression of a trap, wherein the trap is expressed in a tissue susceptible to metastasis, wherein metastasis of the cancer to the tissue is reduced.

13. The method of embodiment 12, wherein the cancer is a solid cancer.

14. The method of embodiments 12-13, wherein the cancer is selected from the group consisting of lung, lymph node, breast, bone, and colorectal cancer.

15. The method of embodiments 12-14, wherein the cancer is CRC and the tissue is liver tissue.

16. The method of embodiments 12-15, wherein the construct comprises a polynucleotide of interest.

17. The method of embodiments 12-16, wherein the trap is a CXCL12 trap.

The present methods overcome insufficient target specificity of most approaches in treating diseases. Furthermore, the shortcomings of gene therapy, due to the numerous extracellular and intracellular barriers has truly hampered clinical treatments of many diseases. Therefore, in order to overcome these barriers disclosed herein is a vector that can find use in clinical applications with high specificity, accumulation, and delivery into target cells, such as, the nucleus of the hepatocytes of the liver. In an embodiment, this vector yields a highly reproducible non-viral vector capable of nuclear delivery of pDNA. The LCP vector described herein provides the ability to incorporate a CMV promoter, extracellular signaling peptide, trap protein, targeting moieties, and nuclear penetrating peptides readily.

The vector can be a liposome. Liposomes are self-assembling, substantially spherical vesicles comprising a lipid bilayer that encircles a core, which can be aqueous, wherein the lipid bilayer comprises amphipathic lipids having hydrophilic headgroups and hydrophobic tails, in which the hydrophilic headgroups of the amphipathic lipid molecules are oriented toward the core or surrounding solution, while the hydrophobic tails orient toward the interior of the bilayer. The lipid bilayer structure thereby comprises two opposing monolayers that are referred to as the "inner leaflet" and the "outer leaflet," wherein the hydrophobic tails are shielded from contact with the surrounding medium. The "inner leaflet" is the monolayer wherein the hydrophilic head groups are oriented toward the core of the liposome. The "outer leaflet" is the monolayer comprising amphipathic lipids, wherein the hydrophilic head groups are oriented towards the outer surface of the liposome. Liposomes typically have a diameter ranging from about 25 nm to about 1 μm. (see, e.g., Shah (ed.) (1998) *Micelles, Microemulsions, and Monolayers: Science and Technology*, Marcel Dekker; Janoff (ed.) (1998) *Liposomes: Rational Design*, Marcel Dekker). The term "liposome" encompasses both multilamellar liposomes comprised of anywhere from two to hundreds of concentric lipid bilayers alternating with layers of an aqueous phase and unilamellar vesicles that are comprised of a single lipid bilayer.

Methods for making liposomes (LCP and LDP types) are well known in the art, e.g., PCT/US2010/044209, herein incorporated by reference in its entirety. A review of methodologies of liposome preparation may be found in *Liposome Technology* (CFC Press NY 1984); Liposomes by Ostro (Marcel Dekker, 1987); Lichtenberg and Barenholz (1988) *Methods Biochem Anal.* 33:337-462 and U.S. Pat. No. 5,283,185, each of which are herein incorporated by reference in its entirety. For example, cationic lipids and optionally co-lipids can be emulsified by the use of a homogenizer, lyophilized, and melted to obtain multilamellar liposomes. Alternatively, unilamellar liposomes can be produced by the reverse phase evaporation method (Szoka and Papahadjopoulos (1978) *Proc. Natl. Acad. Sci. USA* 75:4194-4198, which is herein incorporated by reference in its entirety). In some embodiments, the liposomes are produced using thin film hydration (Bangham et al. (1965) *J. Mol. Biol.* 13:238-252, which is herein incorporated by reference in its entirety). In certain embodiments, the liposome formulation can be briefly sonicated and incubated at 50° C. for a short period of time (e.g., about 10 minutes) prior to sizing (see Templeton et al. (1997) *Nature Biotechnology* 15:647-652, which is herein incorporated by reference in its entirety).

In some embodiments, a targeted liposome or a PEGylated liposome is made as described elsewhere herein, wherein the methods further comprise a post-insertion step following the preparation of the liposome or following the production of the liposome, wherein a lipid-targeting ligand conjugate or a PEGylated lipid is post-inserted into the liposome. Liposomes comprising a lipid-targeting ligand conjugate or a lipid-PEG conjugate can be prepared following techniques known in the art, including but not limited to those presented herein (see Experimental section; Ishida et al. (1999) *FEBS Lett.* 460:129-133; Perouzel et al. (2003) *Bioconjug. Chem.* 14:884-898, which is herein incorporated by reference in its entirety). The post-insertion step can comprise mixing the liposomes with the lipid-targeting ligand conjugate or a lipid-PEG conjugate and incubating the particles at about 50° C. to about 60° C. for a brief period of time (e.g., about 5 minutes, about 10 minutes). In some embodiments, the liposomes are incubated with a lipid-PEG conjugate or a lipid-PEG-targeting ligand conjugate at a concentration of about 5 to about 20 mol %, including but not limited to about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, and about 20 mol %, to form a stealth delivery system. In some of these embodiments, the concentration of the lipid-PEG conjugate is about 10 mol %. The polyethylene glycol moiety of the lipid-PEG conjugate can have a molecular weight ranging from about 100 to about 20,000 g/mol, including but not limited to about 100 g/mol, about 200 g/mol, about 300 g/mol, about 400 g/mol, about 500 g/mol, about 600 g/mol, about 700 g/mol, about 800 g/mol, about 900 g/mol, about 1000 g/mol, about 5000 g/mol, about 10,000 g/mol, about 15,000 g/mol, and about 20,000 g/mol. In certain embodiments, the lipid-PEG conjugate comprises a PEG molecule having a molecular weight of about 2000 g/mol. In some embodiments, the lipid-PEG conjugate comprises DSPE-PEG$_{2000}$. Lipid-PEG-targeting ligand conjugates can also be post-inserted into liposomes using the above described post-insertion methods.

In an embodiment, the liposome contains a vector encoding a CXCL12 trap and PD-1 trap fusion protein linked via a cleavable 2A peptide, which allows for administering just one composition instead of two for the CXCL12/PD-L1 combination trap therapy.

Incorporation of the targeting galactose moiety through conjugation to DSPE-PEG allows for active uptake in the hepatocytes via asialoglycoprotein receptor which is highly expressed on the liver hepatocytes. The use of DOTAP and the acid sensitive calcium phosphate core allows for endosomal escape of the condensed pDNA/mc-CR8C structure, which is released into the cytoplasm. Furthermore, condensation of the pDNA with the membrane penetrating cationic mc-CR8C peptide allows for improved nuclear uptake and release. The incorporation of the CMV promoter within the pDNA allows for high liver expression.

Through incorporation of these parts as described herein an intelligently designed vector which yields high therapeutic levels of expression in the desired targeted cell types is provided. This pTrap LCP vector provides significant decrease the occurrence of colorectal liver metastasis (80%), as well as significantly decrease the tumor burden found within the liver (10 fold). Increased levels of the CXCL12 trap, as well as decreased levels of free CXCL12 protein was found in the liver in a dose dependent manner, as well as a reduction in the recruitment of immune cells (CD8+), demonstrating a biologically specific effect of pTrap LCP treatment.

Thus, it shown herein that delivery of pDNA in a Galactose-LCP vector shows no signs of off-target effects, with minimal to no immune response following three injections QOD. In these studies the His-tag incorporated onto the C-terminal end of the pCXCL12 trap was necessary to determine expression levels through western blot and ELISA assays. However, for further clinical applications the His-tag may not be needed. This would aid in circumventing any immune response such as induction of neutralizing antibodies.

Furthermore, the ability to have transient expression of this small CXCL12 trap (~28 kD) lasting no longer than 8 days, allows clinicians the ability to tightly control/monitor the level and time of expression in order to limit the immune response while still achieving therapeutic efficacy.

Disclosed herein is the affinity and production of the engineered CXCL12 trap (protein) through Bio-Layer Interferometry (BLI) as well as in vitro suppression of migration and invasion (FIG. 2). The engineered CXCL12 trap was found to have a Kd=4 nM through BLI analysis (FIG. 2A). Furthermore, producing one-half maximal inhibition [ND50] against biological active CXCL12 (100 ng/ml) in vitro at a concentration of approximately 120 nM (FIG. 2B). It has also been reported that treatment of CT-26 cells with the endogenous CXCL12 chemokine yields upregulation of the migration/invasion/proliferation pathways. Therefore, we investigated the ability of our CXCL12 trap and a commercially available CXCL12 anti-body (Ab) to suppress the migration and invasion of CT-26 FL3 cells stimulated with endogenous CXCL12. (FIGS. 2B and 2C). These in vitro experiments demonstrate the CXCL12 trap's ability to decrease the migration and invasion of CT-26 FL3 cells stimulated with CXCL12 (100.0 ng/ml) yielding complete suppression at 8.0 µg/ml and 12.0 µg/ml respectively (FIGS. 2B and 2C). Commercially available antibody (ND50 of 2-4 ug/ml; 12-24 nM) was also used as a control.

A useful in vivo pDNA dose (0.5 mg/kg per single injection) is substantially lower than doses previously shown to have in vivo expression. Furthermore, this is the first instance where a therapeutic amount of pDNA has been successfully delivered to the liver via non-viral vectors other than through the use of an invasive hydrodynamic injection which results in liver injury and is not clinically applicable. Such a delivery is attributable to the use of the intelligently designed LCP vector.

In 2013 Hu et al., first reported the use of this vector to elicit high levels of luciferase expression in the liver (Hu, Y., et al., A Highly Efficient Synthetic Vector: Nonhydrodynamic Delivery of DNA to Hepatocyte Nuclei in Vivo. *ACS Nano*, 2013. 7(6): p. 5376-5384). Yet, this level of expression is the highest obtained via non-viral vectors, only behind hydrodynamic injection techniques. Hu et al. found that delivery of Cy-3 labelled pDNA via this Gal-LCP vector preferentially accumulated in the nuclei of hepatocytes 6 h post intravenous tail vein injection (Hu, Y., et al., A Highly Efficient Synthetic Vector: Nonhydrodynamic Delivery of DNA to Hepatocyte Nuclei in Vivo. *ACS Nano*, 2013. 7(6): p. 5376-5384). Organ distribution of radiolabeled Gal-LCP-pDNA/mcCR8C vector demonstrated prominent uptake in the mouse liver. Furthermore, through delivering a CXCL12 trap to the liver we clearly demonstrate that the therapeutic effect was through decreasing free CXCL12 found in the liver microenvironment. (FIG. 5A). This therapy yielded a decrease in liver tumor burden, which subsequently decreased the liver inflammation compared to the untreated diseased liver.

The untreated groups produced higher levels of CXCL12 and further aided in liver metastasis accumulation. Therefore, prophylactic treatment of colorectal patients with this Gal-LCP-pDNA/mcCR8C vector can help decrease inflammation in the liver, which plays a critical role in the livers CXCL12 expression and liver metastasis progression.

Through the use of this vector, a number of applications and therapies can be practiced, such as, the treatment of liver diseases. It is shown herein that this vector has the ability to deliver high levels of therapeutic pDNA to the hepatocytes of the liver. Therefore, the ability to not only treat liver metastasis and primary cancers, but numerous other liver diseases such as HBV, fatty liver, liver cirrhosis and many others are provided herein. In addition to liver diseases, the incorporation of different targeting moieties, such as adenosine analogs, targeting highly expressed Adenosine A2B receptors on lung epithelial cells, will prime this vector to accumulate and deliver pDNA traps against CXCL12 or other microenvironment factors known to play a role in other highly metastatic tissues. Such a strategy can provide modification to the micro-environment factors of numerous tissues known to have high rates of metastasis such as the lung, lymph node, breast, and bone.

III. Compositions

Compositions are provided that are suitable for systemic administration.

Compositions described herein comprise vectors. As used herein, a vector includes viral vectors, non-viral vectors, synthetic vectors and the like. Reference is made to U.S. Pub. Appl. Nos. 2012-0201872; 2011-0117026; and 2011-0117141, each of which is herein incorporated by reference in its entirety. Vectors also include liposome vectors or living cell vectors such as monocytes or stem cells.

Delivery Vectors

Suitable methods for delivering the trap of the invention include viral vectors and non-viral vectors, such as plasmid vectors, liposome vectors, or living cell vectors such as monocytes or stem cells.

The term "vector," as used herein, refers to a nucleic acid construct designed for transfer between different host cells. An "expression vector" or "gene therapy vector" refers to a vector that has the ability to incorporate and express heterologous DNA fragments in a foreign cell. A cloning or expression vector may comprise additional elements, for example, the expression vector may contain an organ-specific promoter for the expression of the trap gene, and contain signaling sequences for desired extracellular or intracellular localization. The expression vector may have two replication systems, thus allowing it to be maintained in two organisms, for example in human cells for expression and in a prokaryotic host for cloning and amplification. The term vector may also be used to describe a recombinant virus, e.g., a virus modified to contain the coding sequence for a therapeutic compound or factor. As used herein, a vector may be of viral or non-viral origin or liposomes or cells such as monocytes or stem cells.

The terms "virus," "viral particle," "vector particle," "viral vector particle," and "virion" are used interchangeably and are to be understood broadly as meaning infectious viral particles that are formed when, e.g., a viral vector of the invention is transduced into an appropriate cell or cell line. Viral particles according to the invention may be utilized for the purpose of transferring DNA into cells either in vitro or in vivo. The terms "vector," "polynucleotide vector," "polynucleotide vector construct," "nucleic acid vector construct," and "vector construct" are used interchangeably herein to mean any nucleic acid construct for gene transfer, as understood by one skilled in the art.

As used herein, the term "viral vector" is used according to its art-recognized meaning. It refers to a nucleic acid vector construct that includes at least one element of viral origin and may be packaged into a viral vector particle. The vector and/or particle may be utilized for the purpose of transferring DNA, RNA or other nucleic acids into cells either in vitro or in vivo. Numerous forms of viral vectors are known in the art, the sources of which include, but are not limited to, adenoviruses, retroviruses, and adeno-associated viruses (AAV).

The present invention contemplates the use of any vector for introduction of the trap of interest into mammalian cells. Exemplary vectors include but are not limited to, viral and non-viral vectors, such as retroviruses (including lentiviruses), adenovirus (Ad) vectors including replication competent, replication deficient and gutless forms thereof, adeno-associated virus (AAV) vectors, simian virus 40 (SV-40) vectors, bovine papilloma virus vectors, Epstein-Barr virus vectors, herpes virus vectors, vaccinia virus vectors, Moloney murine leukemia virus vectors, Harvey murine sarcoma virus vectors, murine mammary tumor virus vectors, Rous sarcoma virus vectors and nonviral plasmid vectors. In one embodiment, the vector is a viral vector. Viruses can efficiently transduce cells and introduce their own DNA into a host cell. In generating recombinant viral vectors, non-essential genes are replaced with a gene or coding sequence for a heterologous (or non-native) protein.

In constructing viral vectors, non-essential genes are replaced with one or more genes encoding one or more therapeutic compounds or factors. Typically, the vector comprises an origin of replication and the vector may or may not also comprise a "marker" or "selectable marker" function by which the vector can be identified and selected. While any selectable marker can be used, selectable markers for use in such expression vectors are generally known in the art and the choice of the proper selectable marker will depend on the host cell. Examples of selectable marker genes which encode proteins that confer resistance to antibiotics or other toxins include ampicillin, methotrexate, tetracycline, neomycin (Southern et al., J., J Mol Appl Genet. 1982; 1(4):327-41 (1982)), mycophenolic acid (Mulligan et al., Science 209:1422-7 (1980)), puromycin, zeomycin, hygromycin (Sugden et al., Mol Cell Biol. 5(2): 410-3 (1985)) or G418.

Reference to a vector or other DNA sequences as "recombinant" merely acknowledges the operable linkage of DNA sequences which are not typically operably linked as isolated from or found in nature. Regulatory (expression/control) sequences are operatively linked to a nucleic acid coding sequence when the expression/control sequences regulate the transcription and, as appropriate, translation of the nucleic acid sequence. Thus expression/control sequences can include promoters, enhancers, transcription terminators, a start codon (i.e., ATG) in front of the coding sequined, splicing signal for introns and stop codons.

Adenovirus gene therapy vectors are known to exhibit strong expression in vitro, excellent titer, and the ability to transduce dividing and non-dividing cells in vivo (Hitt et al., Adv in Virus Res 55:479-505 (2000)). When used in vivo these vectors lead to strong but transient gene expression due to immune responses elicited to the vector backbone. The recombinant Ad vectors for use in the instant invention comprise: (1) a packaging site enabling the vector to be incorporated into replication-defective Ad virions; and (2) a polynucleotide of interest, such as a polynucleotide encoding the trap of interest. Other elements necessary or helpful for incorporation into infectious virions, include the 5' and 3' Ad ITRs, the E2 and E3 genes, etc.

Replication-defective Ad virions encapsulating the recombinant Ad vectors of the instant invention are made by standard techniques known in the art using Ad packaging cells and packaging technology. Examples of these methods may be found, for example, in U.S. Pat. No. 5,872,005, incorporated herein by reference in its entirety. A polynucleotide of interest is commonly inserted into adenovirus in the deleted E1A, E1B or E3 region of the virus genome. Preferred adenoviral vectors for use in practicing the invention do not express one or more wild-type Ad gene products, e.g., E1a, E1b, E2, E3, E4. Preferred embodiments are virions that are typically used together with packaging cell lines that complement the functions of E1, E2A, E4 and optionally the E3 gene regions. See, e.g. U.S. Pat. Nos. 5,872,005, 5,994,106, 6,133,028 and 6,127,175, expressly incorporated by reference herein in their entirety. Adenovirus vectors are purified and formulated using standard techniques known in the art.

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

Recombinant AAV (rAAV) virions for use in practicing the present invention may be produced using standard methodology, known to those of skill in the art and are constructed such that they include, as operatively linked components in the direction of transcription, control sequences including transcriptional initiation and termination sequences, and the coding sequence for a trap of interest. These components are bounded on the 5' and 3' end by functional AAV ITR sequences. By "functional AAV ITR sequences" is meant that the ITR sequences function as intended for the rescue, replication and packaging of the AAV virion. Hence, AAV ITRs for use in the vectors of the invention need not have a wild-type nucleotide sequence, and may be altered by the insertion, deletion or substitution of nucleotides or the AAV ITRs may be derived from any of several AAV serotypes. An AAV vector is a vector derived from an adeno-associated virus serotype, including without limitation, AAV-1, AAV-2, AAV-3, AAV-4, AAV-5, AAV-6, AAV-7, AAV-8, etc. Preferred AAV vectors have the wild type REP and CAP genes deleted in whole or part, but retain functional flanking ITR sequences.

Typically, an AAV expression vector is introduced into a producer cell, followed by introduction of an AAV helper construct, where the helper construct includes AAV coding regions capable of being expressed in the producer cell and which complement AAV helper functions absent in the AAV vector. The helper construct may be designed to down regulate the expression of the large REP proteins (Rep78 and Rep68), typically by mutating the start codon following p5 from ATG to ACG, as described in U.S. Pat. No. 6,548,286, expressly incorporated by reference herein. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety, and include those techniques within the knowledge of those of skill in the art.

Approximately 40 serotypes of AAV are currently known, however, new serotypes and variants of existing serotypes are still being identified today and are considered within the scope of the present invention. See Gao et al (2002), PNAS 99(18):11854-6; Gao et al (2003), PNAS 100(10):6081-6; Bossis and Chiorini (2003), J. Virol. 77(12):6799-810). Different AAV serotypes are used to optimize transduction of particular target cells or to target specific cell types within a particular target tissue. The use of different AAV serotypes may facilitate targeting of malignant tissue. AAV serotypes including 1, 2, 4, 5 and 6 have been shown to transduce brain tissue. See, e.g., Davidson et al (2000), PNAS 97(7)3428-32; Passini et al (2003), J. Virol 77(12):7034-40). Particular AAV serotypes may more efficiently target and/or replicate in target tissue or cells. A single self-complementary AAV vector can be used in practicing the invention in order to increase transduction efficiency and result in faster onset of transgene expression (McCarty et al., Gene Ther. 2001 August; 8(16):1248-54).

Retroviral vectors are a common tool for gene delivery (Miller, 1992, Nature 357: 455-460). Retroviral vectors and more particularly lentiviral vectors may be used in practicing the present invention. Retroviral vectors have been tested and found to be suitable delivery vehicles for the stable introduction of a variety of genes of interest into the genomic DNA of a broad range of target cells. The ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) may also find utility in practicing the present invention. The ability to direct the delivery of retroviral vectors encoding a transgene to a specific type of target cells is highly desirable for gene therapy applications.

The present invention provides retroviral vectors which include e.g., retroviral transfer vectors comprising one or more polynucleotides of interest and retroviral packaging vectors comprising one or more packaging elements. In particular, the present invention provides pseudotyped retroviral vectors encoding a heterologous or functionally modified envelope protein for producing pseudotyped retrovirus.

The core sequence of the retroviral vectors of the present invention may be readily derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods of the present invention includes, but is not limited to, lentivirus. Other retroviruses suitable for use in the compositions and methods of the present invention include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe, J. Virol. 19:19-25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymph-adenopathy associated virus 3 (HTLV-IE) and acquired immune deficiency syndrome (AIDS)-related virus (ARV)), or another virus related to HIV-1 or HIV-2 that has been identified and associated with AIDS or AIDS-like disease. Other lentivirus vectors include, a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768-1771, including Table 1, incorporated herein by reference).

The invention is applicable to a variety of retroviral systems, and those skilled in the art will appreciate the common elements shared across differing groups of retroviruses. All retroviruses share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by the env gene; CA (p24), MA (p117) and NC (p7-11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Synthetic Non-Viral Delivery Agents

Synthetic non-viral agents that are capable of promoting the transfer and expression of a polynucleotide of interest are also suitable for use in the methods of the invention. Such agents include, but are not limited to, cationic lipids and polymers. Non-viral delivery agents that are cationic lipids bind to polyanionic DNA. Following endocytosis, the nucleic acid must escape from the delivery agent as well as the endosomal compartment so that the genetic material is incorporated within the new host. See Felgner, P. L. Non-viral Strategies for Gene Therapy Sci. Am. 1997, 276, 102-106; Felgner, P. L.; Gadek, T. R.; Holm, M.; Roman, R.; Chan, H. W.; Wenz, M.; Northrop, J. P.; Ringgold, G. M.; Danielsen, M. Lipofectin: A highly efficient, lipid mediated DNA-transfection procedure Proc. Natl. Acad. Sci. USA 1987, 84, 7413-7417; Felgner, P. L.; Kumar, R.; Basava, C.; Border, R. C.; Hwang-Felgner, J. In; Vical, Inc. San Diego, Calif.: U.S. Pat. No. 5,264,618, 1993; Felgner, J. H.; Kumar, R.; Sridhar, C. N.; Wheeler, C. J.; Tsai, Y. J.; Border, R.; Ramsey, P.; Martin, M.; Felgner, P. L. Enhanced Gene Delivery and Mechanism Studies with a Novel Series of Cationic Formulations J. Biol. Chem. 1994, 269, 2550-2561; Freidmann, T. Sci. Am. 1997, 276, 96-101; Behr, J. P. Gene Transfer with Synthetic Cationic Amphiphiles: Prospects for Gene Delivery Bioconjugate Chem. 1994, 5, 382-389; Cotton, M.; Wagner, B. Non-viral Approaches to Gene Therapy Curr. Op. Biotech. 1993, 4, 705-710; Miller, A. D. Cationic Liposomes for Gene Therapy Angew. Chem. Int. 1998, 37, 1768-1785; Scherman, D.; Bessodes, M.; Cameron, B.; Herscovici, J.; Hofland, H.; Pitard, B.; Soubrier, F.; Wils, P.; Crouzet, J. Application of Lipids and Plasmid Design for Gene Delivery to Mammalian Cells Curr. Op. Biotech. 1989, 9, 480; Lasic, D. D. In Surfactants in Cosmetics; 2nd ed.; Rieger, M. M., Rhein, L. D., Eds.; Marcel Dekker, Inc.: New York, 1997; Vol. 68, pp 263-283; Rolland, A. P. From Genes to Gene Medicines: Recent Advances in Nonviral Gene Delivery Crit. Rev. Ther. Drug 1998, 15, 143-198; de Lima, M. C. P.; Simoes, S.; Pires, P.; Faneca, H.; Duzgunes, N. Cationic Lipid-DNA Complexes in Gene Delivery from Biophysics to Biological Applications Adv. Drug. Del. Rev. 2001, 47, 277-294.

These synthetic non-viral delivery agents have two main functions, to condense the DNA to be transfected and to promote its cell-binding and passage across the plasma membrane, and where appropriate, the two nuclear membranes. Due to its polyanionic nature, DNA naturally has poor affinity for the plasma membrane of cells, which is also polyanionic. Several groups have reported the use of amphiphilic cationic lipid-nucleic acid complexes for in vivo transfection both in animals and humans. Thus, synthetic non-viral delivery agents have cationic or polycationic charges. See Gao, X; Huang, L. Cationic Liposome-mediated Gene Transfer Gene Therapy 1995, 2, 710-722; Zhu, N.; Liggott, D.; Liu, Y.; Debs, R. Systemic Gene Expression After Intravenous DNA Delivery into Adult Mice Science 1993, 261, 209-211; Thierry, A. R.; Lunardiiskandar, Y.; Bryant, J. L.; Rabinovich, P.; Gallo, R. C.; Mahan, L. C. Systemic Gene-Therapy-Biodistribution and Long-Term Expression of a Transgene in Mice Proc. Nat. Acad. Sci. 1995, 92, 9742-9746. Cationic amphiphilic compounds that possess both cationic and hydrophobic domains have been previously used for delivery of genetic information. In fact, this class of compounds is widely used for intracellular delivery of genes. Such cationic compounds can form cationic liposomes, which are the most popular synthetic non-viral delivery agent for gene transfection studies.

The cationic liposomes serve two functions. First, it protects the DNA from degradation. Second, it increases the amount of DNA entering the cell. Such liposomes have proven useful in both in vitro and in vivo studies. Safinya, C. R. describes the structure of the cationic amphiphile-DNA complex. See Radler, J. O.; Koltover, I.; Salditt, T.; Safinya, C. R. Science 1997, 275, 810-814; Templeton, N. S.; Lasic, D. D.; Frederik, P. M.; Strey, H. H.; Roberts, D. D.; Pavlakis, G. N. Nature Biotech. 1997, 15, 647-652; Koltover, I.; Salditt, T.; Radler, J. O.; Safinya, C. R. Science 1998, 281, 78-81; and Koltover, I.; Salditt, T.; Safinya, C. R. Biophys. J. 1999, 77, 915-924. Many of these systems for gene delivery in vitro and in vivo are reviewed in recent articles. See Remy, J.; Sirlin, C.; Vierling, P.; Behr, J. Bioconj. Chem. 1994, 5, 647-654; Crystal, R. G. Science 1995, 270, 404-410; Blaese, X.; et, a. Cancer Gene Ther. 1995, 2, 291-297; and Behr, J. P. and Gao, X cited above. Unlike viral vectors, the lipid-nucleic acid complexes can be used to transfer expression cassettes of essentially unlimited size. Because these synthetic delivery systems lack proteins, they may evoke fewer immunogenic and inflammatory responses.

Behr discloses numerous amphiphiles including dioctadecylamidologlycylspermine ("DOGS") for gene delivery. This material is commercially available as TRANSFECTAM™. Vigneron describes guanidinium-cholesterol cationic lipids for transfection of eukaryotic cells. Felgner discloses use of positively-charged synthetic cationic lipids including N-1-(2,3-dioleyloxy)propyl-N,N,N-trimethylammonium chloride ("DOTMA"), to form lipid/DNA complexes suitable for transfections. Byk describes cationic lipids where the cationic portion of the amphiphile is either linear, branched, or globular for gene transfection. Blessing and coworkers describe a cationic synthetic vector based on spermine. Safinya describes cationic lipids containing a poly(ethylene glycol) segment for gene delivery. Bessodes and coworkers describe a cationic lipid containing glycosidic linker for gene delivery. Ren and Liu describe cationic lipids based on 1,2,4-butanetriol. Tang and Scherman describe a cationic lipid that contains a disulfide linkage for gene delivery. Vierling describes highly fluorinated cationic amphiphiles as gene carrier and delivery systems. Jacopin describes a cation amphiphile for gene delivery that contains a targeting ligand. Wang and coworkers describe carnitine based cationic esters for gene delivery. Zhu describes the use of a cationic lipid, N[1-(2,3-dioleyloxy)propyl]-N,N,N-trimethylammonium chloride for the intravenous delivery of DNA. See Behr, J. P.; Demeneix, B.; Loeffler, J. P.; Perez-Mutul, J. Efficient Gene Transfer into Mammalian Primary Endocrine Cells with Lipopolyamine Coated DNA Proc. Nat. Acad. Sci. 1989, 86, 6982-6986; Vigneron, J. P.; Oudrhiri, N.; Fauquet, M.; Vergely, L.; Bradley, J. C.; Basseville, M.; Lehn, P.; Lehn, J. M. Proc. Nat. Acad. Sci. 1996, 93, 9682-9686; Byk, G.; B Dubertret, C.; Escriou, V.; Frederic, M.; Jaslin, G.; Rangara, R.; Pitard, B.; Wils, P.; Schwartz, B.; Scherman, D. J. Med. Chem. 1998, 41, 224-235; Blessing, T.; Remy, J. S.; Behr, J. P. J. Am. Chem. Soc. 1998, 120, 8519-8520; Blessing, T.; Remy, J. S.; Behr, J. P. Proc. Nat. Acad. Sci. 1998, 95, 1427-1431; Schulze, U.; Schmidt, H.; Safinya, C. R. Bioconj. Chem. 1999, 10, 548-552; Bessodes, M.; Dubertret, C.; Jaslin, G.; Scherman, D. Bioorg. Med. Chem. Lett. 2000, 10, 1393-1395; Herscovici, J.; Egron, M. J.; Quenot, A.; Leclercq, F.; Leforestier, N.; Mignet, N.; Wetzer, B.; Scherman, D. Org. Lett. 2001; Ren, T.; Liu, D. Tetrahedron Lett. 1999, 40, 7621-7625; Tang, F.; Hughes, J. A. Biochem. Biophys. Res. Commun. 1998, 242, 141-145; Tang, F.; Hughes, J. A. Bioconjugate Chem. 1999, 10, 791-796; Wetzer, B.; Byk, G.; Frederic, M.; Airiau, M.; Blanche, F.; Pitard, B.; Scherman, D. Biochemical J. 2001, 356, 747-756; Vierling, P.; Santaella, C.; Greiner, J. J. Fluorine Chem. 2001, 107, 337-354; Jacopin, J.; Hofland, H.; Scherman, D.; Herscovici, J. J. Biomed. Chem. Lett.

2001, 11, 419-422; and Wang, J.; Guo, X.; Xu, Y.; Barron, L.; Szoka, F. C. J. Med. Chem. 1998, 41, 2207-2215.

In U.S. Pat. No. 5,283,185 to Epand et al., the inventors describe additional examples of amphiphiles including a cationic cholesterol synthetic vector, termed "DC-chol". The inventors describe, in U.S. Pat. No. 5,264,618, more cationic compounds that facilitate transport of biologically active molecules into cells. U.S. Pat. Nos. 6,169,078 and 6,153,434 to Hughes et al. disclose a cationic lipid that contains a disulfide bond for gene delivery. U.S. Pat. No. 5,334,761 to Gebeyehu et al. describes additional cationic amphiphiles suitable for intracellular delivery of biologically active molecules. U.S. Pat. No. 6,110,490 to Thierry describes additional cationic lipids for gene delivery. U.S. Pat. No. 6,056,938 to Unger, et al. discloses cationic lipid compounds that contain at least two cationic groups.

Polymeric systems for gene delivery are known in the art. In Han's review, he discussed most of the common cationic polymer systems including PLL, poly(L-lysine); PEI, polyethyleneimine; pDMEAMA, poly(2-dimethylamino)ethylmethacrylate; PLGA, poly(D,L-lactide-co-glycolide) and PVP (polyvinylpyrrolidone). See Garnett, M. C. Crit. Rev. Ther. Drug Carrier Sys. 1999, 16, 147-207; Han, S.; Mahato, R. I.; Sung, Y. K.; Kim, S. W. Molecular Therapy 2000, 2, 302-317; Zauner, W.; Ogris, M.; Wagner, E. Adv. Drug. Del. Rev. 1998, 30, 97-113; Kabanov, A. V.; Kabanov, V. A. Bioconj. Chem. 1995, 6, 7-20; Lynn, D. M.; Anderson, D. G.; Putman, D.; Langer, R. J. Am. Chem. Soc. 2001, 123, 8155-8156; Boussif, O.; Lezoualc'h, F.; Zanta, M. A.; Mergny, M. D.; Scherman, D.; Demeneix, B.; Behr, J. P. Proc. Natl. Acad. Sci. USA 1995, 92, 7297-7301; Choi, J. S.; Joo, D. K.; Kim, C. H.; Kim, K.; Park, J. S. J. Am. Chem. Soc. 2000, 122, 474-480; Putnam, D.; Langer, R. Macromolecules 1999, 32, 3658-3662; Gonzalez, M. F.; Rueckaite, R. A.; Cuadrado, T. R. Journal of Applied Polymer Science 1999, 71, 1223-1230; Tang, M. X.; Redemann, C. T.; Szoka, F. C. In Vitro Gene Delivery by Degraded Polyamidoamine Dendrimers Bioconjugate Chem. 1996, 7, 703-714; Kukowska-latallo, J. F.; Bielinska, A. U.; Johnson, J.; Spinder, R.; Tomalia, D. A.; Baker, J. R. Proc. Nat. Acad. Sci. 1996, 93, 4897-4902; and Lim, Y.; Kim, S.; Lee, Y.; Lee, W.; Yang, T.; Lee, M.; Suh, M.; Park, J. J. Am. Chem. Soc. 2001, 123, 2460-2461.

Some representative examples of cationic polymers under investigation are described below. For example, poly(beta-amino esters) have been explored and shown to condense plasmid DNA into soluble DNA/polymer particles for gene delivery. To accelerate the discovery of synthetic transfection vectors parallel synthesis and screening of a cationic polymer library was reported by Langer. Wolfert describes cationic vectors for gene therapy formed by self-assembly of DNA with synthetic block cationic co-polymers. Haensler and Szoka describe the use of cationic dendrimer polymers (polyamidoamine (PAMAM) dendrimers) for gene delivery. Wang describes a cationic polyphosphoester for gene delivery. Putnam describes a cationic polymer containing imidazole for the delivery of DNA. See Lynn, D. M.; Langer, R. J. Am. Chem. Soc. 2000, 122, 10761-10768; Wolfert, M. A.; Schacht, E. H.; Toncheva, V.; Ulbrich, K.; Nazarova, O.; Seymour, L. W. Hum. Gene Ther. 1996, 7, 2123-2133; Haensler, J.; Szoka, F. Bioconj. Chem. 1993, 4, 372; and Wang, J.; Mao, H. Q.; Leong, K W. J. Am. Chem. Soc. 2001; Putnam, D.; Gentry, C. A.; Pack, D. W.; Langer, R. Proc. Nat. Acad. Sci. 2001, 98, 1200-1205.

A number of patents are also known that describe cationic polymers for gene delivery. For example, U.S. Pat. No. 5,629,184 to Goldenberg et al. describes cationic copolymers of vinylamine and vinyl alcohol for the delivery of oligonucleotides. U.S. Pat. No. 5,714,166 to Tomalia, et al, discloses dendritic cationic-amine-terminated polymers for gene delivery. U.S. Pat. No. 5,919,442 to Yin et al. describes cationic hyper comb-branched polymer conjugates for gene delivery. U.S. Pat. No. 5,948,878 to Burgess et al. describes additional cationic polymers for nucleic acid transfection and bioactive agent delivery. U.S. Pat. No. 6,177,274 to Park et al. discloses a compound for targeted gene delivery that consists of polyethylene glycol (PEG) grafted poly(L-lysine) (PLL) and a targeting moiety, wherein at least one free amino function of the PLL is substituted with the targeting moiety, and the grafted PLL contains at least 50% unsubstituted free amino function groups. U.S. Pat. No. 6,210,717 to Choi et al. describes a biodegradable, mixed polymeric micelle used to deliver a selected nucleic acid into a targeted host cell that contains an amphiphilic polyester-polycation copolymer and an amphiphilic polyester-sugar copolymer. U.S. Pat. No. 6,267,987 to Park et al. discloses a positively charged poly[alpha-(omega-aminoalkyl) glycolic acid] for the delivery of a bioactive agent via tissue and cellular uptake. U.S. Pat. No. 6,200,956 to Scherman et al. describes a pharmaceutical composition useful for transfecting a nucleic acid containing a cationic polypeptide.

Nanoparticle delivery systems suitable for use in delivering the traps described herein are disclosed in PCT/US2010/044209.

Targeting Ligands

The compositions can further comprise a targeting ligand that is physically associated with the vector.

By "targeting ligand" is intended a molecule that targets the vector or a physically associated molecule to a targeted cell or tissue. Targeting ligands can include, but are not limited to, small molecules, peptides, lipids, sugars, oligonucleotides, hormones, vitamins, antigens, antibodies or fragments thereof, specific membrane-receptor ligands, ligands capable of reacting with an anti-ligand, fusogenic peptides, nuclear localization peptides, or a combination of such compounds. Non-limiting examples of targeting ligands include asialoglycoprotein, insulin, low density lipoprotein (LDL), folate, benzamide derivatives, and monoclonal and polyclonal antibodies directed against cell surface molecules. In some embodiments, the small molecule comprises a benzamide derivative. In some of these embodiments, the benzamide derivative comprises anisamide.

By "targeted cell" is intended the cell to which a targeting ligand recruits a physically associated molecule. The targeting ligand can interact with one or more constituents of a target cell. The targeted cell can be any cell type or at any developmental stage, exhibiting various phenotypes, and can be in various pathological states (i.e., abnormal and normal states). For example, the targeting ligand can associate with normal, abnormal, and/or unique constituents on a microbe (i.e., a prokaryotic cell (bacteria), viruses, fungi, protozoa or parasites) or on a eukaryotic cell (e.g., epithelial cells, muscle cells, nerve cells, sensory cells, cancerous cells, secretory cells, malignant cells, erythroid and lymphoid cells, stem cells). Thus, the targeting ligand can associate with a constitutient on a target cell which is a disease-associated antigen including, for example, tumor-associated antigens and autoimmune disease-associated antigens. Such disease-associated antigens include, for example, growth factor receptors, cell cycle regulators, angiogenic factors, and signaling factors.

In some embodiments, the targeting ligand interacts with a cell surface protein on the targeted cell. In some of these embodiments, the expression level of the cell surface protein that is capable of binding to the targeting ligand is higher in the targeted cell relative to other cells. For example, cancer cells overexpress certain cell surface molecules, such as the HER2 receptor (breast cancer) or the sigma receptor. In certain embodiments wherein the targeting ligand comprises a benzamide derivative, such as anisamide, the targeting ligand targets the associated molecule to sigma-receptor overexpressing cells, which can include, but is not limited to, cancer cells such as small- and non-small-cell lung carcinoma, renal carcinoma, colon carcinoma, sarcoma, breast cancer, melanoma, glioblastoma, neuroblastoma, and prostate cancer (Aydar, Palmer, and Djamgoz (2004) *Cancer Res.* 64:5029-5035).

The terms "cancer" or "cancerous" refer to or describe the physiological condition in mammals that is typically characterized by unregulated cell growth. As used herein, "cancer cells" or "tumor cells" refer to the cells that are characterized by this unregulated cell growth. The term "cancer" encompasses all types of cancers, including, but not limited to, all forms of carcinomas, melanomas, sarcomas, lymphomas and leukemias, including without limitation, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer.

The targeted cell is one that is susceptible to metastases of a distant cancer. As such, the targeted cell can be in any organ. In a particular embodiment, the targeted cell is a liver cell.

The targeting ligand can be physically associated a vector. As used herein, the term "physically associated" refers to either a covalent or non-covalent interaction between two molecules. As used herein, the term "covalent bond" or "covalent interaction" refers to a chemical bond, wherein a pair of electrons is shared between two atoms. Two molecules are said to be chemically bound to one another when the molecules have at least one chemical bond between atoms that make up the molecules. One chemical bond between two molecules is therefore comprised of the sharing of one pair of electrons between an atom in one molecule with an atom in another molecule. For example, a targeting ligand can be covalently bound to a lipid of the invention through one of the nitrogen atoms or one of the R groups of the cationic lipids. A "conjugate" refers to the complex of molecules that are covalently bound to one another. For example, the complex of a lipid covalently bound to a targeting ligand can be referred to as a lipid-targeting ligand conjugate.

Alternatively, the targeting ligand can be non-covalently bound to the lipids of formula (I) or active derivatives thereof. "Non-covalent bonds" or "non-covalent interactions" do not involve the sharing of pairs of electrons, but rather involve more dispersed variations of electromagnetic interactions, and can include hydrogen bonding, ionic interactions, Van der Waals interactions, and hydrophobic bonds. Such lipid-targeting ligand conjugates can be readily obtained according to techniques widely described in the literature.

Polynucleotide of Interest

The term "polynucleotide" is intended to encompass a singular nucleic acid, as well as plural nucleic acids, and refers to a nucleic acid molecule or construct, e.g., messenger RNA (mRNA), plasmid DNA (pDNA), or short interfering RNA (siRNA). A polynucleotide can be single-stranded or double-stranded, linear or circular. A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. The term "polynucleotide" can refer to an isolated nucleic acid or polynucleotide, wherein by "isolated" nucleic acid or polynucleotide is intended a nucleic acid molecule, DNA or RNA, that has been removed from its native environment. Examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. Isolated polynucleotides also can include isolated expression vectors, expression constructs, or populations thereof. "Polynucleotide" also can refer to amplified products of itself, as in a polymerase chain reaction. The "polynucleotide" can contain modified nucleic acids, such as phosphorothioate, phosphate, ring atom modified derivatives, and the like. The "polynucleotide" can be a naturally occurring polynucleotide (i.e., one existing in nature without human intervention), or a recombinant polynucleotide (i.e., one existing only with human intervention). While the terms "polynucleotide" and "oligonucleotide" both refer to a polymer of nucleotides, as used herein, an oligonucleotide is typically less than 100 nucleotides in length.

As used herein, the term "polynucleotide of interest" refers to a polynucleotide that is to be delivered to a cell to elicit a desired effect in the cell (e.g., a therapeutic effect, a change in gene expression). A polynucleotide of interest can be of any length and can include, but is not limited to a polynucleotide comprising a coding sequence for a polypeptide of interest. In certain embodiments, when the polynucleotide is expressed or introduced into a cell, the polynucleotide of interest or polypeptide encoded thereby has therapeutic activity.

i. Polynucleotides Encoding Polypeptides

In some embodiments, the polynucleotide delivery systems comprise a polynucleotide comprising a coding sequence for a polypeptide of interest.

For the purposes of the present invention, a "coding sequence for a polypeptide of interest" or "coding region for a polypeptide of interest" refers to the polynucleotide sequence that encodes that polypeptide. As used herein, the terms "encoding" or "encoded" when used in the context of a specified nucleic acid mean that the nucleic acid comprises the requisite information to direct translation of the nucleotide sequence into a specified polypeptide. The information by which a polypeptide is encoded is specified by the use of codons. The "coding region" or "coding sequence" is the portion of the nucleic acid that consists of codons that can be translated into amino acids. Although a "stop codon" or "translational termination codon" (TAG, TGA, or TAA) is not translated into an amino acid, it can be considered to be part of a coding region. Likewise, a transcription initiation codon (ATG) may or may not be considered to be part of a coding region. Any sequences flanking the coding region, however, for example, promoters, ribosome binding sites, transcriptional terminators, introns, and the like, are not considered to be part of the coding region. In some embodiments, however, while not considered part of the coding region per se, these regulatory sequences and any other regulatory sequence, particularly signal sequences or sequences encoding a peptide tag, may be part of the polynucleotide sequence encoding the polypeptide of interest. Thus, a polynucleotide sequence encoding a polypeptide of interest comprises the coding sequence and optionally any sequences flanking the coding region that contribute to expression, secretion, and/or isolation of the polypeptide of interest.

The term "expression" has its meaning as understood in the art and refers to the process of converting genetic information encoded in a gene or a coding sequence into RNA (e.g., mRNA, rRNA, tRNA, or snRNA) through "transcription" of a polynucleotide (e.g., via the enzymatic action of an RNA polymerase), and for polypeptide-encoding polynucleotides, into a polypeptide through "translation" of mRNA. Thus, an "expression product" is, in general, an RNA transcribed from the gene (e.g., either pre- or post-processing) or polynucleotide or a polypeptide encoded by an RNA transcribed from the gene (e.g., either pre- or post-modification).

As used herein, the term "polypeptide" or "protein" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

The term "polypeptide of interest" refers to a polypeptide that is to be delivered to a cell or is encoded by a polynucleotide that is to be delivered to a cell to elicit a desired effect in the cell (e.g., a therapeutic effect). The polypeptide of interest can be of any species and of any size.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank at the website www.ncbi.nlm.nih.gov/Entrez. Additional information can also be obtained from GeneCards, an electronic encyclopedia integrating information about genes and their products and biomedical applications from the Weizmann Institute of Science Genome and Bioinformatics (bioinformatics.weizmann.ac.il/cards), nucleotide sequence information can be also obtained from the EMBL Nucleotide Sequence Database (www.ebi.ac.uk/embl) or the DNA Databank or Japan (DDBJ, www.ddbi.nig.acjp). Additional sites for information on amino acid sequences include Georgetown's protein information resource website (www.pir.georgetown.edu) and Swiss-Prot (au.expasy.org/sprot/sprot-top.html).

As discussed above, the compositions of the invention can comprise genetic material, such as a polynucleotide of interest, e.g., pDNA (plasmid DNA), which when transcribed produces a trap. In such embodiments, the genetic material can be part of an expression cassette. In addition, polynucleotides comprise a coding sequence found in an expression cassette.

The terms "introduction" or "introduce" when referring to a polynucleotide refers to the presentation of the polynucleotide to a cell in such a manner that the polynucleotide gains access to the intracellular region of the cell.

The expression cassette comprises one or more regulatory sequences, selected on the basis of the cells to be used for expression, operably linked to a polypeptide of interest. "Operably linked" is intended to mean that the nucleotide sequence of interest (i.e., a coding sequence for a polypeptide of interest) is linked to the regulatory sequence(s) in a manner that allows for expression of the nucleotide sequence (e.g., in an in vitro transcription/translation system or in a cell when the expression cassette or vector is introduced into a cell). "Regulatory sequences" include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression cassette can depend on such factors as the choice of the host cell to be transformed, the level of expression of the silencing element or polypeptide of interest desired, and the like. Such expression cassettes typically include one or more appropriately positioned sites for restriction enzymes, to facilitate introduction of the nucleic acid into a vector.

It will further be appreciated that appropriate promoter and/or regulatory elements can readily be selected to allow expression of the relevant transcription units/silencing elements in the cell of interest. In certain embodiments, the promoter utilized to direct intracellular expression of a silencing element is a promoter for RNA polymerase III (Pol III). References discussing various Pol III promoters, include, for example, Yu et al. (2002) *Proc. Natl. Acad. Sci.* 99(9), 6047-6052; Sui et al. (2002) *Proc. Natl. Acad. Sci.* 99(8), 5515-5520 (2002); Paddison et al. (2002) *Genes and Dev.* 16, 948-958; Brummelkamp et al. (2002) *Science* 296, 550-553; Miyagashi (2002) *Biotech.* 20, 497-500; Paul et al. (2002) *Nat. Biotech.* 20, 505-508; Tuschl et al. (2002) *Nat. Biotech.* 20, 446-448. According to other embodiments, a promoter for RNA polymerase I, e.g., a tRNA promoter, can be used. See McCown et al. (2003) *Virology* 313(2):514-24; Kawasaki (2003) *Nucleic Acids Res.* 31 (2):700-7. In some embodiments in which the polynucleotide comprises a coding sequence for a polypeptide of interest, a promoter for RNA polymerase II can be used.

The regulatory sequences can also be provided by viral regulatory elements. For example, commonly used promoters are derived from polyoma, Adenovirus 2, cytomegalovirus, and Simian Virus 40. For other suitable expression systems for both prokaryotic and eukaryotic cells, see Chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.).

In vitro transcription can be performed using a variety of available systems including the T7, SP6, and T3 promoter/polymerase systems (e.g., those available commercially from Promega, Clontech, New England Biolabs, and the like). Vectors including the T7, SP6, or T3 promoter are well known in the art and can readily be modified to direct transcription of silencing elements.

PEGylation

PEGylation of the vector enhances the circulatory half-life of the delivery system by reducing clearance of the vector by the reticuloendothelial (RES) system. While not being bound by any particular theory or mechanism of action, it is believed that a PEGylated vector can evade the RES system by sterically blocking the opsonization of the particles (Owens and Peppas (2006) *Int J Pharm* 307:93-

102). In order to provide enough steric hindrance to avoid opsonization, the exterior surface of the vector must be completely covered by PEG molecules in the "brush" configuration. At low surface coverage, the PEG chains will typically have a "mushroom" configuration, wherein the PEG molecules will be located closer to the surface of the lipid vehicle. In the "brush" configuration, the PEG molecules are extended further away from the particle surface, enhancing the steric hindrance effect. However, over-crowdedness of PEG on the surface may decrease the mobility of the polymer chains and thus decrease the steric hindrance effect (Owens and Peppas (2006) *Int J Pharm* 307:93-102). The conformation of PEG depends upon the surface density and the molecular mass of the PEG on the surface of the vector. The controlling factor is the distance between the PEG chains on the vehicle surface (D) relative to their Flory dimension, $R_F$, which is defined as $aN^{3/5}$, wherein a is the persistence length of the monomer, and N is the number of monomer units in the PEG (Nicholas et al. (2000) *Biochim Biophys Acta* 1463:167-178). Three regimes can be defined: (1) when D>2 RF (interdigitated mushrooms); (2) when D<2 RF (mushrooms); and (3) when D<RF (brushes) (Nicholas et al.).

Pharmaceutical Compositions

The lipids and delivery systems of the invention are useful in mammalian tissue culture systems, in animal studies, and for therapeutic purposes. The cytotoxic cationic lipids of formula (I), and delivery systems comprising a cationic lipid of formula (I), wherein the cationic lipids of formula (I) have cytotoxic activity, delivery systems comprising a cationic lipid of formula (I), wherein the bioactive compound has therapeutic activity, and delivery systems comprising a cytotoxic cationic lipid of formula (I) and a bioactive compound with therapeutic activity can be used in therapeutic applications. The presently disclosed subject matter therefore provides pharmaceutical compositions comprising cytotoxic cationic lipids of formula (I) or delivery systems comprising cationic lipids of formula (I).

The presently disclosed compositions can be formulated for delivery, i.e., administering to the subject, by any available route including, but not limited, to parenteral (e.g., intravenous), intradermal, subcutaneous, oral, nasal, bronchial, ophthalmic, transdermal (topical), transmucosal, rectal, and vaginal routes. In some embodiments, the route of delivery is intravenous, parenteral, transmucosal, nasal, bronchial, vaginal, and oral.

Compositions can be formulated as a pharmaceutically acceptable salt. The phrase "pharmaceutically acceptable salt(s)," as used herein, means those salts of the presently disclosed compounds that are safe and effective for use in a subject and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, borate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, pamoate (i.e., 1,1'-methylene-bis-(2-hydroxy-3-naphthoate)), mesylate salts. Certain of the presently disclosed compounds can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al. (1977) *J. Pharm. Sci.* 66:1-19, which is incorporated herein by reference. The salts of the lipids described herein can be prepared, for example, by reacting the appropriate equivalent of the compound with the desired acid or base in solution. After the reaction is complete, the salts are crystallized from solution by the addition of an appropriate amount of solvent in which the salt is insoluble.

As used herein the term "pharmaceutically acceptable carrier" includes solvents, dispersion media, coatings, antibacterial and antifungal agents, isotonic and absorption delaying agents, and the like, compatible with pharmaceutical or cosmetic administration. Supplementary active compounds also can be incorporated into the compositions.

As one of ordinary skill in the art would appreciate, a presently disclosed pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). The composition should be sterile and should be fluid to the extent that easy syringability exists. In some embodiments, the pharmaceutical compositions are stable under the conditions of manufacture and storage and should be preserved against the contaminating action of microorganisms, such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, isotonic agents, for example, sugars, polyalcohols, such as mannitol or sorbitol, or sodium chloride are included in the formulation. Prolonged absorption of the injectable formulation can be brought about by including in the formulation an agent that delays absorption, for example, aluminum monostearate and gelatin.

Sterile injectable solutions can be prepared by incorporating the active compound (e.g., cytotoxic cationic lipid of formula (I) or a delivery system comprising a cationic lipid of formula (I)) in the required amount in an appropriate solvent with one or a combination of ingredients enumerated above, as required, followed by filtered sterilization. In certain embodiments, solutions for injection are free of endotoxin. Generally, dispersions are prepared by incorporating the active compound into a sterile vehicle which contains a basic dispersion medium and the required other ingredients from those enumerated above. In those embodiments in which sterile powders are used for the preparation of sterile injectable solutions, the solutions can be prepared by vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions also can be prepared using a fluid carrier for use as a mouthwash. Pharmaceutically or cosmetically compatible binding agents, and/or adjuvant materials can be included as part of the composition. The tablets, pills, capsules, troches, and the like can contain any of the following ingredients, or compounds of a similar nature: a binder, such as microcrystalline cellulose, gum tragacanth or gelatin; an excipient, such as starch or lactose, a disintegrating agent, such as alginic acid, Primogel, or corn starch; a lubricant, such as magnesium stearate or Sterotes; a glidant, such as colloidal silicon dioxide; a sweetening agent, such as sucrose or saccharin; or a flavoring agent, such as peppermint, methyl salicylate, or orange flavoring. Compositions for oral delivery can advantageously incorporate agents to improve stability within the gastrointestinal tract and/or to enhance absorption.

For administration by inhalation, the presently disclosed compositions can be delivered in the form of an aerosol spray from a pressured container or dispenser which contains a suitable propellant, e.g., a gas such as carbon dioxide, or a nebulizer. Liquid aerosols, dry powders, and the like, also can be used.

Systemic administration of the presently disclosed compositions also can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions described herein also can be prepared in the form of suppositories (e.g., with conventional suppository bases such as cocoa butter and other glycerides) or retention enemas for rectal delivery.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical or cosmetic carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals. Guidance regarding dosing is provided elsewhere herein.

As used herein, "therapeutic activity" when referring to the compositions described herein is intended one that is able to elicit a desired pharmacologic and/or physiologic effect when administered to a subject in need thereof.

As used herein, the terms "treatment" or "prevention" refer to obtaining a desired pharmacologic and/or physiologic effect. The effect may be prophylactic in terms of completely or partially preventing a particular infection or disease or sign or symptom thereof and/or may be therapeutic in terms of a partial or complete cure of an infection or disease and/or adverse effect attributable to the infection or the disease. Accordingly, the method "prevents" (i.e., delays or inhibits) and/or "reduces" (i.e., decreases, slows, or ameliorates) the detrimental effects of a disease or disorder in the subject receiving the compositions of the invention. The subject may be any animal, including a mammal, such as a human, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Any type of unwanted condition or disease can be treated therapeutically with the presently disclosed compositions. In some embodiments, the disease or unwanted condition that is to be treated is a cancer. As described elsewhere herein, the term "cancer" encompasses any type of unregulated cellular growth and includes all forms of cancer. In some embodiments, the cancer to be treated is a colorectal cancer. Methods to detect the inhibition of cancer growth or progression are known in the art and include, but are not limited to, measuring the size of the primary tumor to detect a reduction in its size, delayed appearance of secondary tumors, slowed development of secondary tumors, decreased occurrence of secondary tumors, and slowed or decreased severity of secondary effects of disease.

It will be understood by one of skill in the art that the administration of the compositions described herein can be used alone or in conjunction with other therapeutic modalities, including, but not limited to, surgical therapy, radiotherapy, or treatment with any type of therapeutic agent, such as a drug. In those embodiments in which the subject is afflicted with cancer, the compositions described herein can be delivered in combination with any chemotherapeutic agent well known in the art.

In some embodiments, the cytotoxic bioactive compound and the compositions described herein can be administered simultaneously to the subject, wherein the cytotoxic bioactive compound and the compositions described herein are both present within a single composition that is administered to the subject. Alternatively, in other embodiments, the cytotoxic bioactive compound and the compositions described herein are administered in separate compositions sequentially. By "sequentially" is intended that the two compositions are administered one after the other to the subject, with two separate administrations of two distinct compositions, wherein one composition comprises the cytotoxic bioactive compound and the other composition comprises the compositions described herein.

When administered to a subject in need thereof, the compositions described herein can further comprise a targeting ligand, as discussed elsewhere herein. In these embodiments, the targeting ligand will target the physically associated ligand or complex to a targeted cell or tissue within the subject. In some embodiments, the targeted delivery system is cytotoxic. In certain embodiments, the targeted cell or tissue will be diseased or characterized by the unwanted condition.

Dosing

Delivery of a therapeutically effective amount of the compositions described herein can be obtained via administration of a pharmaceutical composition comprising a therapeutically effective dose of this agent. By "therapeutically effective amount" or "dose" is meant the concentration of the compositions described herein that is sufficient to elicit the desired therapeutic effect.

As used herein, "effective amount" is an amount sufficient to effect beneficial or desired clinical or biochemical results. An effective amount can be administered one or more times.

The effective amount of the compositions described herein will vary according to the weight, sex, age, and medical history of the subject. Other factors which influence the effective amount can include, but are not limited to, the severity of the subject's condition, the disorder being treated, and, if desired, the adjuvant therapeutic agent being administered along with the lipid or lipid-comprising complex. Methods to determine efficacy and dosage are known to those skilled in the art. See, for example, Isselbacher et al. (1996) *Harrison's Principles of Internal Medicine* 13 ed., 1814-1882, herein incorporated by reference.

The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, and the like. The skilled artisan will appreciate that certain factors can influence the dosage and timing required to effectively treat a subject, including but not limited to the severity of the disease, disorder, or unwanted condition, previous treatments, the general health and/or age of the subject, and other diseases or unwanted conditions present. Generally, treatment of a subject can include a single treatment or, in many cases, can include a series of treatments.

It is to be understood that appropriate doses of the compositions described herein depend upon its potency and can optionally be tailored to the particular recipient, for example, through administration of increasing doses until a preselected desired response is achieved. It is understood that the specific dose level for any particular animal subject can depend on a variety of factors including the activity of the specific compositions described herein employed, the age, body weight, general health, gender, and diet of the subject, the time of administration, the route of administration, the rate of excretion, any drug combination, and the degree of expression or activity to be modulated.

In another embodiment of the invention, a therapeutically effective dose of the compositions described herein is administered intermittently. By "intermittent administration" is intended administration of a therapeutically effective dose of the compositions described herein, followed by a time period of discontinuance, which is then followed by another administration of a therapeutically effective dose, and so forth. Administration of the therapeutically effective dose can be achieved in a continuous manner, as for example with a sustained-release formulation, or it can be achieved according to a desired daily dosage regimen, as for example with one, two, three, or more administrations per day. By "time period of discontinuance" is intended a discontinuing of the continuous sustained-released or daily administration of the compositions described herein. The time period of discontinuance may be longer or shorter than the period of continuous sustained-release or daily administration. During the time period of discontinuance, the level of the effect of the compositions described herein in the relevant tissue is substantially below the maximum level obtained during the treatment. In some embodiments, the discontinuance period depends on the concentration of the effective dose. The discontinuance period can be at least 2 days, at least 4 days or at least 1 week. In other embodiments, the period of discontinuance is at least 1 month, 2 months, 3 months, 4 months or greater. When a sustained-release formulation is used, the discontinuance period must be extended to account for the greater residence time of the compositions described herein at the therapeutic site. Alternatively, the frequency of administration of the effective dose of the sustained-release formulation can be decreased accordingly. An intermittent schedule of administration of the compositions described herein can continue until the desired therapeutic effect, and ultimately treatment of the disease or unwanted condition is achieved.

One of ordinary skill in the art upon review of the presently disclosed subject matter would appreciate that the presently disclosed compositions, including pharmaceutically acceptable salts and pharmaceutical compositions thereof, can be administered directly to a cell, a cell culture, a cell culture medium, a tissue, a tissue culture, a tissue culture medium, and the like. When referring to the compositions described herein, the term "administering," and derivations thereof, comprises any method that allows for the compound to contact a cell. The presently disclosed compositions, or pharmaceutically acceptable salts or pharmaceutical compositions thereof, can be administered to (or contacted with) a cell or a tissue in vitro or ex vivo. The presently disclosed compositions, or pharmaceutically acceptable salts or pharmaceutical compositions thereof, also can be administered to (or contacted with) a cell or a tissue in vivo by administration to an individual subject, e.g., a patient, for example, by systemic administration (e.g., intravenous, intraperitoneal, intramuscular, subdermal, or intracranial administration) or topical application, as described elsewhere herein.

IV. Articles of Manufacture

The article of manufacture can include a vial or other container that contains a composition suitable for the present method together with any carrier, either dried or in liquid form. The article of manufacture further includes instructions in the form of a label on the container and/or in the form of an insert included in a box in which the container is packaged, for carrying out the method of the invention. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

The following examples are offered by way of illustration and not by way of limitation.

EXAMPLES

The development and use of a reliable syngeneic orthotopic colorectal liver metastasis animal model has allowed for further investigation into the role of CXCL12 in driving colorectal liver metastasis formation. This model, first reported by Zhang et al., involves CT-26 FL3 cells ($2.0 \times 10^6$) being inoculated into the cecum wall and yielding a high occurrence of liver metastasis (~90%) (Zhang, Y., et al., Development and Characterization of a Reliable Mouse Model of Colorectal Cancer Metastasis to the Liver. *Clin Exp Metastasis*, 30(7), 2013). Through the establishment of a CT-26 FL3 (stably expressing RFP/Luc marker genes) cell line, luciferase bioluminescent analysis was used to demonstrate that intravenous (IV) injection of Galactose-PEG-LCP nanoparticles delivering pDNA encoding a small engineered antibody binding domain CXCL12/SDF-1-trap protein (28.6 kD), primes the liver to resist metastatic lesions.

Materials and Methods

1. Materials 1,2-Distearoyl-sn-glycero-3-phosphatidyl ethanolamine-N-[succinyl (polyethyleneglycol)-2000]-N-hydroxysuccinimide(DSPE-PEG2000-N-hydroxyl succinimide (NHS)) was purchased from NOF Corporation (Tokyo, Japan). Radioactive $^{177}$LuCl$_3$ in 0.05 N HCl was purchased from PerkinElmer, Inc. and utilized immediately upon receipt. DSPE-PEG2000-galactose was synthesized through the conjugation of 10 eq. of 4-aminophenyl β-d-galactopyranoside and 1 eq. of DSPE-PEG2000-NHS in PBS buffer, followed by chloroform extraction and dialysis against water using a MWCO 1000 dialysis tube. All other lipids were purchased from Avanti Polar Lipids, Inc. (Alabaster, Ala.). Peptides were purchased from Elim Biopharmaceuticals, Inc. (Hayward, Calif.); monocyclic abbreviated to mc. Hoechst nucleic acid stain 3342 was purchased from ThermoFischer Scientific (Grand Island, N.Y.). Fluorescent Cy3 cDNA labelling kit was acquired via (Mirus LabelIT kit, Minis Bio, Madison, Wis.). Luciferin was purchased from Promega Corporation (Madison, Wis.). Plasmids encoding green fluorescence protein (GFP) driven by the cytomegalovirus (CMV) promoter were custom prepared by Bayou Biolabs (Harahan, La.). ELISA, IF, and IHC kits as well as all antibodies including anti-His-tag, anti-CXCL12, and anti-CD8, as well as secondary antibodies were purchases through Abcam (Cambridge, Mass.). Invasion and Migration assay kits were purchases through EMD Millipore, (Billerica, Mass.). All other chemicals were obtained from Sigma-Aldrich (St. Louis, Mo.) and used without further purification. Six-week-old BALB/c female mice (~18 g each) were purchased from Charles River Laboratories (Wilmington, Mass.).

2. Methods

In Vitro Suppression of Migration and Invasion Via CXCL12 Trap Protein:

The engineered protein (CXCL12 trap) was tested to determine its ability to suppress CT-26 FL3 migration and invasion. The Chemotaxis 96-well Cell Migration and 24 well Cell Invasion Assay (EMD Millipore, Billerica, Mass.) was used. Cells were starved for 24 h and seeded on the trans-well plates at a density of $0.5 \times 10^6$ cells/ml in serum free medium. One group of cells remained in serum free medium, while all other groups allowed for the addition of the chemokine (chemoattractant) CXCL12 (100 ng/ml) in the feeder tray. Furthermore, three groups in which CXCL12 was present, allowed for the addition of serum free medium (no treatment), CXCL12 trap (2, 4, 8, 12 μg/ml), or a commercially available CXCL12 mAb (Abcam) (1, 2, 4 μg/ml). Incubation at 37° C. in a 5% CO$_2$ environment for 4 and 24 h (Migration), and for 24 h (Invasion). Cells were dislodged, collected, and lysed from the underside of the migration/invasion plate. Lysis buffer was added along with luciferin (luciferase assay solution), which is analyzed through bioluminescent plate reader. Background wells were subtracted and quantification was reported as relative to untreated (no CXCL12 chemoattractant).

Preparation and Characterization of LCP Loaded with DNA:

LCP was prepared using a modified protocol. Two separate microemulsions (60 mL each) were prepared of Igepal 520 and cyclohexane (3:7 v/v) and placed under stirring. A DNA (180 μg) solution was prepared, in which 1,800 μL of 2.5 M CaCl$_2$ was added. To this solution, octaarginine peptide (mc-CR8C) was added at an N:P ratio of 2:1 (~200 μg) and immediately added to the microemulsion. A Na$_2$HPO$_4$ solution (1,800 μL, 50 mM) was also prepared and added to the other microemulsion. Each microemulsion was allowed to stir for 20 min. The microemulsion containing Na$_2$HPO$_4$ was added to the microemulsion containing the DNA/Peptide/CaCl$_2$. This solution was allowed to stir for 5 min before addition of 1,200 μL of 20 mM DOPA (in CHCl$_3$). After addition of DOPA the microemulsion was left to stir an additional 30 min. An equal volume of 100% EtOH (120 ml) was added to disrupt the emulsion. The mixture was transferred to 50 ml conical centrifuge tubes and centrifuged at 10,000 g for 20 min. After decanting the supernatant, the precipitate was washed twice thereafter with 100% EtOH to remove traces of Igepal and/or cyclohexane. The precipitate was then dried under N$_2$, and resuspended in CHCl$_3$. This solution was centrifuged at 10,000 rpm for 5 min for the removal of large aggregates, and the supernatant containing the LCP "cores" (DNA and peptide entrapped within a calcium phosphate nanoprecipitate, supporting and surrounded by a lipid monolayer of DOPA) was recovered.

To characterize DNA entrapment efficiency, cDNA was labeled with Cy3 (Minis LabelIT kit, Minis Bio, Madison, Wis.) according to manufacturer instructions. Such Cy3-DNA was formulated into the LCP cores, after which recovery was assessed via fluorescence spectrometry. Further studies used Hoescht nucleic acid stain to confirm DNA entrapment efficiency in which pDNA/peptide was encapsulated, cores were lysed in acetic acid buffer, peptide/DNA was dissociated through addition of protease K, and Hoescht stain was added and assessed via fluorescence spectrometry. $^{177}$Lu-labeled LCP cores were prepared as described above, in which pDNA/peptide along with $^{177}$LuCl$_3$ was incorporated into the CaCl$_2$ solution of the calcium emulsion. Upon co-precipitation of the two emulsions, $^{177}$Lu-labeled LCP cores were collected as described above, with centrifugation in CHCl$_3$ removing aggregates containing $^{177}$Lu. The final LCP cores encapsulated 80% of $^{177}$Lu. Final Gal-LCP-pDNA/mc-CR8C was produced through desiccation of a mixture of free lipids and cores and rehydration via 5% aqueous sucrose solution. The ratio of cores to outer leaflet lipids for optimal final particle formulation was found to be 11 mg core: 600 μl DOTAP (20 mM): 600 μl Cholesterol (20 mM): 500 μl DSPE-PEG2000 (20 mM). Therein, 35 mol % DOTAP, 35 mol % cholesterol, and 30 mol % DSPE-PEG2000 (or 25 mol % DSPE-PEG and 5 mol % DSPE-PEG-Gal) were utilized as outer leaflet lipids. Zeta potential and particle size of LCP were measured using a Malvern ZetaSizer Nano Series (Westborough, Mass.). TEM images of LCP were acquired using a JEOL 100CX II TEM (JEOL, Japan).

Pharmacokinetics, Biodistribution, and Cellular Distribution of Gal-LCP-pDNA/mc-CR8C:

Pharmacokinetics and quantitative biodistribution were determined via co-encapsulation of pDNA with $^{177}$Lu, as described above. Such methods have been utilized previously to accurately determine LCP biodistribution. 8-week-old BALB/c female mice (6 mice utilized for each group) were injected individually (0.2 mL, balanced in osmolarity with the addition of sucrose) with LCP at 0.5 mg pDNA/kg, corresponding to a dose of 1×10$^8$ cpm/kg of $^{177}$Lu. For pharmacokinetic analysis, blood was recovered at various time points (0.5, 1, 2, 4, 8, 12, and 16 h) via tail-nick bleed. For biodistribution analysis, 16 h after the administration of LCP, the blood and major organs were collected (6 mice utilized for each time point). Radioactivity in the blood and tissues in both studies was measured using a γ-counter. Analysis was conducted under a two-compartment model utilizing Phoenix WinNonlin (Version 6.3, Pharsight Corporation; Mountain View, Calif.).

In Vivo Gene Dose Escalation and Expression Time:

Formulation of Galactose targeted LCPs containing pCXCL12 Trap DNA, which contains a His-Tag at the C-terminal end were injected (0.2 mL, balanced in osmolarity with the addition of sucrose) into 8-week-old BALB/c female mice (0.1, 0.5, or 1 mg DNA/kg, 3 mice utilized for each group) through the tail vein. Western Blot analysis and quantification after tail vein IV administration of increasing concentrations of pCXCL12 trap DNA LCP in order to determine if the expression is dose dependent. Mice were sacked 24 h after administration. Liver, spleen, lungs, kidney, heart, and blood were collected and homogenized in RIPA buffer. Total protein concentration in the lysate was determined through a bicinchoninic acid protein assay kit (BCA Protein Assay Kit, Pierce, Rockford, Ill.). Subsequently, 50 μg of total protein was loaded for western analysis. The desired CXCL12 trap protein has a molecular weight of 28.6 kD. GAPDH was used as a loading control. His (6×)-tag mouse antibody was used as the primary antibody. The expression of pCXCL12 trap was quantified as the relative HRP intensity increase over PBS treated group.

His-tag ELISA kit was also used in which 5 μg of total protein was loaded for further expression analysis. The kit provided standard proteins containing a His-tag to be used as a standard calibration control. Therefore, quantification of protein expression can be measured through ELISA analysis. Following the dose escalation and expression studies, the 0.5 mg DNA/kg dose was chosen for in vivo therapeutic studies.

Formulation of Galactose targeted LCPs containing pDNA encoding pCXCL12 Trap, which contains a His-Tag at the C-terminal end were injected (0.2 mL, balanced in osmolarity with the addition of sucrose) into 8-week-old BALB/c female mice (0.5 mg DNA/kg×3 QOD, 3 mice utilized for each group) through the tail vein. Western Blot analysis and quantification after tail vein IV administration of pCXCL12 trap DNA LCP in order to determine the transient time of expression. Mice were sacked 1, 2, 4, or 8 days after administration. Liver, spleen, lungs, kidney, heart, and blood were collected and homogenized in RIPA buffer. Protein content was measured using BCA. Subsequently, 50 μg of total protein was loaded for western analysis. All gels were loaded with a specific organ and a standard liver sample in order to analyze organ versus liver expression levels and maintain consistency in quantification of organ and liver expression. The expression of pCXCL12 trap was quantified as the relative HRP intensity increase over PBS treated group.

Toxicity and Pathology Studies:

Mice were treated with pCXCL12 trap, pGFP, blank loaded LCP (0.5 mg DNA/kg×3, QOD) (three mice utilized for each group). Furthermore, another treatment group was administered free CXCL12 trap protein (1.0 mg protein/kg× 3, QOD). Mice were sacked 24 h post final tail vein injection. Serum was obtained from the mice via cardiac puncture and centrifugation. Hepatic and renal damage was assessed by measuring the levels of AST, ALT and BUN in the serum samples. Blood cell levels including, white blood cells, lymphocytes, granulocytes, and monocytes were measured with whole blood analysis. These measurements were quantified by the Animal Clinical Chemistry and Gene Expression Laboratories at UNC Chapel Hill. Further, the major organs of each mouse were collected, fixed, and processed thereafter for trichrome staining. Images of tissue sections were collected using a Nikon light microscope with 10× objective.

In Vivo Liver Metastasis Suppression:

Mice were inoculated with 2×10$^6$ CT-26 FL3 RFP/Luc cells into the cecum wall. Treatment of 10 μg (pDNA) Gal-LCP-pCXCL12 trap/mc-CR8C on days 10, 12, and 14 was administered through tail vein IV (n=7). Control groups included PBS/untreated (n=7) and Gal-LCP-GFP/mc-CR8C (n=6). Progression of tumor mass was followed by administration of 200 μl luciferin (10 mg/ml) IP Luciferase bioluminescent imaging was recorded 10 min after administration of luciferin. Mouse tumor mass on day 24 is shown above in bioluminescent image using IVIS with Kodak camera. After 24 days, the mice were sacked and livers were extracted. Quantification of tumor burden on livers was quantified using image J software. Quantification is shown above in which tumor burden was found to be reduced by over 85% compared to control groups. Further analysis of other organs metastatic burden post treatment were studied. Mouse metastasis was assessed on day 24 in which mice were treated with 200 μl of Luciferin (10 mg/ml). Mice were imaged, sacked, and organs were then extracted and placed in solution of luciferin (1 mg/ml) and imaged for bioluminescence.

Statistical Analysis:

Data were expressed as the mean±standard deviation (SD). Statistical analysis was performed by the Students' t-test when only two value sets were compared, and one-way analysis of variance (ANOVA) followed by Dunnett's test when the data involved three or more groups. *, , * denotes p<0.05, 0.01, and 0.001 respectively and was considered significant and documented on figure or figure legend. In all statistics the groups are compared against the untreated control.

Example 1

Formulation of Galactose-LCP pDNA/Mc-CR8C Nanoparticles

Figure 3C:
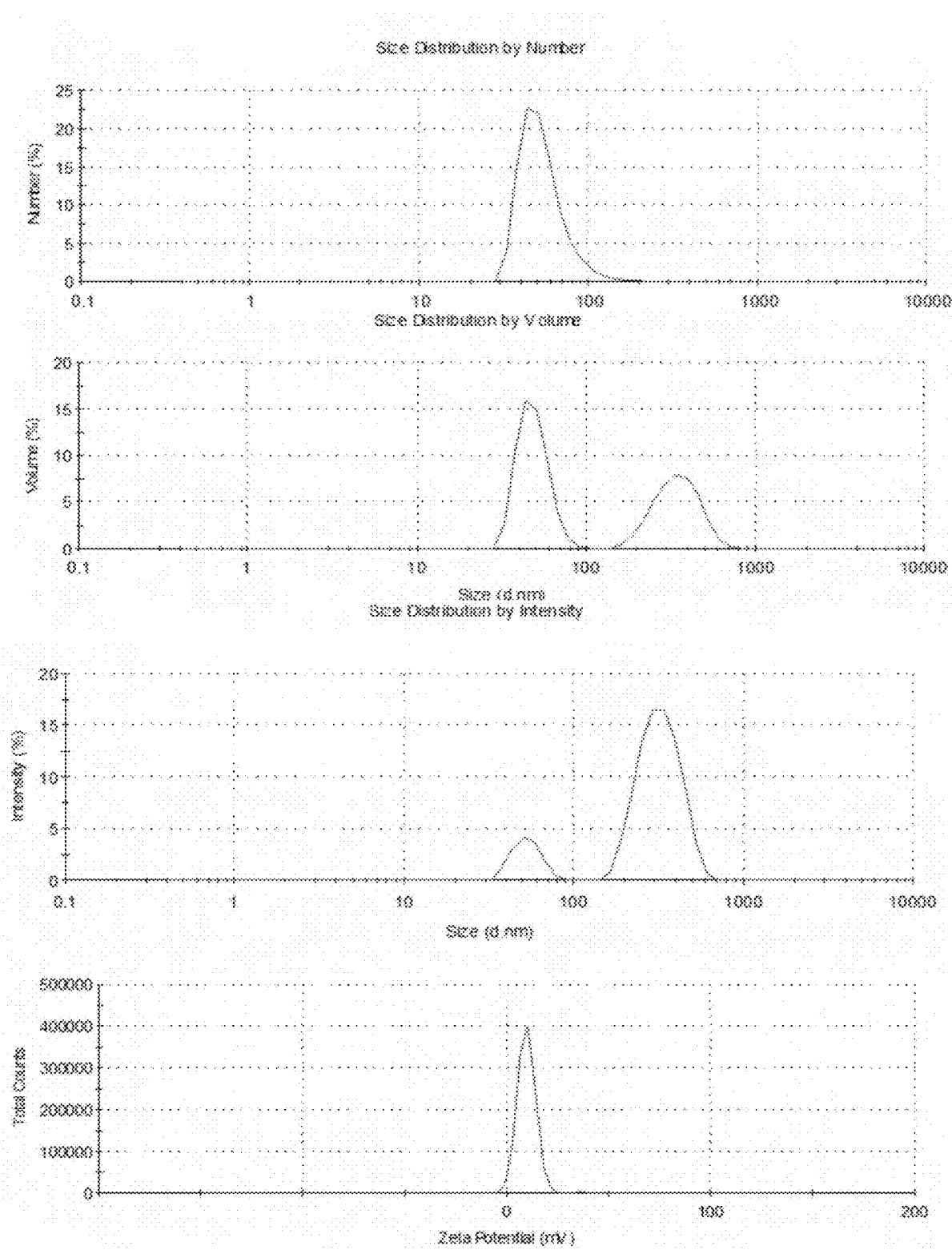
FIG. 3 depicts the LCP nanoparticle characterization by TEM and DLS. (A) LCP core containing pDNA/mc-CR8C peptide (B) Final galactose-LCP containing pDNA/mc-CR8C, with negative uranyl acetate stain (C) Dynamic light scattering (DLS) analysis of final galactose-LCP containing pDNA/mc-CR8C, yielding 45 nanometers in diameter and Zeta potential of +10.0. Number, volume, and intensity weighted size distribution illustrates two particle distribution. The smaller population (~45 nm) is the desired LCP particles, and the larger population (~350 nm) is due to excess DOTAP and cholesterol which form liposomes following thin-film hydration yielding a Z-average of ~236±32 nm; n=6. (D) The stability of the LCP over time in a 10% serum solution was measured through DLS. The LCP was suspended in 10% serum solution and incubated at 37° C. The z-average was recorded over 24 hours in order to observe any protein/LCP aggregation indicated by increased z-average. Data was expressed as mean±s.d., calculated from samples ran in triplicate. The z-average (~30 nm) is consistent over the 24 hours, yielding no significant increase in the z-average, indicating minimal formation of protein/LCP aggregates. (E) The vector map of the pCXCL12 plasmid encapsulated into the LCP. (F) The DNA sequence of the pCXCL12 gene.

Hu et al. first reported the formulation and delivery of the Galactose-LCP with pDNA/mc-CR8C cargo to the liver (hepatocytes) of mice (Hu, Y., et al., A Highly Efficient Synthetic Vector: Nonhydrodynamic Delivery of DNA to Hepatocyte Nuclei in Vivo. *ACS Nano*, 2013. 7(6): p. 5376-5384). As reported a reverse micro-emulsion was used to prepare, 1,2-dioleoyl-sn-glycero-3-phosphate (DOPA)-coated Calcium Phosphate (CaP) nanoparticles (LCP "amorphous cores"). These cores can encapsulate both DNA (60% efficiency) and the cationic peptides, yielding a core size ranging from 15 to 25 nm in diameter. The hollow core structure can be visualized under Transmission Electron Microscopy (TEM) (FIG. 3A/B). Subsequently, the DOPA monolayer surrounding the CaP core allows for the addition of the cationic outer leaflet lipids (1,2-dioleoyl-3-trimethylammonium-propane (DOTAP), helper lipid cholesterol, and 1,2-distearoyl-sn-glycero-3-phosphatidylethanolamine-N-[succinyl(polyethylene glycol)-2000 (DSPE-PEG2000)) to assist in RES evasion, producing sub-60 nm particles ("final" LCP, 40-60 nm in diameter, shown in FIG. 3A-C which can easily penetrate hepatic sinusoidal fenestrations.

Example 2

Determination of LCP Nanoparticle Size

The hydrodynamic diameter and the surface charge of the LCP particle were found via dynamic light scattering to be approximately 45 nm and 10 mV (FIG. 3C). Dynamic light scattering indicated that LCP was narrowly dispersed around 45 nm in diameter, with a positive zeta potential (around +10 mV) due to cationic charge of DOTAP along with the cation shielding ability of DSPE-PEG2000. The LCP and liposome mixture result in a z-average of 236±32 nm; n=6. The solution was found to be stable in 10% fetal bovine serum for at least 24 hours at 37° C. in which no significant increase in the z-average was observed. (FIG. 3D).

Example 3 pDNA Encapsulation Efficiency in LCP Cores

Determination of the pDNA loading of Galactose-LCP pDNA/mc-CR8C was accomplished through lysing the cores in an acetic acid buffer environment (pH=4). The DNA was dissociated from the peptide through addition of a protease K solution. The addition of Hoechst stain allowed for quantitative fluorescent reading to determine DNA encapsulation efficiency. The DNA encapsulation efficiency was found to the approximately 50-60%, which corresponds closely to Hu et al. formulation (Hu, Y., et al., A Highly Efficient Synthetic Vector: Nonhydrodynamic Delivery of DNA to Hepatocyte Nuclei in Vivo. *ACS Nano*, 2013. 7(6): p. 5376-5384).

Example 4

Galactose-LCP-pDNA/mc-CR8C Nanoparticle PK and Organ/Liver Accumulation

Liver specificity, pharmacokinetics, and organ distribution was determined through incorporation of $Lu^{177}$ radioisotope into the pDNA/mcCR8C LCP core. The Galactose-LCP pCXCL12 trap/mc-CR8C (pTrap LCP) particles containing the $Lu^{177}$ were injected through the tail vein into normal BALB/c mice. The PK and organ distribution profile found that the galactose-LCP nanoparticles exhibits a two-phase distribution with a $T^{1/2}\alpha$ and $T^{1/2}\beta$ of 20 min and 1054 minutes respectively, as well as approximately 50% of the LCP accumulating in the liver 16 h post IV injection. (FIG. 4). Tail vein injection of the pTrap LCP particles without Galactose targeting showed a significant decrease in liver accumulation, approximately 10-15% accumulation, which is comparable to the values Hu et al reported.

Example 5

In Vivo Liver Expression Profile of Endogenous CXCL12

To validate the expression levels of endogenous CXCL12 in the liver of diseased (colorectal liver metastasis model) BALB/C mice, we extracted, formalin fixed, paraffin sectioned, and assessed the amount of CXCL12 through immunofluorescent staining with a primary CXCL12 antibody and fluorescently tagged (Alexa Fluor 594) secondary antibody. We furthered assessed whether the delivery of our pTrap LCP would yield decreased fluorescent signal due to CXCL12 trapping as well as decreased inflammation due to decreased metastatic lesions. Therefore, 10 days post final IV administration of pTrap LCP (10 µg pDNA QOD×3), we collected the livers, formalin fixed the livers, paraffin sectioned and used immune-fluorescent staining against CXCL12 (Red). Five groups (four of which contained CRC) were studied, including untreated (without CRC), untreated (PBS), Galactose-LCP pGFP/mc-CR8C (pGFP LCP), pTrap LCP (10 µg), pTrap LCP (10 µg QOD×3). Results are shown in FIG. 5a, in which the untreated and pGFP had no significant difference in fluorescent intensity, and had approximately a 5 to 6 fold increase in CXCL12 expression compared to untreated liver from mice without CRC. However, both pTrap LCP (10 µg×1 and 10 µg QOD×3) groups showed a 2.5 and 5 fold decrease in fluorescent intensity respectively compared to the untreated, ultimately reaching baseline levels of CXCL12 found in untreated liver from mice without CRC. ($p<0.05$) (FIG. 5A). Due to the decrease in CXCL12 found in the liver after treatment of the pTrap LCP (10 µg×1 and 10 µg QOD×3), we further stained sections to determine the effect on the liver CD8 T-cell population (Green), MDSC, and T-regulatory cells which is believed to be recruited by endogenous CXCL12. Four groups were studied, including healthy (No CRC), untreated (Tumor), untreated (Stroma), and pTrap LCP (10 µg every other day ×3). Results are shown in FIG. 5B, in which pTrap LCP (10 µg QOD×3) groups showed a decrease fluorescent intensity compared to the untreated. ($p<0.05$) (FIG. 5B).

Example 6

Figure 5F:
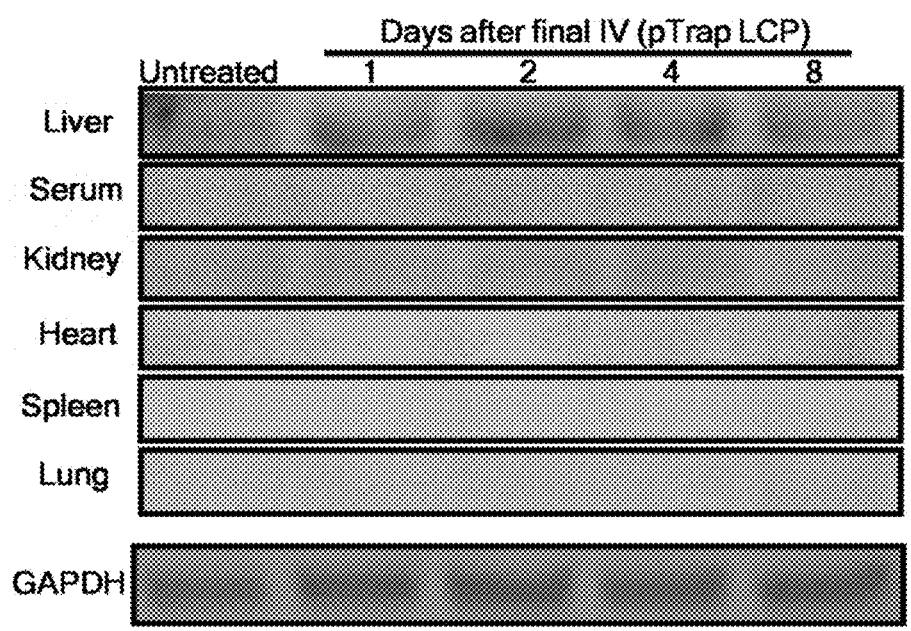
FIG. 5 depicts the biological trapping of endogenous CXCL12 and its role on immune cell recruitment as well as the transient and liver specifi expression of the pCXCL12 trap. (A) Endogenous CXCL12 expression in paraffin-embedded sections of liver tissues from BALB/c mouse models of colorectal cancer sacrificed 10 days after the final treatment injection and control healthy livers [healthy (No CRC)]. Immunofluorescent stain for CXCL12 (red), along with DAPI nuclear stain (blue). Five groups were studied, including healthy (No CRC), untreated (PBS), pGFP LCP control (10 µg every other day×3), pTrap LCP (10 µg), pTrap LCP (10 µg every other day ×3). All data were expressed as mean±s.d., calculated from samples run in triplicate and reported as fluorescent intensity. N.S. denotes no significance, N.D. denotes under detection limit. The p-values of individual groups compared to corresponding untreated control are displayed in graphs. Scale bar: 250 µm. (B) Additional sections were stained to determine the recruitment of immune cells to the liver, including immunosuppressive anti-inflammatory MDSCs [CDllb+(Green)/GR1+(Red)] and $T_{reg}$ [CD4+(Green)/Foxp3+(Red)] as well as the CD8+ T cell population (Green). Four groups were studied, including healthy (No CRC), untreated (Tumor), untreated (Stroma), and pTrap LCP (10 µg every other day×3). Trichrome staining is also shown to distinguish normal and diseased liver. White arrows indicate metastatic lesions. All data were expressed as mean±s.d., calculated from samples run in triplicate and reported as fluorescent intensity. N.S. denotes no significance, N.D. denotes under detection limit. The p-values of individual groups compared to corresponding untreated control are displayed in graphs. Scale bar: 250 µm demonstrates the transient liver-specific expression of pGFP and engineered pCXCL12 trap. (C) Microscopy analysis of GFP expression in major LCP-accumulating organs. The liver sections demonstrate transient expression for at least 4 days after final injection (10 µg every other day ×3. Scale bar: 250 µm. Data were expressed as mean±s.d., calculated from at least triplicated samples and reported as a fluorescent intensity quantified by Image J software. N.S. denotes no significance, N.D. denotes under detection limit, p-values represent significance to untreated sample. Scale bar 250 µm. (D) His(6×)-tag ELISA and (E) Western blot analysis were conducted to determine the organ distribution/expression of the pCXCL12 trap in all major LCP-accumulating organs and serum. Doses were escalated from 2.0, 10.0, or 20.0 µg pDNA administered via tail vein. (F) Western blot analysis of organs show CXCL12 trap expression through use of His(6×) mAb. The expression is transient and only lasts for at least 4 days and no longer than 8 days after the final injection (10 µg every other day ×3). Total protein concentrations were determined by BCA and 50 µg of total protein was loaded per well/lane. Trap protein was detected at 28.6 kDa, as confirmed by a protein standard ladder, consistent with the theoretical value. GAPDH was used as a loading control, except in the serum samples, where GAPDH is not present. Data were expressed as mean±s.d., calculated from samples run in triplicate and shown as a fold increase compared to untreated control. N.S. denotes no significance, N.D. denotes under detection limit. The p-values of groups compared to corresponding untreated control are displayed in graphs.

In Vivo Organ Expression/Distribution of CXCL12-Trap Post pTrap LCP Administration Delivery of pTrap LCP via IV tail vein administration in BALB/c mice yields nearly 50% of the injected dose accumulating in the liver. (FIG. 4B). Hu et al. reported that the majority of LCP is taken up and expressed in the hepatocytes. Hu et al. also showed that decreased PEG density and the absence of galactose targeting ligand, shifted the uptake preferentially into the Kupffer cells, decreasing expression levels of the pDNA. Therefore, to insure hepatocyte uptake and expression we mirror the PEG density (30% mol. input) and galactose targeting ligand used in Hu et al, formulation. We further investigated the preferential expression of the pCXCL12 trap in the liver versus other organs/serum to insure we have preferential liver specific expression of this CXCL12 trap. In order to determine the organ expression of the pCXCL12 trap, we have incorporated a His-tag at the C-terminus, which allows for ELISA and western blot analysis via a His-Tag mAb. (FIGS. 5D, 5E, and 5F). Mice were treated with increasing dose of pTrap LCP (0.1 mg/kg, 0.5 mg/kg, and 1.0 mg/kg). Through ELISA and Western blot analysis we see after 24 h a dose dependent increase in liver expression with no expression being found in other off-target organs or serum (FIGS. 5D and 5E). Further studies in which pTrap LCP (0.5 mg/kg QOD×3) was administered and the mice were sacked on days 1, 2, 4, and 8. Organs were collected and analyzed through western blot by using anti-His-tag mAb (FIG. 5F). These results clearly demonstrate that the Galactose-LCP vector allows for preferential transient expression in the liver, with minimal expression in any other organ or serum. (FIGS. 5D, 5E, and 5F). Subsequently, we report that the liver expression holds transient properties in which expression is found to last up to 8 days post final injection (10 µg pDNA; 0.5 mg/kg QOD×3). (FIG. 5F).

The preferential expression of Green Fluorescent Protein Plasmid (pGFP) and CXCL12 trap plasmid (pTrap) in the liver versus other organs/serum is shown in FIG. 5A. Through fluorescent microscopy analysis of organ sections on day 2, 4 and 8 after final pGFP LCP injection, we were able to demonstrate transient liver-specific expression lasting up to 4 days. No GFP signal was found in any other major organ sections. Furthermore, expression of GFP was found to be predominantly in the hepatocyte population within the liver (FIG. 5A).

Example 7

Figure 6A:
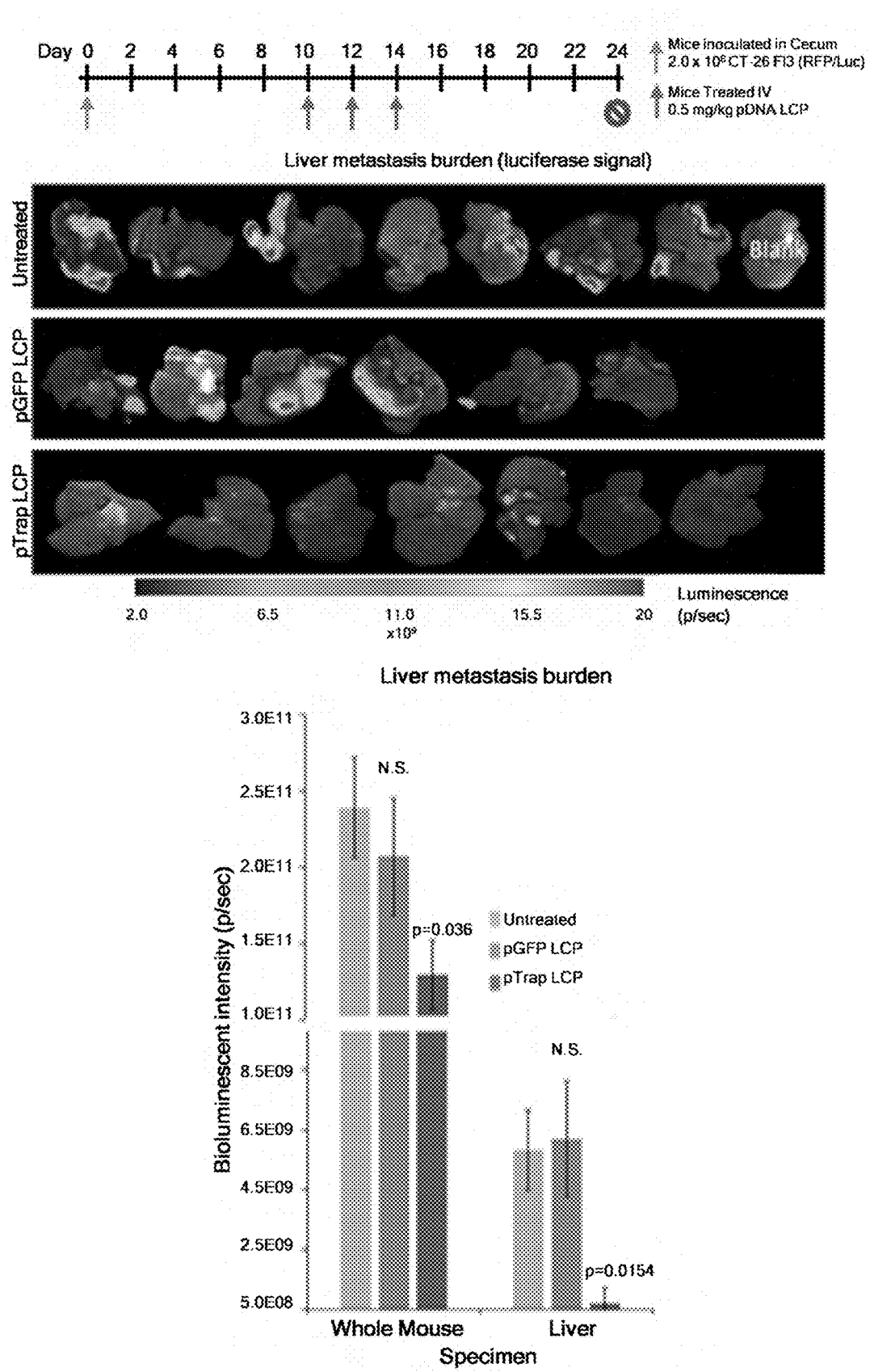

Decreased Occurrence and Tumor Burden of Colorectal Liver Metastasis in Mice Post pTrap LCP Administration We examined the effect of pTrap LCP on the incidence and metastasis burden found in mice. Mice were inoculated with $2.0 \times 10^6$ CT-26 FL3 (RFP/Luc) cells orthotopically into the cecum wall. In this series of experiments, treatments began 10 days post cecum inoculation. Three treatment groups were explored, including PBS (untreated), a vector control consisting of pGFP LCP, and pTrap LCP. Administration of the three treatment groups was initiated on day 10 post inoculation, in which IV tail vein injections (10 µg pDNA) on day 10, 12, and 14. The total mouse tumor burden was followed through IP administration of 200 µl of luciferin (10 mg/ml) followed by bioluminescent analysis. The whole mouse tumor burden was recorded weekly, and used to sort mice into treatment groups before day 10, whole mouse tumor burden on day 24 after inoculation is shown in FIG. 13. On day 24, 200 µl of luciferin (10 mg/ml) was administered IP, mice were sacked due to heavy primary tumor burden in the cecum. Organs were collected and rinsed in PBS before being placed in a diluted luciferin solution (1 mg/ml). Livers and other organs were analyzed by bioluminescent imaging to determine metastasis tumor burden. (FIGS. 6A and 6B). Following bioluminescent analysis, livers were rinsed in PBS, fixed in formalin solution, sectioned, and trichrome stained for further morphological analysis. (FIG. 6C). It is clear from the luciferase (bioluminescent intensity) that the PBS and pGFP LCP have large metastatic tumor burdens on the liver (FIGS. 6A and 6B), which subsequently is causing cirrhosis and fibrotic tissue to become more prominent (FIG. 6C). In contrast, mice treated with pTrap LCP (10 µg pDNA) three times (QOD) showed a significant (10 fold reduction in liver metastasis burden) and approximately a 70-80% decrease in the incidence of liver metastasis formation. The fibrotic area detected via microscope analysis of the trichrome stained liver sections was significantly less in specimens from pGFP LCP mice than in control specimens (p<0.01) (FIG. 6C). This is the first report to our knowledge that has successfully expressed a therapeutic protein, via delivery of pDNA in a liver specific non-viral vector, yielding therapeutic efficacy. Furthermore, we observe that the metastasis is not only reduced in burden and incidence, but the metastasis is not found to migrate and invade other organs. (FIG. 6B).

Example 8

Cancer-Specific T Cells Enhance the Anti-Metastasis Efficacy of pTrap LCP Therapy The decreased MDSC and Treg populations in the liver after pTrap LCP treatment, along with the presence of CD8+ lymphocytes, implicate a shift from a pro-tumor (immunosuppressive) to anti-tumor environment within the liver. Therefore, we examined the cytotoxic T lymphocytes' (CTLs') ability to decrease the establishment of metastasis in the liver after pTrap LCP therapy. To investigate the pTrap LCPs' ability to enhance cancer-specific CD8 T cell killing, we studied the anti-cancer efficacy of the pTrap LCP in mice with a depleted CD8+ T cell population. We followed a protocol similar to that reported by Harimoto et al., in which ≥95% of the CD8+ T cell population was depleted after two intraperitoneal injections of 400 anti-Lyt2.2 (2.43; rat IgG2b)(14). Mice were inoculated with CRC according to the orthotopic syngeneic model described earlier, followed by T cell depletion before treatment. In this series of experiments, treatments began 10 days after cecum inoculation. The animals were divided into three treatment groups: untreated (PBS), pTrap LCP with anti-CD8 (Anti-Lyt2.2), and pTrap LCP with an antibody isotype control (rat IgG2b isotype control). To maintain the depletion of the CD8+ T cell population, an intraperitoneal injection of the Anti-Lyt2.2 or isotype control IgG (400 µg) was administered on day 8 and 10. Treatment was initiated on day 10 after inoculation, with IV tail vein injection (10 µg pDNA) on days 10, 12, and 14. Mice were euthanized because of heavy primary tumor burden in the cecum on day 21, and the liver tumor burden was determined through bioluminescent imaging (FIG. 7). All mice treated with the PBS developed large metastatic tumor lesions in the liver (FIG. 7). The T cell-depleted mice treated with anti-Lyt2.2 followed by three doses of pTrap LCP (10 µg pDNA) showed similar liver tumor burden to the untreated mice. In contrast, mice treated with the isotype control IgG2b antibody followed by pTrap LCP showed a 5-fold reduction in liver metastasis burden and approximately 80% decrease in the incidence of liver metastasis compared to untreated animals. These results show that the presence of CTLs along with reduction in CXCL12 decreases the risk of establishing metastatic lesions in the liver.

Example 9

Figure 8A:
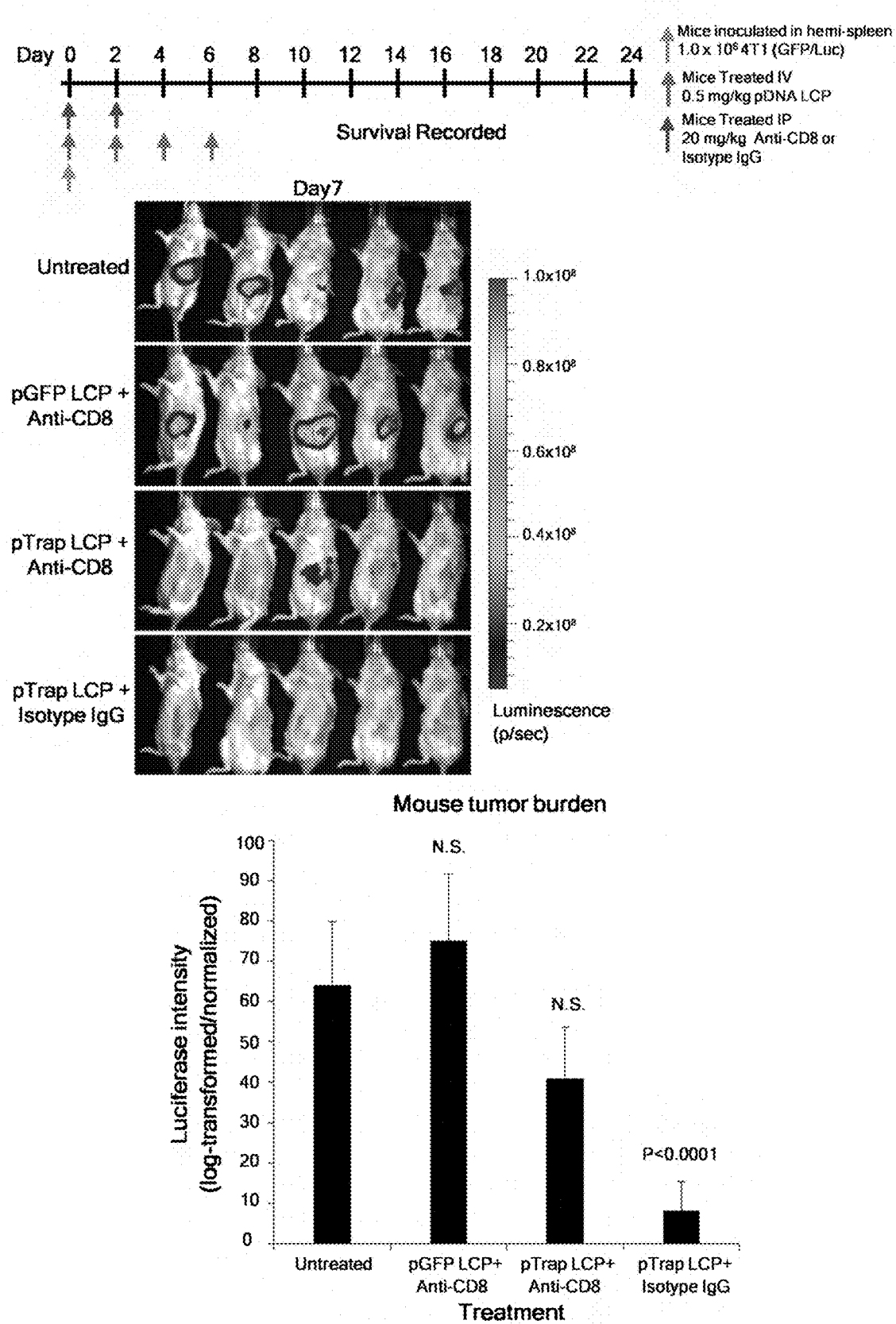

Reduced Metastatic Burden is Associated with Increased Survival in Breast Cancer Liver Metastasis Model We examined the effect of pTrap LCP on the median survival and liver tumor burden in an aggressive mouse breast cancer liver metastasis model. The breast cancer liver metastasis model consists of the hemi-splenic implantation of a highly metastatic murine breast cancer cell line 4T1. These studies modeled the clinical standard of care, in which the primary tumor is resected and death usually results from the metastatic burden. BALB/c mice were inoculated with $1.0 \times 106$ (0.1 mL) of 4T1(GFP/Luc) cells into one half of the spleen, which had been tied off and separated into two halves before the tumor inoculation. The hemi-spleen that received the cells was resected 10 min after inoculation to decrease primary tumor growth. In this series of experiments, treatments began on the day of inoculation because of the rapid migration of cells to the liver, often within 5 min after inoculation (15). We studied four treatment groups for the breast cancer liver metastasis model: untreated (PBS), pGFP LCP with anti-CD8 (10 µg, 0.5 mg/kg pDNA and 400 µg, 20 mg/kg anti-Lyt2.2), pTrap LCP with anti-CD8 (10 µg, 0.5 mg/kg pDNA and 400 µg, 20 mg/kg anti-Lyt2.2), and pTrap LCP with isotype IgG (10 µg, 0.5 mg/kg pDNA and 400 µg, 20 mg/kg Isotype IgG). PBS, pGFP LCP, or pTrap LCP was administered IV via tail vein injections every other day starting on day 0 and ending on day 6. Administration of the anti-Lyt2.2 or Isotype IgG control involved two IP injections on days 0 and 2. Tumor progression was monitored by bioluminescent imaging (FIG. 8A). Mice were euthanized when one of the following conditions applied: drastic weight gain or loss greater than 10% within one week or clear signs of distress, such as dehydration, inactivity, or shortness of breath/weak breathing. Three mice from each group were euthanized 10 days after inoculation, their organs were collected and rinsed in PBS, and the livers were analyzed for tumor burden by flow cytometry analysis (FIG. 8B). Mice that did not receive pTrap LCP treatment developed large metastatic tumor lesions in the liver within the first week after inoculation (FIGS. 8A and 8B). In contrast, mice treated with pTrap LCP showed a reduction in liver metastasis burden and decrease in the incidence of liver metastasis formation, as well as an almost 2-fold increase in the median survival versus all other treatment groups (14 vs 25 days) (FIG. 8C).

Example 10

Reducing the Establishment of Liver Metastasis by pTrap LCP, Trap Protein, and CXCR4 Antagonist We compared the efficacy of different therapeutic modalities [anti-CXCL12 trap protein, CXCR4 small molecule antagonist (AMD3100), and the pTrap LCP] in reducing the establishment of liver metastasis using a human colorectal cancer cell line (HT-29) in immunodeficient athymic mice. The human colorectal cancer liver metastasis model was established according to the same hemi-splenic implantation procedure as above, using colorectal cancer cell line HT-29, which has high expression of CXCR4 (FIG. 11). In this series of experiments, treatments again began on the day of inoculation because of the rapid migration of cells to the liver within 5 min after inoculation (15). The five treatment groups studied for the colorectal cancer liver metastasis model were untreated (PBS), pGFP LCP (10 µg, 0.5 mg/kg pDNA), pTrap LCP (10 µg, 0.5 mg/kg pDNA), free CXCL12 trap protein (10 µg, 0.5 mg/kg protein), and AMD3100 (100 µg, 5.0 mg/kg). The treatments were administered IV by tail vein injection every other day, initiated on day 0 and terminated on day 16 (FIG. 9A). Mice were euthanized on day 36, their livers were collected and rinsed in PBS, and tumor nodules were resected from the livers and weighed (FIG. 9B). Mice that did not receive pTrap LCP or AMD3100 treatment developed numerous metastatic tumor lesions in the liver (FIG. 9B). In contrast, mice treated with pTrap LCP or AMD3100 showed a reduction in liver metastasis burden and decreased incidence of liver metastasis formation during the treatment compared to all other treatment groups.

Example 11

Effects of pTrap LCP on Liver, Kidney, and Blood Function (Toxicity Analysis)

Figure 10A:
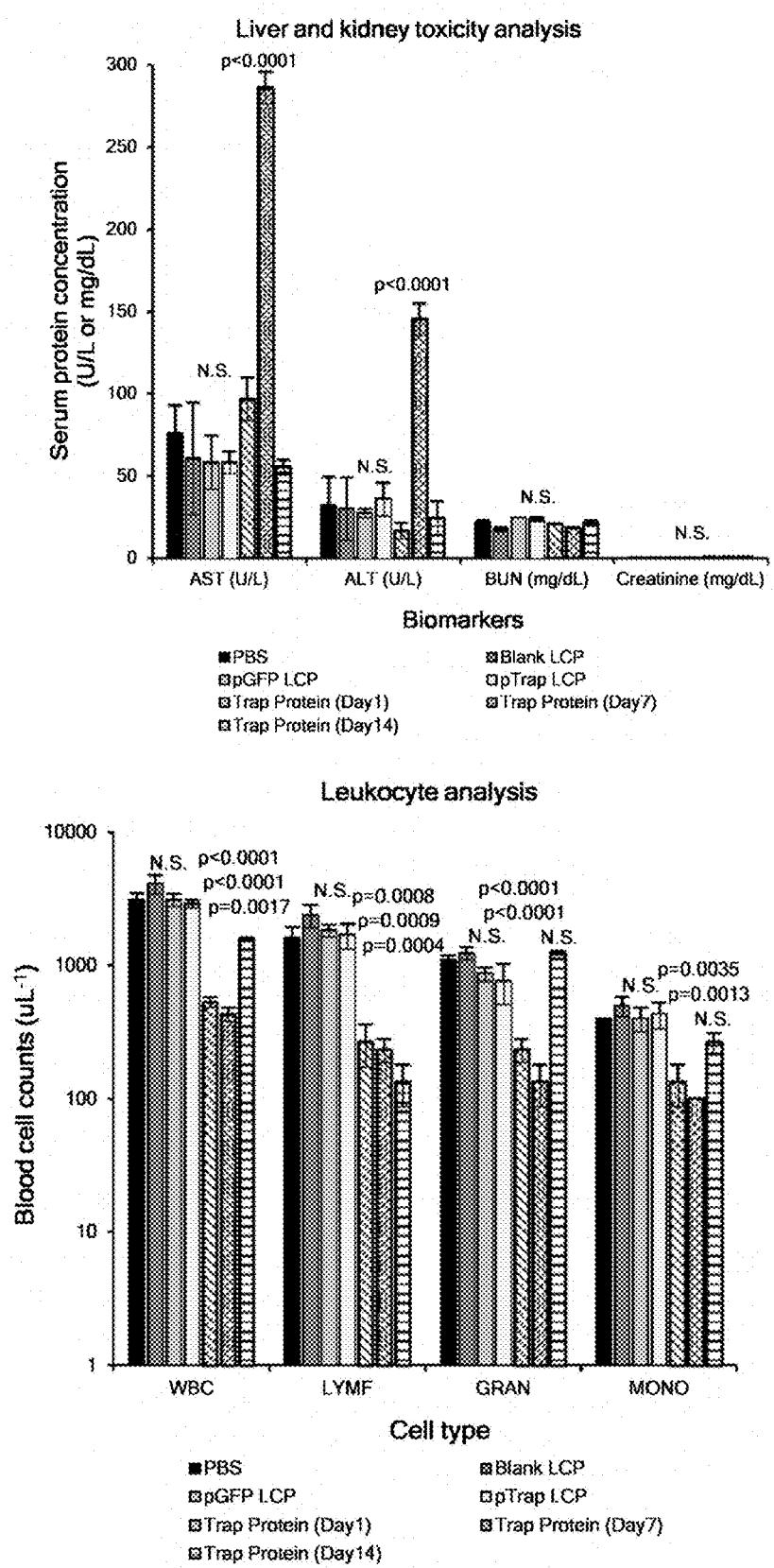
Figure 10B:
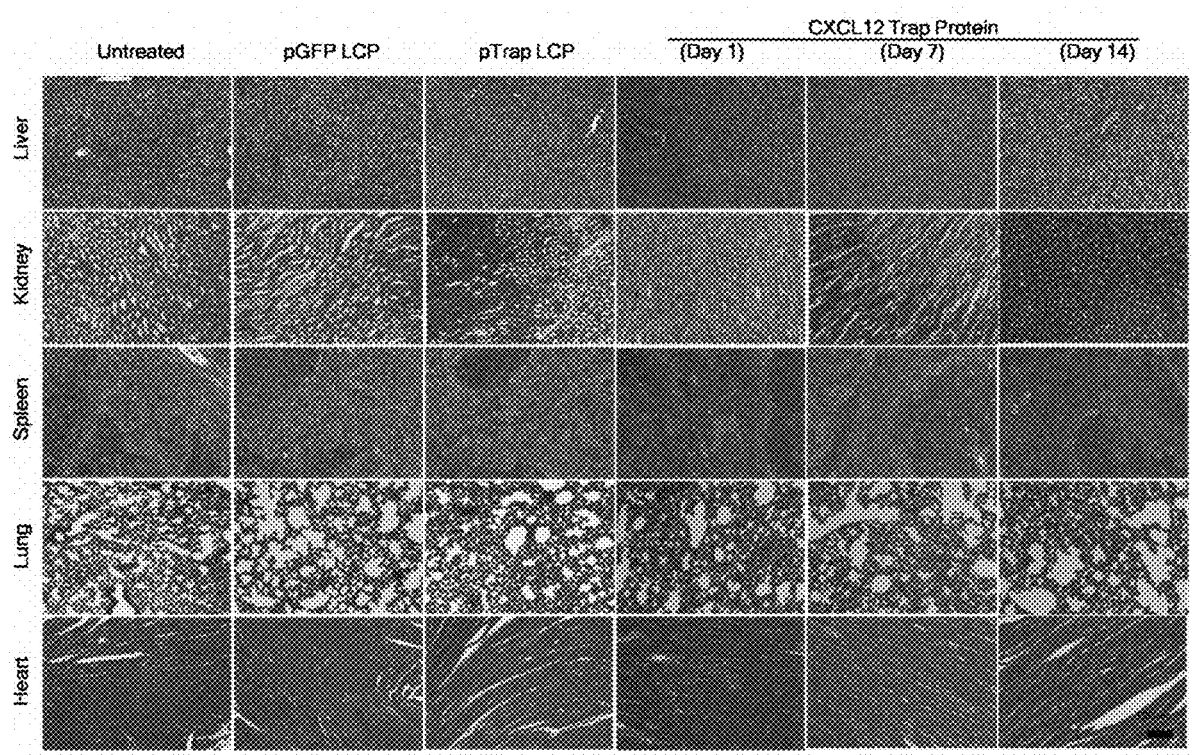

Administration of pTrap LCP (10 µg QOD×3) showed no significant changes in ALT, AST, creatinine, or BUN levels, as well as no sign of toxicity in analyzing trichrome histology sections of any organ 24 h post final IV tail vein injection (FIGS. 10A and 10B). Further analysis of blood/immune cell levels showed no signs of change compared to untreated mice (FIG. 10A). Toxicological analysis was also confirmed in histological trichrome organ sections in which all treatments showed normal tissue/cell morphology. (FIG. 10B).

Example 12

Combination Therapy

Materials and Methods 1,2-distearoyl-sn-glycero-3-phosphoethanolamine-N-[methoxy (polyethyleneglycol-2000)] ammonium salt (DSPE-PEG) were purchased from NOF (Ebisu Shibuya-ku, Tokyo). Dioleoyl phosphatidic acid (DOPA) and 1,2-Dioleoyl-3-trimethylammonium-propane chloride salt (DOTAP) were purchased from Avanti Polar Lipids (Alabaster, Ala., USA). Cholesterol and protamine were purchased from Sigma-Aldrich (St. Louis, Mo., USA). All other chemicals were purchased from Sigma-Aldrich if not specifically mentioned (St. Louis, Mo., USA).

CXCL12 trap gene construction: The coding sequences of the CXCL12-binding VH and VL domains were used for assembly of the trap gene. The final sequence for the CXCL12 trap codes for a signaling peptide, VH domain, a flexible linker, VL domain, E tag, and His(6×) tag, respectively. The complete cDNA was cloned into pCDNA3.1 between NheI and XhoI sites and the accuracy was confirmed by DNA sequencing.

PDL1 trap gene construction: The coding sequences of the extracellular domain of mouse or human PD-1 and the trimerization domain of mouse or human CMP1 were used for assembly of the PD-L1 trap gene. The final sequence for the PD-L1 trap codes for a signaling peptide, the PD-L1 binding domain of PD-1, a flexible linker, a trimerization domain, E tag, and His(6×) tag, respectively. The complete cDNA was cloned into pCDNA3.1 between NheI and XhoI sites and the accuracy was confirmed by DNA sequencing.

Cell lines: Primary tumor cell line KPC98027 derived KPC pancreatic ductal adenocarcinoma mouse model (LSL-Kras$^{G12D/}$ +; LSL-Trp53$^{R172H/}$ +; Pdx-1-Cre, on C57Bl/6 background) were provided by Dr. Serguei Kozlov (National Cancer Institute, Center for Advanced Preclinical Research) and cultivated in Dulbecco's Modified Eagle Medium: Nutrient Mixture F-12 (DMEM/F12) supplemented with 10% fetal bovine serum (FBS) (Gibco) and 1% Penicillin/Streptomycin at 37° C. and 5% $CO_2$ in a humidified atmosphere. Lentivirus transfection of cell lines was performed in which KPC98027 cells were stably transfected with the vector carrying the mCherry red fluorescent protein (RFP), firefly luciferase (Luc), and the puromycin resistance gene. Stable transfected KPC98027 cells (KPC98027 RFP/Luc) were selected in the presence of puromycin.

Orthotopic allografting KPC model in mice: Sub-confluent KPC98207 (with or without RFP/Luc) cells were harvested and washed in phosphate buffered saline (PBS) just prior to implantation. Orthotopic allografting KPC model was established by orthotopic injection of 1×10$^6$ cells into the tail of pancreas. In brief, eight-week-old C57Bl/6 mice were anesthetized by IP injection of ketamine/xylazine solution and placed in supine position. A midline incision was made to exteriorize the spleen and pancreas. Using an insulin-gage syringe, 1×10$^6$ cells in 40 µL were injected into the tail of pancreas. And the abdominal wall and skin closed with 6-0 polyglycolic acid sutures. The injection site was sealed with a tissue adhesive (3M, St. Paul, Minn.) and sterilized with 70% alcohol to kill cancer cells that may have leaked out.

Antibodies: Primary antibodies, fluorescent conjugated primary and secondary used for immunostainings (IF) and flow cytometry (flow cytr) were listed in Table 3 below.

TABLE 3

Antibodies Used in the Study

| Antibodies | Company | Catalog | Application |
| --- | --- | --- | --- |
| Anti-αSMA | Abcam | Ab5694 | IF |
| Anti-CD31 | Abcam | Ab28364 | IF |
| Anti-SDF1 (CXCL12) | Abcam | Ab9797 | IF |
| Anti-PDL1 | Abcam | Ab80276 | IF |
| Ant CD8α (FITC-conjugated) | BD | 553031 | flow cyt |
| Ant CD4 (FITC-conjugated) | BD | 561828 | flow cyt |
| Anti-FOXP3 (PE-conjugated) | BD | 560408 | flow cyt |
| Anti-CD11b (FITC-conjugated) | BD | 553310 | flow cyt |
| Anti-Gr1 (Ly-6G and Ly-6C) (PE-conjugated) | BD PharmingenTM | 553128 | flow cyt |
| Anti-CD206 (PE-conjugated) | BD | | flow cyt |
| Anti-CCR7 (APC-conjugated) | BD | | flow cyt |
| APC Rat IgG2b, κ Isotype Control | BD PharmingenTM | 553991 | flow cyt |
| Anti-Rabbit IgG (Alex Fluor ® 647 Conjugate) | Cell Signaling | 4414 | IF, flow cyt |
| Goat anti-rabbit IgG-HRP | Santa Cruz | Sc-2030 | WB |
| Anti-RFP | Invitrogen | R10367 | WB |

Preparation and Characterization of LPD:

LPD were prepared through a stepwise self-assembly process based on a well-established protocols in the art. Briefly, DOTAP and cholesterol (1:1, mol/mol) were dissolved in chloroform, and the solvent was removed. The lipid film was then hydrated with distilled water to make the final concentration of 10 mmol/L cholesterol and DOTAP. Then, the liposome was sequentially extruded through 200 nm and 100 nm polycarbonate membranes (Millipore, Mass.) to form 70-100 nm unilamellar liposomes. The LPD polyplex cores were formulated by mixing 140 μL of 36 μg protamine in 5% glucose with equal volume of 50 μg plasmid (either pcDNA 3.1 as a control plasmid, or plasmids encoding CXCL12 or PDL1 trap) in 5% glucose. The mixture was incubated at room temperature for 10 min and then 60 μl cholesterol/DOTAP liposomes (10 mmol/L each) were added. Post insertion of 15% DSPE-PEG was further performed at 60° C. for 15 minutes. The size and surface charge of the NPs were determined by a Malvern ZetaSizer Nano series (Westborough, Mass.). TEM images were acquired where NPs were negatively stained using a JEOL 100 CX II TEM (JEOL, Japan).

Biodistribution and Cellular Distribution of LPD NPs:

Approximately 0.1% of hydrophobic dye DiI was incorporated into DOTAP liposomes to formulate the DiI-labeled LPD NPs. Twenty-four hour after intravenously injection of the DiI-labeled LPD NPs, mice were euthanized, major organs and tumors were collected. The distribution of LPD NPs in major organs were quantitatively visualized with IVIS® Kinetics Optical System (Perkin Elmer, CA). The excitation wavelength was set at 520 nm, while the emission wavelength was set at 560 nm. Livers and tumors were further sectioned by a cryostat (H/I Hacker Instruments & Industries, Winnsboro, S.C.) to quantify the distribution of LPD NPs within the tissues. Accumulation and distribution of NPs before or after Combo trap LPD NPs treatment in tumors were further compared and quantified (n=4).

Transient, Local, and Intra-Tumoral Cellular Distribution of Trap Protein:

Formulation of LPD NPs encapsulated pCXCL12 trap DNA, pPD-L1 trap DNA were injected (50 μg plasmid/mice) intravenously into mice bearing KPC98027 RFP/Luc allografts (Daily injection, twice in total). Both pCXCL12 trap DNA and pPD-L1 trap DNA contain His-Tag at the C-terminal end, which can be used as a tracker for the expression of the trap protein. At day 1, 3, 5 post the final injection, mice were sacrificed, major organs and tumors were collected and homogenized in RIPA buffer. Total protein concentration in the lysate was determined through a bicinchoninic acid protein assay kit (BCA Protein Assay Kit, Pierce, Rockford, Ill.). The transfection and expression efficiency of His-tag protein in organs and tumors of different time points were quantified using ELISA (Cell biolabs, INC., n=4). CXCL12 trap protein was also directly intravenously injected into mice and compared with the plasmid counterpart in biodistribution and accumulation level at the time points monitored. Mice bearing KPC98027 RFP/Luc were also given two doses daily injection of LPD NPs encapsulating pGFP DNA. Three days after final injection, tumor tissues were cyro-sectioned and processed with staining of fibroblast marker αSMA, leucocyte marker CD45 and the endothelial marker CD31. Tumor cells were pre-transfected with RFP. GFP protein expression in different cell populations within the tumor tissues were observed using a Nikon light microscope (Nikon Corp., Tokyo). The % of GFP positive cells in each cell populations were quantified using image J from 5 representative images from each type of staining. Here's an example of the calculation:

$$\% \text{ of } CD45^+ GFP \text{ cells} = \frac{\% \ CD45^+ GFP^+ \text{ Cells}}{\% \ GFP^+ \text{ Cells}}$$

Tumor Growth Inhibition, Metastasis Suppression and Survival Analysis:

Mice bearing KPC98027 RFP/Luc allografts were established as mentioned above. Treatments were initiated on day 13. Mice were then randomized into 6 group (n=5-7) as follows: Untreated group (PBS), Ctrl LPD NP (encapsulated with pcDNA3.1 backbone), CXCL12 trap/Ctrl NPs, PD-L1 trap/Ctrl NP, Combo trap NP, and free combo trap protein. Intravenous injections were performed every two days for a total of 4 doses of 50 μg per plasmid/mice. Tumor growth was monitored using IVIS® Kinetics Optical System (Perkin Elmer, CA) every five days. The increases of tumor volumes were calculated as the radiance of the intensities and standardized with the initial tumor volume (Vt/V0). Long term survival was also monitored on mice bearing the KPC98027 RFP/Luc allografts with different treatments (n=7, in each treatment groups). Mice were monitored for over two months. Kaplan-Meier curves and Median Survival were quantified and calculated using Image J. For the study of metastasis, mice bearing tumors were treated with PBS (n=5), CXCL12 trap NPs (n=4), PD-L1 trap NPs (n=4), and Combo traps (n=5). One month after inoculation, mice were injected with 10 mg/mL luciferin and sacrificed. Major organs and tumors were then extracted and placed in solution of luciferin (5 m/mL) and imaged for bioluminescence.

Major organs were then fixed and processed with H&E staining to observe the pathology of tumor metastasis in each organs.

ELISpot Assay for IFN-γ Production:

Re-stimulation of spleen cells for mice bearing KPC98027 or KPC98027 RFP/Luc allografts was performed as described previously. In brief, 13 days after tumor inoculation, spleens in healthy mice, mice bearing KPC98027, and KPC98027 RFP/Luc were harvested and separated into single cell suspensions in a sterile condition. Following the BD™ ELISPOT assay instructions, cells were seeded at $2\times10^5$ per well in a capture antibody coated 96 well plate. The single cell suspensions were then co-cultured with either inactivated KPC98027, KPC98027 RFP/Luc cell lysates or healthy mice spleen cell lysates at 37° C. for 40 h. At the due time, cells were removed by several washing steps. The production of INF-γ was measured by detection antibody addition followed by enzyme conjugate magnification. Red dots signals were developed with a BD ELISpot substrate set and calculated manually.

Quantitative Real-Time PCR (qPCR) Assay:

Total RNA was extracted from the tumor tissues using an RNeasy kit (Qiagen, Valencia, Calif.). cDNA was reverse-transcribed using the First-Strand Synthesis System for RT-PCR (Invitrogen, Grand Island, N.Y.). One hundred ng of cDNA was amplified with the Taqman Universal Probes Supermix system (Bio-rad, Hercules, Calif.). All the mouse-specific primers for RT-PCR reactions are listed in Table 4 (Life Technologies, Grand Island, N.Y.). GAPDH was used as the endogenous control. Reactions were conducted using the 7500 Real-Time PCR System and the data were analyzed with the 7500 Software.

TABLE 4

| Primer | Applied Biosystems/Ref |
|---|---|
| Mouse IFN-γ | Mm01178820_m1 |
| Mouse IL12 α | Mm00446190_m1 |
| Mouse TNF-a | Mm00443260_g1 |
| Mouse IL4 | Mm00441242_m1 |
| Mouse IL10 | Mm00441242_m1 |
| Mouse GAPDH | Mm99999915_g1 |

Flow Cytometry Assay:

Tumor-infiltrating immune lymphocytes were analyzed by flow cytometry. In brief, tissues were harvested and digested with collagenase A and DNAase at 37° C. for 40-50 min. After red blood cell lysis, cells were dispersed with 1 mL of PBS. For intracellular cytokine staining, the cells from the tissues were penetrated with penetration buffer (BD) following the manufacturer's instructions. Different immune lymphocytes ($5\times10^6$/mL) were stained with the fluorescein-conjugated antibodies mentioned in the previous section.

Immunofluorescence Staining:

After the deparaffinizing step, antigen retrieval and permeabilization, tissue sections were blocked in 1% bovine serum albumin (BSA) at room temperature for 1 h. Primary antibodies conjugated with fluorophores (BD, Franklin Lakes, N.J.) were incubated overnight at 4° C. and nuclei were counterstained with DAPI containing mounting medium (Vector Laboratories Inc., Burlingame, Calif.). All antibodies were diluted according to the manufacturer's manual. Images were taken using fluorescence microscopy (Nikon, Tokyo, Japan). Three randomly selected microscopic fields were quantitatively analyzed using Image J software.

TUNEL Assay:

TUNEL assays were carried out using a DeadEnd Fluorometric TUNEL System (Promega, Madison, Wis.) according to the manufactures instructions. Cell nuclei that were fluorescently stained with FITC (green) were defined as TUNEL-positive nuclei. Slides were cover-slipped with 4,6-diaminidino-2-phenyl-indole (DAPI) Vectashield (Vector laboratories, Burlingame, Calif.). TUNEL-positive nuclei were monitored using fluorescence microscopy (Nikon, Tokyo, Japan). Three randomly selected microscopic fields were quantitatively analyzed using Image J.

H&E Morphology Evaluation and Blood Chemistry Analysis:

Four days after the final treatment of the tumor inhibition study, mice with different treatments were all subjected to a toxicity assay. Both whole blood and serum were collected. Whole blood cellular components were counted and compared. Creatinine, blood urea nitrogen (BUN), serum aspartate aminotransferase (AST) and alanine aminotransferase (ALT) in the serum were assayed as indicators of renal and liver function. Organs including the heart, liver, spleen, lungs and kidneys were collected and fixed for H&E staining by UNC histology facility to evaluate the organ-specific toxicity.

Statistical Analysis:

A two-tailed Student's t-test or a one-way analysis of variance (ANOVA) were performed when comparing two groups or larger than two groups, respectively. Statistical analysis was performed using Prism 5.0 Software. Differences were considered to be statistically significant if the P-value was less than 0.05.

Transient and Local Distribution and Expression of pDNA (Trap or GFP) within Tumor Microenvironment Post pDNA LPD Administration LPD preferentially deliver macromolecules, including plasmid DNA, siRNA, mRNA to tumors for anticancer therapy. To prepare LPD, plasmid DNA (pDNA) was condensed with cationic protamine to form a slightly anionic complex core. The core was further coated with the preformulated cationic liposomes (DOTAP, Cholesterol and DSPE-PEG). TEM images confirm the size of LPD (~70 nm) and indicate its spherical shape and homogenous distribution (FIG. 14A). Approximately 0.1% of DiI was incorporated into the lipid membrane of LPD as an in vivo tracker for evaluating the biodistribution of DiI-labeled LPD.

Desmoplastic KPC pancreatic tumor model was generated from orthotopic injection of the primary KPC98027 cells into the tail of the pancreas. DiI-labeled LPD NPs were intravenously injected into mice. Twenty-four hour after injection, NPs accumulation in major organs were analyzed. Consistent with other NPs of similar size, liver were the major organs taken up LPD NPs (FIG. 14B). Besides liver, tumor is another major NP accumulation site (FIG. 14B). Tissue cyrosection data suggest the scattered distribution of DiI-labeled NP over all the liver tissues, with more than 40% of liver cells were labelled (FIG. 14C). In contrast, only less than 25% of tumor cells took up DiI NPs, and the distribution of NPs within tumors were heterogeneous and uneven, mostly due to the high interstitial fluidic pressure (IFP) and thick extracellular matrix within pancreatic tumor microenvironment. The distribution of GFP protein in liver and tumor were further compared as an indication of the transfection efficiency of the LPD delivered plasmid (pGFP). Despite the higher accumulation of NPs in liver, the expression of GFP is extremely low in comparison to tumors (FIG.

14C). This can be attributed to that, the Kupffer cells, which localized in vicinity of blood vessels, nonspecifically phagocytosed the LPD NPs. The transfection efficiency of plasmid in Kupffer cells are relatively low. Therefore, our results demonstrate that LPD encapsulating plasmid can be locally delivered and expressed within the KPC pancreatic cancer.

Immunofluorescence staining was performed to determine the LPD accumulation in various cell populations within the bulk tumor mass (FIG. 14D). Stable transgene expression of RFP and fluorophore-conjugated antibody against mouse αSMA, CD45 and CD31 defined tumor cells, fibroblasts, leukocytes and endothelial populations, respectively. Results show that tumor cells are one of the major cell populations that take up NPs; more than 60% of the tumor cells expressed GFP. In addition, more than ~30% of fibroblasts take up LPD four days post intravenous injection of LPD pGFP (two doses, daily), accounting for ~30% of the total GFP-positive cells. In contrast, the expression of GFP in leucocytes and endothelial are negligible, confirming that fibroblasts are the major stroma off-target sites for NP distribution and plasmid expression. Due to the adjacent distribution of fibroblasts to tumor cells, fibroblasts' expression of the secreted trap would benefit their neighboring effect to tumor cells rather than as an off-targeting site that diminishes the therapeutic concentration of drugs approaching tumor cells.

Figure 14E:
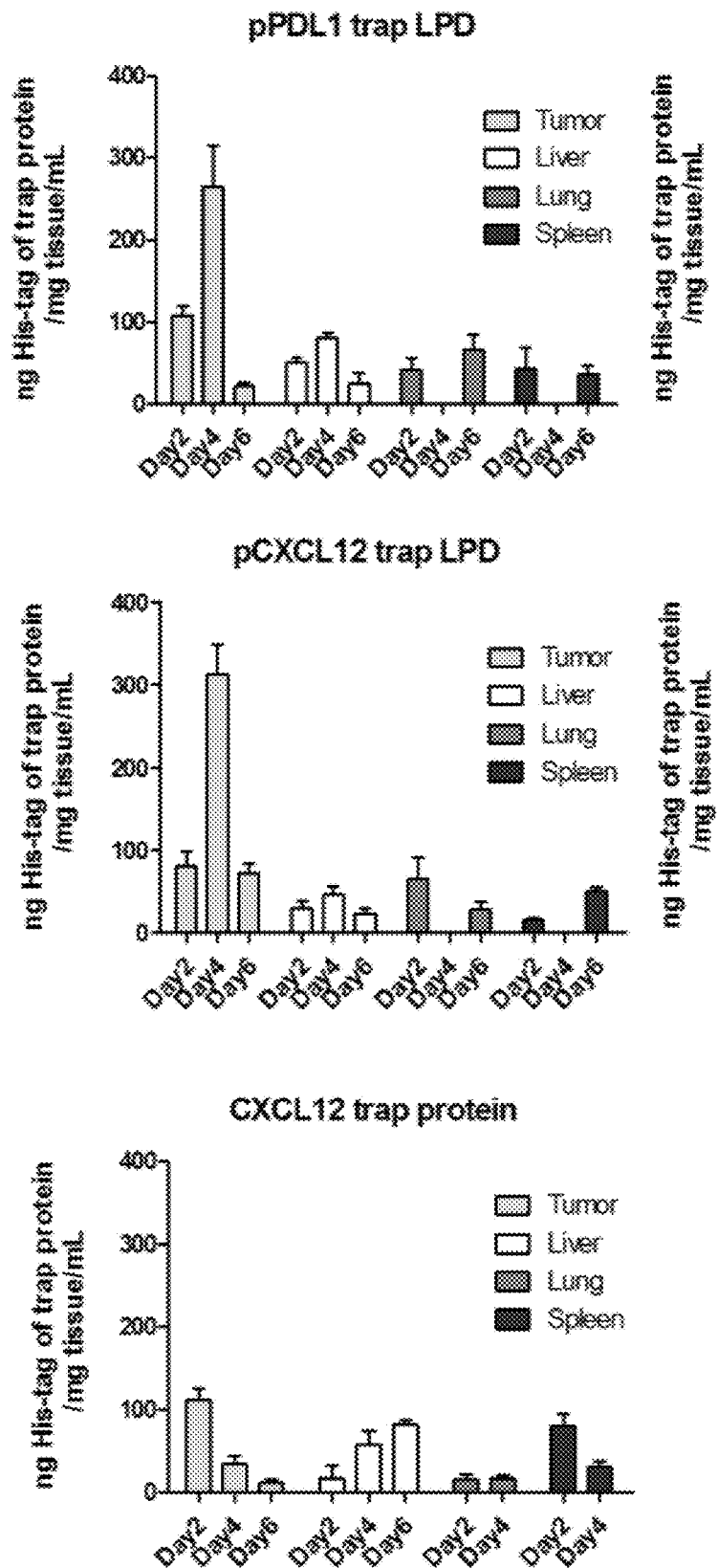

Subsequently, distribution and expression of the trap protein (either PDL1 or CXCL12) was assessed through ELISA via the targetable His-tag incorporated into the C-terminus of the trap (FIG. 14E). The pure trap protein (CXCL12 trap) was also injected and compared. After two daily doses of the trap plasmid NP and trap protein, the mice were sacrificed on days 2, 4, 6, and demonstrated of transient plasmid transfection and expression in the tumor (FIG. 14E) rather than other organs. In contrast, protein trap was cleared rapidly, with significantly lower concentration in all the organs at time monitored.

These results demonstrate that LPD vector allows for preferential transient expression of trap plasmid within the tumors, in particular, fibroblasts and tumor cells, with minimal expression in any other organs. We report that the tumor expression holds transient properties in which expression is found to last up to 4 days post trap plasmid injection (FIG. 14E).

Combined Therapy with LPD NP Encapsulating pCXCL12 Trap DNA and LPD NP Encapsulating pPD-L1 Trap DNA Improved Antitumor Response Against KPC Allografts and Suppressed Metastasis Previous study by Feig et al. suggested that inhibiting the interaction of CXCL12 with CXCR4 uncovers the antitumor activity of anti PD-L1 (Feig et al., Targeting CXCL12 from FAP-expressing carcinoma-associated fibroblasts synergizes with anti-PD-L1 immunotherapy in pancreatic cancer, *PNAS*, 2013 Dec. 10; 110(50):20212-7). Due to the local and transient expression feature of plasmid delivered by LPD vector, plasmid encoding PD-L1 trap and CXCL12 trap were encapsulated into LPD vector, separately, and administered as combined regimens for KPC pancreatic cancer treatment. KPC98027 RFP/Luc was orthotopically inoculated into the tail of the pancreas. The dosing schedule of LPD NPs is presented in FIG. 15A. PBS, LPD NPs encapsulating pcDNA3.1 backbone (Ctrl NP), free combo trap proteins were set as controls. Tumor volume correlated from the number of photons emitted from the tumor were assessed, A) and quantified. B). Results demonstrated that both CXCL12 trap NPs and PDL1 trap NPs monotherapy showed minimal antitumor efficacy at low doses (FIG. 15D). Antitumor efficacy for the monotherapy increased slightly but only partial effective while increasing the dose (FIG. 15E). On the contrary, the combo trap NP group significantly inhibited tumor growth (P<0.01) compared to the PBS group. Tumor weight of the combo group decreased dramatically both at low and high doses (FIG. 15E). Meanwhile, the free combo trap protein only showed slight but not significant anti-cancer effect, suggesting the advantages of using plasmid rather than protein (FIGS. 15A and 15B). Further, in an overall survival analysis after the final day of treatment, median survival was enhanced in the combo trap NP therapy (63.5 days) as compared to other treatment groups (40.5, 49, 47, 50 days for PBS, Ctrl NP, CXCL12 trap NP and PDL1 trap NP groups, respectively; FIG. 15C), conveying not only a potent therapeutic effect but also a long-lasting overall response. This is consistent with the observation by Feig et al. who had used a combination of a CXCR4 antagonist and anti-PD-L1 antibody to inhibit the KPC tumor growth (Feig et al., Targeting CXCL12 from FAP-expressing carcinoma-associated fibroblasts synergizes with anti-PD-L1 immunotherapy in pancreatic cancer, *PNAS*, 2013 Dec. 10; 110(50):20212-7). Data in FIG. 15 suggested that the combined CXCL12 trap NPs with PD-L1 trap NPs indeed exhibited superior antitumor efficacy in the desmoplastic KPC tumor-bearing mouse model.

Further, metastasis of tumors in major organs were monitored one month after the inoculation of KPC allografts. Consistent with the patients bearing pancreatic ductal adenocarcinoma (PDAC), liver and lung are the major metastasis sites for orthotopic KPC models (FIG. 16A). Tumors were also observed in spleen and kidney due to invasion within peritoneal cavity. Histology shows large nodules of metastasis in the lung, spleen and liver of the control group (FIG. 16B). Monotherapy can slightly suppressed tumor metastasis, only the combo therapy was able to significantly inhibit or even abrogate metastasis (FIGS. 16A and 16B). Thus, it was apparent that the combo trap NP strategy was capable of reducing tumor metastasis.

Enhanced T Cells Infiltration into Tumor Microenvironment Explains the Superior Anti-Tumor Effect of the Combo Trap NPs Cancer cell specific T cell response was reported in KPC model previously, and was further confirmed herein by the ELISpot Assay (FIG. 17A). FIG. 17A shows INF-γ ELISpot assay data using splenocytes from tumor bearing animals. Extract from KPC cells, with or without the transfected RFP/Luc markers, could stimulate the splenocytes to secret IFN-γ, but not the extracts from normal splenocytes. The data indicate that KPC tumor could induce tumor specific T-cell response. The immune response seen in the tumor bearing mice was not directed to the luciferase or the red fluorescence markers, but to the yet-to-be identified tumor associated antigens. However, the absence of any significant increase in IFN-γ-secreting CD8+ T cells from the spleens of PD-L1 trap NPs and CXCL12 trap NPs (either mono- or combo-therapy) treated mice indicates that the antitumor effect of combo trap NPs was not accomplished by enhanced systemic priming of cancer-specific CD8+ T cells (FIG. 17B). Since the ELISpot activities were relatively weak (FIGS. 17A and 17B), a vaccine which can boost the cancer-specific cytotoxic T-lymphocyte activity would further enhance the therapeutic activity of the traps.

Figure 18A:
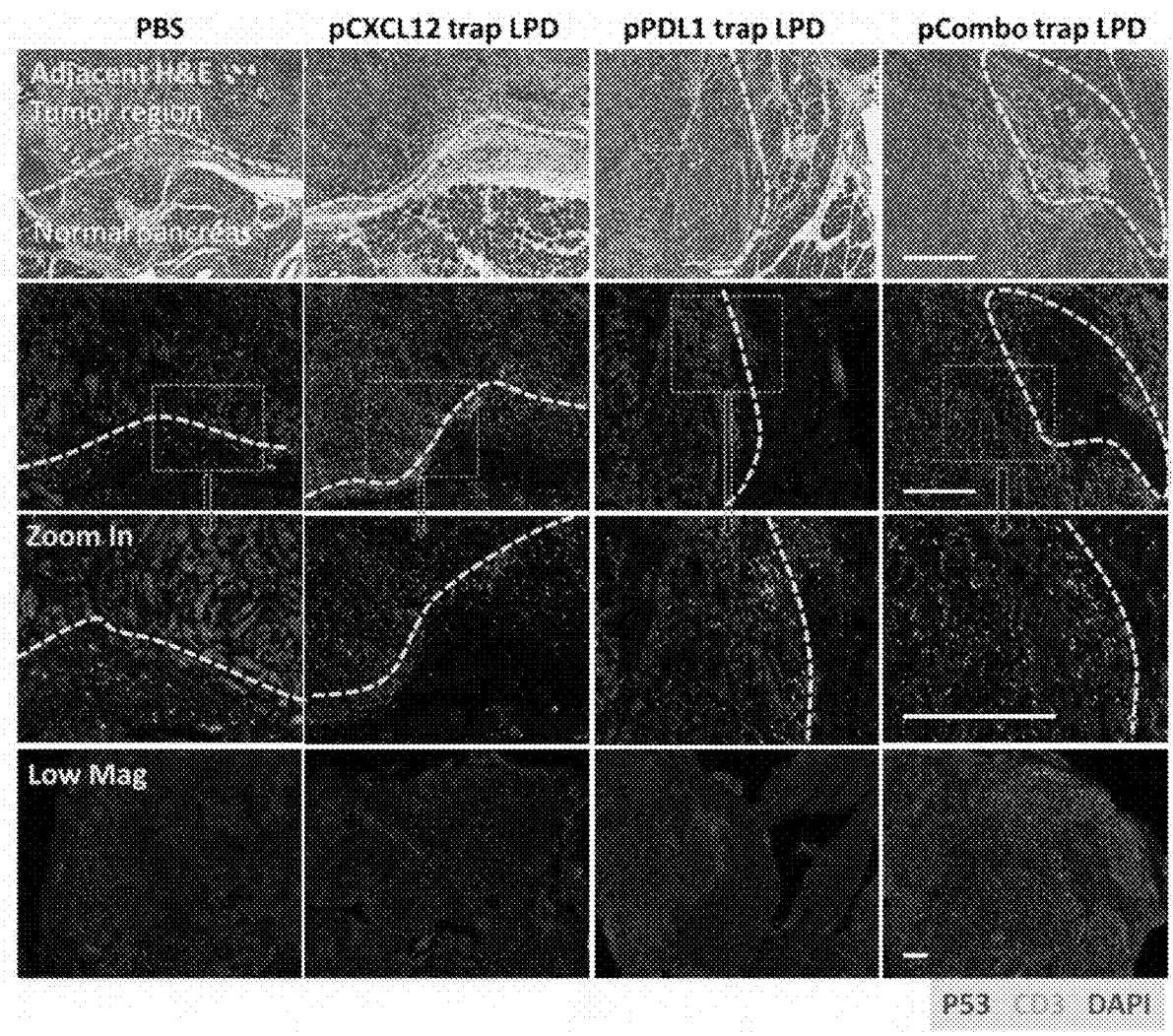

To determine if the immunotherapeutic effect was caused by enhanced T-cell accumulation among cancer cells, the distribution of T-cells (CD3$^+$) in the pancreas was shown by immunofluorescence (FIG. 18A). It was shown that T-cells were mostly located in the border between tumor and normal pancreas tissue in the PBS control. Small amounts of T-cells were found in the tumor region, but they were located in the stroma area. The pancreas from animals treated with PD-L1 trap showed some penetration of T-cells into the tumor region, but the ones treated with CXCL12 trap NP (with or without the PD-L1 trap NP) showed extensive T-cell infiltration into the tumor region. The localization of T-cells in the tumor region is quantified in FIG. 18B. The tumors were further collected and dispersed into single cells. CD3$^+$CD8$^+$ cells were analyzed with flow cytometry (FIG. 18C). Results, again, confirms that the CD8$^+$ T-cells were significantly increased in tumors of the combo trap NPs treated mice. Thus, we conclude that, CXCL12, rather than PD-L1, trap was the major factor that enhanced T-cell infiltration. Further, the role of CD8$^+$ T-cells in the combo trap NPs therapy were evaluated by depleting CD8$^+$ T-cells using monoclonal antibody against CD8 (FIGS. 18D and 18E). It was shown that combo trap NPs significantly slowed tumor growth, but not when CD8 T cells were removed. Collectively, enhanced T-cells infiltration into tumor microenvironment is one major reason resulting in the superior antitumor effect of the combo trap NPs.

Changes of Tumor-Infiltrating Immune Cells and Cytokine Levels in Tumor Microenvironment To further elucidate why the combo trap NP strategy could efficiently improve T cell infiltration and accumulation around tumor cells, we then evaluated the changes of the related distinct myeloid subsets and cytokines in the tumor microenvironment after different trap NP treatments, which, partake in a complicated interplay network to mask CD8+ T-cell anti-tumor activity.

Figure 19A:
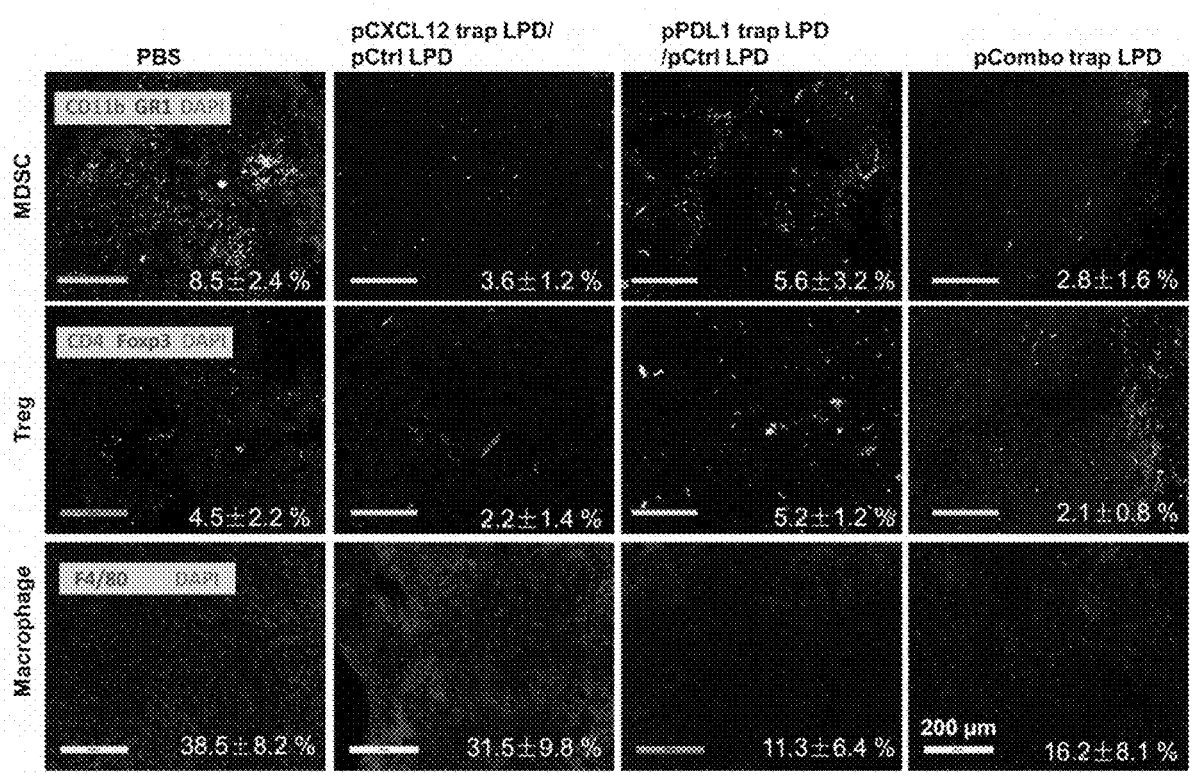
Figure 19B:
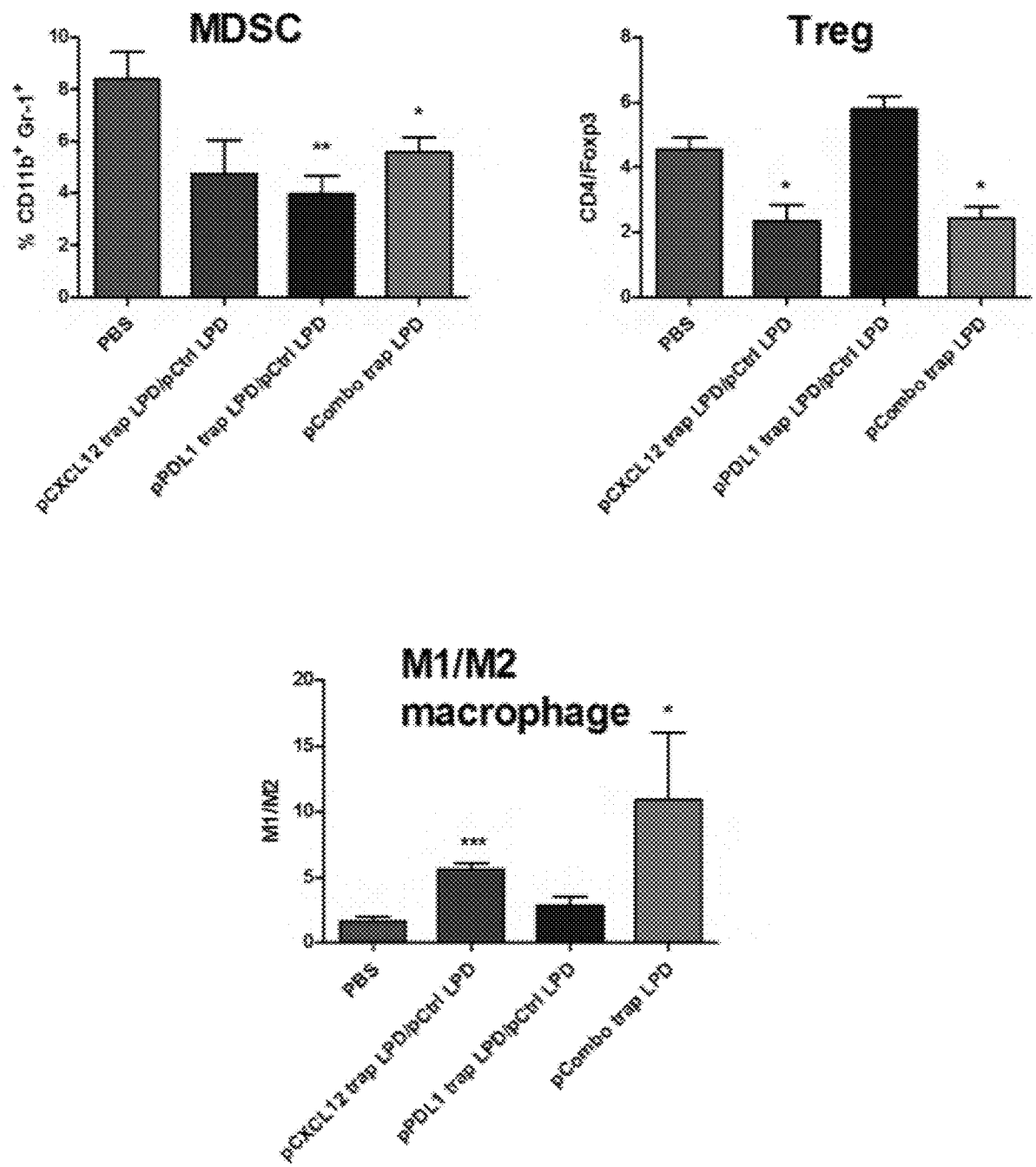

Since immunosuppressive subsets, such as regulatory T cells (Tregs), myeloid-derived suppressor cells (MDSCs), and tumor associated macrophages (TAMs) are the dominate myeloid infiltrates within the desmoplastic PDAC models, we examine the accumulation of these immune suppressive cells within the tumor microenvironments by both flow cytometry and immunostaining of tumor sections. MDSC were checked as the first regulatory subset. As shown in FIGS. 19A and 19B, the percentages of MDSC in the trap only group (either CXCL12 trap and PDL1 trap) and combination group were much lower than the control groups. Since MDSC can establish immune tolerance by induction of Treg development, the blockage of MDSC may lead to inhibition of Treg. We therefore detected the percentage of Treg in tumor tissues, as shown in FIGS. 19A and 19B. Consistent with the trends of MDSC, the CXCL12 trap NP treated group and combination group exhibited fewer Treg cells than the control groups. However, PD-L1 trap NPs slightly increased T cell infiltration, which was also observed by Feig. et al using PD-L1 check point inhibitor (Feig et al., Targeting CXCL12 from FAP-expressing carcinoma-associated fibroblasts synergizes with anti-PD-L1 immunotherapy in pancreatic cancer, PNAS, 2013 Dec. 10; 110(50):20212-7). This is most likely due to the fact that PD-L1/PD1 interaction negatively regulates Treg proliferation and activation by controlling STAT-5 phosphorylation. Macrophage, is another important component of the suppressive tumor immune microenvironment. As shown in FIG. 19A, both PD-L1 monotherapy and combo therapy can significantly decreased the accumulated macrophages, and efficiently turned the macrophages favorable to M1 state (FIG. 19B). Thus, there was a significant remodeling of the suppressive TME by the traps in favor of therapy.

To correlate the observation of immune suppressive subsets with the level of CXCL12 and PD-L1, we next test the neutralizing efficiency of the intravenously delivered trap NPs (FIGS. 20A and 20B). It was shown that CXCL12 trap NPs, but not PD-L1 trap NPs can efficiently neutralize the intratumoral secreted CXCL12, leading to a substantial decrease of the protein detected by an anti-CXCL12 primary antibody, and subsequently inhibit MDSC and Treg infiltration through CXCL12/CXCR4 mediated interaction. Whereas, the overall PD-L1 level was not only diminished by applying PD-L1 trap NPs but also partially affected by CXCL12 trap treatment. This is likely due to the fact that myeloid cells can induce the expression of PD-L1 in tumor cells in an epidermal growth factor receptor (EGFR)/mitogen-activated protein kinases (MAPK)-dependent manner. Therefore, reduced recruitment of myeloid cells by CXCL12 decreased the level of PD-L1. Efficient depletion of MDSC and Treg cells subsequently facilitate the infiltration of effector T cells within the tumor microenvironment, explaining the superior antitumor efficacy.

We then monitored the cytokine levels in the local tumor tissue in order to see whether or not the combo group could reverse the suppressive microenvironment as shown by cytokine levels (FIG. 21). IL-4 and IL-10 are known as Th-2 cytokines which are critical for immunosuppression to promote cancer metastasis. Meanwhile, IFN-γ, IL-12α and TNF-α (considered as Th-1 cytokines) are the cytokines secreted by cytotoxic T cells that facilitate T cell killing and fight against tumor progression. In the CXCL12 trap NP monotherapy group, though IL-12α and IFN-γ increased and IL-4 decreased substantially, IL-10 still increased suggesting a slightly suppressive microenvironment. Similarly, in the PD-L1 trap NP group, despite the increased level of the overall Th1 cytokines, suppressive cytokines remain consistently high. However, in the combination group, both IL-4 and IL-10 were significantly decreased. Meanwhile, IL-12α, TNF-α and IFN-γ were dramatically increased, indicating a M2 to M1 phonotype switch to an immune-stimulating microenvironment. This would consequently activate the recruitment of lymphocytes to act as scavengers, facilitate tumor antigen presentation and result in an intensified cytotoxic T cell mediated, tumor-specific killing.

Changes of the Tumor Vessel and Tumor Associated Fibroblast

Tumor associated fibroblasts (TAFs) and angiogenesis impede the infiltration of cytotoxic T lymphocytes to the tumor tissue. The effect of trap NPs on TAFs was investigated by staining for α-smooth muscle actin (αSMA), a marker of TAFs, and CD31, a marker for the vasculature. The density and mean florescence were detected by fluorescence microscopy. Five microscopic fields were randomly selected for analysis. As shown in FIG. 22A, the density of CD31 in both mono- and combo-groups were lower than that of the control group. The combo group, in particular, demonstrates a substantial blood vessel normalization (FIG. 22B). The blood vessel was decompressed significantly, and subsequently increased NP perfusion and extended distribution after multiple combo trap treatments (FIG. 23). The normalized blood vessel is a result of released IFP, which mostly due to decreased stroma and cell density.

Therefore, we next evaluate the density of fibroblasts. It was shown that the combo trap NP group exhibited the lowest density of αSMA. Interestingly, we found that only CXCL12 trap, but not PD-L1 trap results in the decreasing of αSMA in both the monotherapy and combo therapy (FIGS. 22A and 22B). Consistently, we noted that collagen, one of the major extracellular matrix secreted by fibroblasts were decreased dramatically in both CXCL12 trap NP treated group and combo trap NPs (FIG. 24). Therefore, we conclude that CXCL12 trap NPs not only increased T-cell infiltration, uncovered the antitumor efficacy of PD-L1 trap by tuning the suppressive immune microenvironment, but also by depleting fibroblasts and collagen content. Since fibroblasts are considered as major source of CXCL12 in KPC tumor microenvironment, a CXCR4-mediated autocrine loop may explain the decreasing of fibroblasts and remodeling of the stroma.

Toxicity Evaluation for the Different Treatments and Blood Chemistry Analysis

The results of the toxicological pathology evaluation demonstrated that there were not any noticeable morphological changes in the heart, liver, spleen, lungs and kidneys for monotherapy and combo trap NPs (FIG. 25). However, cellular vacuolization, desquamated-degenerative cells and focal necrosis were detected in liver and renal tissues of mice in PBS and Ctrl NP groups, suggesting severe liver and kidney damages, which were most likely due to the burden of tumors. Consistently, the serum biochemical value analysis demonstrated that liver (AST and ALT) or kidney (creatinine and BUN) toxicity caused by tumor progression in these two groups but not the combo trap NPs treated mice (Table 6). In addition, the whole blood cell counts (Table 5) remain constant within normal ranges for all the groups, suggesting no systemic anemia or inflammation occurred after treatments.

TABLE 5

Whole cell counts of mice treated with different groups

| Sample# | WBC | LYMF | GRAN | MONO | HCT | RBC | HGB | PLT |
|---|---|---|---|---|---|---|---|---|
| Health | 5.8 ± 0.1 | 3.8 ± 0.6 | 1.1 ± 0.3 | 0.8 ± 0.3 | 46.2 ± 3.1 | 9.8 ± 1.0 | 14.9 ± 1.3 | 1036.0 ± 92.7 |
| PBS | 5.5 ± 0.7 | 3.7 ± 0.4 | 1.3 ± 0.2 | 0.6 ± 0.1 | 42.7 ± 0.8 | 9.5 ± 0.2 | 14.0 ± 0.4 | 1159.5 ± 34.7 |
| Protein trap | 6.3 ± 0.2 | 4.0 ± 0.6 | 1.6 ± 0.4 | 0.7 ± 0.1 | 46.8 ± 0.3 | 10.2 ± 0.1 | 14.9 ± 0.3 | 1220.5 ± 46.7 |
| Combo trap NP | 5.8 ± 1.2 | 3.1 ± 0.7 | 2.1 ± 0.3 | 0.6 ± 0.2 | 41.7 ± 0.7 | 9.2 ± 0.2 | 13.6 ± 0.3 | 1182.3 ± 25.8 |
| Ctrl NP | 5.8 ± 1.2 | 1.4 ± 0.2 | 1.8 ± 0.9 | 0.6 ± 0.3 | 38.1 ± 1.9 | 8.6 ± 0.3 | 12.5 ± 0.6 | 951.0 ± 13.1 |

* Numbers in bold indicate that the value is over the normal range

TABLE 6

Serum biochemical value analysis

| Sample# | BUN mg/dL | Creatinine mg/dL | AST U/L | ALT U/L |
|---|---|---|---|---|
| Health | 22.0 ± 2.5 | 0.2 ± 0.0 | 186.7 ± 30.2 | 24.7 ± 10.6 |
| PBS | 24.0 ± 4.8 | 0.4 ± 0.1 | 360.0 ± 58.8 | 68.0 ± 3.6 |
| Protein trap | 33.0 ± 2.5 | 0.2 ± 0.0 | 134.0 ± 8.2 | 21.0 ± 8.9 |
| Combo trap NP | 26.0 ± 2.5 | 0.2 ± 0.0 | 173.3 ± 23.1 | 28.0 ± 8.6 |
| Ctrl NP | 30.0 ± 0.2 | 0.4 ± 0.0 | 406.0 ± 124.1 | 74.0 ± 4.8 |

* Numbers in bold indicate that the value is over the normal range

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A trimer formed from three fusion polypeptides, wherein each fusion polypeptide comprises a PD-1 extracellular domain, a flexible linker, and a trimerization domain, said trimer capable of binding a protein that interacts with the PD-1 extracellular domain, including PD-L1, PD-L2, and CD80, wherein the fusion polypeptide has a sequence with at least 90% identity to SEQ ID NO: 26.

2. A trimer formed from three fusion polypeptides, wherein each fusion polypeptide comprises a PD-1 extracellular domain, a flexible linker, and a trimerization domain, said trimer capable of binding a protein that interacts with the PD-1 extracellular domain, including PD-L1, PD-L2, and CD80, wherein the fusion polypeptide is encoded by a nucleic acid sequence with at least 70% sequence identity to SEQ ID NO: 25.

3. The trimer of claim 1, wherein the fusion polypeptide has a sequence which is SEQ ID NO: 26.

4. The trimer of claim 2, wherein the fusion polypeptide is encoded by a nucleic acid sequence which is SEQ ID NO: 25.

5. A trimer formed from three fusion polypeptides, wherein each fusion polypeptide comprises a PD-1 extracellular domain, a flexible linker, and a trimerization domain, said trimer capable of binding a protein that interacts with the PD-1 extracellular domain, including PD-L1, PD-L2, and CD80, wherein the trimerization domain has a sequence which is SEQ ID NO: 41.

* * * * *

SEQUENCE LISTING

<160> NUMBER OF SEQ ID NOS: 66

<210> SEQ ID NO 1
<211> LENGTH: 175
<212> TYPE: PRT
<213> ORGANISM: Artificial sequence
<220> FEATURE:
<223> OTHER INFORMATION: CXCL12-Trap-hSDA-1

<400> SEQUENCE: 1

```
Met Lys Trp Val Thr Phe Ile Ser Leu Leu Phe Leu Phe Ser Ser Ala
1               5                   10                  15

Tyr Ser Gly Ser Gln Val Gln Leu Leu Glu Ser Gly Gly Gly Leu Val
            20                  25                  30

Gln Pro Gly Gly Ser Leu Arg Leu Ser Cys Ala Ala Ser Gly Val Lys
        35                  40                  45

Val Ser Ala Lys Asn Met Ala Trp Val Arg Gln Ala Pro Gly Lys Gly
50                  55                  60

Leu Glu Trp Val Ser Ser Ile Asn Asn Arg Asp Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Gly Arg Arg Arg Thr Ala Asn Phe Arg Tyr
        115                 120                 125

Trp Gly Gln Gly Thr Leu Val Thr Val Ser Ser Gly Gly Gly Gly Ser
        130                 135                 140

Gly Gly Gly Gly Ser Ala Ala Gly Ala Pro Val Pro Tyr Pro
145                 150                 155                 160

Asp Pro Leu Glu Pro Arg Gly Gly Ser His His His His His
                165                 170                 175

<210> SEQ ID NO 2
<211> LENGTH: 119
<212> TYPE: PRT
<213> ORGANISM: Artificial sequence
<220> FEATURE:
<223> OTHER INFORMATION: VH domain of CXCL12-Trap-hSDA-1

<400> SEQUENCE: 2

Gln Val Gln Leu Leu Glu Ser Gly Gly Gly Leu Val Gln Pro Gly Gly
1               5                   10                  15

Ser Leu Arg Leu Ser Cys Ala Ala Ser Gly Val Lys Val Ser Ala Lys
            20                  25                  30

Asn Met Ala Trp Val Arg Gln Ala Pro Gly Lys Gly Leu Glu Trp Val
        35                  40                  45

Ser Ser Ile Asn Asn Arg Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Arg Arg Arg Thr Ala Asn Phe Arg Tyr Trp Gly Gln Gly
            100                 105                 110

Thr Leu Val Thr Val Ser Ser
        115

<210> SEQ ID NO 3
<211> LENGTH: 10
<212> TYPE: PRT
<213> ORGANISM: Artificial sequence
<220> FEATURE:
<223> OTHER INFORMATION: CDR-H1 of CXCL12-Trap-hSDA-1

<400> SEQUENCE: 3

Gly Val Lys Val Ser Ala Lys Asn Met Ala
```

<210> SEQ ID NO 4
<211> LENGTH: 17
<212> TYPE: PRT
<213> ORGANISM: Artificial sequence
<220> FEATURE:
<223> OTHER INFORMATION: CDR-H2 of CXCL12-Trap-hSDA-1

<400> SEQUENCE: 4

```
Ser Ile Asn Asn Arg Asp Gly Ser Thr Tyr Tyr Ala Asp Ser Val Lys
1               5                   10                  15
Gly
```

<210> SEQ ID NO 5
<211> LENGTH: 10
<212> TYPE: PRT
<213> ORGANISM: Artificial sequence
<220> FEATURE:
<223> OTHER INFORMATION: CDR-H3 of CXCL12-Trap-hSDA-1

<400> SEQUENCE: 5

```
Arg Arg Arg Arg Thr Ala Asn Phe Arg Tyr
1               5                   10
```

<210> SEQ ID NO 6
<211> LENGTH: 176
<212> TYPE: PRT
<213> ORGANISM: Artificial sequence
<220> FEATURE:
<223> OTHER INFORMATION: CXCL12-Trap-hSDA-2

<400> SEQUENCE: 6

```
Met Lys Trp Val Thr Phe Ile Ser Leu Leu Phe Leu Phe Ser Ser Ala
1               5                   10                  15

Tyr Ser Gly Ser Gln Val Gln Leu Glu Ser Gly Gly Gly Leu Val
                20                  25                  30

Gln Pro Gly Gly Ser Leu Arg Leu Ser Cys Ala Ala Ser Gly Phe Lys
            35                  40                  45

Ile Asn Asn Lys Val Met Ala Trp Val Arg Gln Ala Pro Gly Lys Gly
        50                  55                  60

Leu Glu Trp Val Ser Thr Ile Gln Lys Arg Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Glu Ser Ala Arg Thr Ala Asp Lys Leu Gly
        115                 120                 125

Tyr Trp Gly Gln Gly Thr Leu Val Thr Val Ser Ser Gly Gly Gly
    130                 135                 140

Ser Gly Gly Gly Gly Ser Ala Ala Ala Ala Pro Val Pro Tyr
145                 150                 155                 160

Pro Asp Pro Leu Glu Pro Arg Gly Gly Ser His His His His His
                165                 170                 175
```

<210> SEQ ID NO 7
<211> LENGTH: 120
<212> TYPE: PRT
<213> ORGANISM: Artificial sequence
<220> FEATURE:

<223> OTHER INFORMATION: VH domain of CXCL12-Trap-hSDA-2

<400> SEQUENCE: 7

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Lys Ile Asn Asn Lys
            20                  25                  30

Val Met Ala Trp Val Arg Gln Ala Pro Gly Lys Gly Leu Glu Trp Val
        35                  40                  45

Ser Thr Ile Gln Lys Arg Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Ala Arg Thr Ala Asp Lys Leu Gly Tyr Trp Gly Gln
            100                 105                 110

Gly Thr Leu Val Thr Val Ser Ser
        115                 120

<210> SEQ ID NO 8
<211> LENGTH: 10
<212> TYPE: PRT
<213> ORGANISM: Artificial sequence
<220> FEATURE:
<223> OTHER INFORMATION: CDR1-H1 of CXCL12-Trap-hSDA-2

<400> SEQUENCE: 8

Gly Phe Lys Ile Asn Asn Lys Val Met Ala
1               5                   10

<210> SEQ ID NO 9
<211> LENGTH: 17
<212> TYPE: PRT
<213> ORGANISM: Artificial sequence
<220> FEATURE:
<223> OTHER INFORMATION: CDR1-H2 of CXCL12-Trap-hSDA-2

<400> SEQUENCE: 9

Thr Ile Gln Lys Arg Gly Gly Ser Thr Tyr Tyr Ala Asp Ser Val Lys
1               5                   10                  15

Gly

<210> SEQ ID NO 10
<211> LENGTH: 11
<212> TYPE: PRT
<213> ORGANISM: Artificial sequence
<220> FEATURE:
<223> OTHER INFORMATION: CDR3-H3 of CXCL12-Trap-hSDA-2

<400> SEQUENCE: 10

Glu Ser Ala Arg Thr Ala Asp Lys Leu Gly Tyr
1               5                   10

<210> SEQ ID NO 11
<211> LENGTH: 177
<212> TYPE: PRT
<213> ORGANISM: Artificial sequence
<220> FEATURE:
<223> OTHER INFORMATION: CXCL12-Trap-hSDA-3

<400> SEQUENCE: 11

Met Lys Trp Val Thr Phe Ile Ser Leu Leu Phe Leu Phe Ser Ser Ala
1               5                   10                  15

Tyr Ser Gly Ser Gln Val Gln Leu Leu Glu Ser Gly Gly Gly Leu Val
            20                  25                  30

Gln Pro Gly Gly Ser Leu Arg Leu Ser Cys Ala Ala Ser Gly Asp Ser
        35                  40                  45

Phe Thr Thr Lys Asn Met Ala Trp Val Arg Gln Ala Pro Gly Lys Gly
    50                  55                  60

Leu Glu Trp Val Ser Ala Ile Ser Lys Arg Ser Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Gly Leu Thr Gln Arg His Gly His Ala Lys Leu
        115                 120                 125

Lys Tyr Trp Gly Gln Gly Thr Leu Val Thr Val Ser Ser Gly Gly Gly
    130                 135                 140

Gly Ser Gly Gly Gly Gly Ser Ala Ala Ala Gly Ala Pro Val Pro
145                 150                 155                 160

Tyr Pro Asp Pro Leu Glu Pro Arg Gly Gly Ser His His His His His
                165                 170                 175

His

<210> SEQ ID NO 12
<211> LENGTH: 121
<212> TYPE: PRT
<213> ORGANISM: Artificial sequence
<220> FEATURE:
<223> OTHER INFORMATION: VH domain of CXCL12-Trap-hSDA-3

<400> SEQUENCE: 12

Gln Val Gln Leu Leu Glu Ser Gly Gly Gly Leu Val Gln Pro Gly Gly
1               5                   10                  15

Ser Leu Arg Leu Ser Cys Ala Ala Ser Gly Asp Ser Phe Thr Thr Lys
            20                  25                  30

Asn Met Ala Trp Val Arg Gln Ala Pro Gly Lys Gly Leu Glu Trp Val
        35                  40                  45

Ser Ala Ile Ser Lys Arg Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Leu Thr Gln Arg His Gly His Ala Lys Leu Lys Tyr Trp Gly
            100                 105                 110

Gln Gly Thr Leu Val Thr Val Ser Ser
        115                 120

<210> SEQ ID NO 13
<211> LENGTH: 10
<212> TYPE: PRT
<213> ORGANISM: Artificial sequence
<220> FEATURE:
<223> OTHER INFORMATION: CDR-H1 of CXCL12-Trap-hSDA-3

<400> SEQUENCE: 13

```
Gly Asp Ser Phe Thr Thr Lys Asn Met Ala
1               5                  10
```

<210> SEQ ID NO 14
<211> LENGTH: 17
<212> TYPE: PRT
<213> ORGANISM: Artificial sequence
<220> FEATURE:
<223> OTHER INFORMATION: CDR-H2 of CXCL12-Trap-hSDA-3

<400> SEQUENCE: 14

```
Ala Ile Ser Lys Arg Ser Gly Ser Thr Tyr Tyr Ala Asp Ser Val Lys
1               5                   10                  15
Gly
```

<210> SEQ ID NO 15
<211> LENGTH: 12
<212> TYPE: PRT
<213> ORGANISM: Artificial sequence
<220> FEATURE:
<223> OTHER INFORMATION: CDR-H3 of CXCL12-Trap-hSDA-3

<400> SEQUENCE: 15

```
Leu Thr Gln Arg His Gly His Ala Lys Leu Lys Tyr
1               5                   10
```

<210> SEQ ID NO 16
<211> LENGTH: 288
<212> TYPE: PRT
<213> ORGANISM: Artificial sequence
<220> FEATURE:
<223> OTHER INFORMATION: CXCL12-Trap-VH/VL-4

<400> SEQUENCE: 16

```
Met Lys Trp Val Thr Phe Ile Ser Leu Leu Phe Leu Phe Ser Ser Ala
1               5                   10                  15

Tyr Ser Gly Ser Glu Val Gln Leu Val Glu Ser Gly Gly Gly Leu Val
                20                  25                  30

Gln Pro Gly Gly Ser Leu Arg Leu Ser Cys Ala Ala Ser Gly Phe Ser
            35                  40                  45

Leu Thr Val Tyr Ser Val His Trp Val Arg Gln Ala Pro Gly Lys Gly
        50                  55                  60

Leu Glu Trp Val Gly Ala Leu Trp Gly Ser Gly Gly Thr Glu Tyr Asn
65                  70                  75                  80

Ser Asn Leu Lys Ser Arg Phe Thr Ile Ser Arg Asp Thr Ser Lys Asn
                85                  90                  95

Thr Val Tyr Leu Gln Met Asn Ser Leu Arg Ala Glu Asp Thr Ala Val
            100                 105                 110

Tyr Tyr Cys Ala Arg Asp Gln Gly Leu Asn Tyr Gly Ser Leu Phe Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Glu Ser Ile Ser Tyr Ser Leu Ser Trp Tyr Gln
            180                 185                 190

Gln Lys Pro Gly Lys Ala Pro Lys Leu Leu Ile Tyr Asn Ala Val Lys
        195                 200                 205
```

```
Leu Glu Ser Gly Val Pro Ser Arg Phe Ser Gly Ser Gly Thr
        210                 215                 220

Asp Phe Thr Leu Thr Ile Ser Ser Leu Gln Pro Glu Asp Phe Ala Thr
225                 230                 235                 240

Tyr Tyr Cys Lys Gln Tyr Trp Asn Thr Pro Phe Thr Phe Gly Gln Gly
                245                 250                 255

Thr Lys Val Glu Ile Lys Arg Ala Ala Ala Gly Ala Pro Val Pro Tyr
            260                 265                 270

Pro Asp Pro Leu Glu Pro Arg Gly Gly Ser His His His His His His
            275                 280                 285
```

<210> SEQ ID NO 17
<211> LENGTH: 120
<212> TYPE: PRT
<213> ORGANISM: Artificial sequence
<220> FEATURE:
<223> OTHER INFORMATION: VH domain of CXCL12-Trap-VH/VL-4

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Val Tyr
            20                  25                  30

Ser Val His Trp Val Arg Gln Ala Pro Gly Lys Gly Leu Glu Trp Val
        35                  40                  45

Gly Ala Leu Trp Gly Ser Gly Gly Thr Glu Tyr Asn Ser Asn Leu Lys
    50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gln Gly Leu Asn Tyr Gly Ser Leu Phe Asp Tyr Trp Gly Gln
            100                 105                 110

Gly Thr Leu Val Thr Val Ser Ser
        115                 120
```

<210> SEQ ID NO 18
<211> LENGTH: 108
<212> TYPE: PRT
<213> ORGANISM: Artificial sequence
<220> FEATURE:
<223> OTHER INFORMATION: VL domain of CXCL12-Trap-VH/VL-4

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Tyr Ser
            20                  25                  30

Leu Ser Trp Tyr Gln Gln Lys Pro Gly Lys Ala Pro Lys Leu Leu Ile
        35                  40                  45

Tyr Asn Ala Val Lys Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Lys Gln Tyr Trp Asn Thr Pro Phe
                85                  90                  95

Thr Phe Gly Gln Gly Thr Lys Val Glu Ile Lys Arg
            100                 105
```

```
                        100                 105

<210> SEQ ID NO 19
<211> LENGTH: 10
<212> TYPE: PRT
<213> ORGANISM: Artificial sequence
<220> FEATURE:
<223> OTHER INFORMATION: CDR-H1 of CXCL12-Trap-VH/VL-4

<400> SEQUENCE: 19

Gly Phe Ser Leu Thr Val Tyr Ser Val His
1               5                   10

<210> SEQ ID NO 20
<211> LENGTH: 16
<212> TYPE: PRT
<213> ORGANISM: Artificial sequence
<220> FEATURE:
<223> OTHER INFORMATION: CDR-H2 of CXCL12-Trap-VH/VL-4

<400> SEQUENCE: 20

Ala Leu Trp Gly Ser Gly Gly Thr Glu Tyr Asn Ser Asn Leu Lys Ser
1               5                   10                  15

<210> SEQ ID NO 21
<211> LENGTH: 12
<212> TYPE: PRT
<213> ORGANISM: Artificial sequence
<220> FEATURE:
<223> OTHER INFORMATION: CDR-H3 of CXCL12-Trap-VH/VL-4

<400> SEQUENCE: 21

Asp Gln Gly Leu Asn Tyr Gly Ser Leu Phe Asp Tyr
1               5                   10

<210> SEQ ID NO 22
<211> LENGTH: 11
<212> TYPE: PRT
<213> ORGANISM: Artificial sequence
<220> FEATURE:
<223> OTHER INFORMATION: CDR-L1 of CXCL12-Trap-VH/VL-4

<400> SEQUENCE: 22

Arg Ala Ser Glu Ser Ile Ser Tyr Ser Leu Ser
1               5                   10

<210> SEQ ID NO 23
<211> LENGTH: 7
<212> TYPE: PRT
<213> ORGANISM: Artificial sequence
<220> FEATURE:
<223> OTHER INFORMATION: CDR-L2 of CXCL12-Trap-VH/VL-4

<400> SEQUENCE: 23

Asn Ala Val Lys Leu Glu Ser
1               5

<210> SEQ ID NO 24
<211> LENGTH: 9
<212> TYPE: PRT
<213> ORGANISM: Artificial sequence
<220> FEATURE:
<223> OTHER INFORMATION: CDR-L3 of CXCL12-Trap-VH/VL-4

<400> SEQUENCE: 24

Lys Gln Tyr Trp Asn Thr Pro Phe Thr
1               5
```

<210> SEQ ID NO 25
<211> LENGTH: 690
<212> TYPE: DNA
<213> ORGANISM: Artificial sequence
<220> FEATURE:
<223> OTHER INFORMATION: PD-L1 Trap

<400> SEQUENCE: 25

```
atgaaatggg tcacctttat cagcctgctg ttcctgttca gcagcgccta cagcggatcc    60
ggtccgccta cctttagtcc ggcactgctg gttgttaccg aaggtgataa tgcaaccttt   120
acatgcagct ttagcaatac cagcgaaagc tttgttctga attggtatcg tatgagcccg   180
agcaatcaga ccgataaact ggcagcattt ccggaagatc gtagccagcc tggtcaggat   240
agccgtttc  gtgttaccca gctgccgaat ggtcgtgatt ttcatatgag cgttgttcgt   300
gcacgtcgta atgatagcgg cacctatctg tgtggtgcaa ttagcctggc accgaaagca   360
cagattaaag aaagcctgcg tgcagaactg cgtgtgaccg aacgtcgtgc agaaggcccg   420
caaccgcaac cgaaaccgca gccgaaaccg gaaccggaac cgcaaccgca aggcggttct   480
gaggaagacc cctgtgcctg tgagtccata ctgaaatttg aggccaaggt ggagggtctg   540
ctgcaggccc tgaccaggaa gctggaagct gtgagcgggc ggctggctgt cctggagaac   600
agaatcatcg cggccgctgg cgcccctgtg ccttatcctg atcccctgga acctagaggc   660
ggcagccacc accaccatca ccactgatga                                    690
```

<210> SEQ ID NO 26
<211> LENGTH: 228
<212> TYPE: PRT
<213> ORGANISM: Artificial sequence
<220> FEATURE:
<223> OTHER INFORMATION: PD-L1 Trap

<400> SEQUENCE: 26

```
Met Lys Trp Val Thr Phe Ile Ser Leu Leu Phe Leu Phe Ser Ser Ala
1               5                   10                  15

Tyr Ser Gly Ser Gly Pro Pro Thr Phe Ser Pro Ala Leu Leu Val Val
            20                  25                  30

Thr Glu Gly Asp Asn Ala Thr Phe Thr Cys Ser Phe Ser Asn Thr Ser
        35                  40                  45

Glu Ser Phe Val Leu Asn Trp Tyr Arg Met Ser Pro Ser Asn Gln Thr
    50                  55                  60

Asp Lys Leu Ala Ala Phe Pro Glu Asp Arg Ser Gln Pro Gly Gln Asp
65                  70                  75                  80

Ser Arg Phe Arg Val Thr Gln Leu Pro Asn Gly Arg Asp Phe His Met
                85                  90                  95

Ser Val Val Arg Ala Arg Arg Asn Asp Ser Gly Thr Tyr Leu Cys Gly
            100                 105                 110

Ala Ile Ser Leu Ala Pro Lys Ala Gln Ile Lys Glu Ser Leu Arg Ala
        115                 120                 125

Glu Leu Arg Val Thr Glu Arg Arg Ala Glu Gly Pro Gln Pro Gln Pro
    130                 135                 140

Lys Pro Gln Pro Lys Pro Glu Pro Glu Pro Gln Pro Gln Gly Gly Ser
145                 150                 155                 160

Glu Glu Asp Pro Cys Ala Cys Glu Ser Ile Leu Lys Phe Glu Ala Lys
                165                 170                 175

Val Glu Gly Leu Leu Gln Ala Leu Thr Arg Lys Leu Glu Ala Val Ser
```

```
            180                 185                 190
Gly Arg Leu Ala Val Leu Glu Asn Arg Ile Ile Ala Ala Gly Ala
        195                 200                 205

Pro Val Pro Tyr Pro Asp Pro Leu Glu Pro Arg Gly Gly Ser His His
    210                 215                 220

His His His His
225

<210> SEQ ID NO 27
<211> LENGTH: 117
<212> TYPE: PRT
<213> ORGANISM: Homo sapiens

<400> SEQUENCE: 27

Pro Pro Thr Phe Ser Pro Ala Leu Leu Val Val Thr Glu Gly Asp Asn
 1               5                  10                  15

Ala Thr Phe Thr Cys Ser Phe Ser Asn Thr Ser Glu Ser Phe Val Leu
                20                  25                  30

Asn Trp Tyr Arg Met Ser Pro Ser Asn Gln Thr Asp Lys Leu Ala Ala
            35                  40                  45

Phe Pro Glu Asp Arg Ser Gln Pro Gly Gln Asp Ser Arg Phe Arg Val
    50                  55                  60

Thr Gln Leu Pro Asn Gly Arg Asp Phe His Met Ser Val Val Arg Ala
65                  70                  75                  80

Arg Arg Asn Asp Ser Gly Thr Tyr Leu Cys Gly Ala Ile Ser Leu Ala
                85                  90                  95

Pro Lys Ala Gln Ile Lys Glu Ser Leu Arg Ala Glu Leu Arg Val Thr
            100                 105                 110

Glu Arg Arg Ala Glu
        115

<210> SEQ ID NO 28
<211> LENGTH: 130
<212> TYPE: PRT
<213> ORGANISM: Homo sapiens

<400> SEQUENCE: 28

Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Ser Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu
    130
```

<210> SEQ ID NO 29
<211> LENGTH: 143
<212> TYPE: PRT
<213> ORGANISM: Homo sapiens

<400> SEQUENCE: 29

Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140

<210> SEQ ID NO 30
<211> LENGTH: 117
<212> TYPE: PRT
<213> ORGANISM: Mus musculus

<400> SEQUENCE: 30

Ser Leu Thr Phe Tyr Pro Ala Trp Leu Thr Val Ser Glu Gly Ala Asn
1               5                   10                  15

Ala Thr Phe Thr Cys Ser Leu Ser Asn Trp Ser Glu Asp Leu Met Leu
            20                  25                  30

Asn Trp Asn Arg Leu Ser Pro Ser Asn Gln Thr Glu Lys Gln Ala Ala
        35                  40                  45

Phe Cys Asn Gly Leu Ser Gln Pro Val Gln Asp Ala Arg Phe Gln Ile
    50                  55                  60

Ile Gln Leu Pro Asn Arg His Asp Phe His Met Asn Ile Leu Asp Thr
65                  70                  75                  80

Arg Arg Asn Asp Ser Gly Ile Tyr Leu Cys Gly Ala Ile Ser Leu His
                85                  90                  95

Pro Lys Ala Lys Ile Glu Glu Ser Pro Gly Ala Glu Leu Val Val Thr
            100                 105                 110

Glu Arg Ile Leu Glu
        115

<210> SEQ ID NO 31
<211> LENGTH: 147
<212> TYPE: PRT
<213> ORGANISM: Mus musculus

<400> SEQUENCE: 31

Ser Gly Trp Leu Leu Glu Val Pro Asn Gly Pro Trp Arg Ser Leu Thr
1               5                   10                  15

Phe Tyr Pro Ala Trp Leu Thr Val Ser Glu Gly Ala Asn Ala Thr Phe
            20                  25                  30

```
Thr Cys Ser Leu Ser Asn Trp Ser Glu Asp Leu Met Leu Asn Trp Asn
        35                  40                  45

Arg Leu Ser Pro Ser Asn Gln Thr Glu Lys Gln Ala Ala Phe Cys Asn
 50                  55                  60

Gly Leu Ser Gln Pro Val Gln Asp Ala Arg Phe Gln Ile Ile Gln Leu
 65                  70                  75                  80

Pro Asn Arg His Asp Phe His Met Asn Ile Leu Asp Thr Arg Arg Asn
                 85                  90                  95

Asp Ser Gly Ile Tyr Leu Cys Gly Ala Ile Ser Leu His Pro Lys Ala
            100                 105                 110

Lys Ile Glu Glu Ser Pro Gly Ala Glu Leu Val Val Thr Glu Arg Ile
        115                 120                 125

Leu Glu Thr Ser Thr Arg Tyr Pro Ser Pro Ser Pro Lys Pro Glu Gly
    130                 135                 140

Arg Phe Gln
145

<210> SEQ ID NO 32
<211> LENGTH: 143
<212> TYPE: PRT
<213> ORGANISM: Mus musculus

<400> SEQUENCE: 32

Leu Glu Val Pro Asn Gly Pro Trp Arg Ser Leu Thr Phe Tyr Pro Ala
1               5                   10                  15

Trp Leu Thr Val Ser Glu Gly Ala Asn Ala Thr Phe Thr Cys Ser Leu
            20                  25                  30

Ser Asn Trp Ser Glu Asp Leu Met Leu Asn Trp Asn Arg Leu Ser Pro
        35                  40                  45

Ser Asn Gln Thr Glu Lys Gln Ala Ala Phe Cys Asn Gly Leu Ser Gln
 50                  55                  60

Pro Val Gln Asp Ala Arg Phe Gln Ile Ile Gln Leu Pro Asn Arg His
 65                  70                  75                  80

Asp Phe His Met Asn Ile Leu Asp Thr Arg Arg Asn Asp Ser Gly Ile
                 85                  90                  95

Tyr Leu Cys Gly Ala Ile Ser Leu His Pro Lys Ala Lys Ile Glu Glu
            100                 105                 110

Ser Pro Gly Ala Glu Leu Val Val Thr Glu Arg Ile Leu Glu Thr Ser
        115                 120                 125

Thr Arg Tyr Pro Ser Pro Ser Pro Lys Pro Glu Gly Arg Phe Gln
    130                 135                 140

<210> SEQ ID NO 33
<211> LENGTH: 117
<212> TYPE: PRT
<213> ORGANISM: Rattus norvegicus

<400> SEQUENCE: 33

Pro Leu Thr Phe Ser Pro Thr Trp Leu Thr Val Ser Glu Gly Ala Asn
1               5                   10                  15

Ala Thr Phe Thr Cys Ser Phe Ser Asn Trp Ser Glu Asp Leu Lys Leu
            20                  25                  30

Asn Trp Tyr Arg Leu Ser Pro Ser Asn Gln Thr Glu Lys Gln Ala Ala
        35                  40                  45

Phe Cys Asn Gly Tyr Ser Gln Pro Val Arg Asp Ala Arg Phe Gln Ile
 50                  55                  60
```

```
Val Gln Leu Pro Asn Gly His Asp Phe His Met Asn Ile Leu Asp Ala
 65                  70                  75                  80

Arg Arg Asn Asp Ser Gly Ile Tyr Leu Cys Gly Ala Ile Ser Leu Pro
                 85                  90                  95

Pro Lys Ala Gln Ile Lys Glu Ser Pro Gly Ala Glu Leu Val Val Thr
            100                 105                 110

Glu Arg Ile Leu Glu
            115
```

<210> SEQ ID NO 34
<211> LENGTH: 143
<212> TYPE: PRT
<213> ORGANISM: Rattus norvegicus

<400> SEQUENCE: 34

```
Leu Glu Val Leu Asn Lys Pro Trp Arg Pro Leu Thr Phe Ser Pro Thr
 1               5                  10                  15

Trp Leu Thr Val Ser Glu Gly Ala Asn Ala Thr Phe Thr Cys Ser Phe
                20                  25                  30

Ser Asn Trp Ser Glu Asp Leu Lys Leu Asn Trp Tyr Arg Leu Ser Pro
             35                  40                  45

Ser Asn Gln Thr Glu Lys Gln Ala Ala Phe Cys Asn Gly Tyr Ser Gln
 50                  55                  60

Pro Val Arg Asp Ala Arg Phe Gln Ile Val Gln Leu Pro Asn Gly His
 65                  70                  75                  80

Asp Phe His Met Asn Ile Leu Asp Ala Arg Arg Asn Asp Ser Gly Ile
                 85                  90                  95

Tyr Leu Cys Gly Ala Ile Ser Leu Pro Pro Lys Ala Gln Ile Lys Glu
            100                 105                 110

Ser Pro Gly Ala Glu Leu Val Val Thr Glu Arg Ile Leu Glu Thr Pro
            115                 120                 125

Thr Arg Tyr Pro Arg Pro Ser Pro Lys Pro Glu Gly Gln Phe Gln
            130                 135                 140
```

<210> SEQ ID NO 35
<211> LENGTH: 220
<212> TYPE: PRT
<213> ORGANISM: Homo sapiens

<400> SEQUENCE: 35

```
Phe Thr Val Thr Val Pro Lys Asp Leu Tyr Val Val Glu Tyr Gly Ser
 1               5                  10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
             35                  40                  45

Phe Val His Gly Glu Glu Asp Leu Lys Val Gln His Ser Ser Tyr Arg
 50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125
```

```
Val Thr Ser Glu His Glu Leu Thr Cys Gln Ala Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
                195                 200                 205

Pro Glu Leu Pro Leu Ala His Pro Pro Asn Glu Arg
    210                 215                 220

<210> SEQ ID NO 36
<211> LENGTH: 200
<212> TYPE: PRT
<213> ORGANISM: Homo sapiens

<400> SEQUENCE: 36

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
                20                  25                  30

Leu Gly Ala Ile Thr Ala Ser Leu Gln Lys Val Glu Asn Asp Thr Ser
            35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro
        195                 200

<210> SEQ ID NO 37
<211> LENGTH: 219
<212> TYPE: PRT
<213> ORGANISM: Mus musculus

<400> SEQUENCE: 37

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
                20                  25                  30
```

Leu Ala Leu Val Val Tyr Trp Glu Lys Glu Asp Glu Gln Val Ile Gln
                35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
                100                 105                 110

Asn Ala Pro Tyr Arg Lys Ile Asn Gln Arg Ile Ser Val Asp Pro Ala
                115                 120                 125

Thr Ser Glu His Glu Leu Ile Cys Gln Ala Glu Gly Tyr Pro Glu Ala
                130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
                180                 185                 190

Trp Arg Ser Gln Pro Gly Gln Asn His Thr Ala Glu Leu Ile Ile Pro
                195                 200                 205

Glu Leu Pro Ala Thr His Pro Pro Gln Asn Arg
210                 215

<210> SEQ ID NO 38
<211> LENGTH: 200
<212> TYPE: PRT
<213> ORGANISM: Mus musculus

<400> SEQUENCE: 38

Leu Phe Thr Val Thr Ala Pro Lys Glu Val Tyr Thr Val Asp Val Gly
1               5                   10                  15

Ser Ser Val Ser Leu Glu Cys Asp Phe Asp Arg Arg Glu Cys Thr Glu
                20                  25                  30

Leu Glu Gly Ile Arg Ala Ser Leu Gln Lys Val Glu Asn Asp Thr Ser
                35                  40                  45

Leu Gln Ser Glu Arg Ala Thr Leu Leu Glu Glu Gln Leu Pro Leu Gly
    50                  55                  60

Lys Ala Leu Phe His Ile Pro Ser Val Gln Val Arg Asp Ser Gly Gln
65                  70                  75                  80

Tyr Arg Cys Leu Val Ile Cys Gly Ala Ala Trp Asp Tyr Lys Tyr Leu
                85                  90                  95

Thr Val Lys Val Lys Ala Ser Tyr Met Arg Ile Asp Thr Arg Ile Leu
                100                 105                 110

Glu Val Pro Gly Thr Gly Glu Val Gln Leu Thr Cys Gln Ala Arg Gly
                115                 120                 125

Tyr Pro Leu Ala Glu Val Ser Trp Gln Asn Val Ser Val Pro Ala Asn
                130                 135                 140

Thr Ser His Ile Arg Thr Pro Glu Gly Leu Tyr Gln Val Thr Ser Val
145                 150                 155                 160

Leu Arg Leu Lys Pro Gln Pro Ser Arg Asn Phe Ser Cys Met Phe Trp
                165                 170                 175

Asn Ala His Met Lys Glu Leu Thr Ser Ala Ile Ile Asp Pro Leu Ser

Arg Met Glu Pro Lys Val Pro Arg
        195                 200

<210> SEQ ID NO 39
<211> LENGTH: 219
<212> TYPE: PRT
<213> ORGANISM: Rattus norvegicus

<400> SEQUENCE: 39

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Gln Lys Leu Asp Leu
            20                  25                  30

Leu Ala Leu Val Val Tyr Trp Glu Lys Glu Asp Lys Glu Val Ile Gln
        35                  40                  45

Phe Val Glu Gly Glu Glu Asp Leu Lys Pro Gln His Ser Ser Phe Arg
    50                  55                  60

Gly Arg Ala Phe Leu Pro Lys Asp Gln Leu Leu Lys Gly Asn Ala Val
65                  70                  75                  80

Leu Gln Ile Thr Asp Val Lys Leu Gln Asp Ala Gly Val Tyr Cys Cys
                85                  90                  95

Met Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Met Asp Pro Ala
        115                 120                 125

Thr Ser Glu His Glu Leu Met Cys Gln Ala Glu Gly Tyr Pro Glu Ala
    130                 135                 140

Glu Val Ile Trp Thr Asn Ser Asp His Gln Ser Leu Ser Gly Glu Thr
145                 150                 155                 160

Thr Val Thr Thr Ser Gln Thr Glu Glu Lys Leu Leu Asn Val Thr Ser
                165                 170                 175

Val Leu Arg Val Asn Ala Thr Ala Asn Asp Val Phe His Cys Thr Phe
            180                 185                 190

Trp Arg Val His Ser Gly Glu Asn His Thr Ala Glu Leu Ile Ile Pro
        195                 200                 205

Glu Leu Pro Val Pro Arg Leu Pro His Asn Arg
    210                 215

<210> SEQ ID NO 40
<211> LENGTH: 200
<212> TYPE: PRT
<213> ORGANISM: Rattus norvegicus

<400> SEQUENCE: 40

Leu Phe Thr Val Thr Ala Pro Lys Glu Val Tyr Thr Val Asp Phe Gly
1               5                   10                  15

Ser Ser Val Ser Leu Glu Cys Asp Phe Asp Arg Arg Glu Cys Thr Glu
            20                  25                  30

Leu Glu Gly Ile Arg Ala Ser Leu Gln Lys Val Glu Asn Asp Thr Ser
        35                  40                  45

Ser Gln Ser Gln Arg Ala Thr Leu Leu Glu Glu Leu Pro Leu Gly
    50                  55                  60

Lys Ala Ser Phe His Ile Pro Ser Val Gln Val Arg Asp Ser Gly Gln
65                  70                  75                  80

Tyr Arg Cys Leu Val Ile Cys Gly Ala Ala Trp Asp Tyr Lys Tyr Leu

```
                    85                  90                  95
Thr Val Lys Val Lys Ala Ser Tyr Val Arg Ile Asp Thr Gly Ile Leu
                100                 105                 110

Glu Val Pro Gly Thr Gly Glu Val Gln Leu Ile Cys Gln Ala Arg Gly
            115                 120                 125

Tyr Pro Leu Ala Glu Val Ser Trp Gln Asn Val Ser Val Pro Ala Asn
        130                 135                 140

Thr Ser His Ile Arg Thr Pro Glu Gly Leu Tyr Gln Val Thr Ser Val
145                 150                 155                 160

Leu Arg Leu Lys Pro Gln Pro Asn Arg Asn Phe Ser Cys Met Phe Trp
                165                 170                 175

Asn Ala His Met Lys Glu Leu Thr Ser Ala Ile Ile Asp Pro Leu Ser
                180                 185                 190

Trp Met Glu Pro Lys Val Pro Arg
                195                 200

<210> SEQ ID NO 41
<211> LENGTH: 43
<212> TYPE: PRT
<213> ORGANISM: Homo sapiens

<400> SEQUENCE: 41

Glu Glu Asp Pro Cys Ala Cys Glu Ser Leu Val Lys Phe Gln Ala Lys
1               5                   10                  15

Val Glu Gly Leu Leu Gln Ala Leu Thr Arg Lys Leu Glu Ala Val Ser
            20                  25                  30

Lys Arg Leu Ala Ile Leu Glu Asn Thr Val Val
        35                  40

<210> SEQ ID NO 42
<211> LENGTH: 43
<212> TYPE: PRT
<213> ORGANISM: Homo sapiens

<400> SEQUENCE: 42

Glu Glu Asp Pro Cys Ala Cys Glu Ser Leu Val Thr Phe Gln Ala Lys
1               5                   10                  15

Val Glu Gly Leu Leu Gln Ala Leu Thr Arg Lys Leu Glu Ala Val Ser
            20                  25                  30

Lys Arg Leu Ala Ile Leu Glu Asn Thr Val Val
        35                  40

<210> SEQ ID NO 43
<211> LENGTH: 43
<212> TYPE: PRT
<213> ORGANISM: Homo sapiens

<400> SEQUENCE: 43

Glu Glu Asp Pro Cys Ala Cys Glu Ser Leu Val Lys Phe Gln Ala Lys
1               5                   10                  15

Val Glu Gly Leu Leu Gln Ala Leu Thr Ser Pro Leu Glu Ala Val Ser
            20                  25                  30

Lys Arg Leu Ala Ile Leu Glu Asn Thr Val Val
        35                  40

<210> SEQ ID NO 44
<211> LENGTH: 46
<212> TYPE: PRT
<213> ORGANISM: Homo sapiens
```

```
<400> SEQUENCE: 44

Leu Arg Ser Pro Cys Glu Cys Glu Ser Leu Val Glu Phe Gln Gly Arg
1               5                   10                  15

Thr Leu Gly Ala Leu Glu Ser Leu Thr Leu Asn Leu Ala Gln Leu Thr
            20                  25                  30

Ala Arg Leu Glu Asp Leu Glu Asn Gln Leu Ala Asn Gln Lys
        35                  40                  45

<210> SEQ ID NO 45
<211> LENGTH: 44
<212> TYPE: PRT
<213> ORGANISM: Homo sapiens

<400> SEQUENCE: 45

His Asp Gln Cys Lys Cys Glu Asn Leu Ile Met Phe Gln Asn Leu Ala
1               5                   10                  15

Asn Glu Glu Val Arg Lys Leu Thr Gln Arg Leu Glu Glu Met Thr Gln
            20                  25                  30

Arg Met Glu Ala Leu Glu Asn Arg Leu Arg Tyr Arg
        35                  40

<210> SEQ ID NO 46
<211> LENGTH: 45
<212> TYPE: PRT
<213> ORGANISM: Homo sapiens

<400> SEQUENCE: 46

Thr Glu Asp Ala Cys Gly Cys Glu Ala Thr Leu Ala Phe Gln Asp Lys
1               5                   10                  15

Val Ser Ser Tyr Leu Gln Arg Leu Asn Thr Lys Leu Asp Asp Ile Leu
            20                  25                  30

Glu Lys Leu Lys Ile Asn Glu Tyr Gly Gln Ile His Arg
        35                  40                  45

<210> SEQ ID NO 47
<211> LENGTH: 43
<212> TYPE: PRT
<213> ORGANISM: Mus musculus

<400> SEQUENCE: 47

Glu Glu Asp Pro Cys Ala Cys Glu Ser Ile Leu Lys Phe Glu Ala Lys
1               5                   10                  15

Val Glu Gly Leu Leu Gln Ala Leu Thr Arg Lys Leu Gly Ala Val Ser
            20                  25                  30

Gly Arg Leu Ala Val Leu Glu Asn Arg Ile Ile
        35                  40

<210> SEQ ID NO 48
<211> LENGTH: 46
<212> TYPE: PRT
<213> ORGANISM: Mus musculus

<400> SEQUENCE: 48

Leu Arg Ser Pro Cys Glu Cys Glu Ser Leu Val Glu Phe Gln Gly Arg
1               5                   10                  15

Thr Leu Gly Ala Leu Glu Ser Leu Thr Gln Asn Leu Ala Arg Leu Thr
            20                  25                  30

Glu Arg Leu Glu Glu Leu Glu Asn Gln Leu Ala Ser Arg Lys
        35                  40                  45
```

<210> SEQ ID NO 49
<211> LENGTH: 45
<212> TYPE: PRT
<213> ORGANISM: Mus musculus

<400> SEQUENCE: 49

Thr Gln Asp Gln Cys Lys Cys Glu Asn Leu Ile Gln Phe Gln Asn Leu
1               5                   10                  15

Ala Asn Glu Glu Val Arg Lys Leu Thr Gln Arg Leu Glu Glu Met Thr
            20                  25                  30

Gln Arg Met Glu Ala Leu Glu Asn Arg Leu Arg Tyr Arg
        35                  40                  45

<210> SEQ ID NO 50
<211> LENGTH: 43
<212> TYPE: PRT
<213> ORGANISM: Mus musculus

<400> SEQUENCE: 50

Asp Gln Cys Lys Cys Glu Asn Leu Ile Leu Phe Gln Asn Val Ala Asn
1               5                   10                  15

Glu Glu Val Arg Lys Leu Thr Gln Arg Leu Glu Glu Met Thr Gln Arg
            20                  25                  30

Met Glu Ala Leu Glu Asn Arg Leu Lys Tyr Arg
        35                  40

<210> SEQ ID NO 51
<211> LENGTH: 44
<212> TYPE: PRT
<213> ORGANISM: Mus musculus

<400> SEQUENCE: 51

Glu Asp Ala Cys Gly Cys Gly Ala Thr Leu Ala Phe Gln Glu Lys Val
1               5                   10                  15

Ser Ser His Leu Gln Lys Leu Asn Thr Lys Leu Asp Asn Ile Leu Lys
            20                  25                  30

Lys Leu Lys Val Thr Glu Tyr Gly Gln Val His Arg
        35                  40

<210> SEQ ID NO 52
<211> LENGTH: 43
<212> TYPE: PRT
<213> ORGANISM: Ceratotherium simum

<400> SEQUENCE: 52

Glu Glu Asp Pro Cys Ala Cys Glu Ser Ile Val Lys Phe Gln Ala Lys
1               5                   10                  15

Val Glu Gly Leu Leu Gln Ala Leu Thr Arg Lys Leu Glu Ala Val Ser
            20                  25                  30

Lys Arg Leu Ala Val Leu Glu Asn Arg Ile Val
        35                  40

<210> SEQ ID NO 53
<211> LENGTH: 43
<212> TYPE: PRT
<213> ORGANISM: Nannospalax galili

<400> SEQUENCE: 53

Glu Glu Asp Pro Cys Ala Cys Glu Ser Ile Val Arg Phe Glu Ala Lys
1               5                   10                  15

-continued

Val Glu Gly Leu Leu Gln Ala Leu Thr Arg Lys Leu Glu Ala Val Ser
            20                  25                  30

Lys Arg Leu Ala Val Leu Glu Asn Arg Ile Val
        35                  40

<210> SEQ ID NO 54
<211> LENGTH: 43
<212> TYPE: PRT
<213> ORGANISM: Bison bison

<400> SEQUENCE: 54

Glu Glu Asp Pro Cys Ala Cys Glu Ser Ile Val Lys Phe Gln Thr Lys
1               5                   10                  15

Val Glu Gly Leu Leu Gln Ala Leu Thr Arg Lys Leu Glu Ala Val Ser
            20                  25                  30

Lys Arg Leu Ala Val Leu Glu Asn Arg Ile Val
        35                  40

<210> SEQ ID NO 55
<211> LENGTH: 43
<212> TYPE: PRT
<213> ORGANISM: Rattus norvegicus

<400> SEQUENCE: 55

Glu Glu Asp Pro Cys Ala Cys Glu Ser Ile Val Arg Phe Glu Ala Lys
1               5                   10                  15

Val Glu Gly Leu Leu Gln Asp Leu Thr Arg Lys Leu Glu Ala Val Ser
            20                  25                  30

Lys Arg Leu Ala Val Leu Glu Asn Arg Val Ile
        35                  40

<210> SEQ ID NO 56
<211> LENGTH: 46
<212> TYPE: PRT
<213> ORGANISM: Rattus norvegicus

<400> SEQUENCE: 56

Glu Thr Gln Asp Gln Cys Lys Cys Glu Asn Leu Ile Gln Phe Gln Asn
1               5                   10                  15

Leu Ala Asn Glu Glu Val Arg Lys Leu Thr Gln Arg Leu Glu Glu Met
            20                  25                  30

Thr Gln Arg Met Glu Ala Leu Glu Asn Arg Leu Arg Tyr Arg
        35                  40                  45

<210> SEQ ID NO 57
<211> LENGTH: 26
<212> TYPE: PRT
<213> ORGANISM: Rattus norvegicus

<400> SEQUENCE: 57

Glu Asp Ala Cys Ser Cys Gly Ala Thr Leu Ala Phe Gln Glu Lys Val
1               5                   10                  15

Ser Ser His Leu Gln Lys Leu Asn Thr Thr
            20                  25

<210> SEQ ID NO 58
<211> LENGTH: 11
<212> TYPE: PRT
<213> ORGANISM: Artificial sequence
<220> FEATURE:
<223> OTHER INFORMATION: linker sequence -continued

```
<220> FEATURE:
<221> NAME/KEY: REPEAT
<222> LOCATION: (1)..(11)
<223> OTHER INFORMATION: linker sequence can be repeated n times,
      wherein n=1-20

<400> SEQUENCE: 58

Gly Pro Gln Pro Gln Pro Lys Pro Gln Pro Lys
1               5                   10

<210> SEQ ID NO 59
<211> LENGTH: 5
<212> TYPE: PRT
<213> ORGANISM: Artificial sequence
<220> FEATURE:
<223> OTHER INFORMATION: linker sequence
<220> FEATURE:
<221> NAME/KEY: REPEAT
<222> LOCATION: (1)..(5)
<223> OTHER INFORMATION: linker sequence can be repeated n times,
      wherein n=1-20

<400> SEQUENCE: 59

Gly Gly Gly Gly Ser
1               5

<210> SEQ ID NO 60
<211> LENGTH: 15
<212> TYPE: PRT
<213> ORGANISM: Homo sapiens

<400> SEQUENCE: 60

Thr Pro Pro Thr Pro Ser Pro Ser Thr Pro Pro Thr Pro Ser Pro
1               5                   10                  15

<210> SEQ ID NO 61
<211> LENGTH: 16
<212> TYPE: PRT
<213> ORGANISM: Mus musculus

<400> SEQUENCE: 61

Glu Phe Pro Lys Pro Ser Thr Pro Pro Gly Ser Ser Gly Gly Ala Pro
1               5                   10                  15

<210> SEQ ID NO 62
<211> LENGTH: 16
<212> TYPE: PRT
<213> ORGANISM: Camelus dromedarius

<400> SEQUENCE: 62

Pro Gln Pro Gln Pro Gln Pro Lys Pro Gln Pro Lys Pro Glu Pro Glu
1               5                   10                  15

<210> SEQ ID NO 63
<211> LENGTH: 1543
<212> TYPE: DNA
<213> ORGANISM: Artificial Sequence
<220> FEATURE:
<223> OTHER INFORMATION: CXCL12 trap

<400> SEQUENCE: 63
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
```

```
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc tggctaacta    600
gagaacccac tgcttactgg cttatcgaaa ttaatacgac tcactatagg gagacccaag    660
ctggctagcc accatgaaat gggtcacctt tatcagcctg ctgttcctgt tcagcagcgc    720
ctacagcgga tccgaggtgc agctggtgga atctggcgga ggactggtgc agcctggcgg    780
ctctctgaga ctgtcttgtg ccgccagcgg cttcagcctg accgtgtact ctgtgcactg    840
ggtgcgccag gccccaggca aggactgga atgggtggga gccctgtggg gctctggcgg    900
aaccgagtac aacagcaacc tgaagtcccg gttcaccatc agccgggaca ccagcaagaa    960
caccgtgtac ctgcagatga acagcctgcg ggccgaggac accgccgtgt actattgcgc   1020
cagagatcag ggcctgaact acggcagcct gttcgactat ggggccaggg cacactcgt   1080 gaccgtgtct agcggaggcg gaggaagtgg cggaggggga tctggcggcg gaggcagcga   1140
tattcagatg acccagtccc ccagcagcct gagcgcctct gtgggcgaca gagtgaccat   1200
cacctgtcgg gccagcgaga gcatcagcta cagcctgtcc tggtatcagc agaagcccgg   1260
caaggccccc aagctgctga tctacaacgc cgtgaagctg gaaagcggcg tgcccagcag   1320
attttccggc agcggctctg gcaccgactt caccctgacc atcagctccc tgcagcccga   1380
ggacttcgcc acctactact gcaagcagta ctggaacacc cccttcacct tcggacaggg   1440
caccaaggtg gaaatcaaga gcggccgc tggcgcccct gtgccttatc ctgatcccct   1500
ggaacctaga ggcggcagcc accaccacca tcaccactga tga                    1543
```

<210> SEQ ID NO 64
<211> LENGTH: 89
<212> TYPE: PRT
<213> ORGANISM: Homo sapiens

<400> SEQUENCE: 64

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 65
<211> LENGTH: 93
<212> TYPE: PRT
<213> ORGANISM: Homo sapiens

<400> SEQUENCE: 65

```
Met Asn Ala Lys Val Val Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
            50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90
```

<210> SEQ ID NO 66
<211> LENGTH: 18818
<212> TYPE: DNA
<213> ORGANISM: Homo sapiens

<400> SEQUENCE: 66

| | | | | |
|---|---|---|---|---|
| ctttcaggct tctgggacag atcctaggtc cagctgccca cctgattttg tggcaaagaa | 60 |
| aaaaagaaga agaagaagcg agaggcgatg gcgtttgctt tggccagatt taagggcaag | 120 |
| cgaggctgcg cgcggctccc gcagggtcgg atctccgagc tccagggcgc ccctccaccc | 180 |
| gggtgtagat ttcccgcgga ccccttcgcc ctccgggtt tcatcagctg cgcaggaatg | 240 |
| gagctggcca gagctctggg agcggggagg gaggcgccgc caccagaggg cgccggagcc | 300 |
| ccagcgctgc ggccggtgag cggccaggct ccccggccca gcccagcaaa ggcctgggga | 360 |
| cgcccgacgg ctgccttctt cactggacct cactgccttc agttctttaa gagcagggcc | 420 |
| aagtcagtgg ggttcccggc tccaagccca gtgcccaggg tggtgggtg ggtgggtggg | 480 |
| tgggtggatg gatggatgga tggatggatg gagtgccggc ccacagccat ctaacggcca | 540 |
| aagtggtttt ggaaaaaaaa tgcacagaag acacctactc ccaccagcgg agttccggag | 600 |
| ccctcgcagc ctcctgttga ccgctcccgc ctaatgcagc cgctgaccgc ccactccccg | 660 |
| acggccagga ctccccaggg acaggacgt gtccccaggg caggcccctg gatgacgcg | 720 |
| gcgactgacc ccacttcgct ggacgctgtg ctgggaagga cacagagagg tggctggggc | 780 |
| agcctgcggt cacaaagcga ggcccaaagg ggcgctctcc tcaccccac gcctcctggg | 840 |
| tgccgacctg caccctccct tcgccaccgg actggggcca tctgggatgt ctcgggggta | 900 |
| tccggagggc taagcaccgc cgagggacgg ctccgtggga agagttttct ggacccagaa | 960 |
| ggcagacgcc agtagtactg tcctaggagt cggaggtcgg ggtggggag ttctcagctc | 1020 |
| tttgggtcgc acggagcttt tcttgggtaa ggcagtaagt acttaggttt aaaggactta | 1080 |
| cttacagcta ccatttattg agtactgtct gcttgtcaga cacgatgcag agaatttcgc | 1140 |
| ggcgtggggc gggtctcatt gaatctcccg tcccactccg cggggtgggc ctgtgattag | 1200 |
| ctcatttcac cattgagagg tcggaagtac aaaggctaca ttcgctttta ctgagagccg | 1260 |
| ccggcgcctt ctgctttgtt tgtacaggcg aggaaactga ggctcggctg gtggcgccgt | 1320 |
| gggcttggag tccagccac gctgactgca agacgggtc tcattcccgc agatcgagct | 1380 |
| ctgccggcgg ctgcgccgca agccgggcag gtggcgagct tgagccccca cgcacagaaa | 1440 |
| gcaggacccc ctcggctgcc ttgggccgcc accgccagca ggccctccgc ccggactaa | 1500 |
| cttgtttgct tttcattggt tctcattcag ttccgccat cgaaaggccc cgtcccgcag | 1560 |
| cttttccacgc gcgcccact ttacgcctaa ggtcctcagt ctctccagtg gggccctgtc | 1620 |

```
acagggacaa taagcggccc tccagccggc gtcgctcagg ctgcggacct cactgcagac    1680
cgggccagcg gtgcgggcc cagcggagcc tgagaaggtc aaaggccgga gcgcactgcg     1740
cctcgggagc acagagggag cggaggaggg gcgaagggga tgggtggggg gtgccgccga    1800
gggagtcgcg cgtcagagac cccggccacg gccagcactc ggctccgggc ccgcccctca    1860
ccgcgcgccc cgcccgccc cgcctggctc tccctctaa agcgcccggc gcgcgcctcc      1920
caccgccgca ctttcactct ccgtcagccg cattgcccgc tcggcgtccg gccccgacc     1980 cgcgctcgtc cgcccgcccg cccgcccgcc cgcgccatga acgccaaggt cgtggtcgtg    2040
ctggtcctcg tgctgaccgc gctctgcctc agcgacggta agtgcgctcg gcggggaggc    2100
cctggcgagg cggccctggc gaggctctgg gcttcggctc ccgcccggcg cagagccgcg    2160
gctcctctgc ctgcgcccgc agtttgcgcc gcccgacaca gtgggggtgg aggcagctcg    2220
cttagctggg cgctctggtg cggtgtcgcg ttcaaagccc tacttttgcg ccgagggttt    2280
gtgacctgca gagagcgacc gcctgacctc aagctggctg cagagcgagg tcagccggga    2340
caactgggca ggaacgcccc aagagagcgt tcggactgg cgcgggaagg cgcgagggtg     2400
gggagccgcg gaccccagac ccctgcctgc ccaccctcca cccactgcct tcccgctgcg    2460
ggctcggttt ccacaggcga atgggctccg aggtcctgct gcgcacagtg ctggaggtcg    2520
ggcggtgcat ggcgagagcg cgctttgcaa agttcgcctc atgccgcgac ttgaggctgt    2580
gaggtccgat gcagccgcgc agcctccgct ccctgcgaag ccgatcctct ccccacaccc    2640 tcgcgggggct cttggccagg cgcgggcggg ctgcgcggcg cagctgtcgg gcttgtgcca    2700
cccgccaggc cgcgcttctg cacagctccg cggtccgcag cgacgcggac ctgggcgcgc    2760
gtccagccgc tgtcttcctg tctcttctcg ggttcacctg agagaggccc agggaccctc    2820
cgagcctcac acgcccctc cccagctccc caaacacacc tgcagacagg ctcttttgtc     2880
accagctggc caagcgcttt gccccagaat gagagctgca gcaaagttca atctccaagg    2940
ccctgggcca ctgggaaccg tggtgtcccg tttcactggg agagggcttt tttcttttct    3000
ttcgctgaag agaaactcgc tgcgctgtca caggacaccg atgcaaacca aaataaactg    3060
ttgcctctga acacacaaaa caaaaccctg tggctcaggc cgctgagctt ccttggctgt    3120
gaagtttcct gcaaagagtt gaaggacact ctgagtgctc ttgcagccgc gggctgtgca    3180
ggcccagcgc gcctcgagcc cttggctggg ttggtgcaga cgtggcccg cgtcctagc     3240 tggcttggac tgtgcgctgg tgtgagcagg accagcgcag ctgagtcggg ctggagaagc    3300
tgggcagcct ggggtcgtgg cggactgcct aagtgttaag gacacagact gaaggcaatt    3360
gggaatgttc gtcgttgatg aaaagtccct gaggctgtgt ctgcacactg accccccccc    3420 cccccccgcaa gtcatgggc atgtttctag tttttattgc tggatattct tctgttcctg    3480
taaggtctct ggtttgggca gttattgact gattggtggg atgagcgcgg aggtgtcaca    3540
gtgcgccgct ctgggaaatg gtgctgcccc ctccccggag ggctggagag aggattggaa    3600
tgaggaacct cggtctttga gttatgggtg caactgacct gggggaagca cagagacgtg    3660
gggttcatcc cagactcctc ctggcctggg aagggtgaca tggccctcag agttgcccca    3720
ttggcagcca agtaaccagg gcaggagcct gggctccagg cagatctgct ccttacacac    3780
atcgccagaa tgttttgttt tgtttttgttt tcccctcacc tcacagtgcc tatgtgcccc    3840
ctatccccac acttagtcct caagctgcac tacagagaga gcttggccag gggtcctgcc    3900
cctcccccat tggctgactt ccgtcaggca gctgggccct tgggtttccc gggcttaaac    3960
```

```
tcagggtggg cccccttccc aagcctgctt ggaggggcca gctgggctcc tgtctctgca      4020
ttagactgga gggcttctg aaaactcctg gagccaagct cacccggtcc caaatccggg       4080
gtaccatcag agccagtcag gactcttgcc ggtacacgga tttacatcca gaacggttgg     4140
gaaagttagt cttactgaca aaaagctgga ggaaggagca catgaggtac acacgagacc     4200
atgttctttt ggtaagcaca cctgggggct ctgtcacttt aaaaagacct gttgaaattc     4260
gctgcttgac aggcgggcct taggtcctgg gagtagaagc aagaattgct tttgaaggaa    4320
atggataatc ccagggggtg gaggggagag ggagagagag cctgtgtgtt gagctctgaa     4380
taggctctga tttctggcct catcaccact gcttggttgg ggggccagag gagcttctct     4440
cctctgggcg ctggagagtc acagccccac ccatcccagc gggggcggct gcagcacttg     4500
cccttggctg catatcttca agctcactgt tgccggagg gggcttgtgc ctcactaccg       4560
gcctcctatt ctcctgctcc accccccaacc cacccctgc ctcagcttgg aagggcccaa     4620
aagaaatcca gggaaacctg gaggcacaac actcaggagc gtttagctcc tcagttaccc      4680
aggctgcagg ccccggccct gggggtggct ttcccaggtg atctggttac agtgcagtgc    4740
tgacttcccc tgcagggtcc cagtgcagct gctggaagct ggcccagag gtgcctttct       4800 ggagttagat caggtgtaac tgtgaaggct gcttaggtc tctccagtgc catgagtcac       4860
cagcaccctg atgcttggct ttttcctggt tttcagggag ttgcatttgg tcctggggac     4920
aaggaagtgg ggggacaagt ggtccacttt tcctgcaact tggtggctga atacacaatg    4980
caattcctag tccacatcat ccctcaattg attgcagtct gtagaaaaaa taaaataaaa     5040
tgagccccct actcaagatt tcctcctact tccccagcat tctttcccaa aggtgcagaa   5100
tttcagaacc acagaggtct ctcagaactt tgtaaacagg caaacttaaa aaaaaagaaa    5160
aaagaaaaaa aatctctgga ccaaatattc ttagacatat atttaatctc tgatgaaagg    5220
atccacaagt tcaaataatt tggggtatta agtggggctt ggataaaatc ttcaaggaaa    5280
aaagaaaaac aaaaagcaca cacaaatccc agccctccag ggcttgcaat cctatattta   5340
aagggtgagc agtgggttct gcaggagccc cttgctaatt tacactaatg agtgtcaatt    5400
atggcatttt gtaaattggt gattttgcaa agatcttaat acaattcctg aggctacagc    5460
atccctgcct aggcaatgaa accacatttt aactccagct ccactaatct ctaagccttg    5520
gggaaagtgc tggcagaag gtgggtcctt ggcctgctct caggggactc acaggtagga     5580
agccagccag gattctttg tgccttccag agctttaggt gaatgtgagg aggggtctct      5640
ggggtggggg agggcagcat tcctgagtac tactgtgctt cctggctaga ggcctgtgcc    5700
agaggagaga ggccagggag cctggagcct cttgtccccc tttcttttcc ctgagtaggg    5760
agatctttct cagttgtccc ttgaggaatt ttttttacaa agagtaactg gaaatttcag    5820
taccttggac tgaaaccgtt atctactata attactacct ttatcttgag acactgagca    5880
ggtggcttct aatttaatct cccccctcat ctaggctccg gctctcccca ggcctgttgg    5940
gctccttgcc ctgtagaagc tgagcctgag ctcagccagc actcactgtg ttgcctgagg   6000
agatggcctt tcccaacata caccagtaac ctggaactta ccccagtgat gccgtctctt   6060
gatccttaat cgctgcacca actgctgcag cccagacaca cattaccaaa atctggcagg   6120
gtagtaaagt gccttgttgt ccttacctct tctagggaag cccgtcagcc tgagctacag   6180
atgcccatgc cgattcttcg aaagccatgt tgccagagcc aacgtcaagc atctcaaaat    6240
tctcaacact ccaaactgtg cccttcagat tgtgtaagtc ttgaaattga acatcatcta   6300
acgaacatag ttgcatctaa cgaacatagt aacatctaac ccgagtctta ttaaaggtgt    6360
```

```
agaggtgaca agccaagtgt ccaaccttga acttggcata attagtggca gctattctta    6420
tcatgaggac ctttagtatg ccaccaggca ttaattttaa aagccgctct tggcctgggc    6480
accctgctgt gctcgtagta gttctctctt ctttccaaac ctgtgttctt cagcacagca    6540
cagctggatg ctggagaaac tatgggcttc accaaggttt tggctgaagc ctagtaaatt    6600
agccagccct tagctaataa cagtgataac tggcctgcca gtttcgggga tctgatgccc    6660
tacattaact cacaagaccc aaatgcagtt taagtcctct ttaaccattg ggtgaaactt    6720
caacattttc agctcacttg cctgtatttt ctcaagtaca acatatgagg ttttggtgtt    6780
atttggtgtg gatggcagcc actaacattt gattttattc atttgggaaa caaagaccaa    6840
aatcacacat ccacaagaca ggaagatctc agctgggtac agaagaccgg gagaaatgcg    6900
ggaagaaagc catgtgcttg aaagccctct catgctcaag aggtcctgtg tctgaacacg    6960
gggaagcgag ggctcaggga gtctcctgga gaggatttga ttgctcagaa gttctagtgc    7020
taaaaatggg gtggggagac agcagttgga accaaagcta caactttccc aagacttttc    7080
cacccaacac caaatgtttt tacttttgat tttagaaaac tgttttagt tttgagttaa     7140
ccctttactg ccttgaatgt gtttgttatt tacagtatgt tttagggccc tagaaaatga    7200
atgtttttc agtactttgc ctacaacatg atactttatc tcttgtgaag agtattttaa     7260
agatgctcaa tttagctagc ttggacctgc tttacagcac tgatcatgct ggtttactgg    7320
cctggaaatg caccttgaag ttgaagatgc caaatacaat tctcaggtct gagcagacac    7380
taaattaaca aagaatagge cccagatttg accccaatg tgggttgctc cgagccacac     7440
ccatctctgc acccctcttc acctaatgga caggctgctt gaagactccc tgggtgcccc    7500
tgaaccactg ttctggggct tagctgtcct caagacccct aagtacttgg gctgcatgag    7560
attacctggc accaaagggc tttctggcaa gagatccaga gagatgaaat caggccttcc    7620
ccaggagttt gcatgtaggg aagcttttaa gagtgtgaac ttttaaaaaa caaatgagac    7680
caagaaacat tcagtgaact tgtaaaatct ttctagaaac tatttttctgg taagccacct   7740
gcactgcccc tcccctccct ggctggtcac cctcccggtc agaccgcggt gacttctggc    7800
aggcctcctt cctccaggct tcctcatgcc catccttaag tcggccctat atctatcaag    7860
atgacccatc caaataaacc tctgctctgt tgctctccat tctcccctcc ccaggtgcct    7920
agagcatcct gtcgtccct tcctcagttt cctctgtatg ctttgatgac cccctggcg     7980
tatttgctcc tgattttccc ttcccgttta tttactctcc aagctcctac ttatccttca    8040
aaggcagctc aaatgctccc ttacatgaat tcccctgcac tgccccggaa agacttctgt    8100
tcacatttcc atgtctctgc aatggaactt cctgcactgc cagcgctgag cttccccag     8160
cacaccgcga gcacctctgg agcctgagcg taccaagtgg agcacgggt gccagcgagg     8220
gccctagatg ggtgttgggg gagcggatgc acacgttgca gccgcgcctt cctcctgtgc    8280
agccgcacac tgttgccatt ctgttttcac agagcccggc tgaagaacaa caacagacaa    8340
gtgtgcattg acccgaagct aaagtggatt caggagtacc tggagaaagc tttaaacaag    8400
taagcacaac agccaaaaag gactttccgc tagacccact cgaggaaaac taaaaccttg    8460
tgagagatga aagggcaaag acgtggggga gaggggcct taaccatgag gaccaggtgt     8520
gtgtgtgggg tggcacatt gatctgggat cgggcctgag gtttgccagc atttagaccc     8580
tgcatttata gcatacggta tgatattgca gcttatattc atccatgccc tgtacctgtg    8640
cacgttggaa cttttattac tggggttttt ctaagaagaa aattgtatta tcaacagcat    8700
```

```
tttcaagcag ttagttcctt catgatcatc acaatcatca tcattctcat tctcattttt     8760
taaatcaacg agtacttcaa gatctgaatt tggcttgttt ggagcatctc ctctgctccc     8820
ctggggagtc tgggcacagt caggtggtgg cttaacaggg agctggaaaa agtgtccttt     8880
cttcagacac tgaggctccc gcagcagcgc ccctcccaag aggaaggcct ctgtggcact     8940
cagataccga ctggggctgg gcgccgccac tgccttcacc tcctctttca acctcagtga     9000
ttggctctgt gggctccatg tagaagccac tattactggg actgtgctca gagacccctc     9060
tcccagctat tcctactctc tccccgactc cgagagcatg cttaatcttg cttctgcttc     9120
tcatttctgt agcctgatca gcgccgcacc agccgggaag agggtgattg ctggggctcg     9180
tgccctgcat ccctctcctc ccagggcctg ccccacagct cgggccctct gtgagatccg     9240
tctttggcct cctccagaat ggagctggcc ctctcctggg gatgtgtaat ggtcccctg      9300 cttacccgca aaagacaagt ctttacagaa tcaaatgcaa ttttaaatct gagagctcgc     9360
tttgagtgac tgggttttgt gattgcctct gaagcctatg tatgccatgg aggcactaac     9420
aaactctgag gtttccgaaa tcagaagcga aaaaatcagt gaataaacca tcatcttgcc     9480 actacccct cctgaagcca cagcagggtt tcaggttcca atcagaactg ttggcaaggt      9540
gacatttcca tgcataaatg cgatccacag aaggtcctgg tggtatttgt aacttttgc      9600 aaggcatttt tttatatata ttttgtgca cattttttt tacgtttctt tagaaaacaa       9660
atgtatttca aaatatattt atagtcgaac aattcatata tttgaagtgg agccatgat      9720 atgtcagtag tttatacttc tctattatct caaactactg gcaatttgta aagaaatata    9780
tatgatatat aaatgtgatt gcagcttttc aatgttagcc acagtgtatt ttttcacttg    9840
tactaaaatt gtatcaaatg tgacattata tgcactagca ataaaatgct aattgtttca    9900
tggtataaac gtcctactgt atgtgggaat ttatttaccct gaaataaaat tcattagttg   9960
ttagtgatgg agcttataga cgtttctggt ttatatagtt aagcctgcct gcagtcaggt   10020
gtctgagacc ccttctcaca gcccatgtgt gacagtgtat gggcttttct cacgagcaga   10080
ttagatctgc agctcaagtt tttggatctt tttttttttt ttttaacccg attgaaatag   10140
cagtgctggt tttctgaaga ataatatttg actcactaat tcgtcttccc tccctcctcc   10200
tccttggttc tcctaacttc cccatgtaat ccccagagac tcaaccctag taatatcaac   10260
cttttacatt ttcccatgta aaaatcccat gactccaggc catggttaat atgaagcttt   10320
cacagggaca ggtggcctca ccccataaat cattaaatac cattcagctt gaatcatttt   10380
aatgtgacag tcacgagcca gttgctctaa taaaattctg ctaaccagct ctctcccttg   10440
ctctccagaa caatcgcatt cattcccagg agtgttcaca ggcgtctaga aaggggaagg   10500
tgggaccact gccttttttc tcctcttctg aatggcagtc tgaacctggg gcctgcagcc   10560
tccaaaacgt tattcaattt gaaatgcaga catttcttag agaaagctaa gagttcagcc   10620
ctgcattgag aagaagaaaa agtcccatga gagcagggca gggtgggtg acaaggacca    10680 cgatggccag cctggccctg ggtgtaccct gagatgtgga ttccttgtcc ccagtgggaa   10740
tcaggttcag gttggcagat tggcagtcgc tgtaacccat tcacaaaggt gttctaggag   10800
cccattgaac atttgtttga atggaaggaa atgtccaatt tattttaatg aattactgat   10860
aaacagtgct ttgaccaggg gcctccaggc ctgagactga aggcacagtt taaccagtac   10920
acgggccagt gttaaatctt atgcagactg agacgaactt tgttatttt ccacattatt    10980 aatggttcta ctaattttat ctaaggggc gcagagaaga aaagtggggg aaaaagaaa     11040 agataggaaa aaagaagcga cagaagaaga gaaaggctgc ccagaaaagg aaaaactagt   11100
```

```
tatctgccac ctcgagatgg accacagttc acttgctctc ggcgctttgt aaatttgctc   11160
gatcctcctc caggacagac ccccatgcag actgggcagg ggctcagact ccgtgggggg   11220
agcagtgctt tgctgccctg ccagccacac cggcttctgt atttatgtgc tttttaaggc   11280
ccttgttggt ctgctaagtt atgaagaaag tagttgtgca gagactgggg cgggggtctg   11340
tgacgcggag cctgtgtgct caggactctg tccagaatag cctgggagct ccaggaatgc   11400
ccaggttgct gagcccccca gcccgccctc cacttcctct cttagaaggc ctgcgctcac   11460
tggggagctc accagctcca cacacttgca gtctgcattc ctgtggagac caggctgtgg   11520
ccacctggcc agtgtgcagg gcaacctgct agcccagcag aggtggcctc gccaggaagg   11580
gggtgtgcca cccctctgtg gccctcagga aaggtgaaaa ctgactgacc cttaggaatg   11640
ggccctggct ttttccaaat acccattgcc tttccctcca gcactctgcc acctgggaag   11700
gggcttcttc agcccctcct tcctgggttg tgggagtggc tttatcccca gcccgggtg    11760 ggtttctgca aactgtgtgg ggtgagcccg agggaatgct gcattctcag agagcagatg   11820
tggaaacact tctcagggag ctcctctttg ggcaattctc tttagagtct ttaaacgggt   11880
cccccacgtg gaggacagat gtgctatgga actttgcaag ggtcctgaat ccctggggat   11940
cccagcctgt cccctcccgc ctcctgcgtg atggcgtgtg ctccagctgc agggcacagc   12000
tgcctctgtc ctcattcatg ggaaatacct tatctgccta aagcaaatac cacttaagct   12060
ctaggaactt tcctgcaccc tccttccctg cccatgtaga tgtatgtgtg agatttttg    12120 gcaagtttct ctaatctgga ccgggaggat ggaagagcaa ggaccccatt tcagtagtgc   12180
tcggaaaaag gatgcgttga atttctcagc ccttctccac ctcacataaa cacccgccca   12240
ccctgcaccc ggatcctggg tcataatttt aataaatgca gaaagagaaa gtggttggag   12300
gatggagcac atggaattca ggagaaaacc cacaaagacc cctgcatgtc agacacaccc   12360
tgtcccggag cgtggtgtcc ccttgagctt taatgagctc cctgtgatca cagccatgcc   12420
ttctcctcgt tggggaggtg tcctaggatg cttcagccaa agacctttgt ttcccgctgc   12480
tatctctttt acctggacaa ctctcctggc ccacgttcct cttgccagca ctggggtca    12540 caggcctgag ccctgggtac aggggtgccc tagtcttctg ccctcccac ctcttaaggc    12600 acagagctgt tgggtgggct gcctggggct gccatccttc ccgtggaagc cagtagccac   12660
tctagtccat gggactcttg acaaaagcgc cccgagaggg caaacctgtg ccccatact    12720 cgcctgcatt cttcggactc cacatgcagc agggctttgt gcctggggag gggtggccag   12780
tctgtcctgg tcagtatgaa aagctgttgg cccctaggg acagagggcc cagctaaggc    12840
tgcctgagga tacaaactgc ttgctatccc actcctgggg agcagggtct gcaggactg    12900 agagtgggtc ccaccttgag aacgcatgca aggtccgtcc tgtcttgatg tcttgatgtg   12960
actgtatgtg ccctgggggc tcactgtggt ttacaagtgg cttgtgaagc tcctgggagc   13020
aggtggtaca cccagtgctg aagacagggt cgccgtggaa gagcgaagag cctgaccggg   13080
attcctggtg ggttgaaaact aggaagtgct cacaccagtc agagccaaat gagggggtgcg  13140 ctatggtcac tgctctgtcc agcatgcgtt cctcctggga ggtcctggcc acctgtgcac   13200 ccaccccgt gccacctcca gcagtcccac ctggggccac ctacggtggc atggcccctg    13260
gctgagaggc cccgagggcg aagggttact ggaagccacg aaagtgcctc ttgggacagc   13320
cgaggccagg atgcagggca gcagcatcct gagcctcagc cccacgccgg tgccgggtaa   13380
gcagtgtgcc ctgtccccgt cgtatgacca ctctgatggg cctctctgtg ccttcgtgcg   13440
```

```
tctgccacgc ccagtgcttg ccacgtgtct gtcctctgct ttctgccatc catgggtccc    13500
tccgcttcag cctggctgcg tctcgcactc ccctcccgtc tgttgtcgca gggcctctga    13560
agggagatgc atggccaagg tggcaacttg gaagtaggga ttggccccag ggcctccgcg    13620
caggccgctg tcctgctgga gctggctggg tgtgggggga acctgcctta atggtgtttc    13680
cctctgttct tgtcaacagg aggttcaaga tgtgagaggg tcagacgcct gaggaaccct    13740
tacagtagga gcccagctct gaaaccagtg ttagggaagg gcctgccaca gcctccctg     13800 ccagggcagg gccccaggca ttgccaaggg ctttgttttg cacactttgc catattttca    13860
ccatttgatt atgtagcaaa atacatgaca tttattttc atttagtttg attattcagt     13920
gtcactggcg acacgtagca gcttagacta aggccattat tgtacttgcc ttattagagt    13980
gtctttccac ggagccactc ctctgactca gggctcctgg gttttgtatt ctctgagctg    14040
tgcaggtggg gagactgggc tgagggagcc tggccccatg gtcagcccta gggtggagag    14100
ccaccaagag ggacgcctgg gggtgccagg accagtcaac ctgggcaaag cctagtgaag    14160
gcttctctct gtgggatggg atggtggagg gccacatggg aggctcaccc ccttctccat    14220
ccacatggga gccgggtctg cctcttctgg gagggcagca gggctaccct gagctgaggc    14280
agcagtgtga ggccagggca gagtgagacc cagccctcat cccgagcacc tccacatcct    14340
ccacgttctg ctcatcattc tctgtctcat ccatcatcat gtgtgtccac gactgtctcc    14400
atggccccgc aaaaggactc tcaggaccaa agctttcatg taaactgtgc accaagcagg    14460
aaatgaaaat gtcttgtgtt acctgaaaac actgtgcaca tctgtgtctt gtttggaata    14520
ttgtccattg tccaatccta tgtttttgtt caaagccagc gtcctcctct gtgaccaatg    14580
tcttgatgca tgcactgttc cccctgtgca gccgctgagc gaggagatgc tccttgggcc    14640
ctttgagtgc agtcctgatc agagccgtgg tcctttgggg tgaactacct tggttccccc    14700
actgatcaca aaaacatggt gggtccatgg gcagagccca agggaattcg tgtgtgcacca   14760 gggttgaccc cagaggattg ctgccccatc agtgctccct cacatgtcag taccttcaaa    14820
ctagggccaa gcccagcact gcttgaggaa acaagcatt cacaacttgt ttttggtttt     14880
taaaacccag tccacaaaat aaccaatcct ggacatgaag attctttccc aattcacatc    14940
taacctcatc ttcttcacca tttggcaatg ccatcatctc ctgccttcct cctgggccct    15000
ctctgctctg cgtgtcacct gtgcttcggg cccttcccac aggacatttc tctaagagaa    15060
caatgtgcta tgtgaagagt aagtcaacct gcctgacatt tggagtgttc cccttccact    15120
gagggcagtc gatagagctg tattaagcca cttaaaatgt tcacttttga caaaggcaag    15180
cacttgtggg ttttttgtttt gttttcatt cagtcttacg aatactttg cccttttgatt    15240 aaagactcca gttaaaaaaa atttaatga agaaagtgga aaacaaggaa gtcaaagcaa     15300
ggaaactatg taacatgtag gaagtaggaa gtaaattata gtgatgtaat cttgaattgt    15360
aactgttctt gaatttaata atctgtaggg taattagtaa catgtgttaa gtattttcat    15420
aagtatttca aattggagct tcatggcaga aggcaaaccc atcaacaaaa attgtccctt    15480
aaacaaaaat taaaatcctc aatccagcta tgttatattg aaaaaataga gcctgaggga    15540
tctttactag ttataaagat acagaactct ttcaaaacct tttgaaatta acctctcact    15600
ataccagtat aattgagttt tcagtggggc agtcattatc caggtaatcc aagatatttt    15660
aaaatctgtc acgtagaact tggatgtacc tgcccccaat ccatgaacca agaccattga    15720
attcttggtt gaggaaacaa acatgaccct aaatcttgac tacagtcagg aaaggaatca    15780
tttctatttc tcctccatgg gagaaaatag ataagagtag aaactgcagg gaaaattatt    15840
```

```
tgcataacaa ttcctctact aacaatcagc tccttcctgg agactgccca gctaaagcaa    15900
tatgcattta aatacagtct tccatttgca agggaaaagt ctcttgtaat ccgaatctct    15960
ttttgctttc gaactgctag tcaagtgcgt ccacgagctg tttactaggg atccctcatc    16020
tgtccctccg ggacctggtg ctgcctctac ctgacactcc cttgggctcc ctgtaacctc    16080
ttcagaggcc ctcgctgcca gctctgtatc aggacccaga ggaaggggcc agaggctcgt    16140
tgactggctg tgtgttggga ttgagtctgt gccacgtgtt tgtgctgtgg tgtgtccccc    16200
tctgtccagg cactgagata ccagcgagga ggctccagag ggcactctgc ttgttattag    16260
agattacctc ctgagaaaaa aggttccgct tggagcagag gggctgaata gcagaaggtt    16320
gcacctcccc caaccttaga tgttctaagt ctttccattg gatctcattg gacccttcca    16380
tggtgtgatc gtctgactgg tgttatcacc gtgggctccc tgactgggag ttgatcgcct    16440
ttcccaggtg ctacacccct ttccagctgg atgagaattt gagtgctctg atccctctac    16500
agagcttccc tgactcattc tgaaggagcc ccattcctgg gaaatattcc ctagaaactt    16560
ccaaatcccc taagcagacc actgataaaa ccatgtagaa aatttgttat tttgcaacct    16620
cgctggactc tcagtctctg agcagtgaat gattcagtgt taaatgtgat gaatactgta    16680
ttttgtattg tttcaattgc atctcccaga taatgtgaaa atggtccagg agaaggccaa    16740
ttcctatacg cagcgtgctt taaaaaataa ataagaaaca actctttgag aaacaacaat    16800
ttctactttg aagtcatacc aatgaaaaaa tgtatatgca cttataattt tcctaataaa    16860
gttctgtact caaatgtagc caccaacagt ttgaaattag tgttactact tggaattttc    16920
tggacgtgct ttttttcccc acaaacccaa aactgagggt tgtgtaatcc tggctacagt    16980
ggttcatgga aaacagggca ttgtaatcat gctaatcaca gctgagaatt ctggaggcat    17040
acttgcctct tctggacagc tgatccttag cagggaaagg tgctcccttt tctctgagtg    17100
tctttgattt tgctagaatt gcttctgaaa ggccagcctg tcctccactc cacaagggat    17160
ggttttgtgc aagggtctca ggtatttctt gacagctgtg aggagggaag cttccactct    17220
gcccttctca gtcctgggag aatgcaacag aggtctggcc ctgatggtaa ttgctgagga    17280
ccagcactct gtgtgtttcc tgcactgcac agagaccttg ctggaagcca gacacgattc    17340
tctcacctag caatggctag ccagcactgt cctggacatg gggcatagga gatgagccca    17400
gcagacaggt tctggtcctc acagaggtca gcccttaaca ctctctagca cattctctgt    17460
catccacagt caactttgtt agaaaggaga gtcagcacaa aagttccgaa tgtctgagtc    17520
agattgtccg gtcctccaag ccctcttccc cattggtcca gatgtgatca catcatccca    17580
tgccaaatct tcccatgact taatgggatg gccgtcatgt gggtgctaag ctgcagatgg    17640
actggggaag gaagaagggt tagagcaggc cgggaagggc agcgtggtgt caggggacct    17700
gtgcaggtgt gaagatcagt agactggggc ttgcgtccca ttcactctct gctccctctg    17760
tgatttgaga tgcatccctt gatctctctg agttccagtc tcccagctgc aacactgaag    17820
cttattactg ccaacggtca agaggattag actgggagag tgtgtggaag aagctagctt    17880
ttgagggaca ggacaaagcc cgcccctcca ccctgaaagt tccccatttt gctccctctc    17940
tccacctcct gtttcctgag gtccacagag ctagaataag acccacatct gcctctgctg    18000
agccccttaa caaagctcag agaccaaggg agcaggaagt gacctggaag ctgagcctgc    18060
ccctcagcta aaggatgggg agaagtcact gggtcgcatc ccctgtatct ccggcacacc    18120
acactgctat cctagcactg ggaatcgaca atgggccaac ccttcaaaat gacctggcat    18180
```

```
cagaaagaaa gcctgagccc tggcatgctt gcattctccc ctcatttact tggccaacaa    18240
cagctgtgat gcctctcctg caccgcagga gtgtggggag caagacacac tcactctaat    18300
tccatgaagc ctgcagtctg gcggctgccg tgtgagaagt gggtattttc atagattgtg    18360
gtgcattcag gcatcaggga agcgtaaaac agaaaagacc cctaacttag gcatcagtaa    18420
ggatttgctt aaaaagcgct ggtgaaggtg agacctgaga aaagtggatt ctttggggag    18480
gtggtctact gagcccatga gggctggcat ggagagccca ggtggtatcc tcctgtgaat    18540
tggaaagggg gcttattcta gaagccggag gtgtagctca cacagggagt ctggcatggg    18600
gggcacaggg cactgggttt cagcttcctt attcccatca cttgtgggag gcacaaacac    18660
agctgagaaa gctggacccc cacggtgatg gggtcccctc agcacggctg attgcatgga    18720
gtggacactg gatgcatatt gcaggccgat ctgattttct gtcacaggag tacaaggctg    18780
tgattcaaca gcatcgggct ttgctcccctt tctctgtg                           18818
```